United States Patent
Berger et al.

(10) Patent No.: US 8,399,480 B2
(45) Date of Patent: Mar. 19, 2013

(54) HYDROXYMETHYL PYRROLIDINES AS BETA 3 ADRENERGIC RECEPTOR AGONISTS

(75) Inventors: Richard Berger, Princeton, NJ (US); Lehua Chang, Ramsey, NJ (US); Scott D. Edmondson, Clark, NJ (US); Stephen D. Goble, Edison, NJ (US); Sookhee Nicole Ha, Warren, NJ (US); Nam Fung Kar, Brooklyn, NY (US); Ihor E. Kopka, Hampton, NJ (US); Bing Li, Towaco, NJ (US); Gregori J. Morriello, Randolph, NJ (US); Chris R. Moyes, Westfield, NJ (US); Dong-Ming Shen, Edison, NJ (US); Liping Wang, Dayton, NJ (US); Cheng Zhu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/936,221

(22) PCT Filed: Apr. 2, 2009

(86) PCT No.: PCT/US2009/039253
§ 371 (c)(1),
(2), (4) Date: Oct. 4, 2010

(87) PCT Pub. No.: WO2009/124167
PCT Pub. Date: Oct. 8, 2009

(65) Prior Publication Data
US 2011/0028481 A1 Feb. 3, 2011

Related U.S. Application Data

(60) Provisional application No. 61/123,063, filed on Apr. 4, 2008, provisional application No. 61/206,043, filed on Jan. 27, 2009.

(51) Int. Cl.
*A61K 43/90* (2006.01)
*A01K 31/44* (2006.01)
*C07D 237/00* (2006.01)

(52) U.S. Cl. ..... 514/306; 514/248; 514/249; 514/266.2; 544/237; 544/253; 544/282; 546/138; 548/159

(58) Field of Classification Search ............... 544/237, 544/253, 282; 546/138; 548/159; 514/248, 514/259, 266.2, 306, 249
See application file for complete search history.

(56) References Cited

U.S. PATENT DOCUMENTS

2002/0028835 A1 3/2002 Hu et al.
2007/0185136 A1 8/2007 Courtemanche et al.

FOREIGN PATENT DOCUMENTS

WO WO03/072572 A1 9/2003

OTHER PUBLICATIONS

H.P. Kaiser, et al., "Catalytic Hydrogenation of Pyrroles at Atmospheric Pressure", J. Org. Chem., vol. 49, No. 22, p. 4203-9, (1984).

*Primary Examiner* — Paul V. Ward
(74) *Attorney, Agent, or Firm* — Patricia A. Shatynski; Valerie J. Camara

(57) ABSTRACT

The present invention provides compounds of Formula (I), pharmaceutical compositions thereof, and method of using the same in the treatment or prevention of diseases mediated by the activation of β3-adrenoceptor.

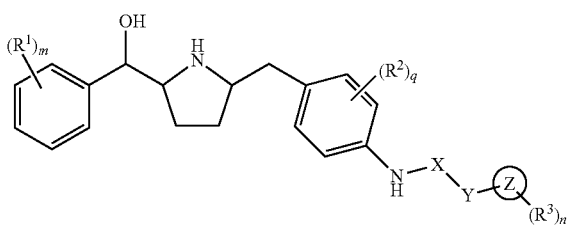

20 Claims, No Drawings

HYDROXYMETHYL PYRROLIDINES AS BETA 3 ADRENERGIC RECEPTOR AGONISTS

CROSS REFERENCE TO RELATED APPLICATIONS

This application is a U.S. National Phase application under 35 U.S.C. §371 of PCT Application No. PCT/US2009/039253, filed Apr. 2, 2009, which claims priority under 35 U.S.C. §119(e) from U.S. Provisional Application Ser. No. 61/123,063, filed Apr. 4, 2008 and 61/206,043, filed Jan. 27, 2009.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

β Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

SUMMARY OF THE INVENTION

The present invention relates to novel β3AR agonists, pharmaceutical compositions containing them, as well as methods for the treatment or prophylaxis of disorders mediated through the β3AR using such novel compounds.

DESCRIPTION OF THE INVENTION

The present invention describes compounds of structural Formula I

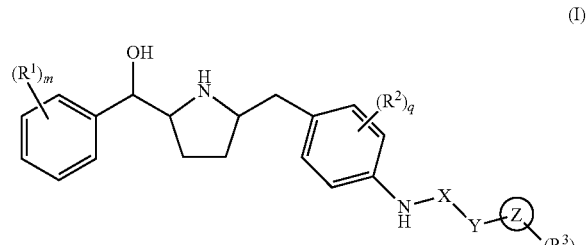

(I)

wherein
m is 0, 1, 2, 3, or 4;
n is 0, 1, 2, 3, 4, or 5;
p is 0, 1, or 2;
q is 0, 1, 2, 3, or 4;
t is 0, 1, 2, 3, 4, or 5;
X is —CO— or —SO$_2$—;
Y is selected from the group consisting of:
  (1) C$_1$-C$_5$ alkanediyl, C$_2$-C$_5$ alkenediyl, and C$_2$-C$_5$ alkynediyl, wherein each of alkanediyl, alkenediyl and alkynediyl is optionally substituted with one to three groups independently selected from halogen, —OR$^a$, S(O)$_p$—C$_1$-C$_3$ alkyl;
  (2) —(CR$^a$R$^a$)$_j$-Q-(CR$^a$R$^a$)$_k$ wherein j and k are integers independently selected from 0, 1 and 2,
  (3) a bond, and
  (4) phenylene optionally substituted with one to three groups independently selected from R$^1$;
Z is selected from the group consisting of:
  (1) phenyl,
  (2) a 5- or 6-membered heterocyclic ring with from 1 to 4 heteroatoms selected from oxygen, sulfur and nitrogen,
  (3) a benzene ring fused to a C$_5$-C$_{10}$ carbocyclic ring, (4) a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, and (5) a 5- or 6-membered heterocyclic ring with from 1 to 4 heteroatoms selected from oxygen, sulfur and nitrogen fused to a $C_5$-$C_{10}$ carbocyclic ring;

$R^1$ is selected from the group consisting of:
(1) $C_1$-$C_5$ alkyl optionally substituted with 1 to 5 halogen atoms,
(2) $C_3$-$C_6$ cycloalkyl,
(3) halogen,
(4) nitro,
(5) cyano,
(6) —C(O)$R^a$,
(7) —C(O)$_2R^a$,
(8) —C(O)N$R^aR^b$, and
(9) -Q$R^b$;

$R^2$ is selected from the group consisting of halogen and $C_1$-$C_5$ alkyl;

$R^3$ is selected from the group consisting of:
(1) $C_1$-$C_6$ alkyl optionally substituted with 1 to 5 groups independently selected from halogen, —O$R^a$, —CO$_2R^a$ and —CON$R^aR^b$,
(2) —(CH$_2$)$_t$-phenyl or —(CH$_2$)$_t$—O-phenyl, and wherein said phenyl in each is optionally substituted with 1 to 3 groups independently selected from halogen, $C_1$-$C_5$ alkyl optionally substituted with 1 to 5 halogen atoms, and —O$R^a$,
(3) oxo,
(4) thioxo,
(5) halogen,
(6) —CN,
(7) $C_3$-$C_6$ cycloalkyl,
(8) —(CH$_2$)$_t$-heterocyclic ring or —(CH$_2$)$_t$—O-heterocyclic ring, and wherein the heterocyclic ring in each is a 5- or 6-membered ring with from 1 to 4 heteroatoms selected from oxygen, sulfur and nitrogen, and wherein said heterocyclic ring is optionally ortho-fused to a benzene ring, and optionally substituted with 1 to 3 groups independently selected from halogen, $C_1$-$C_5$ alkyl optionally substituted with 1 to 5 halogen atoms, and —O$R^a$,
(9) —O$R^a$,
(10) —C(O)O$R^a$,
(11) —C(O)$R^a$,
(12) —C(O)N$R^aR^b$,
(12) —N$R^aR^b$,
(13) —N$R^a$C(O)$R^b$,
(14) —N$R^a$C(O)O$R^b$, and
(15) —N$R^a$C(O)N$R^aR^b$;

$R^a$ is selected from the group consisting of hydrogen and $C_1$-$C_6$ alkyl optionally substituted with 1 to 5 halogen atoms;

$R^b$ is selected from the group consisting of:
(1) hydrogen,
(2) $C_1$-$C_6$ alkyl optionally substituted with 1 to 5 groups selected from the group consisting of:
(a) hydroxy,
(b) halogen,
(c) —CO$_2R^a$,
(d) —S(O)$_p$—$C_1$-$C_3$ alkyl;
(e) $C_3$-$C_9$ cycloalkyl,
(f) $C_1$-$C_6$ alkoxy optionally substituted with 1 to 5 halogens, and
(g) phenyl optionally substituted with 1 to 5 groups independently selected from halogen, nitro, —N$R^aR^a$, trifluoromethyl, trifluoromethoxy, $C_1$-$C_5$ alkyl and —O$R^a$,
(3) $C_3$-$C_8$ cycloalkyl, and (4) phenyl optionally substituted with 1 to 5 groups selected from the group consisting of:
(a) halogen,
(b) nitro,
(c) —N$R^aR^a$,
(d) —OH,
(e) $C_1$-$C_6$ alkoxy optionally substituted with 1 to 5 halogens,
(f) —S(O)$_p$—$C_1$-$C_6$ alkyl; and
(g) $C_1$-$C_6$ alkyl optionally substituted with up to 5 groups selected from hydroxy, halogen, trifluoromethyl, cyano, —CO$_2R^a$, $C_3$-$C_8$ cycloalkyl, and -Q$R^c$;

$R^c$ is selected from the group consisting of:
(1) Z optionally substituted with up to 5 groups selected from halogen, trifluoromethyl, cyano, $C_1$-$C_5$ alkyl and $C_1$-$C_5$ alkoxy, and
(2) $C_1$-$C_6$ alkyl; and Q is selected from
(1) —N($R^a$)—,
(2) —O—, and
(3) —S(O)$_p$—; or a pharmaceutically acceptable salt thereof.

In one embodiment of the compounds of Formula I are compounds of Formula Ia:

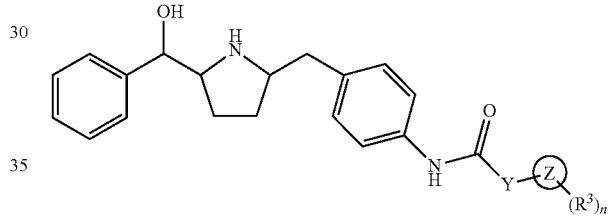

wherein Y, Z, $R^3$ and n are as defined under Formula I.

In one embodiment of Formulas I and Ia are compounds wherein Y is methylene, —CH(CH$_3$)— or a bond. In one subset thereof Y is methylene. In another subset thereof Y is a bond.

In another embodiment of Formulas I and Ia are compounds where Y is phenylene.

In another embodiment of Formulas I and Ia are compounds wherein Z is selecte from the group consisting of:
(1) a 5-membered heterocyclic ring having one nitrogen atom and 0 to 3 additional heteroatoms independently selected from nitrogen, oxygen and sulfur,
(2) a 6-membered heterocyclic ring having 1, 2 or 3 nitrogen atoms, or 1 nitrogen atom and one oxygen or sulfur atom, and
(3) a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, and
(4) a 5- or 6-membered heterocyclic ring with from 1 to 4 heteroatoms selected from oxygen, sulfur and nitrogen fused to a $C_5$-$C_{10}$ carbocyclic ring.

In another embodiment of Formulas I and Ia are compounds wherein Z is a 5- or 6-membered heterocyclic ring with from 1 to 4 heteroatoms selected from oxygen, sulfur and nitrogen. In one subset Z is a 5-membered heterocycle having one nitrogen atom and 0 to 3 additional heteroatoms independently selected from N, O and S. In another subset Z is a 6-membered heterocycle having 1, 2 or 3 nitrogen atoms, or 1 nitrogen atom and an oxygen or sulfur atom. In yet another subset, Z is selected from the group consisting of thiazolyl, oxazolyl, pyridyl, dihydropyridyl, triazolyl (including 1,2,4-triazolyl and 1,2,3-triazolyl), tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, and oxadiazolyl (including 1,2,4-oxadiazolyl and 1,2,5-oxadiazolyl). In one subset of this embodiment, Y is methylene. In another subset of this embodiment Y is a bond.

In another embodiment of Formulas I and Ia are compounds wherein Z is a 5- or 6-membered heterocyclic ring with from 1 to 4 heteroatoms selected from oxygen, sulfur and nitrogen fused to a $C_5$-$C_{10}$ carbocyclic ring. In one subset the carbocyclic ring has 5 or 6 carbon atoms. In another subset the heterocycle is either a 5-membered heterocycle having one nitrogen atom and 0 to 3 additional heteroatoms independently selected from N, O and S, or a 6-membered heterocycle having 1, 2 or 3 nitrogen atoms, or 1 nitrogen atom and an oxygen or sulfur atom, and the carbocycle has 5 or 6 carbon atoms. In yet another subset Z is selected from the group consisting of: indolyl, benzimidazolyl, benzthiazolyl, quinolinyl, isoquinolinyl, tetrahydroquinolinyl, tetrahydroisoquinolinyl, chromenyl, benztriazolyl,

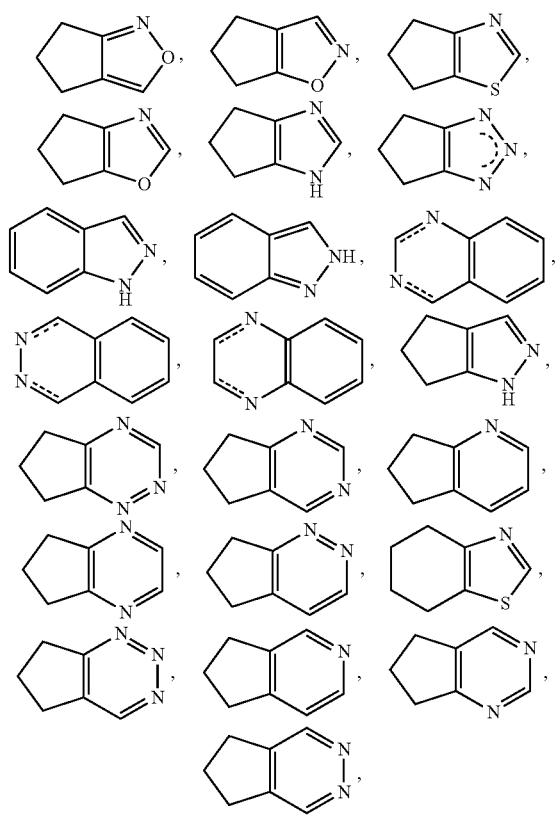

where the dash bond "----" means a single or double bond while conforming to the valency rule for the ring atoms. In one subset of this embodiment Y is methylene. In another subset of this embodiment Y is a bond.

In another embodiment of Formulas I and Ia are compounds wherein Z is a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen. In one subset the fused ring has 2 to 5 heteroatoms, at least one of which is nitrogen. In another subset the fused ring has 2 to 4 nitrogen atoms and no other heteroatoms. In yet another subset the fused ring has one oxygen or sulfur atom, and 1 to 3 nitrogen atoms. In yet another subset. Z is selected from the group consisting of

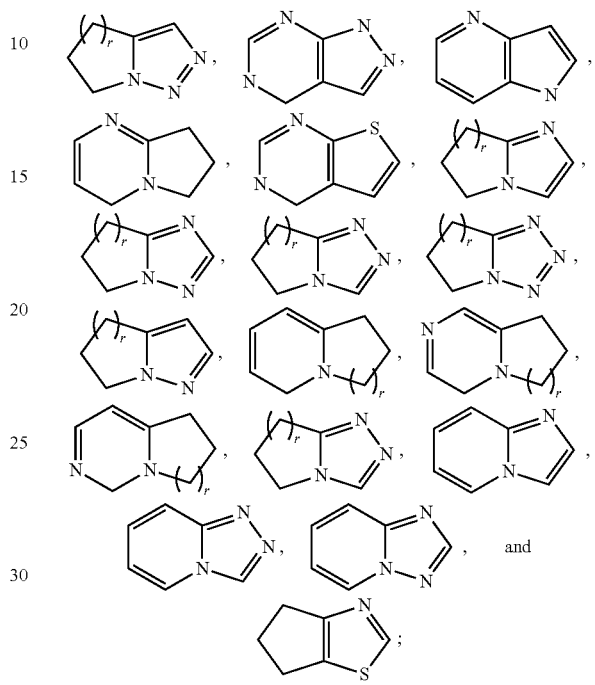

and wherein r is 1 or 2. In one subset of this embodiment Y is methylene. In another subset of this embodiment Y is a bond.

In compounds of Formulas I and Ia, examples of $R^3$ (when n is not 0) include, but are not limited to, —$NR^aR^a$, $C_1$-$C_6$alkyl optionally substituted with halogen or —$OR^a$, —$OR^a$, $C_3$-$C_6$cycloalkyl, phenyl optionally substituted with halogen, benzyl, pyridyl, pyrrolyl, thiazolyl, oxo, halogen, cyano, optionally halo-substituted $C_1$-$C_6$alkanoyl, ($C_1$-$C_6$alkyl)NHC(O)NH—, and —C(O)$NR^aR^a$. More particular examples of $R^3$ include methyl, ethyl, propyl, isopropyl, trifluoromethyl, oxo, fluoro, chloro, pyridyl and pyrrolyl.

In another embodiment of Formulas I and Ia are compounds wherein $R^3$ is selected from the group consisting of:
(1) $C_1$-$C_6$ alkyl optionally substituted with 1 to 5 groups independently selected from halogen, —$OR^a$, —$CO_2R^a$, and —$CONR^aR^b$,
(2) oxo,
(3) halogen,
(4) —$OR^a$,
(5) —C(O)$R^a$,
(6) —C(O)$NR^aR^b$, and
(7) —$NR^aR^b$;
wherein $R^a$ and $R^b$ are as defined above.

In one subset of this embodiment, $R^3$ is selected from the group consisting of:
(1) $C_1$-$C_6$ alkyl optionally substituted with 1 to 5 groups independently selected from halogen, —$OR^a$, —$CO_2R^a$, and —$CONR^aR^b$,
(2) oxo,
(3) halogen, and
(4) —$NR^aR^b$;

wherein each of R$^a$ and R$^b$ is selected from the group consisting of hydrogen and C$_1$-C$_6$ alkyl optionally substituted with 1 to 5 halogen atoms.

In another subset of this embodiment, R$^3$ is selected from the group consisting of:
(1) C$_1$-C$_6$ alkyl,
(2) oxo, and
(3) —NH$_2$.

In another subset of this embodiment, R$^3$ is methyl or ethyl. In another subset, R$^3$ is oxo. In yet another subset, R$^3$ is —NH$_2$.

In another embodiment of Formulas I and Ia are compounds having the specified stereoconfiguration at the indicated chiral center:

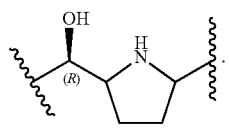

In another embodiment of Formulas I and Ia are compounds having the specified stereoconfiguration at the indicated chiral centers, with the chiral center marked with an asterisk being R or S:

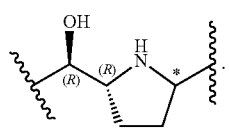

In one subset, the configuration at the chiral center marked with an asterisk is S.

In one embodiment of Formulas I and Ia are compounds as described in Examples 1-313 below.

In another embodiment, the compound of Formulas I or Ia is selected from the group consisting of:

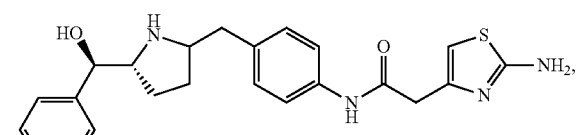

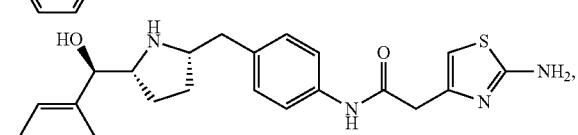

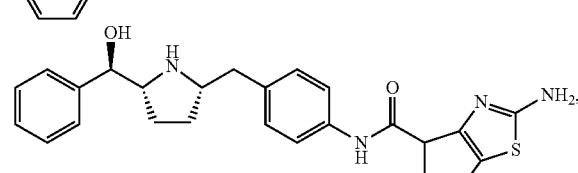

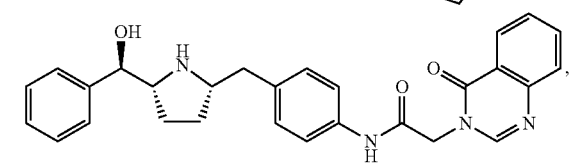

-continued

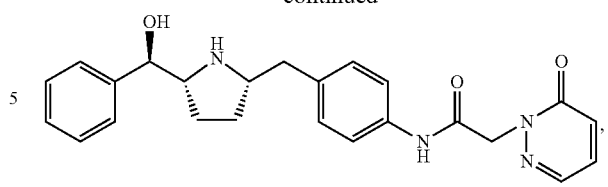

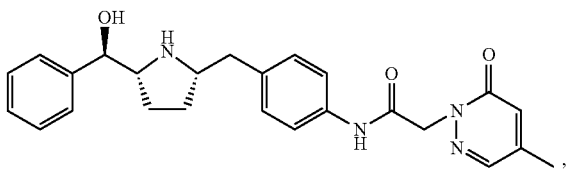

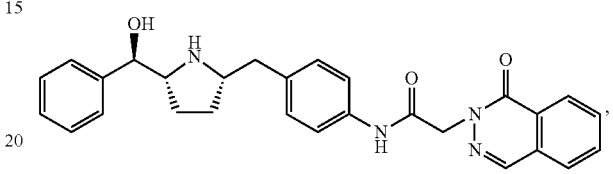

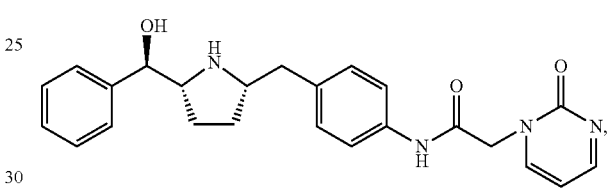

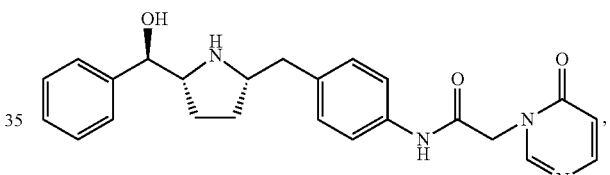

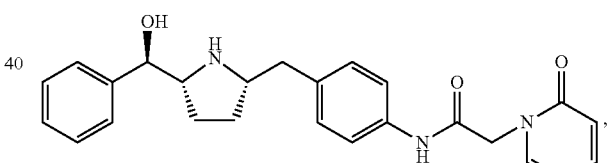

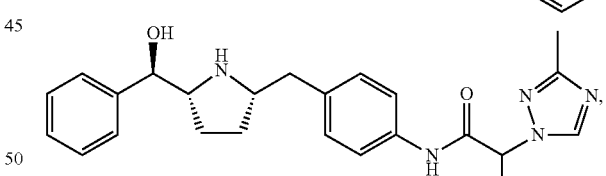

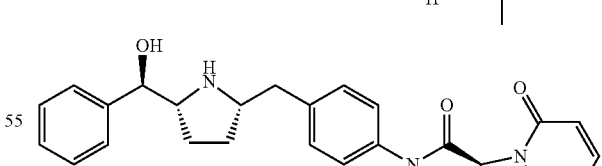

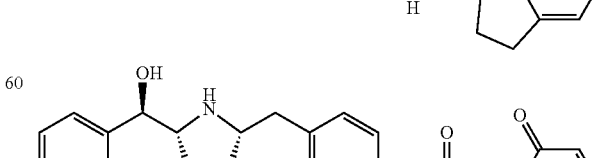

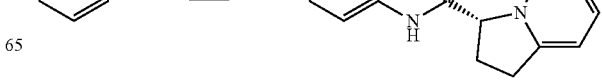

-continued
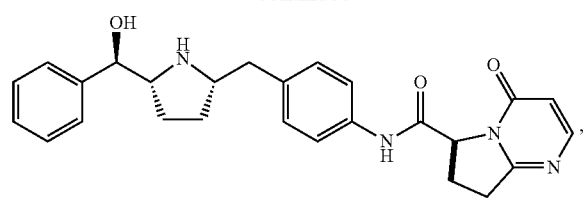
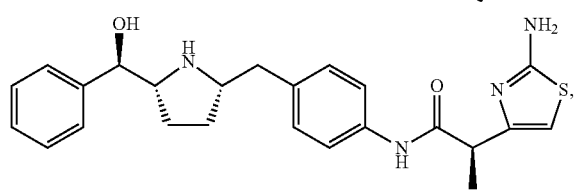
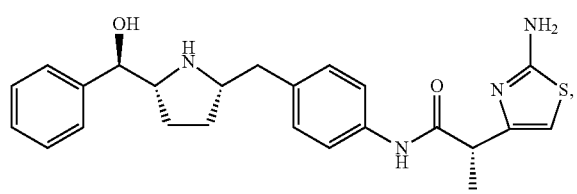
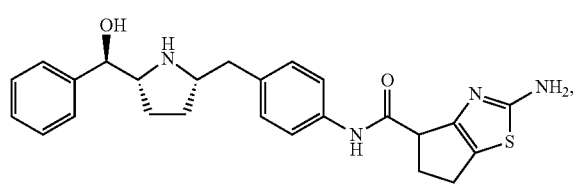
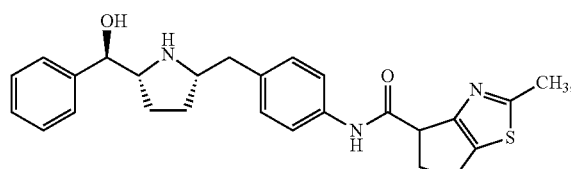
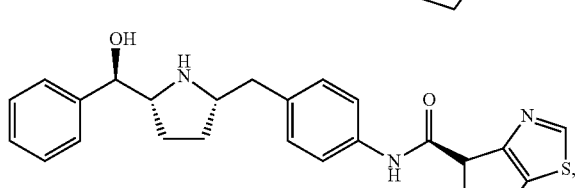
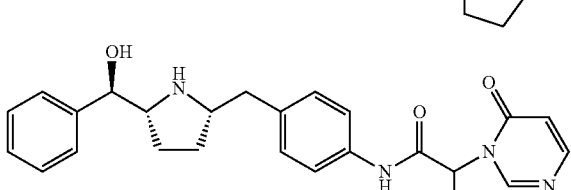
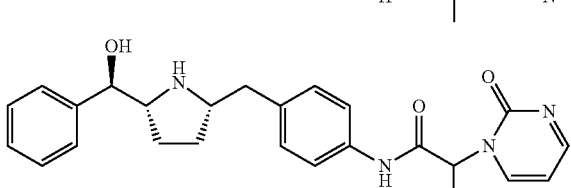
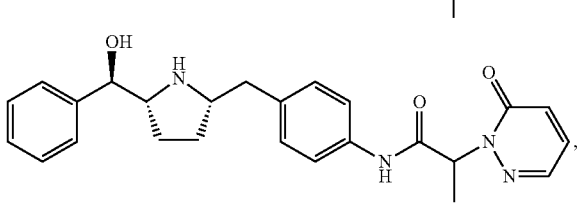
-continued
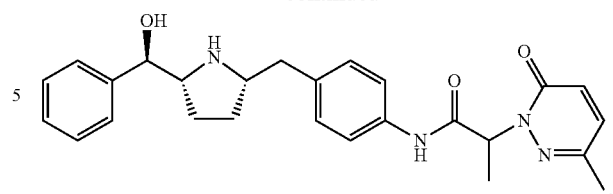
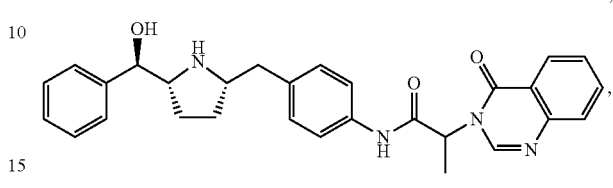
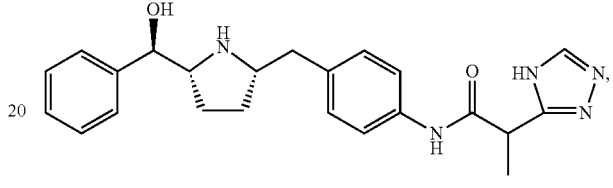
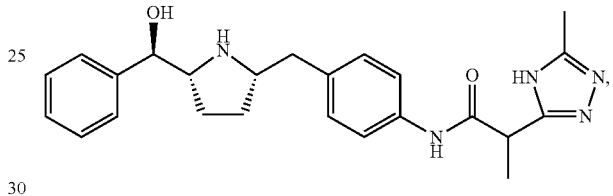
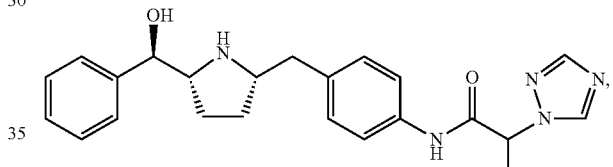
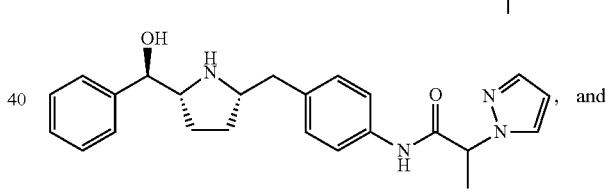
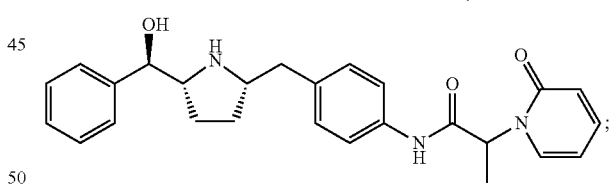, and
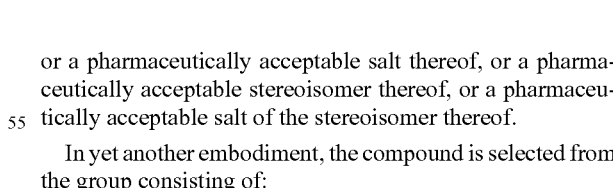;
or a pharmaceutically acceptable salt thereof, or a pharmaceutically acceptable stereoisomer thereof, or a pharmaceutically acceptable salt of the stereoisomer thereof.
In yet another embodiment, the compound is selected from the group consisting of:
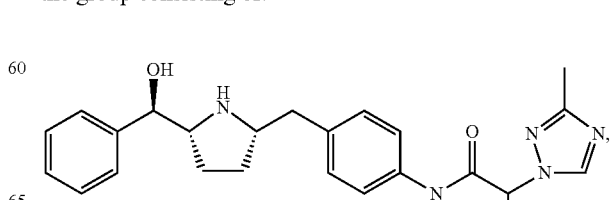

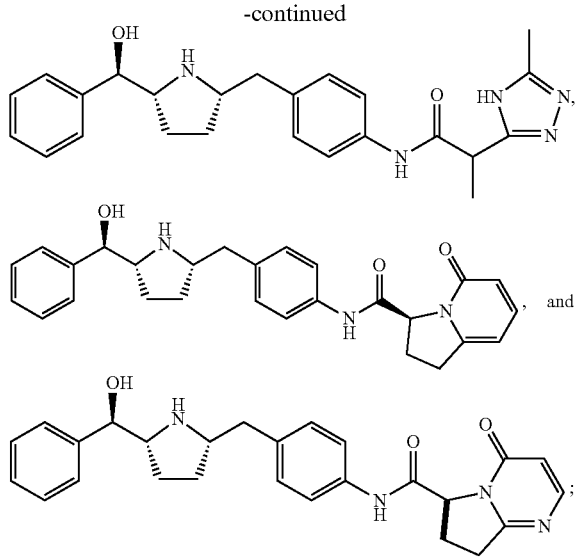

or a pharmaceutically acceptable salt thereof, or a pharmaceutically acceptable stereoisomer thereof, or a pharmaceutically acceptable salt of the stereoisomer thereof.

As used herein "alkyl" is intended to include both branched- and straight-chain saturated aliphatic hydrocarbon groups having the specified number of carbon atoms, e.g., methyl (Me), ethyl (Et), n-propyl (Pr), n-butyl (Bu), n-pentyl, n-hexyl, and the isomers thereof such as isopropyl (i-Pr), isobutyl (1-Bu), secbutyl (s-Bu), tert-butyl (t-Bu), isopentyl, isohexyl and the like. "Cycloalkyl" means a monocyclic saturated carbocyclic ring, having the specified number of carbon atoms, e.g., 3, 4, 5 or 6 carbon atoms. Examples of cycloalkyl include cyclopropyl, cyclobutyl, cyclopentyl and cyclohexyl.

The term "alkanediyl" refers to a straight or branched divalent hydrocarbon radical having the specified number of carbon atoms. "Alkenediyl" and "alkynediyl" refer to straight or branched, unsaturated divalent hydrocarbon radicals. An "alkenediyl" is characterized by a carbon-carbon double bond and an "alkynediyl" is characterized by a carbon-carbon triple bond. Examples of "alkanediyl" include, but are not limited to, methylene (—CH$_2$—), ethylene (—CH$_2$CH$_2$—), 1,1-ethanediyl (—CH(CH$_3$)—), 1,2-propanediyl (—CH(CH$_3$)CH$_2$—), 2-methyl-1,1-propanediyl (—CH[C(CH$_3$)$_2$]—); examples of "alkenediyl" include, but are not limited to, 1,1-ethenediyl (—C(=CH$_2$)—), 1,2-ethenediyl (—CH=CH—), and 2-propen-1,1-diyl (—CH(CH=CH$_2$)—); examples of "alkynediyl" include, but are not limited to, 1,2-ethynediyl (—C≡C—) and 3-butyn-1,1-diyl (—CH(CH$_2$C≡CH)—). Example of a halogen substituted alkanediyl is —C(CH$_3$)(F)—.

The term "optionally substituted" means "unsubstituted or substituted," and therefore, the generic structural Formulas described herein encompass compounds containing the specified optional substituent as well as compounds that do not contain the optional substituent. Each variable is independently defined each time it occurs within the generic structural formula definitions.

The terms "halo" or "halogen" are meant to include fluoro, chloro, bromo and iodo, unless otherwise noted. Fluoro and chloro are preferred.

The terms "carbocycle" or "carbocyclic" refer to saturated, partially unsaturated and aromatic rings having only ring carbon atoms. Examples include, but are not limited to cyclopentyl, cyclohexyl, cycloheptyl, cyclooctyl, cyclopentenyl, cyclohexenyl, cyclohexadienyl, and phenyl. The term "aryl" refers to an aromatic carbocycle. Within the definition for Z, the term "a benzene ring fused to a C$_5$-C$_{10}$ carbocyclic ring" includes, but is not limited to, naphthyl, dihydronaphthyl, tetrahydronaphthyl, indanyl, indenyl, benzocycloheptene, tetrahydrobenzocyloheptene, and the like; preferably benzene is fused to a C$_5$-C$_6$ carbocyclic ring. Such fused ring may be attached to the rest of the molecule via a carbon atom on either ring.

The terms "heterocycle" or "heterocyclic" refer to saturated, partially unsaturated and aromatic rings having at least one ring heteroatom and at least one ring carbon atom; the heterocycle may be attached to the rest of the molecule via a ring carbon atom or a ring nitrogen atom. The terms "heteroaryl" or "heteroaromatic" refer to an aromatic heterocycle. Within the definition for Z, the term "a 5- or 6-membered heterocyclic ring with from 1 to 4 heteroatoms selected from oxygen, sulfur and nitrogen" includes, but is not limited to, pyrrolyl, thienyl, furanyl, imidazoly, pyrazolyl, oxazolyl, isoxazolyl, thiazolyl, isothiazolyl, triazolyl, tetrazolyl, oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, tetrahydroindolizinyl.

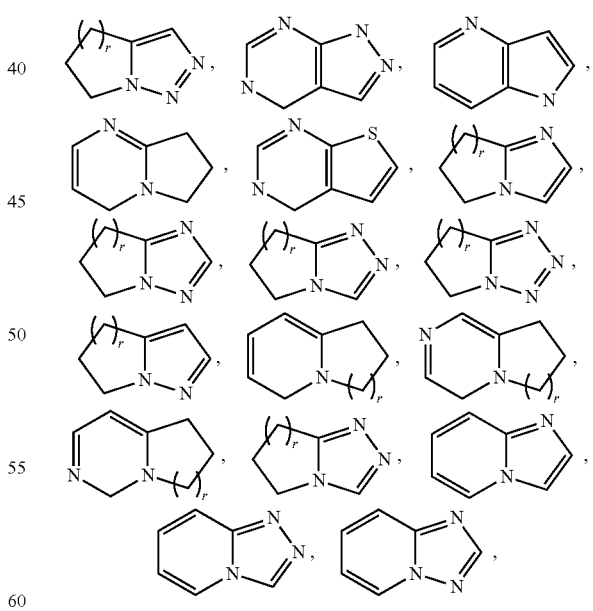

wherein r is 1 or 2. Such fused ring may be attached to the rest of the molecule via a carbon atom or a nitrogen atom on either ring. To avoid any doubt, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" as used herein includes compounds having only one nitrogen as the sole heteroatom when the nitrogen is located at the bridgehead.

Within the definition for Z, the term "a 5- or 6-membered heterocyclic ring with from 1 to 4 heteroatoms selected from oxygen, sulfur and nitrogen fused to a $C_5$-$C_{10}$ carbocyclic ring" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromenyl, chromanyl,

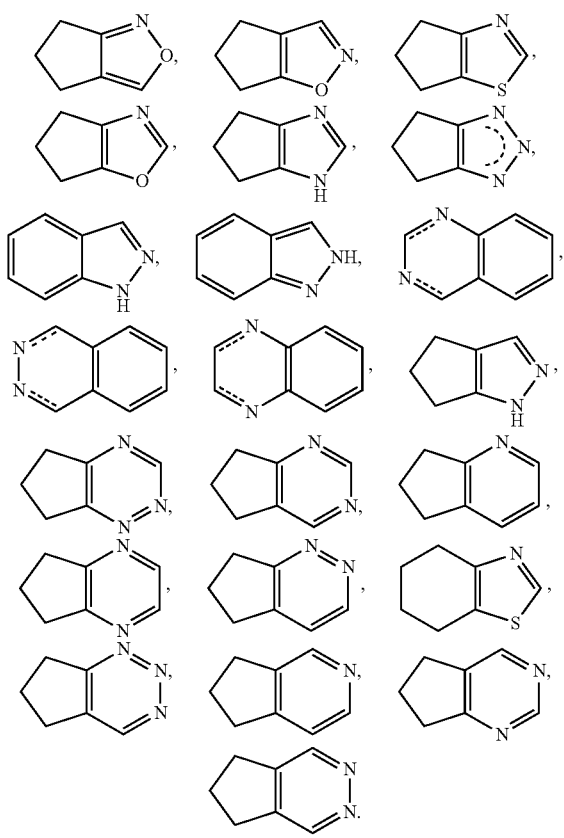

Such fused ring may be attached to the rest of the molecule via a carbon atom or a nitrogen atom on either ring.

For the terms $(R^1)_m$, $(R^2)_q$, $(R^3)_n$, as well as any other similar notations, when m or q or n is 0, then $R^1$, $R^2$ or $R^3$ is hydrogen; when m, q or n is greater than 1, then each occurrence of $R^1$, $R^2$ or $R^3$ is independently selected from other occurrences of $R^1$, $R^2$ or $R^3$, respectively. For example, when n is 2, the two $R^3$ substituents can be the same or different.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. The above Formulas I and Ia are shown without a definitive stereochemistry at certain positions. The present invention includes all stereoisomers of Formulas I and Ia and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I or Ia may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formulas I and Ia. As used herein, the term "solvate" refers to a complex of variable stoichiometry formed by a solute (i.e., a compound of Formula I or Ia) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrates include, but are not limited to, hemi-, mono, sesqui-, di- and trihydrates.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of Formula I or Ia or with a compound which may not be a compound of Formula I or Ia, but which converts to a compound of Formula I or Ia in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound of Formula I or Ia. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19)-elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formulas I and Ia are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams, or more specifically, from about 0.7 milligrams to about 2000 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of Formulas I and Ia are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

In one embodiment, a compound of the present invention is used in the manufacture of a medicament for the treatment or prevention of a disease or disorder mediated by the activation of β3-adrenoceptor.

Another aspect of the present invention provides pharmaceutical compositions which comprises a compound of Formula I or Formula Ia and a pharmaceutically acceptable carrier. The pharmaceutical compositions of the present invention comprise a compound of Formula I or Ia as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formulas I and Ia can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of Formulas I and Ia may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds of Formulas I and Ia may be used in combination with other drugs that are used in the treatment/prevention/suppression or amelioration of the diseases or conditions for which compounds of Formulas I and Ia are useful. Such other drugs may be administered, by a route and in an amount commonly used therefor, contemporaneously or sequentially with a compound of Formula I or Ia. When a compound of Formula I or Ia is used contemporaneously with one or more other drugs, a pharmaceutical unit dosage form containing such other drugs in addition to the compound of Formula I or Ia is preferred. Accordingly, the pharmaceutical compositions of the present invention include those that also contain one or more other active ingredients, in addition to a compound of Formula I or Ia. Examples of other active ingredients that may be combined with a compound of Formula I or Ia, either administered separately or in the same pharmaceutical compositions, include, but are not limited to:

(a) overactive bladder medicines including (i) muscarinic receptor antagonists (e.g. tolterodine, oxybutynin including S-oxybutynin, hyoscyamine, propantheline, propiverine, trospium including trospium chloride, solifenacin, darifenacin, imidafenacin, fesoterodine, temiverine, SVT-40776, 202405 by GlaxoSmithKline, TD6301, RBX9841, DDP200, PLD179, and other anticholinergics. See, for example, U.S. Pat. No. 5,382,600; U.S. Pat. No. 3,176,019; U.S. Pat. No. 3,480,626; U.S. Pat. No. 4,564,621; U.S. Pat. No. 5,096,890; U.S. Pat. No. 6,017,927; U.S. Pat. No. 6,174,896; U.S. Pat. No. 5,036,098; U.S. Pat. No. 5,932,607; U.S. Pat. No. 6,713,464; U.S. Pat. No. 6,858,650; and DD 106643. See also, U.S. Pat. No. 6,103,747; U.S. Pat. No. 6,630,162; U.S. Pat. No. 6,770,295; U.S. Pat. No. 6,911,217; U.S. Pat. No. 5,164,190; U.S. Pat. No. 5,601,839; U.S. Pat. No. 5,834,010; U.S. Pat. No. 6,743,441; WO2002000652; WO200400414853. As will be appreciated by those of skill in the art, these drugs may be administered orally or topically in standard or extended release forms, such as extended release tolterodine, extended release oxybutynin and transdermal oxybutynin), (ii) NK-1 or NK-2 antagonists (e.g. aprepitant, cizolirtine, compounds disclosed in WO2005/073191, WO2005/032464, and other reported NK-1 antagonists), (iii) alpha adrenergic receptor antagonists (e.g. alfuzosin, doxazosin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blocker, (xvi) P2X purinergic receptor antagonists (e.g. P2X1 or P2X3 antagonists), (xvii) PAR2 inhibitors, (xviii) phosphodiesterase inhibitors (e.g. PDE1, PDE4, and PDE5 inhibitors); and (xix) ATP sensitive potassium channel openers, (b) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other β3 adrenergic receptor agonists;

(i) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

In one embodiment, a compound of the present invention and a second active agent as described above are used in the manufacture of a medicament for the treatment or prevention of a disease or disorder mediated by the activation of β3-adrenoceptor.

The compounds of Formula I and Ia of the present invention can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

A variety of chromatographic techniques may be employed in the preparation of the compounds. These techniques include, but are not limited to: High Performance Liquid Chromatography (HPLC) including normal phase, reversed phase, and chiral phase HPLC; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. All temperatures are degrees Celsius unless otherwise noted.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Throughout the application, the following terms have the indicated meanings unless otherwise noted:

| Term | Meaning |
|---|---|
| Ac | Acyl ($CH_3C(O)$—) |
| Aq. | Aqueous |
| Bn | Benzyl |
| BOC (Boc) | t-Butyloxycarbonyl |
| BOP | Benzotriazol-1-yloxytris(dimethylamino)phosphonium hexafluorophosphate |
| °C. | Degree Celsius |
| Calc. or calc'd | Calculated |
| Celite | Celite$^{TM}$ diatomaceous earth |
| DCC | Dicyclohexylcarbodiimide |
| DCM | Dichloromethane |
| DIEA | N,N-diisopropyl-ethylamine |
| DMAP | 4-Dimethylaminopyridine |
| DMF | N,N-dimethylformamide |
| EDC | 1-Ethyl-3-(3-dimethylaminopropyl) carbodiimide |
| Eq. or equiv. | Equivalent(s) |
| ES-MS and ESI-MS | Electron spray ion-mass spectroscopy |
| Et | Ethyl |
| EtOAc | Ethyl acetate |
| g | Gram(s) |
| h or hr | Hour(s) |
| HATU | O-(7-azabenzotriazol-1-yl)-N,N,N',N'-tetramethyluronium hexafluorophosphate |
| HOAc | Acetic acid |
| HOAT | 1-Hydroxy-7-azabenzotriazole |
| HOBT | 1-Hydroxybenzotriazole |
| HPLC | High performance liquid chromatography |
| LC/MS or LC-MASS | Liquid chromatography mass spectrum |
| L | Liter(s) |
| M | Molar(s) |
| Me | Methyl |
| MeOH | Methanol |
| MF | Molecular formula |
| min | Minute(s) |
| mg | Milligram(s) |
| mL | Milliliter(s) |
| mmol | Millimole(s) |
| MOZ (Moz) | p-Methoxybenzyloxycarbonyl |
| MP | Melting point |
| MS | Mass spectrum |
| nM | Nanomolar |
| OTf | Trifluoromethanesulfonyl |
| Ph | Phenyl |
| Prep. | Preparative |
| Ref. | Reference |
| r.t. or rt | Room temperature |
| Sat. | Saturated |
| SCF $CO_2S$ | Super critical fluid carbon dioxide |
| TBAF | Tetrabutylammonium fluoride |
| TBAI | Tetrabutylammonium iodide |
| TBDPS | Tert-butyl diphenylsilyl |

| Term | Meaning |
| --- | --- |
| TBS, TBDMS | Tert-butyl dimethylsilyl |
| TEA or Et₃N | Triethylamine |
| Tf | Triflate or trifluoromethanesulfonate |
| TFA | Trifluoroacetic acid |
| THF | Tetrahydrofuran |
| TLC | Thin-layer chromatography |
| TMS | Trimethylsilyl |

Reaction Schemes below illustrate the methods employed in the synthesis of the compounds of the present invention of Formula Ia. All substituents are as defined above unless indicated otherwise. The synthesis of the novel compounds of Formula Ia which are the subject of this invention may be accomplished by one or more of several similar routes.

In Scheme I, commercially available I-1 is treated with a 1 to 2 M solution of vinyl Grignard in either anhydrous THF or ether at a temperature of 0° C. and allowed to warm to room temperature over a period of time between 1 and 4 h. The reaction is usually performed in an inert organic solvent such as THF and under an inert atmosphere such as nitrogen. The product is an allylic alcohol of structural formula I-2. Conversion of I-2 to I-3 can be achieved by selecting the desired silyl protecting agent, such as tert-butyl dimethyl chloride, and a weak organic base, such as imidazole, and mixing at room temperature between 4 to 16 h. Oxidation of the double bond via the bubbling of ozone gas over a period of time until a blue color persists and then reduction of the ozonide by addition of excess methyl sulfide affords the aldehyde I-4. I-4 is then treated with either R-(+)- or S-(−)-2-methyl-2-propanesulfinamide in the presence of a Lewis acid, such as copper sulfate or titanium tetrachloride, which also acts as a drying agent. The reaction is usually performed in an inert organic solvent, such as dichloromethane, between room temperature and 40° C., for a period of 6-36 h, and the product is the sulfinamide of structural formula I-5. As with I-1, I-5 is treated with vinyl Grignard under similar conditions and time to afford the allyl sulfinamide I-6. To selectively remove the sulfinamide, I-6 is treated with an anhydrous solution of 4 M HCl in dioxane for no more than 15 min. The reaction is then diluted with toluene and concentrated to dryness to afford I-7. Finally, I-7 is converted to I-8 via treatment with benzyl chloroformate in the presence of an anhydrous organic base, such as triethyl amine or diisopropyl ethyl amine, in an inert organic solvent, such as DCM, at 0° C., allowing to warm to room temperature over a period of time between 1 to 3 h.

Scheme I

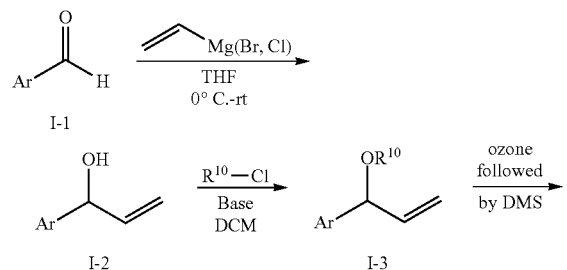

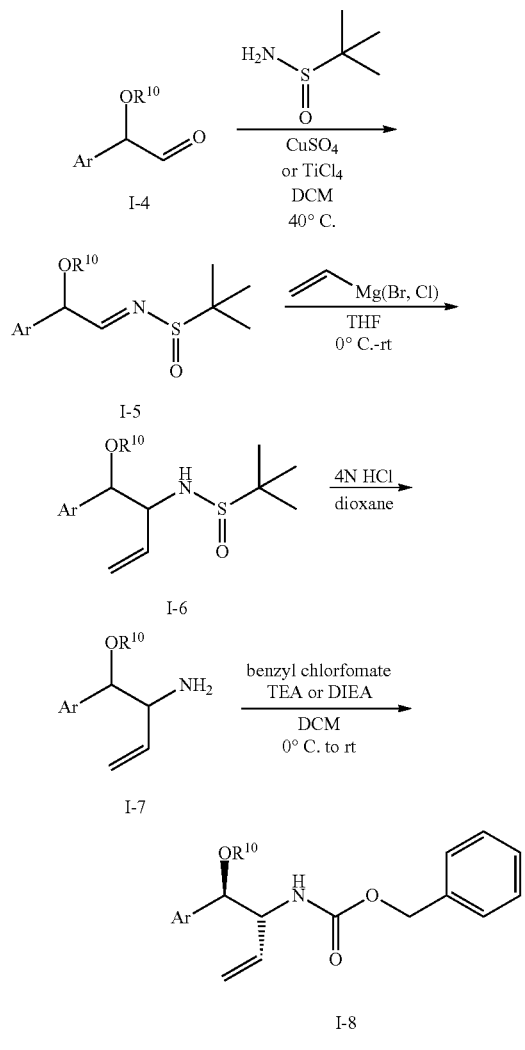

$R^{10}$ = TMS, TBS, TBDPS

Alternatively, aldehyde I-4 can be prepared as shown in Scheme II. Treatment of I-3 with osmium tetraoxide in the presence of N-methyl morpholine N-oxide affords the diol I-9. The reaction is usually performed in a mixture of water and acetone and carefully worked up to remove the toxic osmium tetraoxide before concentrating the solution. The residue, I-9, is then taken up in acetone/water (8:1) and treated with sodium periodate for a period of time between 8 and 24 h at room temperature to afford the aldehyde I-4 as in Scheme I. This is then taken to the final desired intermediate I-8 using the same procedures described in Scheme I.

Scheme II

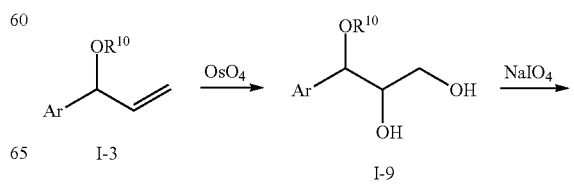

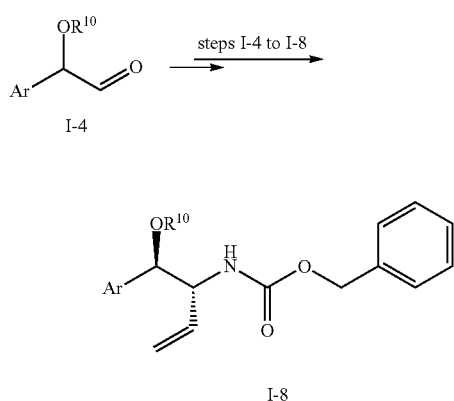

Scheme III describes the synthesis of the pyrrolidine core using the CBz-protected allyl amide I-8 described in Schemes I and II. The vinyl compound I-8 may be reacted in an olefin cross metathesis with the vinyl ketone intermediate I-10 using appropriate catalysts useful in olefin metathesis known to those skilled in the art. Suitable catalysts include, but are not limited to, both "Grubbs" and "Zhan" catalysts and of the type known as Grubbs-II and Zhan I or II to produce the compound of structural formula I-11. Hydrogenation of this intermediate I-11 by treatment with 10% palladium on carbon catalyst under hydrogen atmosphere in a solvent such as ethyl acetate or ethanol over 2-16 h achieves hydrogenation of the olefin along with removal of any Cbz-protecting groups in addition to a ring closure via an intramolecular imine formation between the free amine and ketone and reduction of the imine to form the pyrrolidine ring of the general structure I-12. Depending on the choice of solvent, halogen substituents on the aryl can either remain or be removed at this time depending on preference of the final intermediate. Selective Boc protection of the pyrrolidine may be accomplished by the addition of one equivalent of tert-butyl dicarbonate ($Boc_2O$) to I-12 in the presence of an anhydrous organic base, such as triethylamine (TEA). The reaction is usually performed in an inert organic solvent, such as THF, and under an inert atmosphere, such as nitrogen, affording the product of structural formula I-13. Depending upon the choice of an amide, sulfonamide, or urea, I-13 can be converted to each by using the appropriate method known to those skilled in the art to form those desired compounds. For sulfonamides, I-13 can be treated with the desired sulfonyl chloride containing $R^6$ in the presence of a suitable base, such as pyridine.

As used herein, $R^6$ is selected from:
(1) hydrogen,
(2) $C_1$-$C_{10}$ alkyl optionally substituted with 1 to 5 groups independently selected from halogen, —$OR^a$, —$CO_2R^a$ and —$CONR^aR^b$,
(3) phenyl optionally substituted with 1 to 3 groups independently selected from halogen, $C_1$-$C_5$ alkyl optionally substituted with 1 to 5 halogen atoms, and —$OR^a$, and
(4) a 5- or 6-membered heterocyclic ring with from 1 to 4 heteroatoms selected from oxygen, sulfur and nitrogen, and wherein said heterocyclic ring is optionally ortho-fused to a benzene ring, and optionally substituted with 1 to 3 groups independently selected from halogen, $C_1$-$C_5$ alkyl optionally substituted with 1 to 5 halogen atoms, and —$OR^a$.

The reaction is usually performed in an inert organic solvent such as DMF, between room temperature and 80° C., for a period of 12-24 h, and the product is the sulfonamide of structural formula I-14. For amides, I-13 can be treated with the desired acetyl chloride containing $R^6$ in the presence of a suitable organic base, such as TEA or DIEA. The reaction is usually performed in an inert organic solvent such as DMF, at room temperature for a period of 12-24 h, and the product is the amide of structural formula I-15. Finally, the urea can be formed by treating I-13 with CDI or phosgene in the presence of an amine containing $R^6$ over a period of time between 1 and 24 h, at room temperature to afford the urea of structural formula I-16. Removal of the Boc and silyl protecting groups of I-14, I-15, and I-16 simultaneously via treatment with 6 M HCl in aqueous methanol at room temperature for a period of 12-24 h affords the final desired products of the various amide, sulfonamide and urea containing $R^6$ shown in the general structural formulas I-17, I-18 and I-19.

Additional deprotection steps may be included if there are useful protecting groups on the $R^6$ moiety known to those skilled in the art necessary to allow the chemistry to proceed in a facile fashion. These protecting groups may include trityl groups, tert-butylcarbamate groups or other groups suitable for the protection of heterocyclic compounds or the functional groups attached to the $R^6$ group, such as amines, hydroxyls, carboxylic acids, known to those skilled in the art.

Scheme III

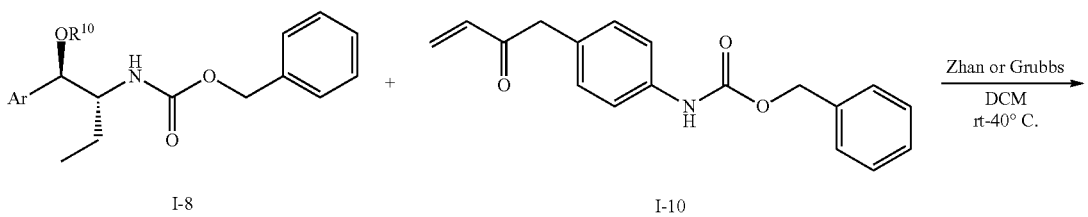

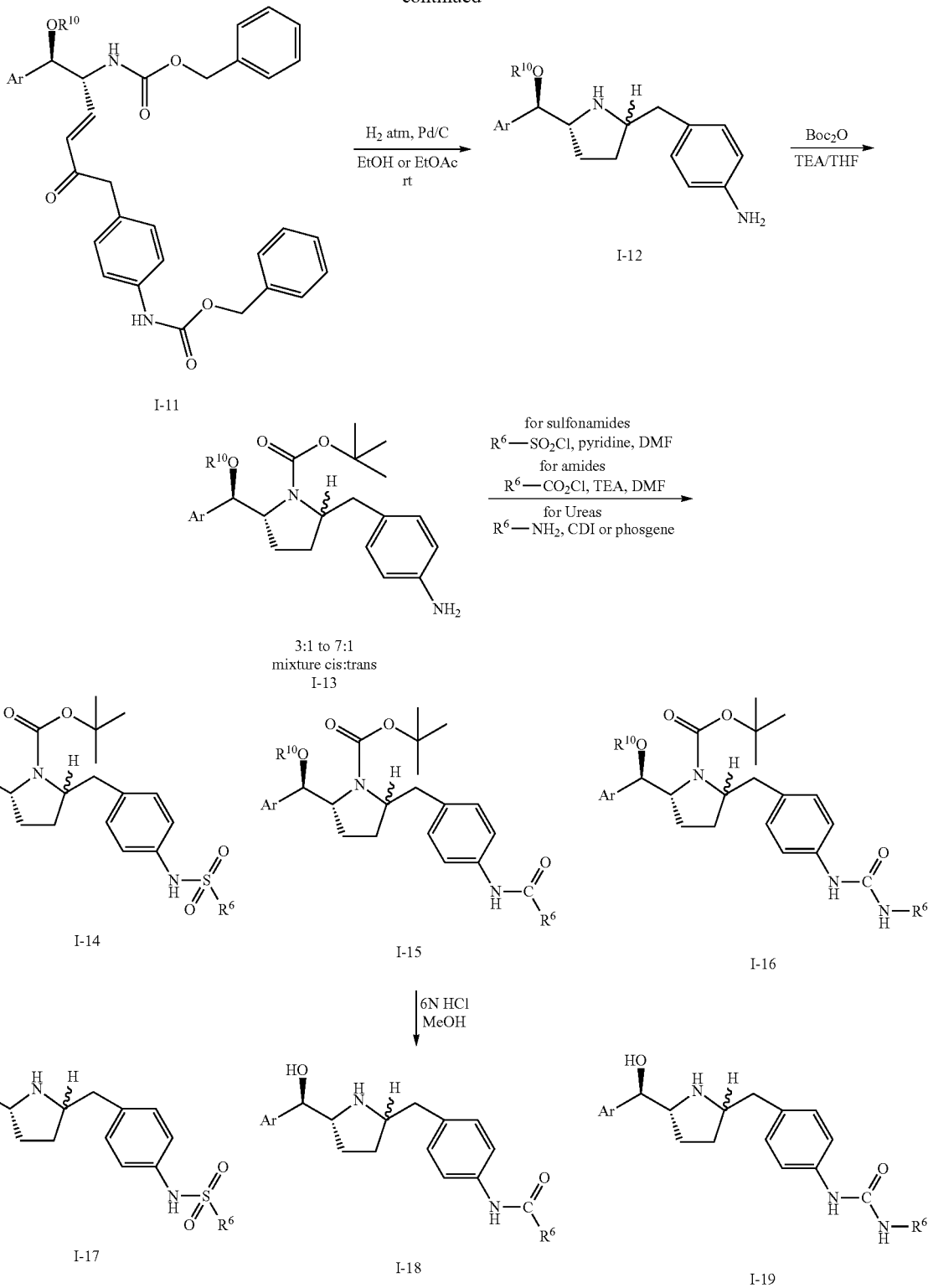

An alternate route as shown in Scheme IV outlines the synthesis which affords both cis- and trans-pyrrolidines that are separated before the final compound is prepared.

The starting 2-amino-arylpropane-1,3-diol (I-20) is first protected as the hemiacetal using acetone in a suitable solvent such as toluene in the presence of acid such as p-toluene sulfonic acid and then the amine is protected by treatment with tert-butyl dicarbonate to give intermediate I-21. Using standard Swern oxidative conditions, the free primary hydroxyl is converted to the aldehyde I-22. Then a Wittig reaction with (triphenylphosphoranylidene) acetaldehyde extends the aldehyde by two carbons and the resulting double bond is reduced via hydrogenation with palladium on carbon to afford I-23. This intermediate then undergoes a second Wittig reaction with (4-nitrobenzyl)triphenyl-phosphonium bromide to give intermediate I-24 which enables the compound to cyclize via Michael addition across the double bond, after protecting group removal. Protection of the amino group with tert-butyl dicarbonate assists in the purification and separation of the substrate to afford both cis and trans isomers, I-25a and I-25b respectively. Hydrogenation of the nitro group to the free amine produces the desired intermediates I-26a and I-26b. Intermediates I-26a and I-26b can be used for standard amide couplings when using EDC, however, the hydroxyl group would need to be selectively protected before treating with either acyl or sulfonyl chlorides or with phosgene when converting to a urea.

Scheme IV

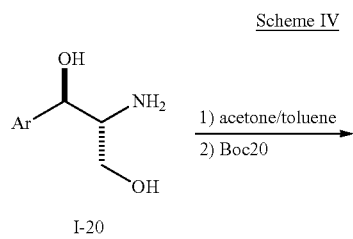

I-20

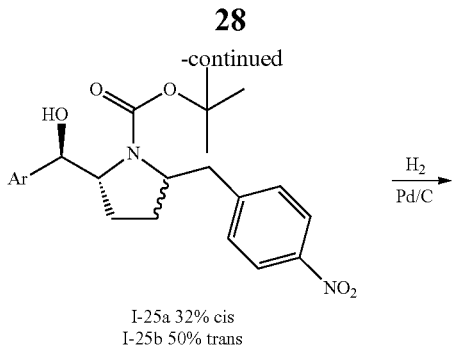

I-25a 32% cis
I-25b 50% trans

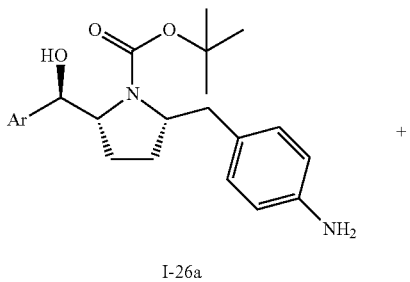

I-26a

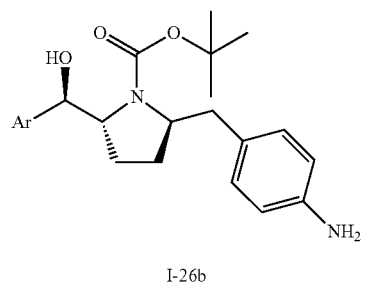

I-26b

Scheme V outlines the synthesis of the pyrrolidine core that interconnects schemes I, III and IV routes to provide pyrrolidine core with diastereoselectivity for the cis 2S, 5R pyrrolidine.

The Wittig reaction is utilized to convert the aldehyde I-22, from scheme IV, to the vinyl analog I-27, via treatment with methyl triphenyl phosphonium bromide. After protecting group manipulation, as seen via intermediate I-28, the scheme becomes convergent to scheme III through intermediate I-8. Using similar procedures as described in Scheme III, intermediate I-11 can then be obtained. Optimization of the hydrogenation by introducing hydrochloric acid and a dilution factor of 0.15 to 0.30 M concentration afforded primarily the cis 2S, 5R pyrrolidine core I-13a.

Scheme V

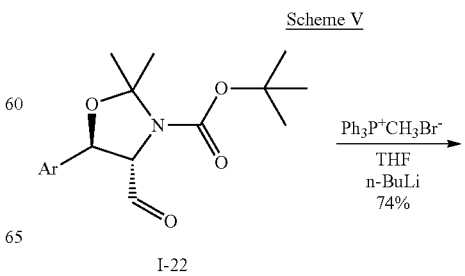

I-22

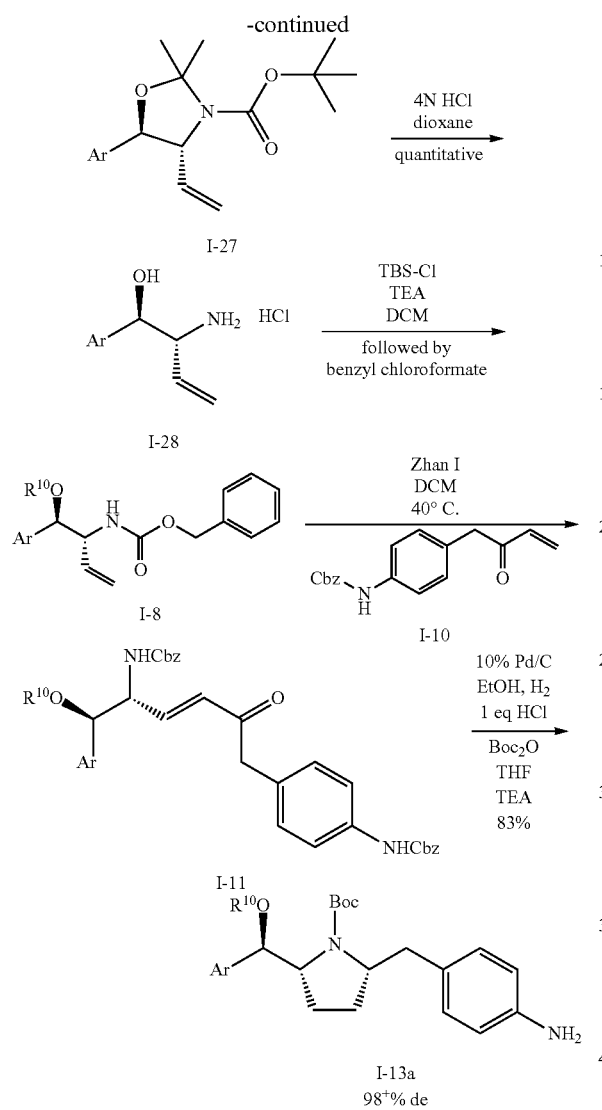

Scheme VI outlines the process of synthesizing the acetylene intermediate via aldol chemistry to set the chirality of both the hydroxyl group and left hand portion of the pyrrolidine. From there, this acetylene intermediate can be used to synthesize both the cis and trans pyrrolidines.

Commercially available I-29 is first treated with trimethylacetyl chloride in the presence of a weak organic base such as triethylamine at −25° C. for 2 h. The sequential addition of anhydrous lithium chloride and either (S)-(−)-4-benzyl or (S)-(−)-4-phenyl-2-oxazolidinone to the mixture followed by gradual warming to room temperature over a period of time between 12 and 24 h affords imide I-30. The reaction is usually performed in an inert organic solvent, such as THF, under an inert atmosphere, such as nitrogen. The alcohol I-32 is prepared according to published procedures (See Evans et al., *J. Am. Chem. Soc.* 2002, 124, 392-394). For example, treatment of I-30 with anhydrous magnesium chloride, triethylamine, the appropriate aldehyde I-31, such as 3-chlorobenzaldehyde or benzaldehyde, and chlorotrimethylsilane at room temperature over a period of 72 h yields the trimethylsilyl ether of the aldol product I-32. The reaction is usually performed in an organic solvent such as ethyl acetate under an inert atmosphere such as nitrogen. Treatment of the trimethylsilyl ether intermediate with a trifluoroacetic acid and methanol mixture affords the desired alcohol I-32. The hydrolysis of the imide I-32 is achieved by treatment with lithium peroxide at 0° C. for a period of 15-18 h. The peroxy acid is subsequently reduced with an aqueous solution of sodium sulfite to afford the carboxylic acid I-33. The reaction is usually performed in a mixture of an inert organic solvent, such as THF, and water under an inert atmosphere, such as nitrogen. Conversion of I-33 to I-34 can be achieved by selecting the desired silyl protecting agent, such as tert-butyl dimethylsilyl trifluoromethanesulfonate, and reacting it in the presence of a weak organic base, such as DBU, at 0° C. for a period of between 12 to 16 h. I-34 can then be treated with diphenylphosphoryl azide in the presence of a weak organic base such as triethylamine for a period of 6 h at room temperature. Addition of the appropriate alcohol, such as 4-methoxybenzyl alcohol, with heating to 100° C. for a period between 12 and 16 h yields the corresponding carbamate I-35. The reaction is usually performed in an inert organic solvent, like toluene, under an inert atmosphere, such as nitrogen. This material forms the basis in which the pyrrolidine core can be synthesized.

Scheme VI

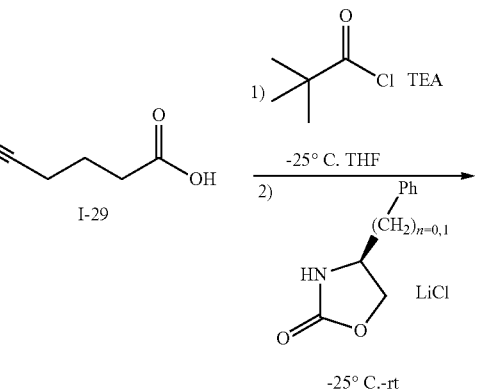

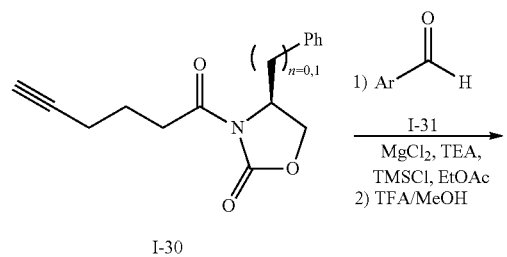

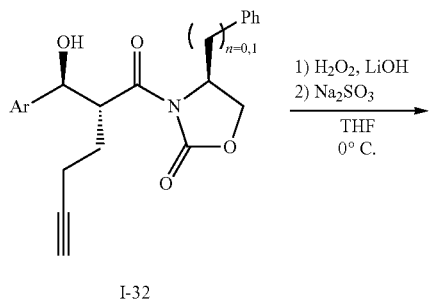

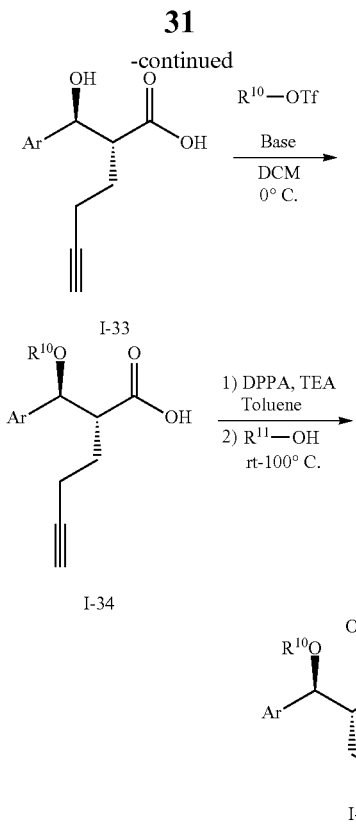

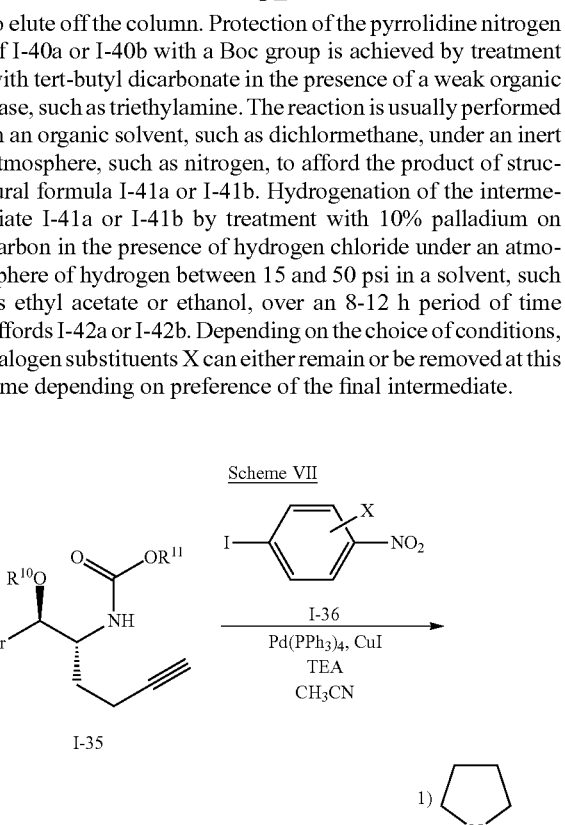

to elute off the column. Protection of the pyrrolidine nitrogen of I-40a or I-40b with a Boc group is achieved by treatment with tert-butyl dicarbonate in the presence of a weak organic base, such as triethylamine. The reaction is usually performed in an organic solvent, such as dichlormethane, under an inert atmosphere, such as nitrogen, to afford the product of structural formula I-41a or I-41b. Hydrogenation of the intermediate I-41a or I-41b by treatment with 10% palladium on carbon in the presence of hydrogen chloride under an atmosphere of hydrogen between 15 and 50 psi in a solvent, such as ethyl acetate or ethanol, over an 8-12 h period of time affords I-42a or I-42b. Depending on the choice of conditions, halogen substituents X can either remain or be removed at this time depending on preference of the final intermediate.

Scheme VII outlines the use of I-35 for conversion of the pyrrolidine core. The pyrrolidine is formed by a ring closer via an intramolecular reductive amination to form both the cis and trans pyrrolidine. Separation of the cis and trans pyrrolidine followed by reduction of the nitro group to an amine gives the final desired pyrroline aniline used for analog synthesis. The alkyne I-35 may be reacted in a Sonagashira type cross-coupling reaction with the corresponding commercially available aryl halide I-36 to afford I-37 using the appropriate reaction conditions known to those skilled in the art. The reaction conditions can include the use of catalysts, such as tetrakis(triphenylphosphine)-palladium(0), with or without copper(I) iodide in the presence of an organic base, such as triethylamine, or palladium(II) acetate with an organic base, such as tetrabutylammonium acetate, in an organic solvent, such as acetonitrile or DMF, under an inert atmosphere, such as nitrogen. Ketone I-38 may be prepared by the reaction of alkyne I-37 with pyrrolidine at a temperature of 80° C. in a solvent such as DMF for a period of between 3-6 h. Subsequent treatment with a 10% aqueous acetic acid solution for a period of between 15-60 min at room temperature yields ketone I-38. The carbamate protecting group of I-38 can be removed using appropriate reaction conditions known to those skilled in the art to afford the corresponding amine, which subsequently undergoes an intramolecular ring closure with the ketone to afford the imine I-39. The reaction conditions can include trifluoroacetic acid in an organic solvent, such as dichloromethane, and hydrochloric acid in an organic solvent such as ether. Reduction of the imine I-39 can be achieved by treatment with sodium cyanoborohydride in an organic solvent, such as methanol, at a temperature of 0° C. under an inert atmosphere, such as nitrogen, for a period of between 18-24 h. This affords the cis-pyrrolidine (I-40a) and trans-pyrrolidine (I-40b) intermediates which can be separated by silica gel chromatography. I-40a is the major diastereomer produced in the reaction and is the first diastereomer

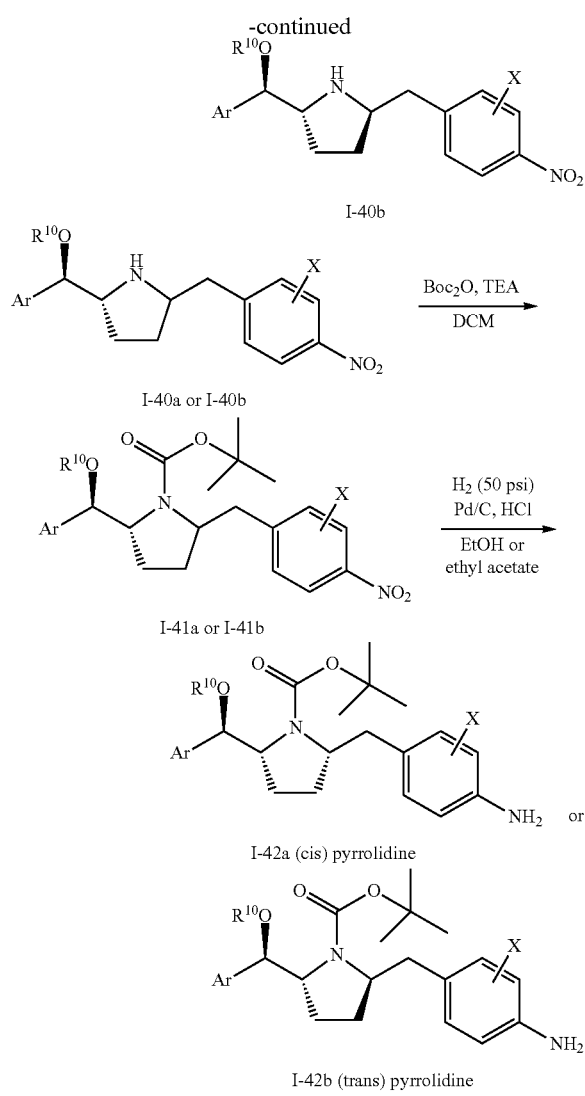

X = H or halogen

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate 1

Benzyl [3-(2-oxobut-3-en-1-yl)phenyl]carbamate (i-1)

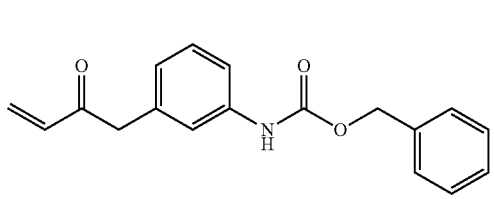

Step A: Ethyl(3-{[(benzyloxy)carbonyl]amino}phenyl)acetate

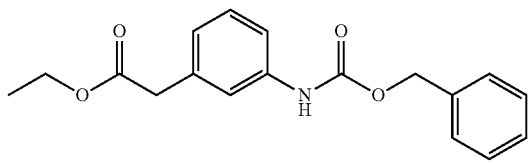 [SMILES: CCOC(=O)Cc1cccc(NC(=O)OCc2ccccc2)c1]

To a solution of methyl (3-aminophenyl)acetate (25 g, 140 mmol) in 250 mL anhydrous DCM was added DIEA (28.5 mL, 155 mmol) and the resulting solution cooled to 0° C. and set under nitrogen atmosphere. To this cooled solution was then added benzyl chloroformate (21.1 mL, 148 mmol) and the resulting mixture stirred overnight allowing to warm to room temperature. The reaction was washed with 1 M HCl, water, and then brine. The organic layer was dried over sodium sulfate, filtered and concentrated under vacuum. No further purification was necessary and the material (44 g, 99%) was used as is for the next step reaction. LC-MS: m/z (ES) 314 (MH)$^+$, 336 (MNa)$^+$.

Step B: (3-{[(Benzyloxy)carbonyl]amino}phenyl)acetic acid

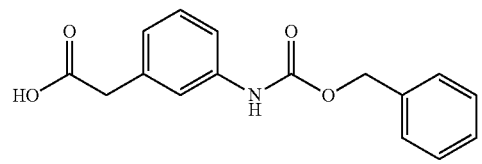 [SMILES: O=C(O)Cc1cccc(NC(=O)OCc2ccccc2)c1]

To a solution of 44.0 g (140 mmol) of ethyl (3-{[(benzyloxy)carbonyl]amino}phenyl)acetate) (from Step A) in THF, ethanol, and water (1:1:1, 1500 mL) was added solid LiOH (16.8 g, 700 mmol) and the resulting solution heated to 60° C. via oil bath for 3 h. The mixture was cooled to room temperature overnight and then 40 mL of concentrate HCl was slowly added, keeping the temperature below 25° C., until the solution was about pH of 2-3. Extract with ethyl acetate (3×750 mL) and then combine and wash organics with water and then brine. Dry organics over sodium sulfate, filter and concentrate under vacuum. The title compound (24.7 g, 87%) was used for the next step reaction without further purification. LC-MS: m/z (ES) 286 (MH)$^+$, 308 (MNa)$^+$.

Step C: Benzyl (3-{2-[methoxy(methyl)amino]-2-oxoethyl}phenyl)carbamate

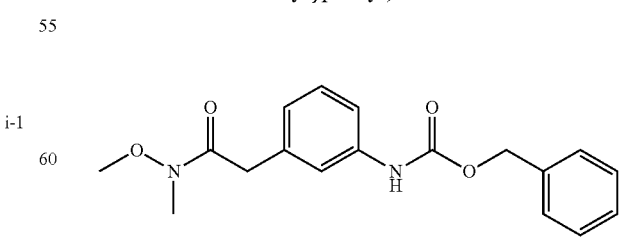

To a suspension of 24.7 g (87 mmol) of (3-{[(benzyloxy)carbonyl]amino}phenyl)acetic acid in 200 mL of dichloromethane (from Step B) was added triethylamine (30.2 mL, 173 mmol) which resulted in some exotherming (+5° C.) and the suspension becoming a solution. After 10 min cooling, HOBt (13.2 g, 87 mmol), N,O-dimethylhydroxylamine HCl (8.5 g, 87 mmol) was added to the solution followed by EDC (16.6 g, 87 mmol) and the resulting mixture stirred at room temperature overnight under nitrogen atmosphere. The solution was transferred to a separatory funnel and washed with 1 M HCl which caused an emulsion. Methanol was added to break up the emulsion and the aqueous was partitioned off. The organics were dried over sodium sulfate, filtered and concentrated under vacuum. Recrystallization of the residue from 1000 mL of 70% hexane in ethyl acetate (heated to reflux and then cooled to room temperature overnight) afforded the title compound (21 g, 74%) as a white solid. LC-MS: m/z (ES) 329 (MH)$^+$.

Step D: Benzyl [13-(2-oxobut-3-en-1-yl)phenyl] carbamate (i-1)

To a solution of 15 g (45.7 mmol) of benzyl (3-{2-[methoxy(methyl)amino]-2-oxoethyl}phenyl)carbamate (from Step C) in 1000 mL anhydrous THF under nitrogen atmosphere cooled to 0° C. via ice/water bath was added dropwise via cannula a 1.0 M solution of vinyl magnesium bromide (100 mL in THF, 100 mmol) and the resulting solution stirred for 1 h at 0° C. The reaction was quenched by a slow addition of 500 mL 1 M HCl keeping the temperature below 5° C. and stirred for 30 min. The mixture was then extracted with ethyl acetate and the combined organics washed with water followed by brine. The organics were then dried over sodium sulfate, filtered, and concentrate under vacuum. The residue was purified by Biotage 75M flash eluting with 30% ethyl acetate in hexane to afford the title compound (11 g, 78%) as a light yellow solid. LC-MS: m/z (ES) 310 (MH)$^+$, 332 (MNa)$^+$. $^1$HNMR (500 MHz, CDCl$_3$) δ: 7.44-7.36 (m, 7H), 7.18 (d, J=8.4 Hz, 2H), 6.70 (br s, 1H), 6.44 (dd, J=10.5, 17.6 Hz, 1H), 6.32 (dd, J=1.1, 17.6 Hz, 1H), 5.85 (dd, J=1.1, 10.5 Hz, 1H), 5.22 (s, 2H), 3.86 (s, 2H).

Intermediate 2

((1R)-1-[(R)-{[tert-butyl(dimethyl)silyl]oxy)(3-chlorophenyl)methyl]prop-2-en-1-yl}carbamate (i-2)

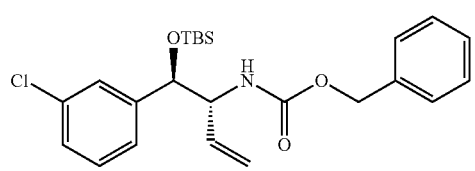

Step A: 1-(3-Chlorophenyl)prop-2-en-1-ol

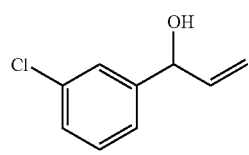

To a cooled solution of 3-chlorobenzaldehyde (22.5 g, 160 mmol) in 100 mL anhydrous THF under inert nitrogen atmosphere was added slowly via syringe a 1.6 M solution of vinyl magnesium chloride in THF (100 mL, 160 mmol) and the solution stirred for three h allowing to warm to room temperature. The reaction was quenched with saturated solution of ammonium chloride and the organic layer was separated, extracted with ethyl acetate (2×200 mL), and organic layers were combined, dried over magnesium sulfate, filtered and concentrated under vacuum. Purification by Horizon MPLC with a 40M+ silica gel column using a gradient eluent of 0-40% ethyl acetate in hexane afforded the title compound (22.4 g, 44%). m/z (ES) 168, 170 (M, M+2)$^+$, 190, 192 (MNa, MNa+2)$^+$. $^1$HNMR (500 MHz, CDCl$_3$) δ: 7.38 (s, 1H), 7.35-7.22 (m, 3H), 5.90 (ddd, J=7.3, 10.0, 17.4 Hz, 1H), 5.38 (d, J=17.5 Hz, 1H), 5.18 (d, J=7.2 Hz, 1H), 5.15 (d, J=10.1 Hz, 1H), 0.96 (s, 9H), 0.18 (s, 3H), 0.08 (s, 3H).

Step B: Tert-butyl {[1-(3-chlorophenyl)prop-2-en-1-yl]oxy}dimethylsilane

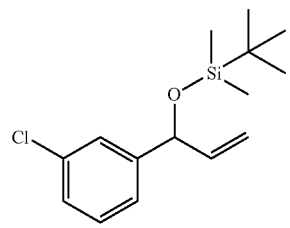 [SMILES: C=CC(O[Si](C)(C)C(C)(C)C)c1cccc(Cl)c1]

To a solution of 22.4 g (133 mmol) of 1-(3-chlorophenyl)prop-2-en-1-ol in 90 mL anhydrous DMF (from Step A) was added t-butyldimethylsilyl chloride (20.0 g, 133 mmol) and imidazole (18.1 g, 266 mmol) and the resulting solution was stirred overnight under nitrogen at room temperature. Wash with water and extract with ethyl acetate. Separate organics, dry over magnesium sulfate, filter, and concentrate under vacuum. The residue was purified by flash silica gel column eluting with a gradient eluent of 0-15% ethyl acetate in hexane to afford the title compound (16.6 g, 46%). m/z (ES) 282, 284 (M, M+2)$^+$; 151, 153 (M-OTBS, M-OTBS+2)$^+$.

Step C: {[Tert-butyl(dimethyl)silyl]oxy}(3-chlorophenyl)acetaldehyde

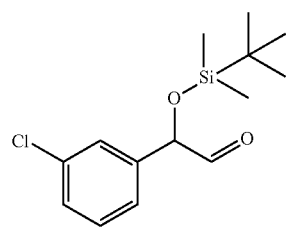 [SMILES: CC(C)(C)[Si](C)(C)OC(C=O)c1cccc(Cl)c1]

To a solution of 4.0 g (14.2 mmol) of tert-butyl {[1-(3-chlorophenyl)prop-2-en-1-yl]oxy}dimethylsilane in dichloromethane cooled to −78° C. via dry ice/acetone bath (from Step B) was bubbled ozone until the solution maintained a slight blue color. Nitrogen gas was then bubbled into the solution until it turned clear. Methyl sulfide was added to the solution and the resulting mixture was allowed to stir overnight at room temperature. The material was concentrated under vacuum and the residue purified via Horizon MPLC with a 40M+ silica gel column, eluting with a gradient eluent of 0-50% ethyl acetate in hexane to afford the product (3.57 g, 89%).

Step D: N-[(1E)-2-{[tert-butyl(dimethyl)silyl]oxy}-2-(3-chlorophenyl)ethylidene]-2-methylpropane-2-sulfinamide

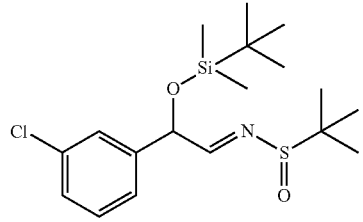 [SMILES: CC(C)(C)S(=O)/N=C/C(O[Si](C)(C)C(C)(C)C)c1cccc(Cl)c1]

To a solution of 3.0 g (10.6 mmol) of {[tert-butyl (dimethyl)silyl]oxy}(3-chlorophenyl)acetaldehyde (from Step C) and 1.3 g (10.6 mmol) of (R or S)-2-methyl-2-propanesulfinamide in 50 mL anhydrous dichloromethane was added copper(II) sulfate (3.4 g, 21.2 mmol) and the resulting mixture was stirred at room temperature under nitrogen atmosphere for 16 h. Wash reaction with water and extract with dichloromethane. Dry the organics with magnesium sulfate, filter and concentrate under vacuum. The residue was purified by Horizon MPLC, with a 40M+ silica gel column, eluting with a gradient eluent system of 0-25% ethyl acetate in hexane to afford the title compound (3.26 g, 80%). %). m/z (ES) 387, 390 (M, M+2)$^+$.

Step E: N-{1-[{[tert-but dimethyl)silyl]oxy}(3-chlorophenyl)methyl]-prop-2-en-1-yl}2-methylpropane-2-sulfinamide

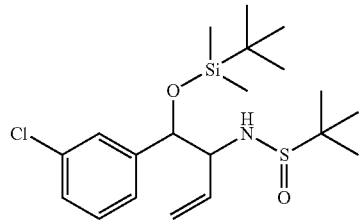 [SMILES: C=CC(NS(=O)C(C)(C)C)C(O[Si](C)(C)C(C)(C)C)c1cccc(Cl)c1]

To a solution of 2.4 g (6.20 mmol) of N-[(1E)-2-{[tert-butyl(dimethyl)silyl]oxy}-2-(3-chlorophenyl)ethylidene]-2-methylpropane-2-sulfinamide in 20 mL anhydrous THF cooled to 0° C. under nitrogen atmosphere (from Step D) was added a 1.6 M solution of vinyl magnesium chloride in THF (3.90 mL, 6.2 mmol) via syringe and the resulting mixture stirred for 1 h. The mixture was allowed to warm to room temperate and stirred for an additional hour. The reaction was quenched with saturated solution of ammonium chloride and extract with ethyl acetate. Combine organics, dry over magnesium sulfate, filter and concentrate under vacuum. The residue was purified by Horizon MPLC, with a 40M+ silica gel column, eluting with a gradient eluent system of 0-35% ethyl acetate in hexane to afford all four diastereomers as single isomers.

By NMR the four products obtained were diastereomers of each other. The isomers were labeled as they eluted off the silica gel column. The first isomer that eluted off was named isomer 1 and then isomers 2, 3 and lastly isomer 4.

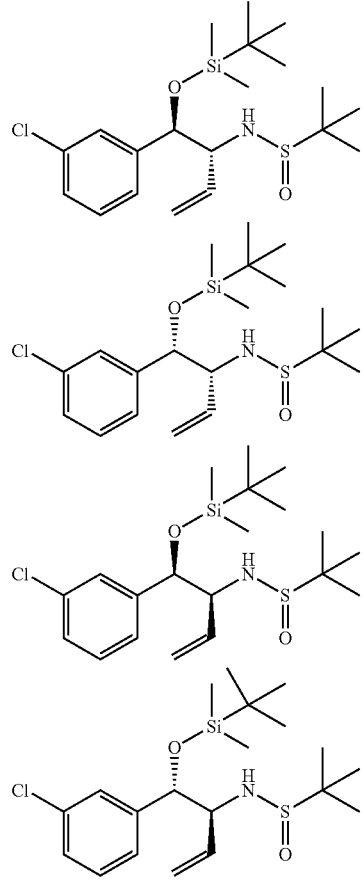

Isomer 1: m/z (ES) 416, 418 (M, M+2)$^+$, 438, 440 (MNa, MNa+2)$^+$. $^1$HNMR (500 MHz, CDCl$_3$) δ: 7.32 (s, 1H), 7.30 (br d, J=7.5, 1H), 7.26 (br d, J=6.2 Hz, 2H), 7.22-7.18 (m, 1H), 5.60 (ddd, J=7.3, 10.3, 17.4 Hz, 1H), 5.15 (d, J=10.3 Hz, 1H), 5.00 (d, J=17.3 Hz, 1H), 4.57 (d, J=7.4 Hz, 1H), 3.98-3.94 (m, 2H), 1.64 (br s, 1H), 1.23 (s, 9H), 0.91 (s, 9H), 0.08 (s, 3H), −0.18 (s, 3H).

Isomer 2: m/z (ES) 416, 418 (M, M+2)$^+$, 438, 440 (MNa, MNa+2)$^+$. $^1$HNMR (500 MHz, CDCl$_3$) δ: 7.33-7.31 (m, 2H), 7.26 (br d, J=5.0 Hz, 2H), 7.20-7.16 (m, 1H), 5.44 (ddd, J=7.2, 10.0, 17.4 Hz, 1H), 5.26 (overlapping d, J=7.3 Hz, 1H), 5.25 (overlapping d, J=17.3 Hz, 1H), 4.84 (d, J=4.4 Hz, 1H), 4.02 (dt, J=4.4, 7.8 Hz, 1H), 3.80 (d, J=4.4 Hz, 1H), 1.20 (s, 9H), 0.94 (s, 9H), 0.14 (s, 3H), −0.12 (s, 3H).

Isomer 3: m/z (ES) 416, 418 (M, M+2)$^+$, 438, 440 (MNa, MNa+2)$^+$. $^1$HNMR (500 MHz, CDCl$_3$) δ: 7.32-7.29 (m, 2H), 7.26-7.24 (m, 2H), 7.22-7.20 (m, 1H), 6.04 (ddd, J=7.1, 10.4, 17.4 Hz, 1H), 5.40 (d, J=10.2 Hz, 1H), 5.32 (d, J=17.3 Hz, 1H), 4.80 (d, J=4.0 Hz, 1H), 3.88-3.80 (m, 1H), 3.55 (d, J=9.4 Hz, 1H), 1.09 (s, 9H), 0.95 (s, 9H), 0.09 (s, 3H), −0.10 (s, 3H).

Isomer 4: m/z (ES) 416, 418 (M, M+2)$^+$, 438, 440 (MNa, MNa+2)$^+$. $^1$HNMR (500 MHz, CDCl$_3$) δ: 7.32 (s, 1H), 7.30 (br d, J=7.5, 1H), 7.27-7.25 (m, 2H), 7.21-7.18 (m, 1H), 5.92 (ddd, J=7.1, 10.3, 17.4 Hz, 1H), 5.23 (d, J=10.4 Hz, 1H), 5.18

(d, J=17.4 Hz, 1H), 4.75 (d, J=4.2 Hz, 1H), 3.88-3.82 (m, 1H), 3.33 (d, J=9.4 Hz, 1H), 1.19 (s, 9H), 0.94 (s, 9H), 0.09 (s, 3H), −0.14 (s, 3H).

Step F: ((1R)-1-[(R)-{[tert-butyl(dimethyl)silyl]oxy}(3-chlorophenyl)methyl]prop-2-en-1-yl}carbamate (i-2)

To isomer 1 (510 mg, 2.22 mmol) of N-{1-[{[tert-butyl(dimethyl)silyl]oxy}(3-chlorophenyl)methyl]-prop-2-en-1-yl}2-methylpropane-2-sulfinamide (from Step E) was added 5 mL anhydrous 4 M HCl in dioxane and the solution stirred for 15 min at room temperature. The reaction was concentrated to dryness and azeotroped with toluene (2×5 mL) to remove excess HCl. The residue was then taken up in anhydrous dichloromethane, set under nitrogen atmosphere, cooled to 0° C. with ice/water bath and then benzyl chloroformate (0.32 mL, 2.22 mmol) was slowly added via syringe followed by diisopropylethyl amine (1.19 mL, 6.66 mmol) and the resulting solution stirred for 2 h at 0° C. The solution was concentrated to dryness under vacuum and the residue was purified via preparative plates (4×1000 µM) eluding with 20% ethyl acetate in hexane to afford the title compound (703 mg, 71%). m/z (ES) 446, 448 (M, M+2)⁺, 468, 470 (MNa, MNa+2)⁺. ¹HNMR (500 MHz, CDCl₃) δ: 7.32 (s, 1H), 7.30 (br d, J=7.5, 1H), 7.27-7.25 (m, 2H), 7.21-7.18 (m, 1H), 5.92 (ddd, J=7.1, 10.3, 17.4 Hz, 1H), 5.23 (d, J=10.4 Hz, 1H), 5.18 (d, J=17.4 Hz, 1H), 4.75 (d, J=4.2 Hz, 1H), 3.88-3.82 (m, 1H), 3.33 (d, J=9.4 Hz, 1H), 1.19 (s, 9H), 0.94 (s, 9H), 0.09 (s, 3H), −0.14 (s, 3H).

Intermediates related to those described above of varying stereoechemistry may be prepared from the appropriate starting materials using the procedure described above.

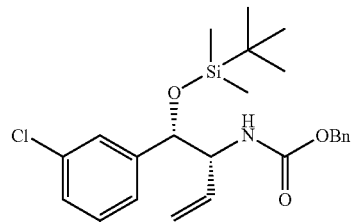

i-2b

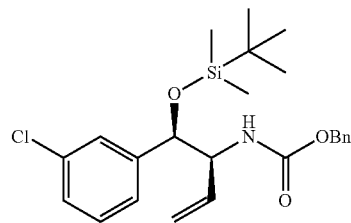

i-2c

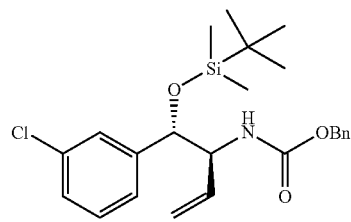

i-2d

Intermediate 3

Tert-butyl(5R)-2-(4-aminobenzyl)-5-[(R)-{[tert-butyl(dimethyl)silyl]oxy}(phenyl)methyl]pyrrolidine-1-carboxylate (i-3)

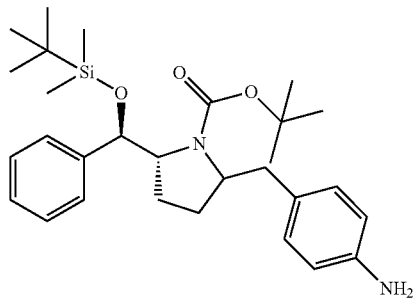

i-3

Step A: Benzyl{4-[(3E,5R,6R)-5-{[(benzyloxy)carbonyl]amino-6-{[tert-butyl (dimethyl)silyl]oxy}-6-(3-chlorophenyl)-2-oxohex-3-en-1-yl]phenyl}carbamate

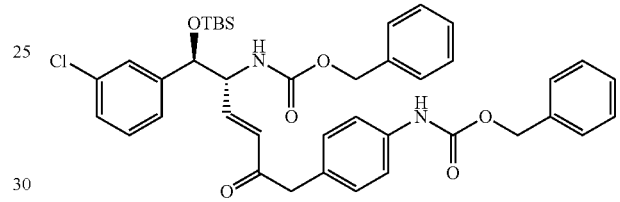

To a solution of benzyl[3-(2-oxobut-3-en-1-yl)phenyl]carbamate (i-1) (820 mg, 2.80 mmol) and ((1R)-1-[(R)-{[tert-butyl(dimethyl)silyl]oxy}(3-chlorophenyl)methyl]prop-2-en-1-yl}carbamate (i-2) (500 mg, 1.12 mmol) in 7 mL of anhydrous dichloromethane was added the Zhan I catalyst (740 mg, 1.12 mmol) and the resulting green solution was heated to 40° C. overnight under nitrogen atmosphere. The reaction was concentrated to dryness and the residue purified via preparative plates (4×1000 µM) eluting with 40% ethyl acetate in hexane to afford the title compound (348 mg, 50%). m/z (ES) 713, 715 (M, M+2)⁺, 735, 737 (MNa, MNa+2)⁺.

Step B: 4-({(5R)-5-[(R)-([tert-butyl(dimethyl)silyl]oxy}(phenyl)methyl]pyrrolidin-2-yl}methyl) aniline

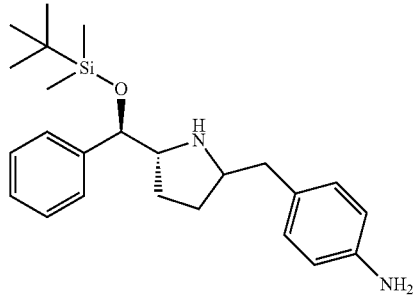

To a solution of 328 mg (0.46 mmol) of benzyl {4-[(3E,5R,6R)-5-{[(benzyloxy)carbonyl]amino-6-{[tert-butyl (dimethyl)silyl]oxy}-6-(3-chlorophenyl)-2-oxohex-3-en-1-yl]phenyl}carbamate (from Step A) in 25 mL ethanol was added 10% palladium on carbon and the suspension was set under hydrogen atmosphere via a balloon of hydrogen gas. The reaction was stirred under hydrogen for 1 h at room temperature. TLC proved that the reaction was complete. The catalyst was filtered off using a Gilmen 0.45 μM PTFE syringe filter and washed with ethanol (4×5 mL). The filtrate was concentrated to dryness under vacuum and the residue purified by preparative plate (3×1000 μM) eluding with 5% methanol in dichloromethane to afford the title compound (121 mg, 66%). m/z (ES) 397 (MH)$^+$.

Step C: Tert-butyl(5R)-2-(4-aminobenzyl)-5-[(R)-{[tert-butyl(dimethyl)silyl]oxy}(phenyl)methyl]pyrrolidine-1-carboxylate (i-3)

To a solution of 121 mg (0.315 mmol) of 4-({(5R)-5-[(R)-([tert-butyl(dimethyl)silyl]oxy}(phenyl)methyl]pyrrolidin-2-yl}methyl)aniline in 5 mL of anhydrous THF (from Step B) was added tert-butyl carbonate (69 mg, 0.315 mmol), followed by TEA (44 μL, 0.315 mmol) and the resulting solution stirred at room temperature under nitrogen atmosphere overnight. The reaction mixture was put directly on a preparative plate (1500 μM) and eluted with 30% ethyl acetate in hexane to afford the title compound (100 mg, 64%). m/z (ES) 497 (MH)$^+$, 397 (M-Boc)$^+$. $^1$HNMR (500 MHz, CDCl$_3$) δ: 7.40-7.30 (m, 5H), 6.75-6.68 (m, 2H), 6.56-6.51 (m, 2H), 5.52-5.48 (m, 1H), 5.32-5.28 (m, 1H), 4.16-4.06 (m, 2H), 3.88-3.82 (m, 1H), 3.76-3.70 (m, 1H), 3.55-3.48 (m, 2H), 2.74 (br d, J=11.8 Hz, 1H), 2.44 (br d, J=11.8 Hz, 1H), 2.05-1.94 (m, 1H), 1.90-1.82 (m, 1H), 1.60 (s, 9H), 1.50-1.42 (m, 1H), 1.32-1.22 (m, 2H), 1.10-1.02 (m, 1H), 0.95 (s, 9H), 0.08 (s, 3H), −0.15 (s, 3H).

Separation of Intermediate 4a And Intermediate 4b

Tert-butyl (2S,5R)-2-(4-aminobenzyl)-5-[(R)-{[tert-butyl(dimethyl)silyl]oxy}(phenyl)methyl]pyrrolidine-1-carboxylate (i-4a)

Tert-butyl (2R,5R)-2-(4-aminobenzyl)-5-[(R)-{[tert-butyl(dimethyl)silyl]oxy}(phenyl)methyl]pyrrolidine-1-carboxylate (i-4-b)

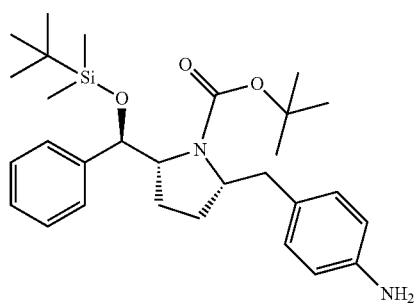

i-4a

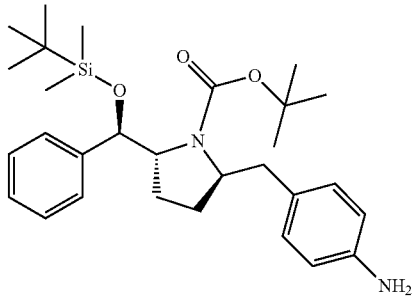

i-4b

Step A: Tert-butyl (2S,5R)-2-(4-aminobenzyl)-5-[(R)-{[tert-butyl(dimethyl)silyl]oxy}(phenyl)methyl]pyrrolidine-1-carboxylate (i-4a) and tert-butyl (2R,5R)-2-(4-aminobenzyl)-5-[(R)-{[tert-butyl(dimethyl)silyl]oxy}(phenyl)methyl]pyrrolidine-1-carboxylate (i-4-b)

The intermediate i-3 (tert-butyl(5R)-2-(4-aminobenzyl)-5-[(R)-{[tert-butyl(dimethyl)silyl]oxy}(phenyl)methyl]pyrrolidine-1-carboxylate (4:1 mixture of cis and trans) was taken up in methanol and purified via the Berger Multigram SFC (supercritical) using an eluent of 30% methanol:60% carbon dioxide to separate the two diastereomers. The first isomer of the column was labeled minor isomer 1 and the second isomer was labeled major isomer 2.

i-4a: m/z (ES) 497 (MH)$^+$, 397 (M-Boc)$^+$. $^1$HNMR (500 MHz, CDCl$_3$) δ: 7.40-7.30 (m, 5H), 6.75-6.68 (m, 2H), 6.56-6.51 (m, 2H), 5.52-5.48 (m, 1H), 5.32-5.28 (m, 1H), 4.16-4.06 (m, 2H), 3.88-3.82 (m, 1H), 3.76-3.70 (m, 1H), 3.55-3.48 (m, 2H), 2.74 (br d, J=11.8 Hz, 1H), 2.44 (br d, J=11.8 Hz, 1H), 2.05-1.94 (m, 1H), 1.90-1.82 (m, 1H), 1.60 (s, 9H), 1.50-1.42 (m, 1H), 1.32-1.22 (m, 2H), 1.10-1.02 (m, 1H), 0.95 (s, 9H), 0.92 (d, J=11.8 Hz, 1H), 0.12 (br d, J=14.0 Hz, 3H), −0.04 (s, 3H). Eluted 8.70 min on SFC, isomer 2 i-4-b: m/z (ES) 497 (MH)$^+$, 397 (M-Boc)$^+$. $^1$HNMR (500 MHz, CDCl$_3$) δ: 7.40-7.30 (m, 5H), 6.76-6.68 (m, 2H), 6.56-6.51 (m, 2H), 5.52-5.48 (m, 1H), 5.32-5.28 (m, 1H), 4.16-4.06 (m, 2H), 3.88-3.82 (m, 1H), 3.76-3.70 (m, 1H), 3.60-3.46 (m, 2H), 2.72 (br d, J=12.0 Hz, 1H), 2.44 (br d, J=12.2 Hz, 1H), 2.05-1.94 (m, 1H), 1.90-1.82 (m, 1H), 1.64 (s, 9H), 1.50-1.42 (m, 1H), 1.32-1.22 (m, 2H), 1.10-1.02 (m, 1H), 0.95 (s, 9H), 0.14 (br d, J=13.8 Hz, 3H), 0.09 (s, 3H). Eluted 7.78 min on SFC, isomer 1.

Synthesis of Intermediate 4a and Intermediate 4b

Tert-butyl (2S,5R)-2-(4-aminobenzyl)-5-[(R)-{[tert-butyl(dimethyl)silyl]oxy}(phenyl)methyl]pyrrolidine-1-carboxylate (i-4a)

Tert-butyl (2R,5R)-2-(4-aminobenzyl)-5-[(R)-{[tert-butyl(dimethyl)silyl]oxy}(phenyl)methyl]pyrrolidine-1-carboxylate (i-4-b)

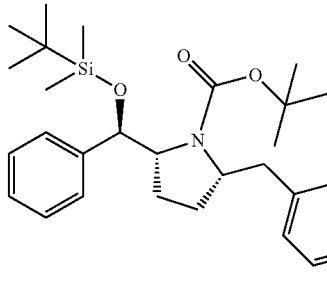

i-4a i-4b

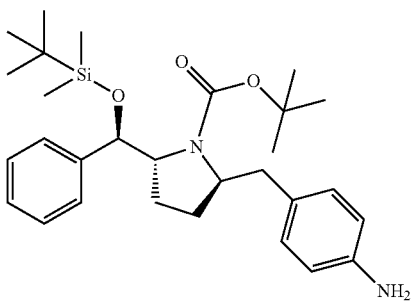

Step A: (4S)-3-Hex-5-ynoyl-4-phenyl-1,3-oxazolidin-2-one

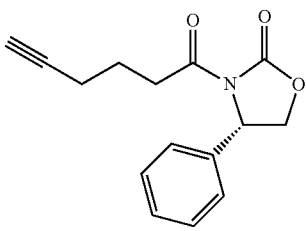 [SMILES: C#CCCCC(=O)N1C(=O)OC[C@@H]1c1ccccc1]

To a solution of 69.0 g (615 mmol) of 5-hexynoic acid and 214 mL (1540 mmol) of triethylamine in 1.0 L of anhydrous tetrahydrofuran at −25° C. under an atmosphere of nitrogen was added 83.0 mL (677 mmol) of trimethylacetyl chloride over 20 min. Upon addition a white precipitate formed and the resulting suspension was stirred for 2 h. Next, 28.7 g (677 mmol) of anhydrous lithium chloride and 100.0 g (615.0 mmol) of (4S)-4-phenyl-1,3-oxazolidin-2-one were added sequentially and the mixture was allowed to gradually warm to ambient temperature over 12 h. All volatiles were removed in vacuo and the residue was diluted with water (1 L) and extracted with ethyl acetate (3×300 mL). The combined organic layers were washed with brine (250 mL), dried over magnesium sulfate, filtered and concentrated in vacuo. The crude residue was purified by silica gel chromatography eluting with a 5-50% ethyl acetate in hexanes gradient to afford the title compound as a colorless solid (135 g, 85.4%). $^1$H NMR (500 MHz, CDCl$_3$): δ 7.40-7.37 (m, 2H), 7.36-7.32 (m, 1H), 7.31-7.28 (m, 2H), 5.42 (dd, J=8.9, 3.7 Hz, 1H), 4.69 (t, J=8.9 Hz, 1H), 4.28 (dd, J=9.2, 3.7 Hz, 1H), 3.13-3.02 (m, 2H), 2.24-2.21 (m, 2H), 1.94 (t, J=2.6 Hz, 1H), 1.84 (quintet, J=7.1 Hz, 2H). LC-MS: m/z (ES) 258.2 (MH)$^+$.

Step B: (4S)-3-{(2R)-2-[(S)-Hydroxy(phenyl)methyl]hex-5-ynoyl}-4-phenyl-1,3-oxazolidin-2-one

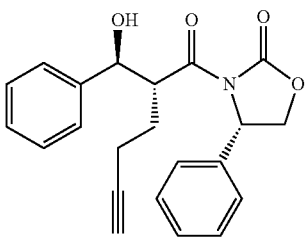 [SMILES: C#CCC[C@@H](C(=O)N1C(=O)OC[C@@H]1c1ccccc1)[C@H](O)c1ccccc1]

To a stirred solution of 56.8 g (221 mmol) of (4S)-3-hex-5-ynoyl-4-phenyl-1,3-oxazolidin-2-one from step A above in 265 mL of anhydrous ethyl acetate at ambient temperature under an atmosphere of nitrogen was added 6.31 g (66.2 mmol) of anhydrous magnesium chloride, 61.5 mL (442 mmol) of triethylamine, 26.9 mL (265 mmol) of benzaldehyde and 42.3 mL (331 mmol) of chlorotrimethylsilane and the resulting mixture was stirred for 72 h. The heterogeneous reaction mixture was filtered through a 300 mL plug of silica gel eluting with an additional 1 L of ethyl acetate. The filtrate was evaporated to dryness in vacuo and the residue suspended in 265 mL of methanol and 10 mL of trifluoroacetic acid. The resulting mixture was stirred at ambient temperature under nitrogen for 5 h during which time the reaction became homogeneous. All volatiles were then removed in vacuo and the residue was purified by silica gel chromatography eluting with a 5-15% ethyl acetate in hexanes gradient to afford the title compound as a white solid (65.0 g, 81.2%). $^1$H NMR (500 MHz, CDCl$_3$): δ 7.30-7.28 (m, 8H), 7.09-7.07 (m, 2H), 5.42 (dd, J=8.7, 3.7 Hz, 1H), 4.76-4.72 (m, 1H), 4.72-4.67 (m, 1H), 4.65 (t, J=8.7 Hz, 1H), 4.18 (dd, J=8.7, 3.7 Hz, 1H), 3.05 (d, J=7.8 Hz, 1H), 2.24 (td, J=7.1, 2.5 Hz, 2H), 2.00-1.93 (m, 2H), 1.67-1.61 (m, 1H). LC-MS: m/z (ES) 346.1 (MH-H$_2$O)$^+$, 386.0 (MNa)$^+$.

Step C: (2R)-2-[(S)-Hydroxy(phenyl)methyl]hex-5-ynoic acid

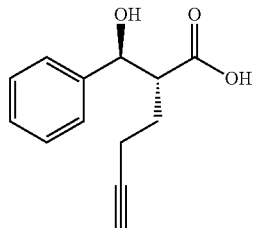 [SMILES: C#CCC[C@@H](C(=O)O)[C@H](O)c1ccccc1]

To a stirred solution of 65.0 g (179 mmol) of OS)-3-{(2R)-2-[(S)-hydroxy(phenyl)methyl]hex-5-ynoyl}-4-phenyl-1,3-oxazolidin-2-one from Step B above in 1050 mL of a 20 to 1 mixture of anhydrous tetrahydrofuran to water at 0° C. under an atmosphere of nitrogen was added 77.0 mL (894 mmol) of a 35% aqueous hydrogen peroxide solution at a rate slow enough to keep the internal temperature below 3° C. Next, 395 mL (395 mmol) of a 1.0 M aqueous lithium hydroxide solution was added at a rate slow enough to keep the internal temperature of the reaction below 5° C. and the resulting mixture was stirred for 3 h at 0° C. The reaction was quenched with 755 mL (984 mmol) of a 1.3 M aqueous sodium sulfite solution at a rate slow enough to keep the internal temperature of the mixture below 5° C. All volatiles were removed in vacuo and the remaining aqueous phase was extracted with ethyl acetate (3×200 mL). The aqueous phase was then cooled to 0° C. and acidified with a 6 M aqueous hydrogen chloride solution until a pH of 3 was achieved. The aqueous phase was then extracted with ethyl acetate (3×300 mL) and the combined organics were washed with brine (100 ml), dried over magnesium sulfate, filtered and evaporated in vacuo. The residue was purified by silica gel chromatography eluting with a 5-10% ethyl acetate and 3% acetic acid in hexanes gradient to afford the title compound as a colorless gum (32.0 g, 82.0%). $^1$H NMR (500 MHz, CDCl$_3$): δ 7.39-7.28 (m, 5H), 4.85 (d, J=8.2, 1H), 3.03-2.97 (m, 1H), 2.29-2.15 (m, 2H), 1.97 (t, J=2.5 Hz, 1H), 1.93-1.82 (m, 1H), 1.62-1.55 (m, 1H). LC-MS: m/z (ES) 201.0 (MH-H$_2$O)$^+$.

Step D: (2R)-2-[(S)-{[Tert-butyl(dimethyl)silyl]oxy}(phenyl)methyl]hex-5-ynoic acid

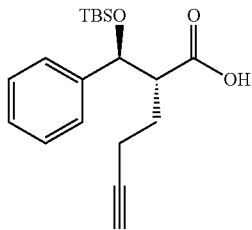 [SMILES: C#CCC[C@@H](C(=O)O)[C@H](O[Si](C)(C)C(C)(C)C)c1ccccc1]

To a stirred solution of 32.0 g (147 mmol) of (2R)-2-[(S)-hydroxy(phenyl)methyl]hex-5-ynoic acid from Step C above in 500 mL of anhydrous acetonitrile at ambient temperature under an atmosphere of nitrogen was added 77.0 mL (513 mmol) of 1,8-diazabicyclo[5.4.0]undec-7-ene 22 mL followed by 66.3 g (440 mmol) of tert-butyldimethylsilyl chloride in three portions over 10 min. The reaction mixture was stirred for 4 h then evaporated in vacuo to remove all volatiles. The residue was diluted with 300 mL of dichloromethane and 100 mL of water. A 1.0 M aqueous hydrogen chloride solution was added to the mixture until a pH of 3 was achieved in the aqueous layer. The phases were separated and the aqueous phase was extracted with dichloromethane (2×100 mL). The combined organics were washed with water (50 mL), brine (50 mL) then dried over magnesium sulfate. After filtration and evaporation in vacuo the residue was dissolved in 350 mL of methanol and 350 mL (280 mmol) of a 0.8 M aqueous potassium carbonate solution was added. The resulting mixture was stirred for 1.5 h then evaporated in vacuo to remove all volatiles. The residue was diluted with 300 mL of dichloromethane and the aqueous phase was acidified with a 5.0 M aqueous hydrogen chloride solution until a pH of 3 was achieved. The phases were separated and the aqueous phase was extracted with dichloromethane (2×100 mL). The combined organics were washed with water (50 mL), brine (50 mL) then dried over magnesium sulfate, filtered and evaporated in vacuo. The residue was purified by silica gel chromatography eluting with a 3-15% ethyl acetate in hexanes gradient to afford the title compound as a colorless solid (42.3 g, 86.6%). $^1$H NMR (500 MHz, CDCl$_3$): δ 7.36-7.27 (m, 5H), 4.78 (d, J=8.7, 1H), 2.90-2.86 (m, 1H), 2.19-2.11 (m, 1H), 2.10-2.03 (m, 1H), 1.90 (t, J=2.6 Hz, 1H), 1.75-1.67 (m, 1H), 1.41-1.34 (m, 1H), 0.83 (s, 9H), 0.02 (s, 3H), −0.27 (s, 3H). LC-MS: m/z (ES) 333.2 (MH)$^+$.

Step E: 4-Methoxybenzyl {(1R)-1-[(R)-{[tert-butyl(dimethyl)silyl]oxy}(phenyl)methyl]pent-4-yn-1-yl}carbamate

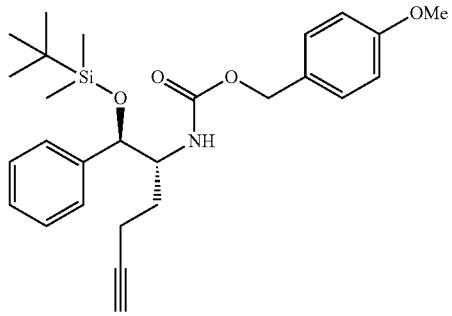 [SMILES: C#CCC[C@@H](NC(=O)OCc1ccc(OC)cc1)[C@H](O[Si](C)(C)C(C)(C)C)c1ccccc1]

To a solution of 40.0 g (120 mmol) of (2R)-2-[(S)-{[tert-butyl(dimethyl)silyl]oxy}(phenyl)methyl]hex-5-ynoic acid from Step D above and 33.5 mL (241 mmol) of triethylamine in 400 mL of anhydrous toluene at ambient temperature under an atmosphere of nitrogen was added 37.5 mL (132 mmol) of diphenylphosphoryl azide. The mixture was stirred for 5 h and then 37.5 mL (301 mmol) of 4-methoxybenzyl alcohol was added. The resulting mixture was heated to 105° C. for 16 h, cooled to ambient temperature and then diluted with 250 mL of a saturated aqueous bicarbonate solution. The phases were separated and the aqueous phase was extracted with ethyl acetate (2×150 mL). The combined organics were washed with water (100 mL), brine (100 mL) then dried over magnesium sulfate, filtered and evaporated in vacuo. The crude residue was purified by silica gel chromatography eluting with 3-10% ethyl acetate in hexanes to afford the title compound as a colorless oil (50.9 g, 90.5%). $^1$H NMR (500 MHz, CDCl$_3$): 7.28-7.21 (m, 7H), 6.87 (d, J=8.4 Hz, 2H), 4.92 (s, 2H), 4.77-4.59 (m, 2H), 3.89-3.84 (m, 1H), 3.81 (s, 3H), 2.30-2.22 (m, 2H), 1.95 (m, 1H), 1.91-1.85 (m, 1H), 1.57-1.50 (m, 1H), 0.89 (s, 9H), 0.06 (s, 3H), −0.15 (s, 3H). LC-MS: m/z (ES) 468.1 (MH)$^+$, 490.0 (MNa)$^+$.

Step F: 4-methoxybenzyl[(1R)-1-[(R)-{[tert-butyl(dimethyl)silyl]oxy}(phenyl)methyl]-5-(4-nitrophenyl)pent-4-yn-1-yl]carbamate

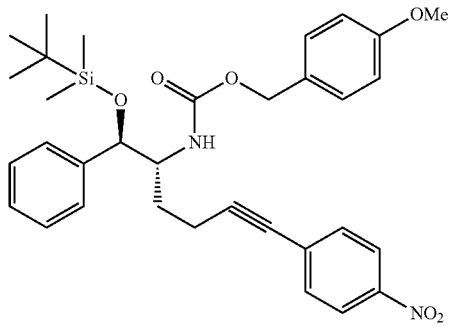 [SMILES: COc1ccc(COC(=O)N[C@H](CCC#Cc2ccc([N+](=O)[O-])cc2)[C@H](O[Si](C)(C)C(C)(C)C)c2ccccc2)cc1]

To a solution of acetylene (from Step E, 40 g, 80 mmol) and 4-iodonitrobenzene (21.8 g, 88 mmol) in anhydrous DMF (500 ml) was added triethylamine (111 mL, 797 mmol). Pd(dppf)Cl$_2$ (1.95 g, 2.39 mmol) and copper(I) iodide (910 mg, 4.78 mmol) was added and the mixture degassed with nitrogen (bubble 15 min) and the resulting solution stirred at room temperature for 5 h. The mixture was poured into water (1200 m) and extracted with EtOAc (3×300 mL). The combined organics were then washed with water (2×500 mL), sat. NaCl (200 mL), dried over magnesium sulfate, filtered and evaporated under vacuum. Residue was purified by MPLC (Horizon Biotage 2× Flash 65i) eluting with a gradient of 0-30% ethyl acetate in hexane to give 41 g (84%) as a dark red oil. %). $^1$H NMR (500 MHz, CDCl$_3$): 8.11-8.04 (m, 2H), 7.94-8.01 (m, 1H), 7.38-7.21 (m, 8H), 6.87 (d, J=8.4 Hz, 2H), 4.98 (s, 2H), 4.77-4.59 (m, 2H), 4.00-3.95 (m, 3H), 3.81 (s, 3H), 2.56 (t, J=7.1 Hz, H=2H), 2.00-1.95 (m, 1H), 1.66-1.61 (m, 1H), 0.93 (s, 9H), 0.10 (s, 3H), −0.10 (s, 3H). LC-MS: m/z (ES) 589.3 (MH)$^+$, 611.2 (MNa)$^+$.

Step G: 4-methoxybenzyl[(1R)-1-[(R)-{[tert-butyl (dimethyl)silyl]oxy}(phenyl)methyl]-5-(4-nitrophenyl)-4-oxopentyl]carbamate

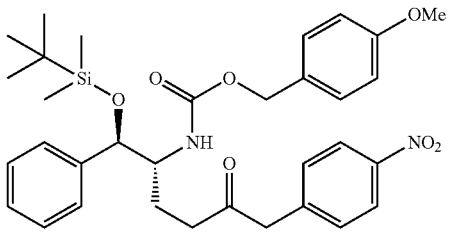 [SMILES: COc1ccc(COC(=O)N[C@H](CCC(=O)Cc2ccc([N+](=O)[O-])cc2)[C@H](O[Si](C)(C)C(C)(C)C)c2ccccc2)cc1]

To a solution of nitrophenyl acetylene (from Step F, 41 g, 65.5 mmol) in DMF (40 ml) was added pyrrolidine (14 mL, 196.5 mmol) and the resulting mixture heated at 80° C. for 3 h. The mixture was cooled to room temperature and a 10% solution of acetic acid in water (110 ml) was added, and the resulting solution stirred at room temperature for another 3 h. The mixture was poured into water (300 ml) and extracted with EtOAc (3×250 ml); combined EtOAc layers were washed with water (2×250 ml), sat. NaCl (100 ml), dried over MgSO$_4$, filtered and evaporated. The residue was purified by Horizon Flash 75 eluting with a gradient rising from 100% Hexanes to 50% EtOAc in Hexanes to give 34 g (81%) as a dark orange oil. $^1$H NMR (500 MHz, CDCl$_3$): 8.17-8.14 (m, 2H), 7.32-7.23 (m, 9H), 6.87 (d, J=8.4 Hz, 2H), 4.96 (d, J=12.2 Hz, 1H), 4.90 (d, J=12.1 Hz, 1H), 4.72 (d, J=3 Hz, 1H), 4.16-4.13 (m, 1H), 3.81 (s, 3H), 3.71-3.77 (m, 2H), 2.65-2.52 (m, 2H), 1.97-1.92 (m, 1H), 1.72-1.60 (m, 1H), 0.93 (s, 9H), 0.05 (s, 3H), −0.13 (s, 3H).

Step H: (2R,5S)-2-[(R)-{[tert-butyl(dimethyl)silyl]oxy}(phenyl)methyl]-5-(4-nitrobenzyl)pyrrolidine (2R,5R)-2-[(R)-{[tert-butyl(dimethyl)silyl]oxy}(phenyl)methyl]-5-(4-nitrobenzyl)pyrrolidine isomer 1

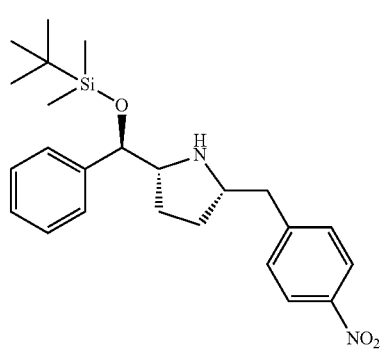

isomer 2

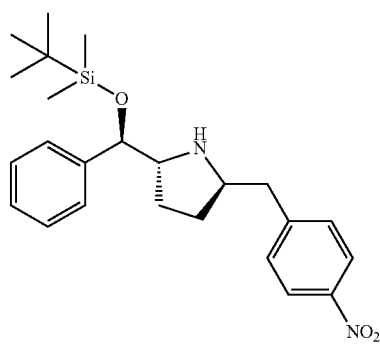

To a solution of MOZ protected ketone amine (from Step G, 34 g, 56 mmol) in DCM (350 ml) was added TFA (256 ml) and the resulting mixture stirred at room temperature for 1.5 h. The solution was evaporated under vacuum and residue partitioned between DCM and sat. NaHCO$_3$. The organic layer was dried over MgSO$_4$, filtered and evaported. The residue was dissolved in MeOH (750 ml) and cooled to 0° C. via ice/water bath. Sodium cyanoborohydride (21.2 g, 337 mmol) was then added and the resulting mixture was stirred overnight to allow to warm to room temperature. The mixture was quenched by addition of water and the organics removed under vacuum. The aqueous layer was then extracted with EtOAc (×2) and the combined EtOAc layers washed with sat. NaCl, dried over MgSO$_4$, filtered and evaporated under vacuum. The residue was purified by column chromatography on silica (eluent: gradient rising from 100% Hexanes to 35% EtOAc in Hexanes) to give 16.4 g (63.4%) of the first isomer, (2R,5S)-2-[(R)-{[tert-butyl(dimethyl)silyl]oxy}(phenyl)methyl]-5-(4-nitrobenzyl)pyrrolidine, and 3.1 g (12%) of the second isomer (2R,5R)-2-[(R)-{[tert-butyl(dimethyl)silyl]oxy}(phenyl)methyl]-5-(4-nitrobenzyl)pyrrolidine.

Isomer 1: LC-MS: m/z (ES) 427.3 (MH)$^+$
Isomer 2: LC-MS: m/z (ES) 427.3 (MH$^+$)$^+$ Step I: Tert-butyl (2R,5S)-2-[(R)-{[tert-butyl(dimethyl)silyl]oxy}(phenyl)methyl]-5-(4-nitrobenzyl)pyrrolidine-1-carboxylate

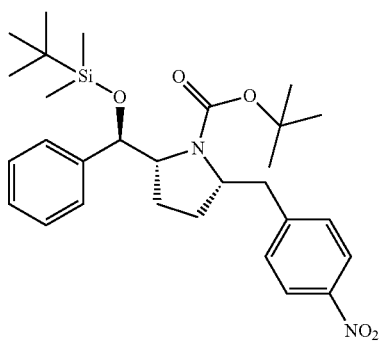 [SMILES: CC(C)(C)OC(=O)N1[C@H](Cc2ccc([N+](=O)[O-])cc2)CC[C@@H]1[C@H](O[Si](C)(C)C(C)(C)C)c1ccccc1]

To a solution of tert-butyl (2R,5S)-2-[(R)-{[tert butyl(dimethyl)silyl]oxy}(phenyl)methyl]-5-(4-nitrobenzyl)pyrrolidine-1-carboxylate (12 g, 42.5 mmol) in anhydrous THF was added Boc anhydride (9.3 g, 42.5 mmol) followed by TEA (17.76 mL, 127.4 mmol) and the resulting solution stirred at room temperature under nitrogen atmosphere for 2 h. The mixture was washed with water (100 mL) and extracted with ethyl acetate (2×200 mL). The organics were dried over sodium sulfate, filtered, and concentrated under vacuum. The residue was purified via Horizon Biotage MPLC (65i silica gel column) eluting with a gradient of 20-75% ethyl acetate in hexane to afford the desired product. LC-MS: m/z (ES) 527.3 (MH)$^+$, 549.2 (MNa)$^+$.

Step J: Tert-butyl (2R,5R)-2-[(R)-{[tert-butyl(dimethyl)silyl]oxy}(phenyl)methyl]-5-(4-nitrobenzyl)pyrrolidine-1-carboxylate

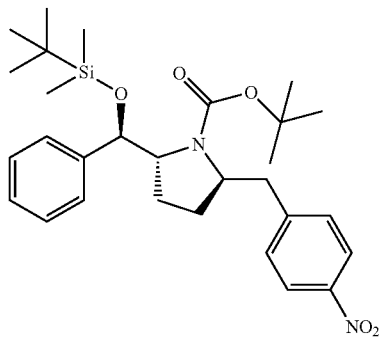

Prepared in the same manner as Step I but replacing the cis pyrrolidine isomer with the trans isomer, (2R,5R)-2-[(R)-{[tert-butyl(dimethyl)silyl]oxy}(phenyl)methyl]-5-(nitrobenzyl)pyrrolidine. LC-MS: m/z (ES) 527.3 (MH)+, 549.2 (MNa)+.

Step K: Tert-butyl (2S,5R)-2-(4-aminobenzyl)-5-[(R)-{[tert-butyl(dimethyl)silyl]oxy}(phenyl)methyl]pyrrolidine-1-carboxylate (i-4a)

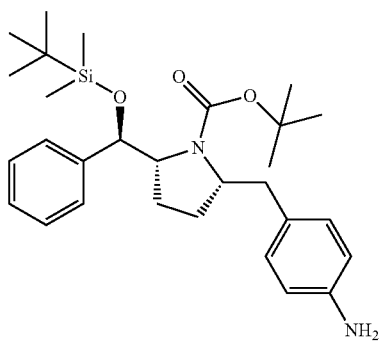

A 500 mL parr shaker flask was charged with 10% Pd/c (4.75 g) and to this was added 100 mL of methanol to cover the catalyst. A solution of the nitro intermediate from Step I (8.5 g, 18.5 mmol) in methanol (80 mL) was then added to the suspension, followed by 15.4 mL of 1.0 M hydrogen chloride in methanol solution. The reaction vessel was set under 50 PSI hydrogen gas and the mixture aggitated overnight. An aliquot was taken and analyzed through the LC-MS which showed complete reaction.

The catalyst was filtered off using celite and washed with methanol (2×100 mL). The filtrate was concentrated to dryness and the product was purified via Horizon MPLC (65i silica column) eluting with a gradient rising from 0% to 30% ethyl acetate in hexane to afford the title compound (6.2 g, 72%). m/z (ES) 497 (MH)+, 397 (M-Boc)+. $^1$HNMR (500 MHz, CDCl$_3$) δ: 7.38-7.29 (m, 5H), 6.76-6.68 (m, 2H), 6.55-6.50 (m, 2H), 5.52-5.49 (m, 1H), 5.30-5.27 (m, 1H), 4.15-4.05 (m, 2H), 3.86-3.81 (m, 1H), 3.76-3.71 (m, 1H), 3.55-3.47 (m, 2H), 2.74 (br d, J=11.7 Hz, 1H), 2.44 (br d, J=11.7 Hz, 1H), 2.05-1.93 (m, 1H), 1.90-1.83 (m, 1H), 1.60 (s, 9H), 1.50-1.42 (m, 1H), 1.31-1.21 (m, 2H), 1.10-1.02 (m, 1H), 0.95 (s, 9H), 0.92 (d, J=11.8 Hz, 1H), 0.13 (br d, J=14.0 Hz, 3H), −0.05 (s, 3H)

Step L: Tert-butyl (2R,5R)-2-(4-aminobenzyl)-5-[(R)-{[tert-butyl(dimethyl)silyl]oxy}(phenyl)methyl]pyrrolidine-1-carboxylate (i-4-b)

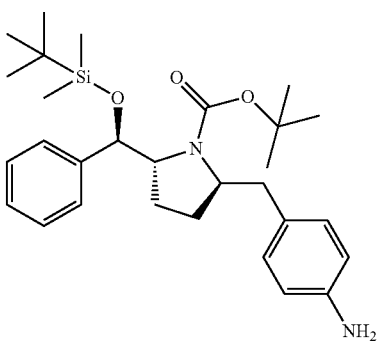 [SMILES: CC(C)(C)OC(=O)N1[C@@H](Cc2ccc([N+](=O)[O-])cc2)CC[C@@H]1[C@H](O[Si](C)(C)C(C)(C)C)c1ccccc1]

Prepared in the same manner as Step K but replacing the cis pyrrolidine isomer with the trans isomer, Tert-butyl (2R,5R)-2-[(R)-{[tert-butyl(dimethyl)silyl]oxy}(phenyl)methyl]-5-(4-nitrobenzyl)pyrrolidine-1-carboxylate. m/z (ES) 497 (MH)+, 397 (M-Boc)+. $^1$HNMR (500 MHz, CDCl$_3$) δ: 7.41-7.30 (m, 5H), 6.73-6.67 (m, 2H), 6.56-6.50 (m, 2H), 5.52-5.48 (m, 1H), 5.33-5.28 (m, 1H), 4.15-4.06 (m, 2H), 3.86-3.81 (m, 1H), 3.76-3.70 (m, 1H), 3.59-3.46 (m, 2H), 2.72 (br d, J=12.0 Hz, 1H), 2.44 (br d, J=12.0 Hz, 1H), 2.05-1.93 (m, 1H), 1.90-1.82 (m, 1H), 1.64 (s, 9H), 1.49-1.42 (m, 1H), 1.32-1.20 (m, 2H), 1.10-1.02 (m, 1H), 0.95 (s, 9H), 0.14 (br d, J=13.7 Hz, 3H), 0.10 (s, 3H).

The following intermediates were prepared from the appropriate starting materials using the procedures described above for intermediate i-4a.

TABLE 1

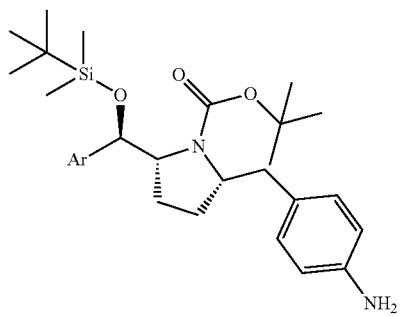

| Intermediate | Ar | Calc. Mass | MS (e/z) (MH)+ |
|---|---|---|---|
| i-4c | (3-fluorophenyl) | 514.30 | 515.30 |

TABLE 1-continued

| Intermediate | Ar | Calc. Mass | MS (e/z) (MH)+ |
|---|---|---|---|
| i-4d | 4-F-C6H4- | 514.30 | 515.30 |
| i-4e | 3,5-diF-C6H3- | 532.30 | 533.30 |
| i-4f | 3,4-diF-C6H3- | 532.30 | 533.30 |

The following intermediates were prepared from the appropriate starting materials using the procedures described above for intermediate i-4-b.

TABLE 2

| Intermediate | Ar | Calc. Mass | MS (e/z) (MH)+ |
|---|---|---|---|
| i-4g | 3-F-C6H4- | 514.30 | 515.30 |
| i-4h | 4-F-C6H4- | 514.30 | 515.30 |

Intermediate 5

Tert-butyl(5R)-2-(4-aminobenzyl)-5-[(R)-{[tert-butyl (dimethyl)silyl]oxy}(3-chlorophenyl)methyl]pyrrolidine-1-carboxylate (i-5)

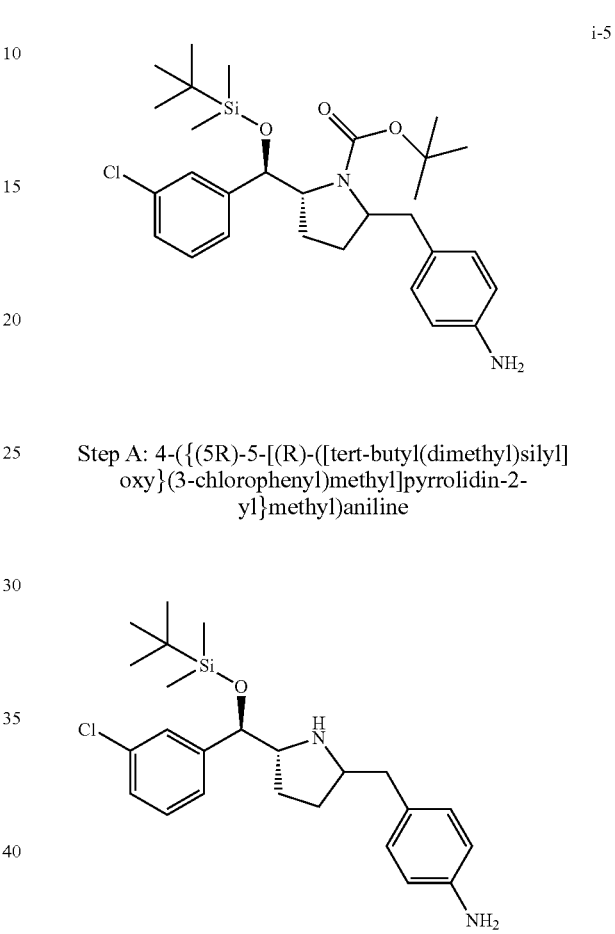

Step A: 4-({(5R)-5-[(R)-([tert-butyl(dimethyl)silyl] oxy}(3-chlorophenyl)methyl]pyrrolidin-2-yl}methyl)aniline To a solution of 100 mg (0.15 mmol) of benzyl{4-[(3E,5R,6R)-5-{[(benzyloxy)carbonyl]amino-6-{[tert-butyl (dimethyl)silyl]oxy}-6-(3-chlorophenyl)-2-oxohex-3-en-1-yl]phenyl}carbamate (from Step A, i-3) in 8 mL ethyl acetate was added 10% palladium on carbon and the suspension was set under hydrogen atmosphere via a balloon of hydrogen gas. The reaction was stirred under hydrogen for 8 h at room temperature. The catalyst was filtered off using a Gilmen 0.45 uM PTFE syringe filter and washed with ethyl acetate (4×2 mL). The filtrate was concentrated to dryness under vacuum and the residue purified by preparative plate (1000 µM) eluding with 5% methanol in dichloromethane to afford the title compound (33 mg, 51%). m/z (ES) 430, 432 (M, M+2)+.

Step B: Tert-butyl(5R)-2-(4-aminobenzyl)-5-[(R)-{[tert-butyl(dimethyl)silyl]oxy}(3-chlorophenyl) methyl]pyrrolidine-carboxylate (i-5)

To a solution of 33 mg (0.07 mmol) of 4-({(5R)-5-[(R)-([tert-butyl(dimethyl)silyl]oxy}(3-chlorophenyl)methyl] pyrrolidin-2-yl}methyl)aniline in 1 mL of anhydrous THF (from Step A) was added tert-butyl carbonate (15.3 mg, 0.07 mmol), followed by TEA (13 uL, 0.07 mmol) and the resulting solution stirred at room temperature under nitrogen atmosphere overnight. The reaction mixture was put directly on a preparative plate (500 uM) and eluted with 30% ethyl acetate in hexane to afford the title compound (25 mg, 78%). m/z (ES) 530, 532 (M, M+2)$^+$, 430, 432 (M-Boc, M-Boc+2)$^+$.

Intermediate 6

4-{4-[4-(Trifluoromethyl)phenyl]-1,3-thiazol-2-yl}benzenesulfonyl chloride (i-6)

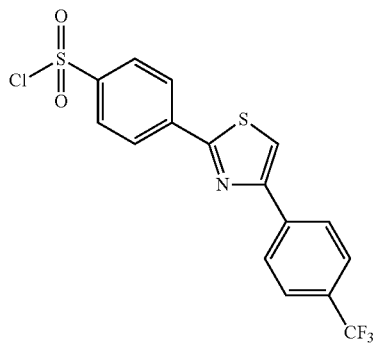

i-6

Intermediate 6 can be prepared according to published procedures, for example, Ikemoto et al., *Tetrahedron* 2003, 59, 1317-1325.

Intermediate 7

2-Methyl-5,6-dihydro-4H-cyclopenta[α][1,3]thiazole-4-carboxylic acid (i-7)

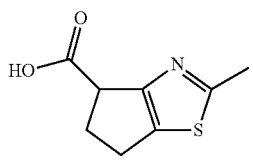

i-7

Step A: Ethyl 2-methyl-5,6-dihydro-4H-cyclopenta[α][1,3]thiazole-4-carboxylate

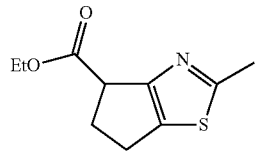

To a solution of ethyl 2-oxocyclopentane-2-carboxylate (56 g, 359 mmol) in chloroform (500 mL) cooled at 0° C. was added bromine (18.5 mL, 359 mmol) over ~20 min. After complete addition mixture allowed to warm to room temperature and stirred overnight. Nitrogen gas bubbled through mixture for 90 min to remove most of HBr. Washed with water (500 mL), sat. NaHCO$_3$ (250 mL), sat. NaCl (200 mL), dried over MgSO$_4$, filtered and evaporated. Residue dissolved in EtOH (500 mL) and thioacetamide (26.9 g, 359 mmol) added, mixture stirred at room temperature for 1 h then at reflux overnight. The mixture was cooled and evaporated, and the residue partitioned between DCM and sat. NaHCO$_3$, organic layer washed with sat. NaCl, dried over MgSO$_4$, filtered and evaporated. The Residue purified by MPLC (Biotage Horizon: 2×FLASH 65i) eluent: 100% Hexanes (450 mL), gradient rising from 100% Hexanes to 25% EtOAc in Hexanes (1400 mL), then 25% EtOAc in Hexanes to give the title compound (32 g, 42%) as a dark oil. $^1$HNMR (500 MHz, CDCl$_3$) δ: 4.22 (q, J=7.0 Hz, 2H), 3.96 (m, 1H), 3.04 (m, 1H), 2.88 (m, 1H), 2.76 (m, 2H), 2.70 (s, 3H), 1.30 (t, J=7.0 Hz, 3H).

Step B: 2-Methyl-5,6-dihydro-4H-cyclopenta[α][1,3]thiazole-4-carboxylic acid (i-7)

To a solution of 31.5 g (149 mmol) of ethyl 2-methyl-5,6-dihydro-4H-cyclopenta [α][1,3]thiazole-4-carboxylate in THF (450 mL) and methanol (100 mL) (from step A) was added a solution of lithium hydroxide (149 mL of a 1M solution, 149 mmol) and the resulting mixture stirred at room temperature for 3 h. Organics removed by evaporation and aqueous residue extracted with Et$_2$O (2×250 mL) and acidified to pH 3 by the addition of 1 M HCl (~170 mL) and saturated with solid NaCl. Extracted with DCM (3×250 mL), combined DCM layers dried over MgSO$_4$, filtered and evaporated. Extracted with DCM (3×250 mL), combined DCM layers dried over MgSO$_4$, filtered and evaporated. Residue triturated with acetonitrile, filtered and dried to give the title compound (7.1 g, 26%) as an off white solid. $^1$HNMR (500 MHz, CDCl$_3$) δ: 11.75 (br s, 1H), 4.02 (m, 1H), 3.00 (m, 1H), 2.90-2.66 (m, 6H).

Intermediate 8

2-[(Tert-butoxycarbonyl)amino]-5,6-dihydro-4H-cyclopenta[α][1,3]thiazole-4-carboxylic acid

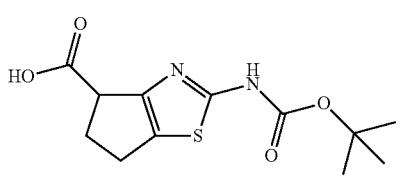

i-8

Step A: Ethyl 2-amino-5,6-dihydro-4H-cyclopenta[α][1,3]thiazole-4-carboxylate

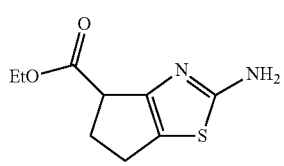

Prepared in the same manner as intermediate (i-7) replacing the thioacetamide in Step A with thiourea. $^1$HNMR (500

MHz, CDCl₃) δ: 5.30 (br s, 2H), 4.21 (q, J=7.0, 2H), 3.81 (m, 1H), 2.91 (m, 1H), 2.78 (m, 1H), 2.66 (m, 2H), 1.30 (t, J=7.0, 3H).

Step B: Ethyl 2-[(tert-butoxycarbonyl)amino]-5,6-dihydro-4H-cyclopenta[α][1,3]thiazole-4-carboxylate

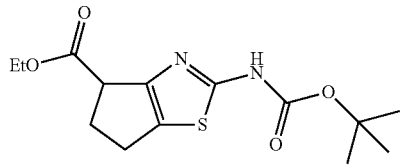 [SMILES: CCOC(=O)C1CCc2sc(NC(=O)OC(C)(C)C)nc21]

To a solution of 230 mg (1.08 mmol) of ethyl 2-amino-5,6-dihydro-4H-cyclopenta [α][1,3]thiazole-4-carboxylate in dichloromethane (5 mL) (from step A) was added di-tert butyldicarbonate (236 mg, 1.08 mmol), triethylamine (0.15 mL, 1.08 mmol) and DMAP (13 mg, 0.11 mmol) and the resulting mixture stirred at room temperature for 2 h. Mixture washed with 1N HCl (10 mL), sat. NaCl (5 mL), dried over MgSO₄, filtered and evaporated.

Residue purfied by MPLC (Biotage Horizon: FLASH 25+S) eluent: 100% Hexanes (100 mL), gradient 0-15% EtOAc in Hexanes (900 mL) then 15% EtOAc in Hexanes (500 mL) to give the title compound (160 mg, 47%) as a white foam. ¹HNMR (500 MHz, CDCl₃) δ: 9.23 (br s, 1H), 4.17 (q, J=7.1 Hz, 2H), 3.95 (t, J=6.6 Hz, 1H), 3.04 (m, 1H), 2.86 (m, 1H), 2.76 (m, 2H), 1.55 (s, 9H), 1.23 (t, J=7.1 Hz, 3H).

Step C: 2-[(Tert-butoxycarbonyl)amino]-5,6-dihydro-4H-cyclopenta[α][1,3]thiazole-4-carboxylic acid (i-8)

Prepared from ethyl 2-[(tert-butoxycarbonyl)amino]-5,6-dihydro-4H-cyclopenta [α][1,3]thiazole-4-carboxylate (from step B) using a procedure analogous to that found in intermediate (i-7) step B. ¹HNMR (500 MHz, CDCl₃) δ: 3.96 (m, 1H), 3.06 (m, 1H), 2.88 (m, 2H), 2.71 (m, 1H), 1.55 (s, 9H).

Intermediate 9

2-(4-Fluorophenyl)-5,6-dihydro-4H-cyclopenta[α][1,3]thiazole-4-carboxylic acid (i-9)

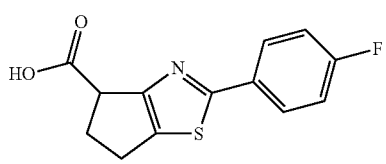

Prepared using procedures analogous to those found in intermediate 7 (i-7) replacing thioacetamide with 4-fluorothiobenzamide in step A. ¹HNMR (500 MHz, DMSO-d6) δ: 7.90 (m, 2H), 7.29 (t, J=8.7, 2H), 3.81 (m, 1H), 2.99 (m, 1H), 2.86 (m, 1H), 2.70-2.58 (m, 2H).

Intermediate 10

2-Methyl-4,5,6,7-tetrahydro-1,3-benzothiazole-4-carboxylic acid (i-10)

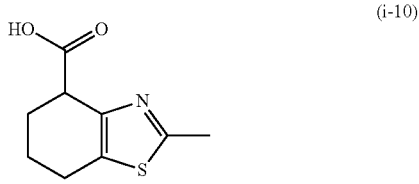

Step A: Ethyl 2-methyl-4,5,6,7-tetrahydro-1,3-benzothiazole-4-carboxylate

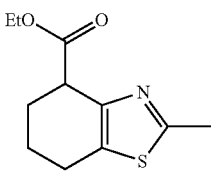

To a solution of ethyl 2-oxocyclohexanecarboxylate (15 g, 88 mmol) in anhydrous diethyl ether (40 mL) cooled at 0° C. was added bromine (4.5 mL, 88 mmol) dropwise over 15 mins. After complete addition mixture allowed to warm to room temp over 90 min. Mixture diluted with EtOAc (100 mL) and washed with sat. NaHCO₃, sat. NaCl, dried over MgSO₄, filtered and evaporated. Residue taken up in ethanol (100 mL) and thioacetamide (6.6 g, 88 mmol) added. Mixture stirred at room temp for 1 h then at reflux overnight. Mixture evaporated and residue partitioned between sat. NaHCO₃ and DCM. Organic layer dried over MgSO₄, filtered and evaporated. Residue purified by MPLC (Biotage Horizon: FLASH 65i) eluent: 100% Hexanes (500 mL), gradient 0 to 25% EtOAc in Hexanes (1200 mL) then 25% EtOAc in Hexanes (1200 mL) to give the title compound (6.14 g, 31%) as a pale orange oil. ¹HNMR (500 MHz, CDCl₃) δ: 4.22 (q, J=7.1, 2H), 3.84 (t, J=5.5, 1H), 2.80 (m, 1H), 2.73 (m, 1H), 2.65 (s, 3H), 2.18 (m, 1H), 2.11-1.95 (m, 2H), 1.85 (m, 1H), 1.29 (t, J=7.1, 3H).

Step B: 2-Methyl-4,5,6,7-tetrahydro-1,3-benzothiazole-4-carboxylic acid (i-10)

Prepared from ethyl 2-methyl-4,5,6,7-tetrahydro-1,3-benzothiazole-4-carboxylate (from step A) according to the procedure outlined in intermediate (i-7) step B. ¹HNMR (500 MHz, CDCl₃) δ: 9.26 (br s, 1H), 3.81 (q, J=7.3 and 5.9, 1H), 2.75 (m, 2H), 2.68 (s, 3H), 2.24 (m, 1H), 2.18-2.01 (m, 2H), 1.82 (m, 1H).

Intermediate 11

2-[(Tert-butoxycarbonyl)amino]-4,5,6,7-tetrahydro-1,3-benzothiazole-4-carboxylic acid (i-11)

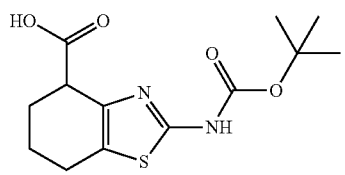
(i-11)

Step A: Ethyl 2-amino-4,5,6,7-tetrahydro-1,3-benzothiazole-4-carboxylate

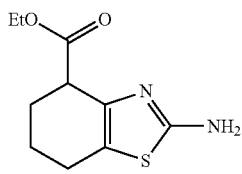 [SMILES: CCOC(=O)C1CCCc2sc(N)nc21]

Prepared according to the procedures outlined in intermediate 10 (i-10) step A replacing thioacetamide with thiourea. $^1$HNMR (500 MHz, DMSO-$d_6$) δ: 9.28 (br s, 2H), 4.11 (q, J=7.3, 2H), 3.71 (t, J=5.0, 1H), 2.57-2.39 (m, 2H), 1.90 (m, 2H), 1.78 (m, 1H), 1.59 (m, 1H), 1.17 (t, J=7.3, 3H).

Step B: 2-[(Tert-butoxycarbonyl)amino]-4,5,6,7-tetrahydro-1,3-benzothiazole-4-carboxylic acid (i-11)

Prepared from ethyl 2-amino-4,5,6,7-tetrahydro-1,3-benzothiazole-4-carboxylate (from step A) according to the procedures outlined in intermediate 8 (i-8) steps B and C. $^1$HNMR (500 MHz, CDCl$_3$) δ: 3.70 (t, J=5.2, 1H), 2.74 (m, 1H), 2.64 (m, 1H), 2.25 (m, 1H), 2.10-1.94 (m, 2H), 1.87 (m, 1H), 1.55 (s, 9H).

Intermediate 12

Indan-1-carboxylic acid (i-12)

Prepared according to the literature procedure Journal of Organic Chemistry (2000), 65(4), 1132-1138.

Intermediate 13a and Intermediate 13b

Tert-butyl (2S,5R)-2-(4-aminobenzyl)-5-[(R)-hydroxy(phenyl)methyl]pyrrolidine-1-carboxylate (i-13a)

Tert-butyl (2R,5R)-2-(4-aminobenzyl)-5-[(R)-hydroxy(phenyl)methyl]pyrrolidine-1-carboxylate (i-13b)

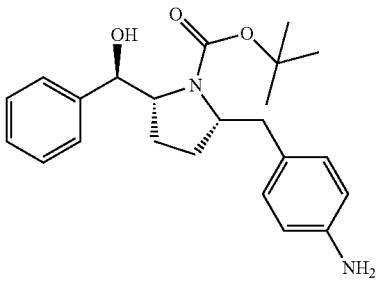
i-13a

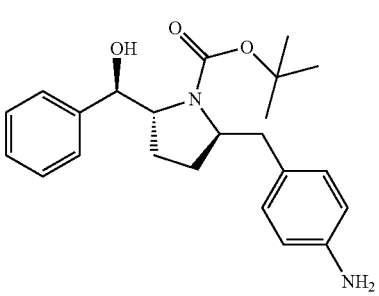
i-13b

Step A: Tert-butyl (4R,5R)-2,2-dimethyl-4-[(1E)-3-oxoprop-1-en-1-yl]-5-phenyl-1,3-oxazolidine-3-carboxylate

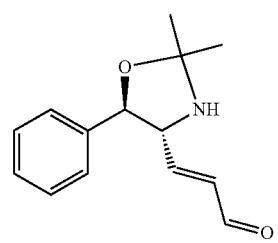

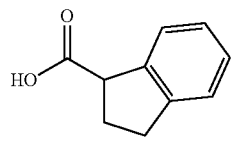 [SMILES: O=C(O)C1CCc2ccccc21]

To a solution of tert-butyl (4S,5R)-4-formyl-2,2-dimethyl-5-phenyl-1,3-oxazolidine-3-carboxylate (20.9, 89.1 mmol) in CH$_2$Cl$_2$ (150 mL) was added (triphenylphosphoranylidene) acetaldehyde (27.1 g, 89.1 mmol) and the resulting mixture was stirred at ambient temperature for 40 h. After removal of ⅓ of the solvent, hexanes was generously added and the resulting solid was filtered off. Flash chromatography Step B: Tert-butyl (4R,5R)-2,2-dimethyl-4-(3-oxo-propyl)-5-phenyl-1,3-oxazolidine-3-carboxylate

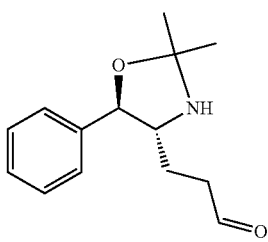 [SMILES: CC1(C)N[C@H](CCC=O)[C@@H](c2ccccc2)O1]

To a solution of tert-butyl (4R,5R)-2,2-dimethyl-4-[(1E)-3-oxoprop-1-en-1-yl]-5-phenyl-1,3-oxazolidine-3-carboxylate (19.6 g, 59.1 mmol) (from Step A) in acetone (150 mL) was added 1.9 g of 10% Pd/C and the resulting suspension was stirred under a hydrogen balloon at ambient temperature for 24 h. The solid was filtered off on celite and the filtrate concentrated under vacuum. The residue was purified by flash chromatography on a Biotage Horizon® system (silica gel, 0 to 20% ethyl acetate in hexanes gradient then 20% ethyl acetate in hexanes) to afford 11.5 g (58%) of the title compound as a colorless oil. LC/MS 356.3 (M+23).

Step C: Tert-butyl (4R,5R)-2,2-dimethyl-4-[(3E)-4-(4-nitrophenyl)but-3-en-1-yl]-5-phenyl-1,3-oxazolidine-3-carboxylate and tert-butyl (4R,5R)-2,2-dimethyl-4-[(3Z)-4-(4-nitrophenyl)but-3-en-1-yl]-5-phenyl-1,3-oxazolidine-3-carboxylate

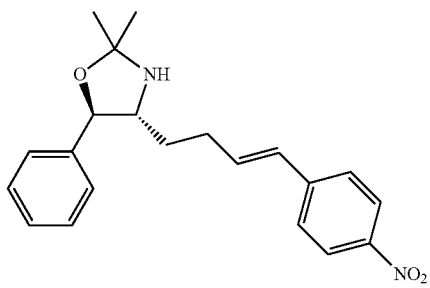 [SMILES: CC1(C)N[C@H](CC/C=C/c2ccc([N+](=O)[O-])cc2)[C@@H](c2ccccc2)O1]

To a solution of tert-butyl (4R,5R)-2,2-dimethyl-4-(3-oxo-propyl)-5-phenyl-1,3-oxazolidine-3-carboxylate (10.0 g, 30.0 mmol) from Step B in CH$_2$Cl$_2$ (200 mL) was added (4-nitrobenzyl)triphenyl-phosphonium bromide (21.5 g, 45.0 mmol) followed by Et$_3$N (8.36 mL, 60.0 mmol). The red reaction mixture was stirred at ambient temperature for 48 h. Hexane (200 mL) was poured into the reaction mixture and the solid was filtered off. Flash chromatography on a Biotage Horizon® system (silica gel, 0 to 10% ethyl acetate in hexanes gradient then 10% ethyl acetate in hexanes) afforded 10.7 g (79%) of the title compounds (cis trans mixture) as pale yellow foam. LC/MS 475.4 (M+23).

Step D: Tert-butyl (2R,5S)-2-[(R)-hydroxy(phenyl)methyl]-5-(4-nitrobenzyl)pyrrolidine-1-carboxylate and tert-butyl (2R,5R)-2-[(R)-hydroxy(phenyl)methyl]-5-(4-nitrobenzyl)pyrrolidine-1-carboxylate

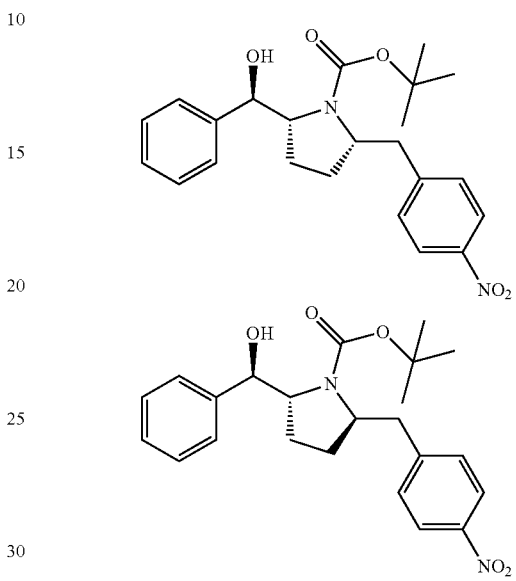

To a solution of the above cis/trans mixture (7.86 g, 17.4 mmol) from Step C in ethyl acetate (100 mL) was added 50 mL of 2N HCl solution and the resulting mixture was stirred at ambient temperature for 2 h then heated to 45° C. for 3 h. The volatiles were removed under reduced pressure. The resulting white solid was dissolved in N,N-dimethylformamide (100 mL) and 15.1 mL (86.7 mmol) of $^i$Pr$_2$Net was added. The reaction mixture was stirred at ambient temperature for 7 h. Di-tert-butyl dicarbonate (4.55 g, 20.8 mmol) was then added and the reaction mixture was stirred at ambient temperature overnight. Water (200 mL) was added and it was extracted with ethyl acetate (200 mL×3). The combined organic layers were dried over Na$_2$SO$_4$, filtered and concentrated under reduced pressure. The residue was purified by flash chromatography on a Biotage Horizon® system (silica gel, 0 to 30% ethyl acetate in hexanes gradient) to afford 1.61 g (22%) of the title compounds tert-butyl (2R,5S)-2-[(R)-hydroxy(phenyl)methyl]-5-(4-nitrobenzyl)pyrrolidine-1-carboxylate (cis) and 3.9 g (54%) of tert-butyl (2R,5R)-2-[(R)-hydroxy(phenyl)methyl]-5-(4-nitrobenzyl)pyrrolidine-1-carboxylate (trans). LC/MS 435.4 (M+23).

Step E: Tert-butyl (2S,5R)-2-(4-aminobenzyl)-5-[(R)-hydroxy(phenyl)methyl]pyrrolidine-1-carboxylate (i-13a)

To a solution of the above (cis) tert-butyl (2R,5S)-2-[(R)-hydroxy(phenyl)methyl]-5-(4-nitrobenzyl)pyrrolidine-1-carboxylate (1.51 g, 3.66 mmol) from Step D in ethanol (20 mL) was added 0.15 g of 10% Pd/C and the resulting suspension was stirred under a hydrogen balloon at ambient temperature for 5 h. Filtration through celite and removal of the solvent gave 1.40 g (100%) of the title compound as white foam which was used without further purification. LC/MS 405.3 (M+23).

Step F: Tert-butyl (2R,5R)-2-(4-aminobenzyl)-5-[(R)-hydroxy(phenyl)methyl]pyrrolidine-1-carboxylate (i-13b)

To a solution of (trans) tert-butyl (2R,5R)-2-[(R)-hydroxy(phenyl)methyl]-5-(4-nitrobenzyl)pyrrolidine-1-carboxylate (3.90 g, 9.46 mmol) from Step D in ethanol (40 mL) was added 0.4 g of 10% Pd/C and the resulting suspension was stirred under a hydrogen balloon at ambient temperature for 6 h. The solid was filtered off through celite. After removal of the solvent, flash chromatography on a Biotage Horizon® system (silica gel, 0 to 30% ethyl acetate in hexanes gradient then 30% ethyl acetate in hexanes) afforded 2.30 g (64%) of the title compound as a white foam. LC/MS 405.3 (M+23).

Intermediate 14

(2S)-1-(1,3-benzothiazol-2-yl)pyrrolidine-2-carboxylic acid (i-14)

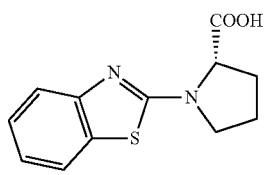 [SMILES: O=C(O)[C@@H]1CCCN1c1nc2ccccc2s1]

To a solution of 28 mg (0.24 mmol) of L-Proline in N,N-dimethylformamide (3 mL) at ambient temperature was added 51 mg (0.24 mmol) of 2-bromobenzothiazole, 100 mg (0.72 mmol) of potassium carbonate, and 6 mg (0.03 mmol) of copper iodide. The reaction mixture was stirred at 100° C. overnight. It was then filtered and purified by reverse-phase HPLC (TMC Pro-Pac C18; 0-60% 0.1% trifluoroacetic acid in acetonitrile/0.1% trifluoroacetic acid in water gradient). The pure fractions were lyophilized overnight to give 35 mg 60% of the title compound as a light brown solid. $^1$H NMR (DMSO-$d_6$): δ 7.78 (d, J=8.0 Hz, 1H), 7.45 (d, J=8.0 Hz, 1H), 7.28 (t, J=7.8 Hz, 1H), 7.08 (t, J=7.8 Hz, 1H), 4.48 (d, J=7.3 Hz, 1H), 3.52-3.61 (m, 2H), 2.37 (m, 1H), 2.01-2.11 (m, 3H). LC/MS 249.3 (M+1)

Intermediates 15-22

The following N-substituted L-proline intermediates were prepared from the appropriate starting materials using the procedures described above and procedures known in the art.

TABLE 3

| INTERMEDIATE | STRUCTURE | CALC. MASS | MS (E/Z) (MH)$^+$ |
|---|---|---|---|
| i-15 | 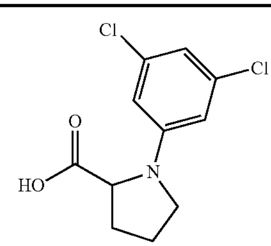 | 260.12 | 260.76 (M) 262.66 (M + 2) |
| i-16 | 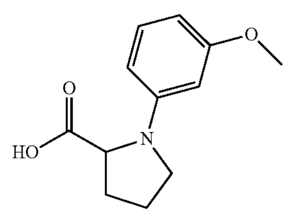 [SMILES: COc1cccc(N2CCCC2C(=O)O)c1] | 221.25 | 222.40 |
| i-17 | 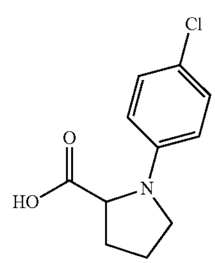 [SMILES: O=C(O)C1CCCN1c1ccc(Cl)cc1] | 225.67 | 225.42 (M) 227.06 (M + 2) |

TABLE 3-continued

| INTERMEDIATE | STRUCTURE | CALC. MASS | MS (E/Z) (MH)+ |
|---|---|---|---|
| i-18 | 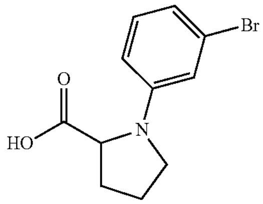 [SMILES: O=C(O)C1CCCN1c1cccc(Br)c1] | 270.12 | 269.98 (M)<br>271.92 (M + 2) |
| i-19 | 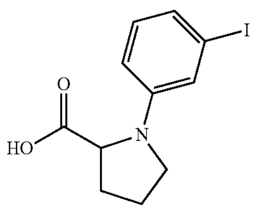 [SMILES: O=C(O)C1CCCN1c1cccc(I)c1] | 317.12 | 317.92 |
| I-20 | | 248.30 | 249.30 |
| i-21 | 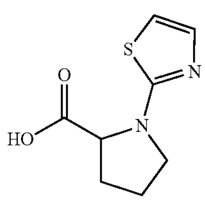 [SMILES: O=C(O)C1CCCN1c1nccs1] | 198.24 | 199.15 |
| i-22 | 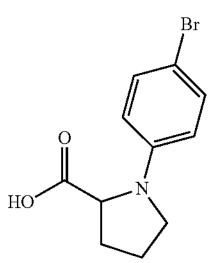 [SMILES: O=C(O)C1CCCN1c1ccc(Br)cc1] | 270.12 | 269.90 (M)<br>271.96 (M + 2) |

Intermediate 23

(6-Oxopyridazin-1(6H)-yl)acetic acid (i-23)

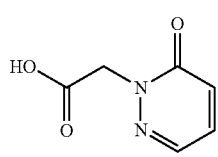 [SMILES: O=C(O)Cn1ncccc1=O]

To a solution of 3-chloro-6-oxopyridazin-1(6H)-yl)acetic acid (1 g, 5.30 mmol, ChemBridge) in 40 mL methanol was added 100 mg 10% palladium on carbon and the resulting suspension was set under hydrogen atmosphere and stirred vigorously for four h at room temperature. The catalyst was filter off via Gilmen 0.45 μM PFTE syringe filter and the filtrate concentrated under vacuum. The residue was used without any further purification. $^1$H NMR (D$_2$O): δ 9.07 (dd, J=1.6, 3.9 Hz, 1H), 7.59 (dd, J=4.1, 9.4 Hz, 1H), 7.14 (dd, J=1.6, 9.3 Hz, 1H), 4.97 (s, 2H). LC/MS 155.09 (M+1)

Intermediate 24

Preparation of 2-bromo-5,6-dihydro-4H-cyclopenta[d][1,3]thiazole-4-carboxylic acid (i-24)

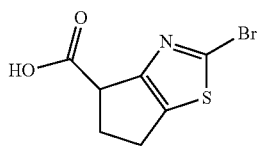 [SMILES: O=C(O)C1CCc2sc(Br)nc21]

Step A: Ethyl 2-bromo-5,6-dihydro-4H-cyclopenta[d][1,3]thiazole-4-carboxylate

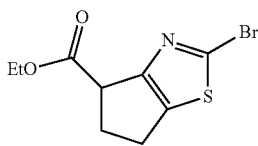 [SMILES: O=C(O)C1CCc2sc(Br)nc21]

To a solution tert-butyl nitrite (4.2 mL, 35.3 mmol) and copper(II) bromide (6.3 g, 28.3 mmol) in acetonitrile (100 mL) was added portionwise ethyl 2-amino-5,6-dihydro-4H-cyclopenta[α][1,3]thiazole-4-carboxylate (5 g, 23.6 mmol). Once the addition was complete the mixture stirred at room temperature for 3 h. Mixture poured into 2 M HCl (600 mL) and extracted with EtOAc (3×200 mL), combined EtOAc layers washed with 1 M HCl (500 mL), water (250 mL), sat. NaHCO$_3$ (200 mL), sat. NaCl (150 mL), dried over MgSO$_4$, filtered and evaporated. Residue purified by MPLC (Biotage Horizon: FLASH 40 M) eluent: 100% hexanes (100 mL), gradient rising from 100% Hexanes to 25% EtOAc in Hexanes (750 mL), then 25% EtOAc in Hexanes (700 mL) to give 1.87 g (29%) as a light orange oil. $^1$H NMR (500 MHz CDCl$_3$) δ: 4.22 (q, J=7.1, 2H), 4.00 (m, 1H), 3.04-3.11 (m, 1H), 2.88-2.94 (m, 1H), 2.77 (q, J=7.3, 2H), 1.31 (t, J=7.1, 3H).

Step B: 2-Bromo-5,6-dihydro-4H-cyclopenta[d][1,3]thiazole-4-carboxylic acid

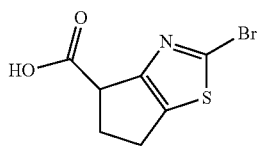 [SMILES: O=C(O)C1CCc2sc(Br)nc21]

A solution of the product from step A (4.92 g, 17.82 mmol) was dissolved in methanol (20 mL) and added dropwise to a mixture of 5 N NaOH (4.25 mL, 21.25 mmol), water (16 mL) and methanol (30 mL). After addition was complete the mixture was stirred for 2 h. The methanol was removed by evaporation and the pH of the remaining aqueous was adjusted to ~2.5 with conc. HCl. The mixture was saturated with solid NaCl and extracted with EtOAc (×3); combined EtOAc layers washed with sat. NaCl, dried over Na$_2$SO$_4$ and treated with activated charcoal overnight. The filtered mixture was evaporated. The residue was triturated with EtOAc, and the solid filtered to give 1.94 g of the desired product. The mother liquors were evaporated and purified by MPLC using a gradient rising from 100% Hexanes to 100% EtOAc in Hexanes to give a further 0.82 g of the title product (2.76 g in total, 62%) as an off white solid. $^1$H NMR (500 MHz CDCl$_3$) δ: 4.04 (m, 1H), 3.02-3.08 (m, 1H), 2.88-2.94 (m, 1H), 2.78-2.83 (m, 2H).

Intermediate 25

Preparation of 2-{2-[(tert-butoxycarbonyl)amino]-1,3-thiazole-4-yl}-4-fluorobutanoic acid (i-25)

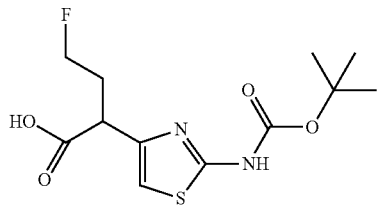 [SMILES: CC(C)(C)OC(=O)Nc1nc(C(CCF)C(=O)O)cs1]

Step A: Tert-butyl (2E)-2-[(tert-butoxycarbonyl)inimo]-4-(2-ethoxy-2-oxoethyl)-1,3-thiazole-3(2H)-carboxylate

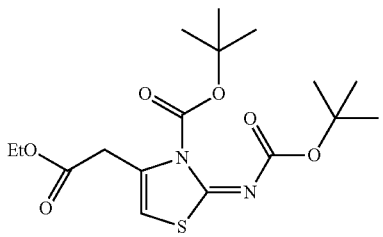 [SMILES: CCOC(=O)Cc1cs/c(=N/C(=O)OC(C)(C)C)n1C(=O)OC(C)(C)C]

To a solution of ethyl 2-amino thiazole-4-acetate (8 g, 43 mmol) in DCM (75 mL) was added di-tert-butyldicarbonate (20.63 g, 95 mmol), Hunig's Base (16.51 mL, 95 mmol) and DMAP (1.57 g, 12.89 mmol) and the resulting mixture stirred at room temperature overnight. The mixture was washed with water, sat. NaCl, dried over MgSO$_4$, filtered and evaporated. The residue was purified by MPLC employing a gradient rising from 100% Hexanes to 50% EtOAc in Hexanes to give the title compound 12.5 g (75%) as a white solid. $^1$H NMR (500 MHz CDCl₃) δ: 7.02 (s, 1H), 4.17 (q, J=7.3, 2H), 3.73 (s, 2H), 1.51 (s, 18H), 1.25 (t, J=7.3, 3H).

Step B: Ethyl 2-(2-[(tert-butoxycarbonyl)amino]-1,3-thiazol-4-yl)-4-fluorobutanoate

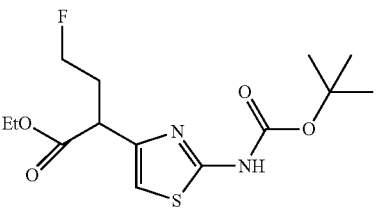 [SMILES: CCOC(=O)C(CCF)c1csc(NC(=O)OC(C)(C)C)n1]

To a solution of the product from step A (7.5 g, 19.4 mmol) in anhydrous THF (100 mL) cooled at −78° C. was added butyl lithium (8.54 mL of a 2.5 M soln, 21.35 mmol), followed by 1-iodo-2-fluoroethane (6.75 g, 38.8 mmol) and the mixture stirred at −78° C. for 1 h then allowed to warm to room temperature. A 10% w/w solution of citric acid (21 mL) was added and the resulting mixture stirred at room temperature overnight. The mixture was evaporated to remove THF and diluted with water (100 mL) and extracted with EtOAc (×3). The combined EtOAc layers were washed with water, sat. NaCl, dried over MgSO₄, filtered and evaporated. Residue purified by MPLC eluent: gradient rising from 100% Hexanes to 25% EtOAc in Hexanes. Further purification by PREP-HPLC on a C18 column employing a gradient rising from 100% water to 95% acetonitrile in water+0.05% TFA gave the title compound 500 mg (7%). ¹H NMR (500 MHz CDCl₃) δ: 8.22 (br s, 1H), 6.75 (s, 1H), 4.32-4.57 (m, 2H), 4.12-4.25 (m, 2H), 3.95 (t, J=7.5, 1H), 2.40-2.52 (m, 1H), 2.18-2.31 (m, 1H), 1.56 (s, 9H), 1.25 (t, J=7.1, 3H).

Step C: 2-{2-[(Tert-butoxycarbonyl)amino]-1,3-thiazole-4-yl}-4-fluorobutanoic acid

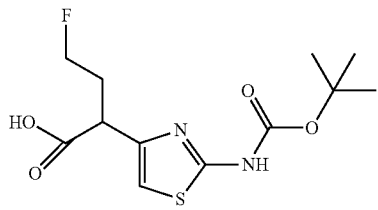 [SMILES: CC(C)(C)OC(=O)Nc1nc(C(CCF)C(=O)O)cs1]

To a solution of the product from step B (100 mg, 0.3 mmol) in a mixture of THF (1 mL) and methanol (0.3 mL) was added a solution of lithium hydroxide (0.3 mL of a 1 M soln, 0.3 mmol) and the resulting mixture stirred at room temperature for 90 min. 1N HCl (0.3 mL, 0.3 mmol) was added and the mixture evaporated to dryness. The resulting crude product was used immediately without purification.

Intermediate 26

Preparation of 2-fluoro-5,6-dihydro-4H-cyclopenta[d][1,3]-thaizole-4-carboxylic acid (i-26)

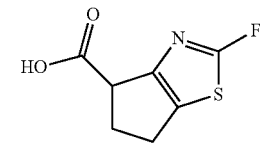 [SMILES: O=C(O)C1CCc2sc(F)nc21]

Step A: Ethyl 2-fluoro-5,6-dihydro-4H-cyclopenta[d]thiazole-4-carboxylate

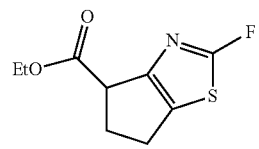 [SMILES: CCOC(=O)C1CCc2sc(F)nc21]

Ethyl 2-amino-5,6-dihydro-4H-cyclopenta[α][1,3]thiazole-4-carboxylate[From Step A, Intermediate 8] (2 g, 9.4 mmol) was dissolved in fluoroboric acid (5.17 g, 28.3 mmol) and the mixture cooled to the point just above it freezes (~5° C.). Nitrosonium tetrafluoroborate (1.1 g, 9.4 mmol) added portionwise and mixture stirred at 0° C. for 20 mins. Diethyl ether (60 mL) added and mixture stirred at −50° C. for 30 min. Filtered and the solid washed with diethyl ether and air dried. The solid was taken up in toluene (70 mL) and warmed to 90° C. for 30 min. The mixture was cooled and evaporated, and the crude residue purified by MPLC (eluent: gradient rising from 100% Hexanes to 40% EtOAc in Hexanes) to give the title compound 390 mg (19%) as a yellow oil. ¹H NMR (500 MHz CDCl₃) δ: 4.22 (q, J=7.1, 2H), 3.93 (dd, J=7.0 and 5.0, 1H), 3.08 (m, 1H), 2.91 (m, 1H), 2.71 (m, 2H), 1.31 (t, J=7.1, 3H).

Step B: 2-Fluor-5,6-dihydro-4H-cyclopenta[d][1,3]-thaizole-4-carboxylic acid

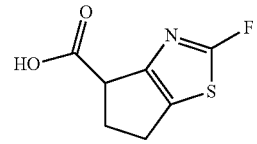 [SMILES: O=C(O)C1CCc2sc(F)nc21]

To a solution of the product from step A (100 mg, 0.456 mmol) in a mixture of THF (1.5 mL) and methanol (0.5 mL) was added a solution of lithium hydroxide (0.558 mL of a 1 M soln, 0.588 mmol) and the resulting mixture stirred at room temperature for 90 mins. 1N HCl (0.558 mL, 0.558 mmol)

was added and the mixture evaporated to dryness. The resulting crude product was used immediately without purification.

Intermediate 27

Preparation of 6,7-dihydro-5H-pyrrolo[1,2-d]tetrazole-5-carboxylic acid (i-27)

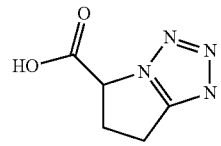

Step A: Methyl 5-methoxy-3,4-dihydro-2H-pyrrole-2-carboxylate

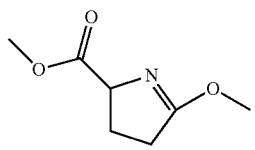

Methyl 5-methoxy-3,4-dihydro-2H-pyrrole-2-carboxylate was prepared using the method as described in Reference: Wick, A., Bartlett, P. and Dolphin, D; Helvetica Chimica Vol. 54 Fasc. 2 (1971).

Step B: Methyl 6,7-dihydro-5H-pyrrolo[1,2-d]tetrazole-5-carboxylate

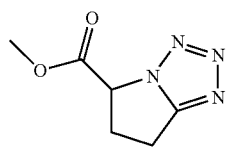

To a solution of starting methyl 5-methoxy-3,4-dihydro-2H-pyrrole-2-carboxylate (900 mg, 6.04 mmol) in 4 mL of acetic acid was added sodium azide (975 mg, 12.08 mmol) and the resulting suspension heat to 60° C. and stirred vigorously for 48 h. The solution was cooled to room temperature and diluted with 35 mL of ethyl ether. Solid potassium carbonate was added to the solution which was stirred at room temperature for 20 min. The solids were filtered off via fritted funnel, washed with cool ethyl ether and concentrated under vacuum. Solid precipitated during concentration and was filtered off after concentrating to one-fifth volume. The solids were washed once with cold ether (3 mL) and dried under high vacuum overnight to afford the title compound (308 mg, 31%). LC-MS: m/z (ES)=169 (MH)+.

Step C: 6,7-Dihydro-5H-pyrrolo[1,2-d]tetrazole-5-carboxylic acid

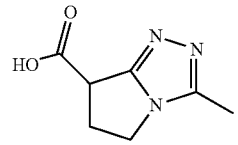

To a solution of methyl 6,7-dihydro-5H-pyrrolo[1,2-d]tetrazole-5-carboxylate (300 mg, 1.78 mmol) in THF/water/MeOH was added LiOH (214 mg, 8.92 mmol) and the resulting solution was heated via oil bath to 60° C. for 16 h. (Round bottom was equipped with a condenser.) The solution was cooled to room temperature and concentrated to remove organic solvents. The aqueous layer was then acidified to pH of ~5 using 2N HCl. The mixture was concentrated to dryness under vacuum, azeotroping with toluene (2×20 mL) to make sure all water was removed. The material was used without further purification with Lithium chloride as a by-product. LC-MS: m/z (ES)=155 (MH)+.

Intermediate 28

Preparation of 3-methyl-6,7-dihydro-5H-pyrrolo[2,1-c][1,2,4]-triazole-7-carboxylic acid (i-28)

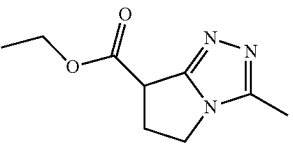

Step A: Ethyl 3-methyl-6,7-dihydro-5H-pyrrolo[2,1-c][1,2,4]-triazole-7-carboxylate Ref: Lawson, Edward C, etc., Tet. Lett. 41 (2000) p. 4533-4536

Dissolved commercially available ethyl 2-oxopyrrolidine-3-carboxylate (2.50 g, 15.91 mmol) in 30 mL dichloromethane in 50 mL round bottom flask. To this solution was added trimethyloxonium tetrafluoroborate (2.59 g, 17.5 mmol) as a solid and rinsed with 20 mL dichloromethane. The resulting mixture was stirred at room temperature for two h and LC/MS indicated that the intermediate methyl 5-methoxy-3,4-dihydro-2H-pyrrole-4-carboxylate had formed. At this point, acetohydrazide (1.18 g, 15.91 mmol) was introduced as a solid to the mixture and the resulting solution was stirred at room temperature for 3 h. The solution was then concentrated under vacuum to remove all dichloromethane and the residue was then taken up in 100 mL n-butanol which was heated to reflux in an oil bath set at 120° C. overnight. The solution was cooled to room temperature and concentrated under vacuum. The residue was purified via sixteen 1500 μm silica gel preparative plates eluting with 90:10 dichloromethane:methanol solvent system. The product was extracted from the silica gel using 85:15 dichloromethane:methanol which afforded the title compound (454 mg, 11%). $^1$H NMR (500 MHz DMSO-d6) δ: 4.16-4.06 (m, 1H), 4.00-3.88 (m, 1H), 2.85-2.78 (m, 1H), 2.29 (s, 3H), 1.55 (dt, J=6.7, 13.9 Hz, 2H), 1.32 (dt, J=6.7, 14.0 Hz, 2H), 0.88 (t, J=7.5 Hz, 3H). LC-MS: m/z (ES)=196 (MH)$^+$.

Step B: 3-Methyl-6,7-dihydro-5H-pyrrolo[2,1-c][1,2,4]-triazole-7-carboxylic acid

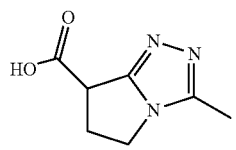

To a solution of ethyl 6,7-dihydro-5H-pyrrolo[2,1-c][1,2,4]-triazole-7-carboxylic acid (400 mg, 2.05 mmol) in THF/water/MeOH was added LiOH (250 mg, 10.25 mmol) and the resulting solution was heated via oil bath to 60° C. for 16 h. (Round bottom was equipped with a condenser.) The solution was cooled to room temperature and concentrated to remove organic solvents. The aqueous layer was then acidified to pH of ~5 using 2N HCl. The mixture was concentrated to dryness under vacuum, azeotroping with toluene (2×20 mL) to make sure all water was removed. The material was used without further purification with lithium chloride as a by-product. LC-MS: m/z (ES)=168 (MH)$^+$.

Intermediate 29

Preparation of 3-methyl-5,6,7,8-tetrahydro-[1,2,4]-triazolo[4,3-d]pyridine-8-carboxylic acid. (i-29)

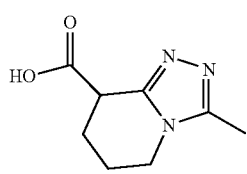

Prepared using procedures analogous to those found in intermediate 28 (i-28) above replacing ethyl 2-oxopyrrolidine-3-carboxylate with ethyl 2-oxopiperidine-3-carboxylate. LC-MS: m/z (ES)=182 (MH)$^+$.

Intermediate 30

Preparation of 3-methyl-6,7-dihydro-5H-pyrrolo[2,1-c][1,2,4]-triazole-5-carboxylic acid (i-30)

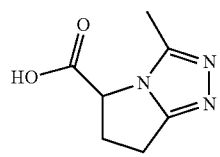

Prepared using procedures analogous to those found in intermediate 28 (i-28) above replacing ethyl 2-oxopyrrolidine-3-carboxylate with methyl 5-oxopyrrolidine-2-carboxylate. LC-MS: m/z (ES)=168 (MH)$^+$.

Intermediate 31

Preparation of [6-oxopyridazin-1(6H)-yl]acetic acid (i-31)

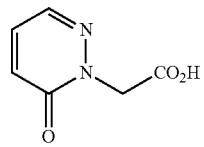 [SMILES: O=C(O)Cn1ncccc1=O]

To 3-chloro-6-oxopyridazin-1(6H)-yl]acetic acid (1.00 g, 5.30 mmol) in methanol (40 mL) was added 100 mg of 10% Pd/C. After the reaction mixture was stirred at ambient temperature under a H$_2$ balloon for 1 h, the Pd was filtered off through celite. The filtrate was concentrated in vacuo and purified by reverse phase HPLC (TMC Pro-Pac C18; 0-40% 0.1% trifluoroacetic acid in acetonitrile/0.1% trifluoroacetic acid in water gradient). Removal of the volatiles in vacuo afforded the title compound as a white crystalline. $^1$H NMR (D$_2$O): δ 8.06 (dd, J=3.9, 1.4 Hz, 1H), 7.56 (dd, J=9.4, 3.9 Hz, 1H), 7.12 (dd, J=9.4, 1.5 Hz, 1H), 4.95 (s, 2H). LC/MS 155.2 (M+1).

Intermediate 32

Preparation of [2-oxopyrimidin-1(2H)-yl]acetic acid (i-32)

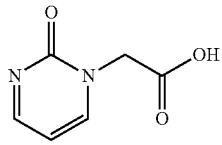 [SMILES: O=C(O)Cn1cccnc1=O]

To 2-hydroxypyrimidine hydrochloride (1.00 g, 7.54 mmol) and chloroacetic acid (0.713 g, 7.54 mmol) was added 5 N sodium hydroxide solution (4.5 mL). The reaction mixture was heated at 105° C. for 2 h. After cooled down to ambient temperature and neutralized with 2 M hydrochloric acid (3.8 mL), the title compound was collected by crystallization and filtration as a pale yellow solid. $^1$H NMR (DMSO-$d_6$): δ 13.2 (s, 1H), 8.59 (dd, J=3.9, 3.0 Hz, 1H), 8.16 (dd, J=6.4, 2.8 Hz, 1H), 6.46 (dd, J=6.4, 4.1 Hz, 1H), 4.58 (s, 2H). LC/MS 155.2 (M+1).

as a white solid. $^1$H NMR (DMSO-$d_6$): δ 13.2 (s, 1H), 8.43 (s, 1H), 7.94 (d, J=6.7 Hz, 1H), 6.43 (d, J=6.6 Hz, 1H), 4.63 (s, 2H). LC/MS 155.1 (M+1).

Intermediate 33

Preparation of 2-[2-oxopyrimidin-1(2H)-yl]propanoic acid (i-33)

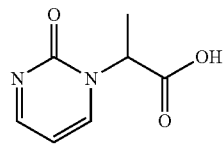

To 2-hydroxypyrimidine hydrochloride (1.27 g, 9.54 mmol) was added 5 N sodium hydroxide solution (5.7 mL) followed by (2S)-2-bromopropanoic acid (0.95 mL, 11 mmol). The reaction mixture was heated at 80° C. for 4 h. After cooled down to ambient temperature, it was neutralized with 2N hydrochloric acid (4.8 mL) and then directly purified by reverse phase HPLC (TMC Pro-Pac C18; 0-50% 0.1% trifluoroacetic acid in acetonitrile/0.1% trifluoroacetic acid in water gradient). Removal of the volatiles in vacuo afforded the title compound as a white solid. LC/MS 169.1 (M+1).

Intermediate 34

Preparation of [6-oxopyrimidin-1(6H)-yl]acetic acid (i-34)

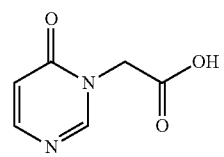 [SMILES: O=C(O)Cn1cnccc1=O]

To pyrimidin-4(3H)-one (0.608 g, 6.33 mmol) was added 5 N sodium hydroxide solution (2.5 mL) followed by chloroacetic acid (0.598 g, 6.33 mmol). The reaction mixture was heated at 105° C. for 2 h. After cooled down to ambient temperature, it was neutralized with 2 N hydrochloric acid (3.2 mL) and then directly purified by reverse phase HPLC (TMC Pro-Pac C18; 0-40% 0.1% trifluoroacetic acid in acetonitrile/0.1% trifluoroacetic acid in water gradient). Removal of the volatiles in vacuo afforded the title compound Intermediate 35

Preparation of 2-[6-oxopyrimidin-1(6H)-yl]propanoic acid (i-35)

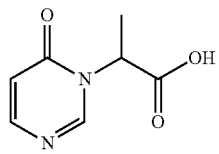

To pyrimidin-4(3H)-one (0.908 g, 9.45 mmol) was added 5 N sodium hydroxide solution (3.8 mL) followed by (2R)-2-bromopropanoic acid (0.95 mL, 11 mmol). The reaction mixture was heated at 85° C. for 1 h. After cooled down to ambient temperature, it was neutralized with 2 M hydrochloric acid (5.2 mL) and then directly purified by reverse phase HPLC (TMC Pro-Pac C18; 0-40% 0.1% trifluoroacetic acid in acetonitrile/0.1% trifluoroacetic acid in water gradient). Removal of the volatiles in vacuo afforded the title compound as a white solid. $^1$H NMR (DMSO-$d_6$): δ 8.48 (d, J=2.7 Hz, 1H), 7.88 (dd, J=7.8, 2.8 Hz, 1H), 6.12 (d, J=7.6 Hz, 1H), 5.04 (q, J=7.3 Hz, 1H), 1.64 (d, J=7.5 Hz, 3H). LC/MS 169.1 (M+1).

Intermediate 36

Preparation of [5-oxo-1,6-naphthyridin-6(5H)-yl]acetic acid (i-36)

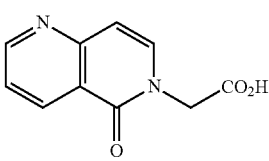 [SMILES: O=C(O)Cn1ccc2ncccc2c1=O]

To 1,6-naphthyridin-5(6H)-one (0.625 g, 4.28 mmol) was added 5 M sodium hydroxide solution (1.7 mL) followed by chloroacetic acid (0.404 g, 4.28 mmol). The reaction mixture was heated at 100° C. for 2 h. After cooled down to ambient temperature and neutralized with 2 N hydrochloric acid (2.1 mL), the title compound was collected by filtration as a yellow solid. $^1$H NMR (DMSO-$d_6$): δ 13.1 (s, 1H), 8.94 (dd, J=4.6, 1.8 Hz, 1H), 8.51 (dd, J=8.0, 1.6 Hz, 1H), 7.72 (d, J=7.6 Hz, 1H), 7.52 (dd, J=8.0, 4.6 Hz, 1H), 6.72 (d, J=7.6 Hz, 1H), 4.72 (s, 2H). LC/MS 205.2 (M+1).

Intermediate 37

Preparation of [4-methyl-6-oxopyridazin-(6H)-yl]acetic acid (i-37)

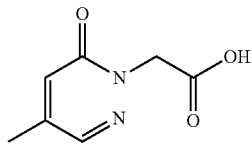

Step A: Ethyl[4-methyl-6-oxopyridazin-1(6H)-yl]acetate

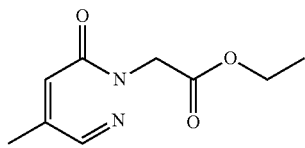

5-Hydroxy-4-methylfuran-2(5H)-one (1.19 g, 10.4 mmol) and ethyl hydrazinoacetate hydrochloride (1.61 g, 10.4 mmol) in 95% ethanol (20 mL) was refluxed for 2 h. Removal of the solvent in vacuo followed by purification using a Biotage Horizon® system (0-50% ethyl acetate/hexanes mixture) gave ethyl [4-methyl-6-oxopyridazin-1(6H)-yl]acetate as a yellow crystalline. LC/MS 219.2 (M+23).

Step B: [4-Methyl-6-oxopyridazin-1(6H)-yl]acetic acid

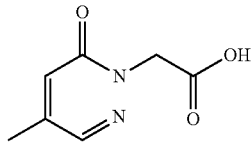

To ethyl [4-methyl-6-oxopyridazin-1(6H)-yl]acetate (0.575 g, 2.93 mmol) in tetrahydrofuran (3 mL), methanol (2 mL) and water (2 mL) was added 1 N lithium hydroxide solution (2.9 mL). The reaction mixture was stirred at ambient temperature for 1.5 h. After neutralized with trifluoro acetic acid, the reaction mixture was directly purified by reverse phase HPLC (TMC Pro-Pac C18; 0-45% 0.1% trifluoroacetic acid in acetonitrile/0.1% trifluoroacetic acid in water gradient). The pure fractions were lyophilized overnight to yield the title compound. LC/MS 169.2 (M+1).

Intermediate 38

Preparation of 2-[4-methyl-6-oxopyridazin-1(6H)-yl]propanoic acid (i-38)

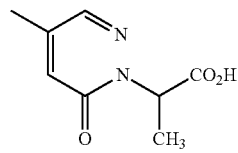

To ethyl [4-methyl-6-oxopyridazin-1(6H)-yl]acetate (0.132 g, 0.673 mmol) in tetrahydrofuran (4 mL) at −78° C. was added 1M lithium hexamethyldisilazane solution (0.74 mL). The reaction mixture was stirred at −78° C. for 15 min then was added methyl iodide (0.046 mL, 0.74 mmol). After being stirred at −78° C. for 2 h, the reaction mixture was allowed to warm to ambient temperature over 0.5 h. Removal of the volatiles in vacuo followed by purification using a Biotage Horizon® system (0-50% ethyl acetate/hexanes mixture) gave ethyl 2-[4-methyl-6-oxopyridazin-1(6H)-yl]propanoate as oil. To 88 mg (0.42 mmol) of the above oil in tetrahydrofuran (0.3 mL), water (0.2 mL) and methanol (0.2 mL) was added 5 N sodium hydroxide solution (0.2 mL). The reaction mixture was stirred at ambient temperature for 3 h then neutralized with 2 N hydrochloric acid and purified by reverse phase HPLC (TMC Pro-Pac C18; 0-40% 0.1% trifluoroacetic acid in acetonitrile/0.1% trifluoroacetic acid in water gradient). Removal of the volatiles in vacuo afforded the title compound as a white solid. LC/MS 183.2 (M+1).

IntermediateS 39 and 40

Preparation of 2-[6-oxopyridazin-1(6H)-yl]propanoic acid and 2-(pyridazin-3-yloxy)propanoic acid (i-39 and i-40)

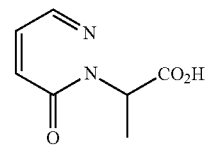

i-39

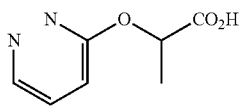

i-40

To 3(2H)-pyridazinone (1.19 g, 12.3 mmol) was added 5 N sodium hydroxide solution (4.9 mL) followed by (2S)-2-bromopropanoic acid (1.11 mL, 12.3 mmol). The reaction mixture was heated at 90° C. for 1 h. After cooled downed to ambient temperature, 2 M hydrochloric acid (6.2 mL) was added and the reaction mixture was directly purified by reverse phase HPLC (TMC Pro-Pac C18; 0-40% 0.1% trifluoroacetic acid in acetonitrile/0.1% trifluoroacetic acid in water gradient). The O-alkylation product 2-(pyridazin-3-yloxy)propanoic acid was eluted fast. The pure fractions were collected and the solvent was removed in vacuo afforded the two title compounds both as pale yellow solid. 2-[6-Oxopyridazin-1(6H)-yl]propanoic acid (i-39): $^1$H NMR (D$_2$O): δ 8.07 (dd, J=4.1, 1.6 Hz, 1H), 7.53 (dd, J=9.3, 3.9 Hz, 1H), 7.09 (dd, J=9.4, 1.6 Hz, 1H), 5.46 (m, 1H), 1.64 (d, J=7.3 Hz, 3H). 2-(pyridazin-3-yloxy)propanoic acid (i-40): $^1$H NMR (D$_2$O): δ 9.01 (d, J=5.3 Hz, 1H), 8.14 (dd, J=9.1, 5.2 Hz, 1H), 7.64 (d, J=9.1 Hz, 1H), 5.45 (q, J=7.2 Hz, 1H), 1.86 (d, J=7.1 Hz, 3H).

Intermediate 41

Preparation of [2-oxopyrazin-1(2H)-yl]acetic acid (i-41)

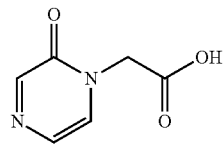

Pyrazin-2(1H)-one (0.333 g, 3.47 mmol) was added 5 N sodium hydroxide solution (2.1 mL) followed by chloroacetic acid (0.524 g, 5.54 mmol). The reaction mixture was heated at 100° C. for 2 h. After cooled down to ambient temperature, 2 N hydrochloric acid (3.5 mL) was added and the reaction mixture was directly purified by reverse phase HPLC (TMC Pro-Pac C18; 0-40% 0.1% trifluoroacetic acid in acetonitrile/0.1% trifluoroacetic acid in water gradient). The pure fractions were lyophilized overnight to yield the title compound as a yellow solid. LC/MS 155.2 (M+1).

IntermediateS 42 and 43

Preparation of 2-[3-methyl-6-oxopyridazin-1(6H)-yl] propanoic acid and 2-[(6-methylpyridazin-3-yl)oxy] propanoic acid (i-42 and i-43)

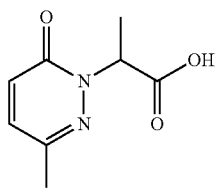
i-42

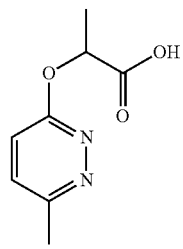
i-43

To 6-methylpyridazin-3(2H)-one (0.510 g, 4.63 mmol) was added 5 N sodium hydroxide solution (1.85 mL) followed by 2-bromopropanoic acid (0.709 g, 4.63 mmol). The reaction mixture was heated at 90° C. for 1 h. After cooled down to ambient temperature, 2 M hydrochloric acid (5.0 mL) was added and the reaction mixture was directly purified by reverse phase HPLC (TMC Pro-Pac C18; 8-20% 0.1% trifluoroacetic acid in acetonitrile/0.1% trifluoroacetic acid in water gradient). The O-alkylation product was eluted fast. The pure fractions were collected and lyophilized overnight to afford the two title compounds. LC/MS 183.2 (M+1). 2-[3-methyl-6-oxopyridazin-1(6H)-yl]propanoic acid (i-42): $^1$H NMR (DMSO-d$_6$): δ 7.34 (d, J=9.7 Hz, 1H), 6.88 (d, J=9.4 Hz, 1H), 5.30 (q, J=7.3 Hz, 1H), 2.26 (s, 3H), 1.49 (d, J=7.3 Hz, 3H). 2-[(6-methylpyridazin-3-yl)oxy]propanoic acid (i-43): $^1$H NMR (DMSO-d$_6$): δ 8.36 (d, J=9.0 Hz, 1H), 7.90 (d, J=9.2 Hz, 1H), 6.00 (q, J=6.6 Hz, 1H), 2.90 (s, 3H), 1.73 (d, J=6.6 Hz, 3H).

Intermediate 44

Preparation of 1(6S)-4-oxo-4,6,7,8-tetrahydropyrrolol[1,2-]pyrimidine-6-carboxylic acid (i-44)

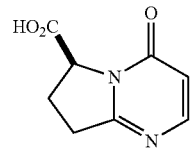 [SMILES: O=C(O)[C@@H]1CCc2nccc(=O)n21]

Step A: Methyl 16(S)-4-oxo-4,6,7,8-tetrahydropyrrolol[1,2-]pyrimidine-6-carboxylate

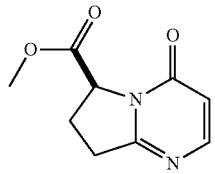

Methyl (2S)-5-methoxy-3,4-dihydro-2H-pyrrole-2-carboxylate (4.19 g, 26.6 mmol) and 3-azatricyclo[4.2.1.0.$^{2,5}$] non-7-en-4-one (2.4 g, 17.8 mmol) was heated at 110° C. overnight. Purification using a Biotage Horizon® system (0-100% ethyl acetate/hexanes mixture) gave the title compound methyl [6(S)-4-oxo-4,6,7,8-tetrahydropyrrolo[1,2-$^\alpha$] pyrimidine-6-carboxylate and intermediate methyl (7S)-9-oxo-3,8-diazatetracyclo[9.2.1.0$^{2,10}$.0$^{4,8}$]tetradeca-3,12-diene-7-carboxylate. The intermediate was heated at 150° C. for 45 min to afford the title compound without further purification. LC/MS 195.2 (M+1).

Step B: 1(6S)-4-oxo-4,6,7,8-tetrahydropyrrolo[1,2-]pyrimidine-6-carboxylic acid

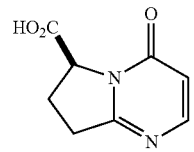 [SMILES: O=C(O)[C@@H]1CCc2nccc(=O)n21]

Methyl [6(S)-4-oxo-4,6,7,8-tetrahydropyrrolo[1,2-$^\alpha$]pyrimidine-6-carboxylate (9.95 g, 51.2 mmol) in tetrahydrofuran (60 mL), methanol (40 mL) and a solution of lithium hydroxide (3.32 g, 77 mmol) in water (40 mL) was stirred at ambient temperature for 1 h. 2 N hydrochloric acid (38.5 mL) was added to neutralize the reaction mixture which was then directly purified by reverse phase HPLC (TMC Pro-Pac C18; 0-40% 0.1% trifluoroacetic acid in acetonitrile/0.1% trifluoroacetic acid in water gradient). The O-alkylation product was eluted fast. The pure fractions were collected and lyophilized overnight to afford the title compound as a pale yellow solid. $^1$H NMR (DMSO-$d_6$): δ 7.89 (d, J=6.6 Hz, 1H), 6.24 (d, J=6.6 Hz, 1H), 4.92 (dd, J=10.0, 3.1 Hz, 1H), 3.12-2.99 (m, 2H), 2.52 (m, 1H), 2.11 (m, 1H). LC/MS 181.2 (M+1).

Intermediate 45

5,6-Dihydro-4H-pyrrolo[1,2-b]pyrazole-6-carboxylic acid (i-45)

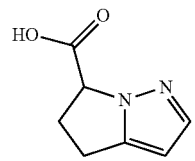 [SMILES: O=C(O)C1CCc2ccnn21]

Step A: 7-(Trimethylsilyl)-5-oxohept-6-ynoic acid

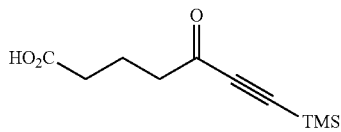 [SMILES: C[Si](C)(C)C#CC(=O)CCCC(=O)O]

This intermediate was prepared according to the procedure found in: Nayyar, N. K.; Hutchison, D. R.; Martinelli, M. J. *J. Org. Chem.* 1997, 62, 982.

Step B: (5Z)-5-[(Tert-butoxycarbonyl)hydrazono]-7-(trimethylsilyl)hept-6-ynoic acid

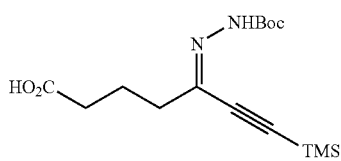 [SMILES: CC(C)(C)OC(=O)N/N=C(\C#C[Si](C)(C)C)CCCC(=O)O]

To a stirred solution of 54.0 g (254 mmol) of 7-(trimethylsilyl)-5-oxohept-6-ynoic acid from step A above in 750 mL of IPA under an atmosphere of nitrogen was added 33.6 g (254 mmol) of tert-butyl carbazate. The reaction mixture was stirred for 4 h at ambient temperature then evaporated in vacuo to remove all volatiles. This afforded the title compound as a yellow gum which was used without further purification (77 g, 93%). LC-MS: m/z (ES) 327 (MH)$^+$.

Step C: 4-[1-(Tert-butoxycarbonyl)-1H-pyrazol-3-yl]butanoic acid

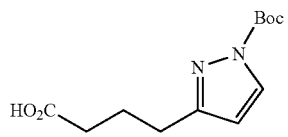

To a stirred solution of 77.0 g, (236 mmol) of (5Z)-5-[(tert-butoxycarbonyl)hydrazono]-7-(trimethylsilyl)hept-6-ynoic acid from step B above in 500 mL of THF was added 350 mL (350 mmol) of a 1.0 M solution of tetrabutylammonium fluoride in THF over 30 min. The resulting mixture was stirred at ambient temperature for 48 h and then evaporated to dryness in vacuo. The residue was diluted with 1 L of a 5% aqueous acetic acid solution and the aqueous phase extracted with ethyl acetate (3×350 mL). The combined organic layers were washed with water (2×100 mL), and brine (150 mL), dried over magnesium sulfate, filtered and evaporated to dryness in vacuo. The crude residue was purified by silica gel chromatography eluting with 3% acetic acid and 35% ethyl acetate in hexanes mixture to afford the title compound as yellow oil (60 g, quantitative yield). LC-MS: m/z (ES) 255 (MH)$^+$.

Step D: Tert-butyl 3-[4-(benzyloxy)-4-oxobutyl]-1H-pyrazole-1-carboxylate

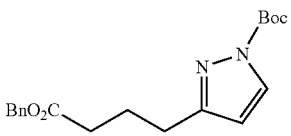

To a stirred solution of 60.0 g (236 mmol) of 4-[1-(tert-butoxycarbonyl)-1H-pyrazol-3-yl]butanoic acid from step C above in 400 mL of DMF was added 48.9 g (354 mmol) of potassium carbonate followed by dropwise addition of 40.0 mL (300 mmol) of benzyl bromide. The resulting mixture was stirred for 24 h, quenched with water, and extracted with ethyl acetate (3×300 mL). The combined organic layers were washed with brine, dried over magnesium sulfate, filtered and evaporated to dryness in vacuo. The crude residue was purified by silica gel chromatography eluting with 30% ethyl acetate in hexanes to afford the title compound as a yellow oil (55.6 g. 68.4%). LC-MS: m/z (ES) 345 (MH)$^+$.

Step E: Tert-butyl 3-[4-(benzyloxy)-3-bromo-4-oxobutyl]-1H-pyrazole-1-carboxylate

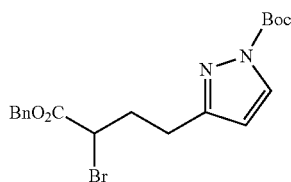

To a stirred solution of 27.5 g (80.0 mmol) of tert-butyl 3-[4-(benzyloxy)-4-oxobutyl]-1H-pyrazole-1-carboxylate from step D above in 250 mL of anhydrous THF at −78° C. under an atmosphere of nitrogen was added 88 mL (88 mmol) of a 1.0 M solution of sodium bis(trimethylsilyl)amide in anhydrous THF. The resulting dark yellow solution was stirred for 1 h at −78° C. and then 12 mL (96 mmol) of chlorotrimethylsilane was added dropwise over 5 min. The resulting mixture was stirred for 25 min during which time the reaction became a light yellow color. Next, 16 g (88 mmol) of solid N-bromosuccinimide was added in one portion and the resulting mixture was stirred for 3 h at −78° C. followed by gradual warming to 0° C. over 1 h. The reaction was quenched with a saturated aqueous ammonium chloride solution and the aqueous phase extracted with ethyl acetate (3×200 mL). The combined organics were washed with brine, dried over magnesium sulfate, filtered and evaporated to dryness in vacuo to afford the title compound as a yellow gum. The crude product appears to be a 1:1 mixture of starting material and desired product by NMR and was used without further purification in the next step. LC-MS: m/z (ES) 424 (MH)$^+$.

Step F: Benzyl 5,6-dihydro-4H-pyrrolo[1,2-b]pyrazole-6-carboxylate

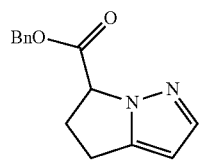 [SMILES: O=C(OCc1ccccc1)C1CCc2ccnn21]

To a stirred solution of 16.9 g (40.0 mmol) of tert-butyl 3-[4-(benzyloxy)-3-bromo-4-oxobutyl]-1H-pyrazole-1-carboxylate from step E above in 50 mL of dichloromethane was added 50 mL of TFA. The resulting mixture was stirred for 2 h at ambient temperature then all volatiles were evaporated in vacuo. The residue was then diluted with 50 mL of toluene and evaporated again in vacuo to remove all residual TFA. The crude material was then dissolved in 125 mL of anhydrous acetone and 14.0 g (100 mmol) of solid potassium carbonate was slowly added over 15 min followed by 1.2 g (8.0 mmol) of sodium iodide. The resulting mixture was then heated at reflux for 16 h, cooled to room temperature and evaporated to dryness in vacuo. The residue was diluted with 100 mL of a saturated, aqueous ammonium chloride solution and then extracted with ethyl acetate (3×100 mL). The combined organic layers were washed with brine, dried over magnesium sulfate, filtered and evaporated in vacuo. The crude residue was purified by silica gel chromatography eluting with a 10-80% ethyl acetate in hexanes gradient to afford the title compound as a clear gum 6.2 g (64% yield). LC-MS: m/z (ES) 243 (MH)$^+$.

Step G: 5,6-Dihydro-4H-pyrrolo[1,2-b]-pyrazole-6-carboxylic acid

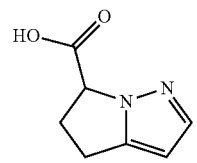 [SMILES: O=C(O)C1CCc2ccnn21]

A 100 mL round bottom flask under an atmosphere of nitrogen was charged with 0.600 mg (0.560 mmol) of 10 weight percent palladium on activated carbon and wet with 10 mL of ethanol. Next, a solution of 6.0 g (0.025 mol) of benzyl 5,6-dihydro-4H-pyrrolo[1,2-b]pyrazole-6-carboxylate from step F above in 40 mL of ethanol was added and the mixture placed under 1 atmosphere of hydrogen. The reaction was stirred for 3 h then filtered through a pad of Celite®. The pad was washed with 20 mL of ethanol and the filtrate was evaporated in vacuo to afford the title compound as a colorless solid (3.7 g, quantitative yield). $^1$H NMR (500 MHz, DMSO-d$_6$): δ 11.90 (br s, 1H), 7.44 (s, 1H), 5.98 (s, 1H), 4.87 (dd, J=8.9, 3.7 Hz, 1H), 2.94-2.82 (m, 3H), 2.58-2.52 (m, 1H). LC-MS: m/z (ES) 153 (MH)$^+$.

Intermediate 46

(3S)-5-Oxo-1,2,3,5-tetrahydroindolizine-3-carboxylic acid (i-46)

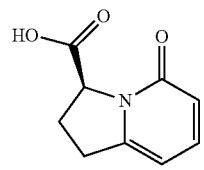 [SMILES: O=C(O)[C@@H]1CCc2cccc(=O)n21]

Step A: (3S,9S)-5-Oxo-1,2,3,5,6,8a-hexahydroindolizine-3-carboxylic acid methyl ester

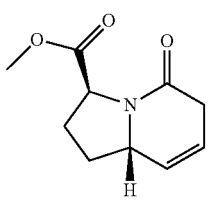

This intermediate was prepared according to the procedures found in: Hanessian, S.; Sailes, H.; Munro, A.; Therrien, E. *J. Org. Chem.* 2003, 68, 7219 and Vaswani, R. G.; Chamberlin, R. *J. Org. Chem.* 2008, 73, 1661.

Step B: Methyl (3S)-5-oxo-1,2,3,5-tetrahydroindolizine-3-carboxylate

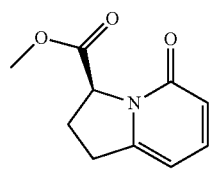

To a stirred solution of 0.850 g (4.06 mmol) of (3S,9S)-5-oxo-1,2,3,5,6,8a-hexahydroindolizine-3-carboxylic acid methyl ester from step A above in 50 mL of dichloromethane was added 6.30 g (72.5 mmol) of manganese(IV) oxide and the resulting mixture was stirred for 12 h at reflux. The reaction was cooled to ambient temperature, filtered through a pad of Celite®, and the solid was then washed with 100 mL of dichloromethane. The filtrate was evaporated to dryness in vacuo and the residue was purified by silica gel chromatography eluting with 10-50% ethyl acetate in hexanes gradient to afford the title compound as a clear gum (0.47 g, 55% yield). LC-MS: m/z (ES) 194 (MH)⁺.

Step C: (3S)-5-Oxo-1,2,3,5-tetrahydroindolizine-3-carboxylic acid

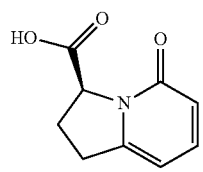 [SMILES: O=C(O)[C@@H]1CCc2cccc(=O)n21]

To a stirred solution of 0.200 mg (1.00 mmol) of methyl (3S)-5-oxo-1,2,3,5-tetrahydroindolizine-3-carboxylate from step B above in 3 mL of THF was added 1.5 mL (1.5 mmol) of a 1.0 M aqueous LiOH solution. The resulting mixture was stirred for 2 h at ambient temperature then quenched with 2.0 mL (2.0 mmol) of a 1.0 M aqueous solution of hydrogen chloride. All volatiles were evaporated in vacuo and the aqueous phase was extracted with a 30% IPA in chloroform mixture (3×5 mL). The combined extract were washed with brine, dried over magnesium sulfate, filtered, and evaporated in vacuo to afford the title compound as a white solid (0.17 g, 92%). ¹H NMR (500 MHz, CD₃OD): δ 7.53 (dd, J=8.9, 7.1 Hz, 1H), 6.38-6.35 (m, 2H), 5.11 (dd, J=9.7, 2.7 Hz, 1H), 3.23-3.12 (m, 2H), 2.62-2.53 (m, 1H), 2.35-2.30 (m, 1H). LC-MS: m/z (ES) 180 (MH)⁺.

Intermediate 47

2-(2-(Benzylamino)-2-oxoethyl)-5,6-dihydro-4H-cyclopenta[d]thiazole-4-carboxylic acid (i-47)

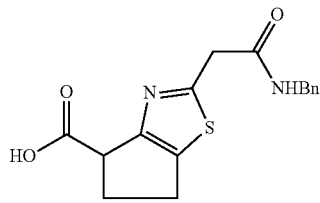

The title compound was prepared according to the procedure used for i-7 except that 3-amino-N-benzyl-3-thioxopanamide was used in place of thioacetamide. LC-MS: m/z (E/S) 317 (MH)⁺.

Intermediate 48

4-Chloro-5-pyrimidinyl acetic acid (i-48)

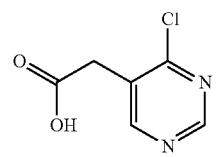

Step A: Ethyl (4-chloro-5-pyrimidinyl)acetate

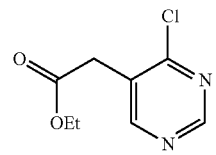 [SMILES: CCOC(=O)Cc1cncnc1Cl]

This material was synthesized according to the procedure of Zymalkowski and Reimann et al. *Archie. Der. Pharmazie* 1966, 299, 362.

Step B: 4-Chloro-5-pyrimidinyl acetic acid

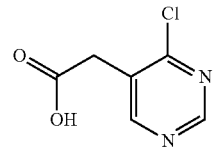 [SMILES: O=C(O)Cc1cncnc1Cl]

To a solution of 0.6 g (3 mmol) of ethyl (4-chloro-5-pyrimidinyl)acetate from Step A above in 0.5 mL of water and 1.5 mL of ethanol was added 215 mg (5.11 mmol) of lithium hydroxide hydrate. The reaction mixture was stirred at ambient temperature for 2 h then concentrated in vacuo to remove all volatiles. The residue was diluted with 7 mL of 2.0 M aqueous hydrogen chloride and then concentrated in vacuo to remove all volatiles to yield the title compound (0.43 g, 83%). $^1$H-NMR (500 MHz, CD$_3$OD) δ: 8.88 (s, 1H), 8.70 (s, 1H), 3.96 (s, 2H). LC-MS: m/z (E/S) 173 (MH)$^+$.

Intermediate 49

4-Methoxy-5-pyrimidinyl acetic acid (i-49)

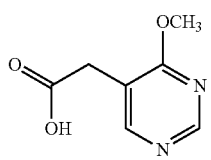 [SMILES: COc1ncncc1CC(=O)O]

Step A: Methyl (4-methoxy-5-pyrimidinyl)acetate

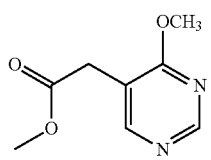

To a solution of 0.250 g (1.25 mmol) of ethyl (4-chloro-5-pyrimidinyl)acetate (see i-48, Step A) in 10 mL of absolute methanol was dissolved 0.060 g (2.50 mmol) of sodium metal. The resulting solution was heated under microwave conditions at 120° C. for 10 min. All volatiles were removed in vacuo and the residue was diluted with saturated sodium bicarbonate and extracted with dichloromethane (3×10 mL). The combined organic layers were washed with brine, dried over magnesium sulfate, filtered and evaporated to dryness in vacuo to afford the title compound as a clear gum (0.21 g, 93%). $^1$H-NMR (500 MHz, CD$_3$OD) δ: 8.72 (s, 1H), 8.35 (s, 1H), 3.96 (s, 2H), 4.01 (s, 3H), 3.70 (s, 3H), 3.57 (s, 2H). LC-MS: m/z (E/S) 183 (MH)$^+$.

Step B: 4-Methoxy-5-pyrimidinyl acetic acid

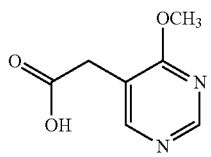

To a stirred solution of 0.21 g (1.14 mmol) of methyl (4-methoxy-5-pyrimidinyl)acetate from Step A above in 0.5 mL of water and 1.5 mL of ethanol was added 81 mg (1.9 mmol) of lithium hydroxide hydrate. The reaction mixture was stirred at ambient temperature for 2 h then concentrated in vacuo to remove all volatiles. The residue was diluted with 3 mL of 2.0 M aqueous hydrogen chloride and then concentrated in vacuo to remove all volatiles to yield the title compound as an off white solid (191 mg, 90%). $^1$H-NMR (500 MHz, CD$_3$OD) δ: 8.72 (s, 1H), 8.35 (s, 1H), 4.01 (s, 3H), 3.57 (s, 2H). LC-MS: m/z (E/S) 169 (MH)$^+$.

Intermediate 50

2-(4-Methoxypyrimidin-5-yl)propanoic acid (i-50)

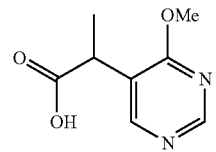

Step A: Ethyl 2-(4-chloropyrimidin-5-yl)propanoate

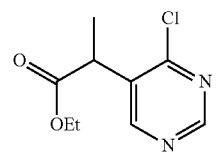

To a stirred, cooled (−78° C. solution of 5.8 g (29 mmol) of ethyl (4-chloro-5-pyrimidinyl)acetate (see i-48, Step A) in 75 mL of anhydrous THF under an atmosphere of nitrogen was added 15.2 mL (30.4 mmol) of a 2.0 M solution of lithium diisopropylamide in anhydrous THF. The resulting mixture was stirred for 15 min then 2.26 mL (36.1 mmol) of iodomethane was added over 5 min. The reaction mixture was stirred for 15 min, allowed to warm to −20° C. over 45 min, then warmed to 0° C. for 15 min. The reaction mixture was then quenched with a saturated ammonium chloride solution and extracted with 50 mL of dichloromethane. The organic layer was dried over magnesium sulfate, filtered, and evaporated in vacuo. The crude residue was purified by silica gel chromatography eluting with a 20% ethyl acetate in hexanes mixture to afford the title compound (1.9 g, 31%). $^1$H-NMR (500 MHz, CD$_3$OD) δ: 8.88 (s 1H), 8.74 (s, 1H), 4.17 (m, 2H), 1.58 (d, J=7 Hz, 3H), 1.29 (t, J=7 Hz, 3H). LC-MS: m/z (E/S) 215 (MH)$^+$.

Step B: Methyl 2-(4-methoxypyrimidin-5-yl)propanoate

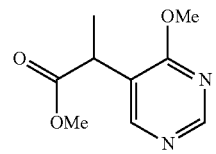

To a solution of 0.250 g (1.17 mmol) of ethyl 2-(4-chloropyrimidin-5-yl)propanoate from step A above in 5 mL of absolute methanol was dissolved 0.054 g (2.34 mmol) of sodium metal. The resulting solution was heated under microwave conditions at 120° C. for 10 min. All volatiles were removed in vacuo and the residue was diluted with saturated sodium bicarbonate and extracted with dichloromethane (3×10 mL). The combined organic layers were washed with brine, dried over magnesium sulfate, filtered and evaporated to dryness in vacuo to afford the title compound as a clear gum (0.21 g, 93%). $^1$H-NMR (500 MHz, CD$_3$OD) δ: 8.65 (s 1H), 8.36 (s, 1H), 4.0 (s, 3H), 3.9 (q, J=7 Hz, 2H), 3.66 (s, 3H), 1.58 (d, J=7 Hz, 3H). LC-MS: m/z (E/S) 197 (MH)$^+$.

Step C: 2-(4-Methoxypyrimidin-5-yl)propanoic acid

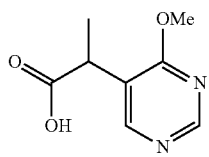

To a stirred solution of 0.21 g (1.06 mmol) of methyl 2-(4-methoxypyrimidin-5-yl)propanoate from Step B above in 0.5 mL of water and 1.5 mL of ethanol was added 81 mg (1.9 mmol) of lithium hydroxide hydrate. The reaction mixture was stirred at ambient temperature for 2 h then concentrated in vacuo to remove all volatiles. The residue was diluted with 3 mL of 2.0 N aqueous hydrogen chloride and then concentrated in vacuo to remove all volatiles to yield the title compound as an off white solid (70 mg, 36%). $^1$H-NMR (500 MHz, CD$_3$OD) δ: 8.67 (s 1H), 8.4 (s, 1H), 4.07 (s, 3H), 3.9 (q, J=7 Hz, 2H), 1.58 (d, J=7 Hz, 3H). LC-MS: m/z (E/S) 183 (MH)$^+$.

Intermediate 51

2-(2-Oxopyridin-1(2H)-yl)propanoic acid (i-51)

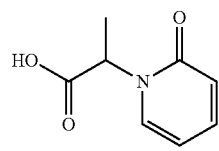

Step A: Tert-butyl 2-(2-oxopyridin-1(2H)-yl)propanoate

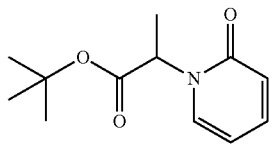

To a stirred solution of 9.5 g (0.10 mol) of 2-hydroxypyridine in 250 mL of DMF was added 16.6 g (0.120 mol) of potassium carbonate followed by 25.0 g (0.120 mol) of 2-bromopropionic acid tert-butyl ester. The resulting mixture was stirred at ambient temperature for 7 h then diluted with 1 L of water. The aqueous phase was extracted with ethyl acetate (3×200 mL) and the combined organics were washed with water (2×100 mL), brine (100 mL), dried over magnesium sulfate, filtered and evaporated in vacuo. The crude residue was purified by silica gel chromatography eluting with 25% ethyl acetate in hexanes to afford the title compound as a clear gum 16 g (72%). LC-MS: m/z (ES) 224 (MH)$^+$ Step B: 2-(2-Oxopyridin-1(2H)-yl)propanoic acid

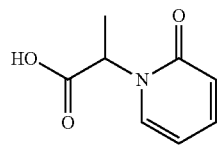

To a stirred suspension of 16.6 g (74.4 mmol) of tert-butyl 2-(2-oxopyridin-1(2H)-yl)propanoate from step A above in 10 mL of anhydrous 1,4-dioxane under an atmosphere of nitrogen was added 150 mL of a 4.0 M hydrogen chloride solution in 1,4-dioxane. The resulting solution was stirred overnight at ambient temperature then evaporated to dryness in vacuo to afford the title compound as a white solid (12.4 g, quantitative yield). LC-MS: m/z (ES) 168 (MH)$^+$ Intermediate 52

2-(2-Oxo-1,3-oxazolidin-3-yl)propanoic acid (i-52)

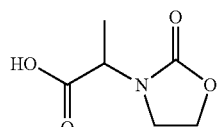

Step A: Benzyl (2-oxo-1,3-oxazolidin-3-yl)acetate

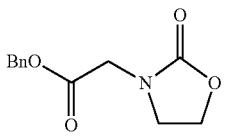

To a stirred solution of 1.0 g (6.9 mmol) of (2-oxo-1,3-oxazolidin-3-yl)acetic acid in 10 mL of anhydrous DMF was added 1.0 g (7.6 mmol) of potassium carbonate followed by 1.0 mL (8.3 mmol) of benzyl bromide. The reaction mixture was stirred for 3 h then quenched with water. The aqueous phase was extracted with ethyl acetate (3×25 mL) and the combined organics were washed with water (2×10 mL), brine (10 mL), dried over magnesium sulfate, filtered and evaporated in vacuo. The crude residue was purified by silica gel chromatography eluting with 50% ethyl acetate in hexanes to afford the title compound as a white solid 0.50 g (31%). LC-MS: m/z (ES) 236 (MH)$^+$.

Step B: Benzyl 2-(2-oxo-1,3-oxazolidin-3-yl)propanoate

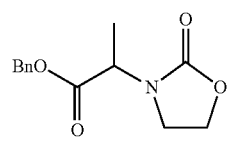

To a stirred solution of 0.50 g (2.1 mmol) of benzyl (2-oxo-1,3-oxazolidin-3-yl)acetate from step A above in 15 mL of anhydrous THF at −78° C. under an atmosphere of nitrogen was added 1.2 mL (2.4 mmol) of a 2.0 M solution of lithium diisopropylamide in anhydrous THF. The resulting yellow solution was stirred for 15 min at −78° C. and then 0.0360 g (2.55 mmol) of iodomethane was added. The resulting mixture was stirred for 2 h with gradual warming to ambient temperature then quenched with a saturated aqueous ammonium chloride solution. The aqueous phase was extracted with ethyl acetate (3×20 mL) and the combined organics were washed with brine, dried over magnesium sulfate, filtered and evaporated to dryness in vacuo. The crude residue was purified by silica gel chromatography eluting with 40% ethyl acetate in hexanes to afford the title compound as a clear gum 0.37 g (70%). LC-MS: m/z (ES) 250 (MH)$^+$.

Step C: 2-(2-Oxo-1,3-oxazolidin-3-yl)propanoic acid

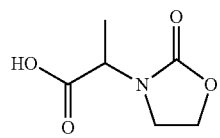

A 25 mL round bottom flask under an atmosphere of nitrogen was charged with 0.030 g (0.028 mmol) of 10 weight percent palladium on activated carbon and wet with 2 mL of ethanol. Next, a solution of 0.37 g (1.5 mmol) of benzyl 2-(2-oxo-1,3-oxazolidin-3-yl)propanoate from step B above in 10 mL of ethanol was added and the mixture placed under 1 atmosphere of hydrogen. The reaction was stirred for 3 h then filtered through a pad of Celite®. The pad was washed with 20 mL of ethanol and the filtrate was evaporated in vacuo to afford the title compound as a colorless solid (0.24 g, quantitative yield). $^1$H-NMR (500 MHz, CD$_3$OD) δ: 4.60-4.30 (m, 3H), 3.80-3.60 (m, 2H), 1.45 (d, J=3.5, 3H). LC-MS: m/z (ES) 160 (MH)$^+$.

Intermediate 53

2-(2H-1,2,3-Triazol-2-yl)propanoic acid (i-53)

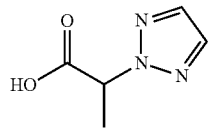

Intermediate 53 was prepared from 2H-1,2,3-triazol-2-ylacetic acid using a procedure analogous to that used to prepare i-51. LC-MS: m/z (ES) 142.2 (MH)$^+$.

142.2

Intermediate 54

6,7-Dihydro-5H-cyclopenta[b]pyridine-7-carboxylic acid, trifluoroacetic acid salt (i-54)

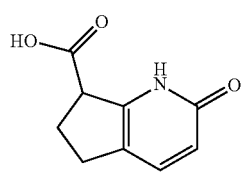

To a cooled (0° C.) solution of 16 mL (25 mmol) of a 1.6 M n-butyl lithium solution in hexane was added 3.9 mL (25 mmol) of N,N,N',N'-tetramethylethylenediamine followed by a solution of 3.0 mL (25 mmol) of 2,3-cyclopentenopyridine in 5 mL of anhydrous tetrahydrofuran. The resulting mixture was allowed to warm to ambient temperature over 15 min and then anhydrous carbon dioxide gas was bubbled through the reaction mixture for 1 h. The solid precipitate was next filtered and the crude solid purified by reverse phase HPLC (TMC Pro-Pac C18; 0-40% 0.01% trifluoroacetic acid in acetonitrile/0.01% trifluoroacetic acid in water gradient) to give the title compound as a yellow solid (2.0 g, 50%). LC-MS: m/z (ES) 164.1 (MH)$^+$.

Intermediate 55

2-Oxo-2,5,6,7-tetrahydro-1H-cyclopenta[b]pyridine-7-carboxylic acid (i-55)

Step A: Methyl
6,7-dihydro-5H-cyclopenta[b]pyridine-7-carboxylate

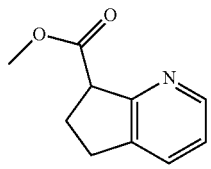

To a solution of 1.0 g (6.1 mmol) of Intermediate 54 in a mixture of 10 mL of methanol and 10 mL of diethyl ether at 0° C. under an atmosphere of nitrogen was added 9.0 mL (18 mmol) of a 2.0 M solution of (trimethylsilyl)diazomethane in diethyl ether. After stirring for 5 min the reaction was quenched with 2 mL of glacial acetic acid. All volatiles were evaporated in vacuo and the residue was purified by silica gel chromatography eluting with 50% ethyl acetate in hexane to afford the title compound as a yellow gum (1.0 g, 92%). LC-MS: m/z (ES) 177.1 (MH)+.

Step B: Methyl
6,7-dihydro-5H-cyclopenta[b]pyridine-7-carboxylate
1-oxide

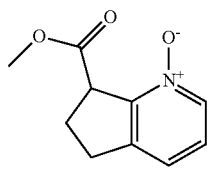

To a cooled (0° C.) solution of 1.53 g (8.47 mmol) of methyl 6,7-dihydro-5H-cyclopenta[b]pyridine-7-carboxylate from step A above in 30 mL of dichloromethane was added 1.61 g (9.31 mmol) of m-CPBA. The solution was allowed to stir for 1 h and then quenched with 50 mL of a saturated aqueous sodium bicarbonate solution. The layers were separated and the aqueous phase extracted with dichloromethane (3×50 mL). The combined organic extracts were washed with brine, dried over magnesium sulfate, filtered and evaporated in vacuo to yield the title compound as a light brown solid that was used without purification. LC-MS: m/z (E/S) 194.2 (MH)+.

Step C: Methyl 2-chloro-6,7-dihydro-5H-cyclopenta
[b]pyridine-7-carboxylate

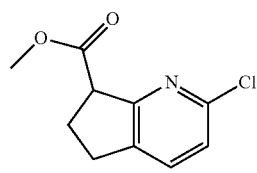

To a cooled (0° C.) solution of 0.21 mL (2.28 mmol) of phosphorous oxychloride in 0.2 mL of anhydrous DMF was added a solution of 1.1 g (5.69 mmol) of methyl 6,7-dihydro-5H-cyclopenta[b]pyridine-7-carboxylate 1-oxide from Step B above in 15 mL chloroform dropwise over 10 min. The resulting solution was allowed to warm to ambient temperature and then refluxed for 4 h. The mixture was cooled and poured into 30 mL of cold water. The aqueous solution was extracted with diethyl ether (3×30 mL) followed by a single extraction with 30 mL of dichloromethane. The combined organic layers were dried over magnesium sulfate, filtered and evaporated in vacuo. The resulting brown residue was purified by silica gel chromatography eluting with 50% ethyl acetate in hexane to afford the title compound as a light brown solid (0.30 g, 25%). LC-MS: m/z (E/S) 212.0 (MH)+.

Step D: 2-Oxo-2,5,6,7-tetrahydro-1H-cyclopenta[b]
pyridine-7-carboxylic acid

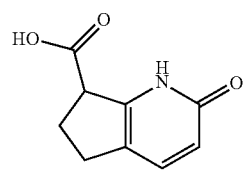

To a 15 mL mixture of tetrahydrofuran, methanol, and a 1.0 N aqueous LiOH solution in a 3:1:1 ratio was added 0.242 g (1.14 mmol) of methyl 2-chloro-6,7-dihydro-5H-cyclopenta[b]pyridine-7-carboxylate from Step C above. The resulting mixture was stirred at ambient temperature for 1 h. The solution was evaporated in vacuo and the resulting light brown residue was purified by reverse phase HPLC(YMC Pack Pro C18, 100×20 mm I.D. column, 0-60% 0.01% trifluoroacetic acid in acetonitrile/0.01% trifluoroacetic acid in water gradient) to give the title compound as a brown oil (184 mg, 90%). LC-MS: m/z (E/S) 180.0 (MH)+.

Intermediate 56

2-(3-methyl-1H-1,2,4-triazol-1-yl)propanoic acid
(i-56)

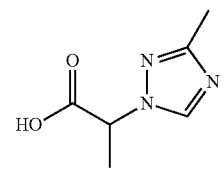

Step A: Tert-butyl
2-(3-methyl-1H-1,2,4-triazol-1-yl)propanoate

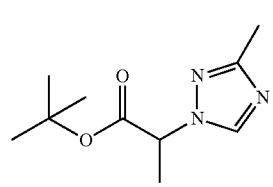

To a solution of 3-methyl-1H-1,2,4-triazole (7.3 g, 88 mmol) in DMF (75 mL) was added K2CO3 (60.7 g, 439 mmol) and 2-bromopropionic acid tert-butyl ester (14.6 mL, 88 mmol). The reaction was stirred at room temperature overnight. The mixture was diluted with EtOAc (500 mL), washed with water (×3) then brine. Dried over MgSO$_4$ and concentrated. The residue was purified by column chromatography on silica gel, eluting with EtOAc/isohexane (20 to 100%) to give 13 g of crude product as a 3:1 mixture of regioisomers. The mixture was purified by Chiralcel OD with a gradient from 4% to 30% IPA/Heptane. Then the first two peaks were separated with Chiracel OD column isocratically eluting with 4% IPA/Heptane. The second peak was collected as the desired single stereoisomer (R or S) (2-(3-methyl-1H-1,2,4-triazol-1-yl)propanoic acid tert-butyl ester) (3.5 g, 19%). $^1$H-NMR (500 MHz, CDCl$_3$) δ 8.05 (s, 1H), 4.90 (q, J=7 Hz, 1H), 2.35 (s, 3H), 1.72 (d, J=7 Hz, 3H), 1.40 (s, 9H). ESI-MS calculated for C$_{10}$H$_{17}$N$_3$O$_2$: Exact Mass: 211.13. Found 156.05 (-tBu).

Step B: 2-(3-methyl-1H-1,2,4-triazol-1-yl)propanoic acid

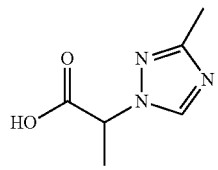

Tert-butyl 2-(3-methyl-1H-1,2,4-triazol-1-yl)propanoate (1.0 g, 4.7 mmol) from step A was dissolved in 4 M HCl in dioxane (100 mL) and stirred at room temperature overnight. The product was concentrated under reduced pressure and dried under high vacuum to give (R or S) tert-butyl 2-(3-methyl-1H-1,2,4-triazol-1-yl)propanoate as the HCl salt (850 mg). ESI-MS calculated for C$_6$H$_9$N$_3$O$_2$: Exact Mass: 155.07. Found 156.05.

Intermediate 57

2-(1-Methyl-1H-pyrazol-3-yl)propanoic acid (i-57)

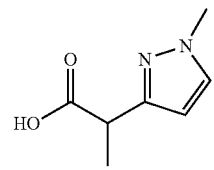

Step A: Benzyl propiolate To a solution of 17.0 g (233 mmol) of propiolic acid in 600 mL of anhydrous DMF was added 39.9 g (233 mmol) of benzyl bromide followed by portionwise addition of 76.0 g (233 mmol) of Cs$_2$CO$_3$. After stirring at room temperature for 24 h, the reaction was quenched with a saturated aqueous ammonium chloride solution and extracted with EtOAc (3×200 mL). The combined extracts were washed with water then brine and dried over anhydrous sodium sulfate. The mixture was then filtered through a silica gel pad washing with hexanes, and the filtrate was evaporated under reduced pressure to afford a crude product. The crude product was purified by silica gel chromatography eluting with a 0-20% ethyl acetate in hexane gradient to afford the title compound as a colorless oil (13.8 g, 35%). $^1$H NMR (CDCl$_3$, 500 MHz) δ 7.41 (m, 5H), 5.25 (s, 2H), 2.92 (s, 1H).

Step B: Benzyl 2-(tributylstannyl)acrylate

To a solution of 6.42 g (40.1 mmol) of benzyl propiolate from step A above in 25 ml of anhydrous THF was added 0.93 g (0.80 mmol) of tetrakis(triphenylphosphine)palladium(0) followed by a solution of 12.6 g (42.1 mmol) of tributyltin hydride in 25 mL of anhydrous THF over 15 min. After stirring at room temperature overnight the solvent was removed under reduced pressure. The residue was filtered through a pad of Celite® which was then washed with hexanes. The filtrate was concentrated in vacuo and the crude product was purified by silica gel chromatography eluting with a 0-15% ethyl acetate in hexane gradient to afford the title compound as a colorless oil (13 g, 73%). $^1$H NMR (CDCl$_3$, 500 MHz) δ 7.39 (m, 5H), 6.99 (d, J=2.7 Hz, 1H), 5.98 (d, J=2.7 Hz, 1H), 5.20 (s, 2H), 1.47 (m, 6H), 1.30 (m, 6H), 0.96 (m, 6H), 0.89 (t, J=7.4 Hz, 9H).

Step C: Benzyl 2-(1-methyl-1H-pyrazol-3-yl)acrylate

To a solution of 0.30 g (1.4 mmol) of 3-iodo-1-methyl-1H-pyrazole in 3 mL of anhydrous THF was added a solution of 0.82 g (1.8 mmol) of benzyl 2-(tributylstannyl)acrylate from step B above in 1 mL of anhydrous THF, 0.18 g (0.15 mmol) of tetrakis(triphenylphosphine)palladium(0) and 0.14 g (1.4 mmol) of copper (I) chloride. The reaction mixture was heated to 55° C. for 12 h, cooled and evaporated to dryness under reduced pressure. The residue was dissolved in 10 mL of a 1:1 mixture of hexane and EtOAc then filtered through a pad of Celite®. The pad was washed with 15 mL of a 1:1 mixture of hexane and EtOAc and the combined filtrates were evaporated to dryness. The crude residue was purified by silica gel chromatography eluting with a 0-80% EtOAc in hexanes gradient to afford the title compound as a colorless oil (0.23 g, 66%). LC-MS: m/z (ES) 265 (M+Na)$^+$.

Step D: 2-(1-Methyl-1H-pyrazol-3-yl)propanoic acid

To 0.10 mg (0.093 mmol) of 10% palladium on carbon was added a solution of (0.23 g, 0.93 mmol) of benzyl 2-(1-methyl-1H-pyrazol-3-yl)acrylate prepared in step C above in 6 mL of methanol. The resulting suspension was stirred under an atmosphere of hydrogen (1 atmosphere) overnight. The residue was filtered through a pad of Celite® and the pad was washed with cold methanol. The combined filtrates were evaporated under reduced pressure to yield the title compound as an off-white gum (0.11 g, 76%). LC-MS: m/z (ES) 155 (MH)⁺.

Intermediate 58

2-(1,3-Thiazol-2-yl)propanoic acid (i-58)

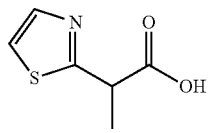

Step A: Ethyl 2-(1,3-thiazol-2-yl)propanoate

Ethyl 2-(1,3-thiazol-2-yl)propanoate was prepared according to the procedure outlined in: Dondoni, A.; Dall'Occo, T.; Giancarlo, F.; Fogagnolo, M.; Medici, A. *Tetrahedron Letters*, 1984, 25, 3633-3636.

Step B: 2-(1,3-Thiazol-2-yl)propanoic acid

To a solution of 0.26 g (1.5 mmol) of ethyl 2-(1,3-thiazol-2-yl)propanoate from step A above in 15 mL of methanol was added 3.0 mL (15 mmol) of an aqueous 5.0 M sodium hydroxide solution. The resulting mixture was stirred at ambient temperature overnight. The reaction mixture was evaporated in vacuo to remove the methanol and the aqueous phase was acidified with a 2 N hydrochloric acid solution until a pH of 4 was achieved. The aqueous solution was purified by reverse phase HPLC (TMC Pro-Pac C18; 0-25% 0.1% trifluoroacetic acid in acetonitrile/0.1% trifluoroacetic acid in water gradient). The pure fractions were lyophilized overnight to afford the title compound as a white solid (0.17 g, 71%). LC-MS: m/z (ES) 158 (MH)⁺.

Intermediate 59

2-(3-Methyl-1H-pyrazol-5-yl)propanoic acid (i-59)

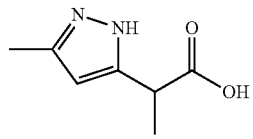

Step A: Ethyl 2-methyl-3,5-dioxohexanoate

Ethyl 2-methyl-3,5-dioxohexanoate was prepared according to the procedure outlined in: Solladie, G.; Gehrold, N.; Maignan, J. *Eur. J. Org. Chem.*, 1999, 2309-2314.

Step B: Ethyl 2-(3-methyl-1H-pyrazol-5-yl)propanoate

To a solution of 18.6 g (100 mmol) of ethyl 2-methyl-3,5-dioxohexanoate from step A above in 200 mL of THF and 50 mL of water was added 3.45 mL (110 mmol) of anhydrous hydrazine. The biphasic reaction mixture was stirred at ambient temperature overnight then evaporated to dryness in vacuo. The crude yellow residue was dissolved in an ethyl acetate and water mixture and flushed through a 50 g silica gel plug. The filtrate was then evaporated to dryness in vacuo and the residue purified by silica gel chromatography eluting with a 0-100% ethyl acetate in hexanes gradient to afford the title compound as a yellow oil (1.89 g, 10%). ¹H NMR (CDCl₃, 500 MHz) δ 7.26 (s, 1H), 5.98 (s, 1H), 4.20-4.12 (m, 2H), 3.81 (q, J=7.3 Hz, 1H), 2.28 (s, 3H), 1.51 (d, J=7.3 Hz, 3H), 1.25 (t, J=7.1 Hz, 3H). LC-MS: m/z (ES) 183 (MH)⁺.

Step C: 2-(3-Methyl-1H-pyrazol-5-yl)propanoic acid

To a solution of 1.24 g (6.8 mmol) of ethyl 2-(3-methyl-1H-pyrazol-5-yl)propanoate from step B above in 20 mL of methanol and 5 mL of water was added 1.5 mL (7.5 mmol) of an aqueous 5.0 M sodium hydroxide solution. The resulting mixture was stirred at ambient temperature for 2.5 h and then evaporated in vacuo to remove the methanol. The aqueous phase was extracted with ethyl acetate (2×75 mL) then acidified with a 2 N hydrochloric acid solution until a pH of 4 was achieved. The aqueous solution was extracted with ethyl acetate (5×50 mL) and the combined organic layers were dried over anhydrous sodium sulfate, filtered and evaporated to yield the title compound as a yellow gum (0.80 g, 76%). ¹H NMR (CDCl₃, 500 MHz) δ 10.23 (br s, 1H), 7.26 (s, 1H), 5.97 (s, 1H), 3.87 (q, J=7.3 Hz, 1H), 2.26 (s, 3H), 1.59 (d, J=7.3 Hz, 3H). LC-MS: m/z (ES) 155 (MH)⁺.

Intermediate 60

2-(1H-Pyrazol-5-yl)propanoic acid (i-60)

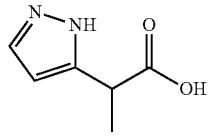

Intermediate 60 was prepared from commercially available ethyl formate and ethyl 2-methyl-3-oxobutanoate using a procedure analogous to that used to prepare Intermediate 59. ¹H NMR (CDCl₃, 500 MHz) δ 7.50 (s, 1H), 7.13 (br s, 1H), 6.22 (s, 1H), 3.95 (q, J=7.3 Hz, 1H), 1.63 (d, J=7.3 Hz, 3H). LC-MS: m/z (ES) 141 (MH)⁺.

Intermediate 61

(2-Oxo-1,3-oxazinan-3-yl)acetic acid (i-61)

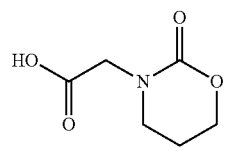

Step A: 1,3-Oxazinan-2-one

To a solution of 4.75 g (29.3 mmol) of 1,1'-carbonyldiimidazole in 260 mL of anhydrous dichloromethane was added 4.6 mL (27 mmol) of DIEA followed by 2.00 g (27 mmol) of 3-aminopropan-1-ol. The resulting mixture was stirred at ambient temperature overnight and then quenched with a saturated aqueous ammonium chloride solution. The layers were separated and the organic phase extracted with dichloromethane (2×30 mL). The combined organic layers were washed with brine, dried over anhydrous sodium sulfate, filtered and evaporated in vacuo. The crude residue was purified by silica gel chromatography eluting with a 5-15% methanol in ethyl acetate gradient to afford the title compound as a clear gum (0.20 g, 7.6%). $^1$HNMR (500 MHz, CDCl$_3$) δ: 6.12 (br s, 1H), 4.29 (t, J=5.4 Hz, 2H), 3.36 (td, J=6.2, 2.3 Hz, 2H), 2.00-1.95 (m, 2H).

Step B: Methyl (2-oxo-1,3-oxazinan-3-yl)acetate

A solution of 0.20 g (2.0 mmol) of 1,3-oxazinan-2-one from step A above in 2 mL of anhydrous DMF was added to a 10 mL round bottom flask containing 0.13 g (3.2 mmol) of a 60% sodium hydride suspension in mineral oil under an atmosphere of nitrogen. After stirring for 10 min 0.37 g (2.4 mmol) of methyl bromoacetate was added in one portion and the reaction mixture was allowed to stir overnight. The reaction mixture was then quenched with 5 mL of a saturated aqueous ammonium chloride solution and then diluted with 20 mL of water. The resulting suspension was extracted with ethyl acetate (3×10 mL) and the combined organics were washed with water (2×3 mL), brine (1×3 mL) and dried over magnesium sulfate. The mixture was filtered, evaporated and purified by silica gel chromatography eluting with a 5% methanol in ethyl acetate mixture to afford the title compound as a clear oil (0.068 g, 20%). $^1$HNMR (500 MHz, CDCl$_3$) δ: 4.28 (t, J=5.4 Hz, 2H), 4.03 (s, 2H), 3.70 (s, 3H), 3.36 (t, J=6.2 Hz, 2H), 2.08-2.04 (m, 2H). LC-MS: m/z (ES) 174 (MH)$^+$.

Step C: (2-Oxo-1,3-oxazinan-3-yl)acetic acid

To a solution of 0.068 g (0.39 mmol) of methyl (2-oxo-1,3-oxazinan-3-yl)acetate from step B above in 6 mL of THF and 2 mL of water and 2 mL of methanol was added 0.60 mL (1.2 mmol) of an aqueous 2.0 M sodium hydroxide solution. The resulting mixture was stirred at ambient temperature for 3 h and then evaporated in vacuo to remove the methanol and THF. The aqueous phase was acidified with a 2 N hydrochloric acid solution until a pH of 2 was achieved and then extracted with a 30% isopropyl alcohol in chloroform mixture (3×10 mL). The combined organic layers were dried over anhydrous sodium sulfate, filtered and evaporated to yield the title compound as an off-white solid (0.06 g, 99%). $^1$H NMR (CD$_3$OD, 500 MHz) δ: 4.32 (t, J=5.4 Hz, 2H), 4.03 (s, 2H), 3.41 (t, J=6.2 Hz, 2H), 2.10-2.05 (m, 2H). LC-MS: m/z (ES) 160 (MH)$^+$.

Intermediate 62

(3-Methyl-2-oxotetrahydropyrimidin-1(2H)-yl)acetic acid (i-62)

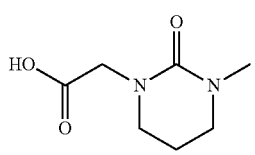

Step A: 1-Methyltetrahydropyrimidin-2(1H)-one

To a solution of 10.1 g (62.4 mmol) of 1,1'-carbonyldiimidazole in 113 mL of anhydrous dichloromethane was added 10.0 mL (56.7 mmol) of DIEA followed by 5.00 g (56.7 mmol) of N-methylpropane-1,3-diamine. The resulting mixture was stirred at ambient temperature overnight and then quenched with a saturated aqueous ammonium chloride solution. The layers were separated and the organic phase extracted with dichloromethane (2×50 mL). The combined organic layers were washed with brine, dried over anhydrous sodium sulfate, filtered and evaporated in vacuo. The crude residue was purified by silica gel chromatography eluting with a 5-15% methanol in ethyl acetate gradient to afford the title compound as a clear gum (0.700 g, 10.0%). $^1$HNMR (500 MHz, CDCl$_3$) δ: 4.69 (br s, 1H), 3.30-3.27 (m, 2H), 3.24 (t, J=6.0 Hz, 2H), 2.92 (s, 3H), 1.96-1.92 (m, 2H).

Step B: Tert-butyl (3-methyl-2-oxotetrahydropyrimidin-1(2H)-yl)acetate

A solution of 0.30 g (2.6 mmol) of 1-methyltetrahydropyrimidin-2(1H)-one from step A above in 5 mL of anhydrous DMF was added to a 10 mL round bottom flask containing 0.16 g (4.2 mmol) of a 60% sodium hydride suspension in mineral oil under an atmosphere of nitrogen. After stirring for 10 min 0.62 g (3.2 mmol) of tert-butyl bromoacetate was added in one portion and the reaction mixture was allowed to stir overnight. The reaction mixture was then quenched with 5 mL of a saturated aqueous ammonium chloride solution and then diluted with 20 mL of water. The resulting suspension was extracted with ethyl acetate (3×10 mL) and the combined organics were washed with water (2×3 mL), brine (1×3 mL) and dried over magnesium sulfate. The mixture was filtered, evaporated and purified by silica gel chromatography eluting with a 0-5% methanol in ethyl acetate gradient to afford the title compound as a clear oil (0.090 g, 15%). $^1$HNMR (500 MHz, CDCl$_3$) δ: 3.88 (s, 2H), 3.23 (t, J=6 Hz, 2H), 3.20 (t, J=6 Hz, 2H), 2.84 (s, 3H), 1.94-1.89 (m, 2H), 1.37 (s, 9H). LC-MS: m/z (ES) 229 (MH)$^+$.

Step C: (3-Methyl-2-oxotetrahydropyrimidin-1(2H)-yl)acetic acid

To a solution of 0.090 g (0.39 mmol) of tert-butyl (3-methyl-2-oxotetrahydropyrimidin-1(2H)-yl)acetate from step B above in 4 mL of anhydrous dichloromethane was added 1 mL of TFA. The resulting mixture was stirred at ambient temperature for 6 h then evaporated to dryness in vacuo to afford the title compound as an off-white gum (0.68 g, 99%). LC-MS: m/z (ES) 173 (MH)$^+$.

Intermediate 63

(3-Methyl-2-oxoimidazolidin-1-yl)acetic acid (i-63)

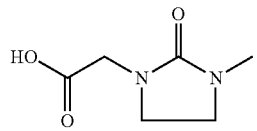

(3-Methyl-2-oxoimidazolidin-1-yl)acetic acid was prepared from commercially available N-methylethane-1,2-diamine using a procedure analogous to that used to prepare Intermediate 62. $^1$HNMR (500 MHz, CDCl$_3$) δ 7.21 (br s, 1H), 3.96 (s, 2H), 3.48-3.42 (m, 2H), 3.39-3.59 (m, 2H), 2.80 (s, 3H). LC-MS: m/z (ES) 159 (MH)$^+$.

Intermediate 64

2-(3-Methyl[1,2,4]triazolo[4,3-a]pyridin-8-yl)propanoic acid (i-64)

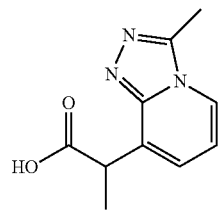

Step A: N-(3-bromopyridin-2-yl)acetohydrazide

To a solution of 0.800 g (3.38 mmol) of 2,3-dibromopyridine in 10 mL of anhydrous 1,4-dioxane was added 0.325 g (10.1 mmol) of anhydrous hydrazine and the resulting mixture was heated to 85° C. for 8 h. The reaction mixture was cooled to ambient temperature then evaporated to dryness in vacuo. The crude residue was dissolved in anhydrous dichloromethane and cooled to –78° C. in a dry ice acetone bath under an atmosphere of nitrogen. Next, 1.0 mL (6.8 mmol) of triethylamine was added followed by 0.210 g (2.72 mmol) of acetyl chloride. The resulting mixture was allowed to warm to ambient temperature over 20 min then all volatiles were removed in vacuo. The residue was suspended in 20 mL of water and extracted with ethyl acetate (3×10 mL). The combined extracts were washed with brine, dried over magnesium sulfate, filtered and evaporated to afford the title compound (0.18 g, 23%). LC-MS: m/z (ES) 230, 232 (MH)$^+$ and 188, 190 (MH-COCH$_3$)$^+$.

Step B: 8-Bromo-3-methyl[1,2,4]-triazolo[4,3-a]pyridine

To a solution of 0.17 g (0.74 mmol) of N-(3-bromopyridin-2-yl)acetohydrazide from step A above in 40 mL of anhydrous toluene was added 3 mL of glacial acetic acid and the resulting mixture was heated to reflux for 20 h employing a Dean-Stark trap. The reaction mixture was cooled to ambient temperature then evaporated to dryness in vacuo to afford the title compound (0.13 g, 84%) LC-MS: m/z (ES) 212, 214 (MH)$^+$.

Step C: Benzyl 2-(3-methyl[1,2,4]-triazolo[4,3-a]pyridin-8-yl)acrylate

To a solution of 0.13 g (0.61 mmol) of 8-bromo-3-methyl[1,2,4]triazolo[4,3-a]pyridine from Step B above in 4 mL of anhydrous THF was added a solution of 0.36 g (0.80 mmol) of benzyl 2-(tributylstannyl)acrylate (see Intermediate 62, Step B) in 1 mL of anhydrous THF, 0.11 g (0.09 mmol) of tetrakis(triphenylphosphine)palladium(0) and 0.067 g (0.67 mmol) of copper (I) chloride. The reaction mixture was heated to 60° C. for 6 h, cooled and filtered through a pad of Celite®. The pad was washed with 15 mL of a dichloromethane and the combined filtrates were evaporated to dryness. The crude residue was purified by silica gel chromatography eluting with a 0-6% methanol in ethyl acetate gradient to afford the title compound (0.13 g, 73%). LC-MS: m/z (ES) 294 (MH)$^+$.

Step D: 2-(3-Methyl[1,2,4]triazolo[4,3-d]pyridin-8-yl)propanoic acid

To 0.040 g (0.038 mmol) of 10% palladium on carbon was added a solution of (0.080 g, 0.27 mmol) of benzyl 2-(3-methyl[1,2,4]triazolo[4,3-a]pyridin-8-yl)acrylate prepared in Step C above in 4 mL of methanol. The resulting suspension was stirred under an atmosphere of hydrogen (1 atmosphere) for 6 h. The residue was filtered through a pad of Celite® and the pad was washed with cold methanol. The combined filtrates were evaporated under reduced pressure to give the title compound (0.043 g, 77%). LC-MS: m/z (ES) 206 (MH)$^+$.

Intermediate 65

4-Methoxy-2-(1H-pyrazol-1-yl)butanoic acid (i-65)

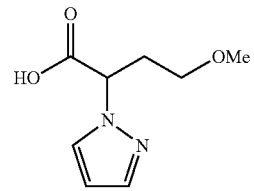 [SMILES: COCCC(C(=O)O)n1cccn1]

Step A: Methyl 4-methoxy-2-(1H-pyrazol-1-yl)butanoate

To a stirred, cooled (–78° C.) solution of 1.32 g (10.0 mmol) of methyl 4-methoxybutanoate in 15 mL of anhydrous THF under an atmosphere of nitrogen was added 10.5 mL (10.5 mmol) of a 1.0 M solution of LiHMDS in tetrahydrofuran. The resulting mixture was stirred for 1 h, then 1.09 g (10 mmol) of chlorotrimethylsilane was added. After stirring for 20 min, 1.78 g (10.0 mmol) of solid N-bromosuccinimide was added and the mixture was stirred for 2 h at –78° C., then slowly warmed to ambient temperature over 40 min. The reaction was quenched with a saturated aqueous ammonium chloride solution and then the aqueous phase was extracted with ethyl acetate (2×20 mL). The combined organic layers were washed with brine, dried over sodium sulfate, filtered and evaporated to dryness in vacuo. The crude residue was dissolved in 15 mL of DMF and 5.5 g (40 mmol) of potassium carbonate followed by 3.4 g (50 mmol) of 1H-pyrazole were added. The resulting mixture was heated to 80° C. for 40 min, then cooled to ambient temperature. The reaction was diluted with 75 mL of water and extracted with ethyl acetate (3×50 mL). The combined extracts were washed with brine, dried over magnesium sulfate, filtered and evaporated to dryness in vacuo. The crude residue was purified by reverse phase HPLC (TMC Pro-Pac C18; 0-75% 0.1% trifluoroacetic acid in acetonitrile/0.1% trifluoroacetic acid in water gradient) to yield the title compound (0.26 g, 13%). LC-MS: m/z (ES) 199 (MH)$^+$.

Step B: 4-Methoxy-2-(1H-pyrazol-1-yl)butanoic acid

To a stirred solution of 0.045 g (0.23 mmol) of methyl 4-methoxy-2-(1H-pyrazol-1-yl)butanoate from step A above in 2 mL of methanol was added a solution of 0.032 g (0.57 mmol) of potassium hydroxide in 0.5 mL of water. The mixture was stirred at ambient temperature for 1.5 h then acidified with a 2 N hydrochloric acid solution until a pH of 4 was achieved. The mixture was evaporated to remove all volatiles then extracted with ethyl acetate. The combined extracts were washed with brine, dried over magnesium sulfate, filtered and evaporated to dryness to afford the title compound (0.040 g, 95%). LC-MS: m/z (ES) 185 (MH)$^+$.

Intermediate 66

(5S)-6,7-Dihydro-5H-pyrrolo[1,2-b][1,2,4]triazole-5-carboxylic acid (i-66)

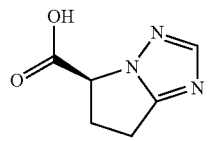 [SMILES: O=C(O)[C@@H]1CCc2ncnn21]

Step A:
(5S)-1-Amino-5-[(trityloxy)methyl]pyrrolidin-2-one

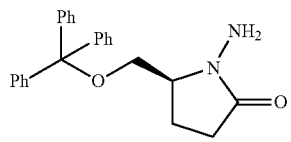 [SMILES: NN1C(=O)CC[C@H]1COC(c1ccccc1)(c1ccccc1)c1ccccc1]

To a cooled (0° C.) solution of 0.550 g (1.54 mmol) of (S)-tritylhydroxymethylpyrrolidinone in 10 mL of 1,2-dimethoxyethane under an atmosphere of nitrogen was added 0.123 g (3.08 mmol) of a 60% sodium hydride suspension in mineral oil. After stirring for 30 min, a solution of 0.828 g (3.85 mmol.) of 2-[(aminooxy)sulfonyl]-1,3,5-trimethylbenzene in 5 mL of diethyl ether was added in small portions over 30 min. The reaction mixture was allowed to warm to ambient temperature overnight then filtered. The filtrand was washed with diethyl ether and the filtrate was washed successively with a saturated aqueous sodium bicarbonate solution and brine. The organic layer was then dried over magnesium sulfate, filtered and evaporated in vacuo to afford the title compound as a colorless solid. The solid is contaminated with mineral oil form the sodium hydride and weighed 0.6 g (quantitative yield). LC-MS: m/z (ES) 395 (M+Na)$^+$.

Step B: (5S)-5-[(Trityloxy)methyl]-6,7-dihydro-5H-pyrrolo[1,2-b][1,2,4]triazole

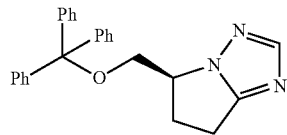 [SMILES: c1ccc(C(OC[C@@H]2CCc3ncnn32)(c2ccccc2)c2ccccc2)cc1]

To a stirred solution of 0.540 g (1.45 mmol) of (5S)-1-amino-5-[(trityloxy)methyl]pyrrolidin-2-one from step A above in 5 mL of anhydrous DMF was added 0.327 g (7.25 mmol) of formamide followed by 0.050 g (0.36 mmol) of zinc(II) chloride. The resulting mixture was heated to 160° C. for 48 h, cooled to ambient temperature and diluted with 25 mL of ethyl acetate. The solution was washed sequentially with an aqueous sodium bicarbonate solution, water and then brine and the organic layer dried over magnesium sulfate. The mixture was then filtered, evaporated to dryness in vacuo and purified by silica gel chromatography eluting with a 0-100% ethyl acetatae in hexanes gradient to afford the title compound (0.27 g, 49%). LC-MS: m/z (ES) 382 (MH)$^+$.

Step C: (5S)-6,7-Dihydro-5H-pyrrolo[1,2-b][1,2,4]triazol-5-ylmethanol

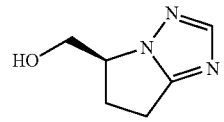

The product form step B above, 0.27 g (0.71 mmol) of (5S)-5-[(trityloxy)methyl]-6,7-dihydro-5H-pyrrolo[1,2-b][1,2,4]triazole, was dissolved in 35 mL of a 4.0 M solution of hydrogen chloride in anhydrous 1,4-dioxane. The reaction mixture was stirred for 10 min, quenched with 20 mL of methanol, then evaporated to dryness in vacuo. The residue was purified by reverse phase HPLC (TMC Pro-Pac C18; 0-90% 0.1% trifluoroacetic acid in acetonitrile/0.1% trifluoroacetic acid in water gradient) to yield the title compound (0.050 g, 50%). LC-MS: m/z (ES) 140 (MH)$^+$.

Step D: ((5S)-6,7-Dihydro-5H-pyrrolo[1,2-b][1,2,4]-triazole-5-carboxylic acid

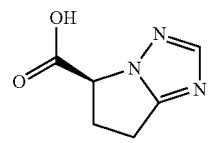 [SMILES: O=C(O)[C@@H]1CCc2ncnn21]

To a stirred solution of 0.025 g (0.18 mmol) of (5S)-6,7-dihydro-5H-pyrrolo[1,2-b][1,2,4]triazol-5-ylmethanol from step C above in 1 mL of a pH 6.7 aqueous phosphate buffer and 1 mL of acetonitrile was added 0.0020 g (0.013 mmol) of 2,2,6,6-tetramethylpiperidine 1-oxyl, 0.033 g (0.36 mmol) of sodium chlorite (33 mg, 0.36 mmol) and 0.0044 mL (0.0036 mmol) of sodium hypochlorite. The resulting mixture was stirred at 35° C. for 72 h, then concentrated to dryness in vacuo. The residue was dissolved in 1 mL (4 mmol) of a 4.0 M solution of hydrogen chloride in anhydrous 1,4-dioxane and concentrated in vacuo. The crude residue was purified by reverse phase HPLC (TMC Pro-Pac C18; 0-70% 0.1% trifluoroacetic acid in acetonitrile/0.1% trifluoroacetic acid in water gradient) to yield the title compound as the TFA salt. The product was then dissolved in 1 mL (4 mmol) of a 4.0 M solution of hydrogen chloride in anhydrous 1,4-dioxane and concentrated in vacuo to afford the title compound as the hydrogen chloride salt. LC-MS: m/z (ES) 154 (MH)+.

Intermediate 67

2-(1,3-Thiazol-4-yl)propanoic acid (i-67)

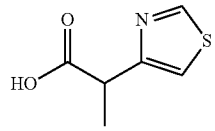

Step A: Ethyl 2-(1,3-thiazol-4-yl)propanoate

To a cooled (0° C.) solution of 43.3 g (300 mmol) of ethyl 2-methylacetoaceate in 270 mL of chloroform was added a solution of 15.5 mL (300 mmol) of bromine in 30 mL of chloroform dropwise over 30 min. After complete addition the mixture was allowed to warm to room temperature and stirred overnight. Air was bubbled through the reaction mixture for 70 min, then the solution was dried over sodium sulfate, filtered and evaporated to give 66.0 g (99.0%) of a pale orange oil. To a cooled (0° C.) mixture of 40.0 g (180 mmol) of this intermediate and 10.7 mL (269 mmol) of formamide in 400 mL of anhydrous 1,4-dioxane was added 15.0 g (67.2 mmol) of phosphorous pentasulfide. The mixture was warmed to room temperature and stirred for 1.5 h, then heated to 93° C. for 2.5 h. After cooling to ambient temperature overnight all voliatiles were removed in vacuo and the residue was basified by the addition of a saturated aqueous sodium bicarbonate solution. The aqueous phase was extracted with dichloromethane (3×300 ml) and the combined organic layers were washed with a saturated aqueous sodium bicarbonate solution, water, brine and then dried over magnesium sulfate. The mixture was filtered, evaporated and the residue purified by MPLC (Biotage Horizon 2×FLASH 65i) eluent: 100% Hexanes (450 ml), then a gradient rising from 100% Hexanes to 25% EtOAc in Hexanes (2400 ml), then 25% EtOAc in Hexanes (1200 ml) to yield the title compound as an orange oil (20.0 g, 60.0%). $^1$H NMR (500 MHz, CDCl$_3$) δ: 1.24 (t, J=7.1, 3H), 1.58 (d, J=7.3, 3H), 4.05 (q, J=7.3, 1H), 4.17 (m, 2H), 7.18 (d, J=1.3, 1H), 8.76 (d, J=1.6, 1H).

Step B: 2-(1,3-Thiazol-4-yl)propanoic acid

A solution of 5.0 g (27 mmol) of ethyl 2-(1,3-thiazol-4-yl)propanoate from step A above in 25 mL of methanol was added dropwise to a mixture of 6.6 mL (33 mmol) of a 5 N aqueous NaOH solution, water (16 ml) and methanol (30 ml). After addition was complete the mixture was stirred for 2 h. The methanol was removed by evaporation and the pH of the remaining aqueous was adjusted to ~2.5 with a concentrated hydrogen chloride solution. The mixture was saturated with solid sodium chloride and extracted with EtOAc (3×100 mL). The combined organic layers were washed with brine, dried over sodium sulfate and treated with activated charcoal overnight. The mixture was filtered and evaporated to afford the title compound as an off-white solid 4.0 g (95%). $^1$H NMR (500 MHz, CDCl$_3$) δ: 1.63 (d, J=7.3, 3H), 4.11 (q, J=7.3), 7.25 (d, J=1.8, 1H), 8.88 (d, J=1.8, 1H), 10.25 (br s, 1H).

IntermediateS 68 and 69

(4R)-5,6-Dihydro-4H-cyclopenta[d][1,3]thiazole-4-carboxylic acid (i-68) and (4S)-5,6-dihydro-4H-cyclopenta[d][1,3]thiazole-4-carboxylic acid (i-69)

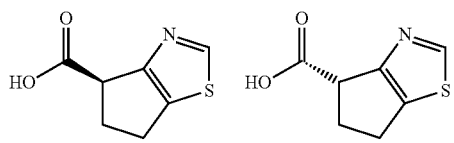

Intermediates 68 and 69 were prepared from ethyl 2-oxo-cyclopentane carboxylate using a procedure analogous to that used to prepare Intermediate 47. The two enantiomers were separated by SFC CO$_2$S using an AD-H column 10% MeOH/ 90% CO$_2$, 2.1 ml/min 100 bar 40° C. The first eluting enantiomer, (4S)-5,6-dihydro-4H-cyclopenta[d][1,3]thiazole-4-carboxylic acid, was designated as Intermediate 68 (i-68) and the second eluting enantiomer, (4R)-5,6-Dihydro-4H-cyclopenta[d][1,3]thiazole-4-carboxylic acid, was designated as Intermediate 69 (i-69). $^1$H NMR (500 MHz, CDCl$_3$) δ: 2.59-2.68 (m, 1H), 2.71-2.79 (m, 1H), 2.83-2.90 (m, 1H), 2.92-3.00 (m, 1H), 3.86 (m, 1H), 8.82 (s, 1H), 12.45 (s, 1H).

Intermediate 70

2-(1,3-Thiazol-4-yl)butanoic acid (i-70)

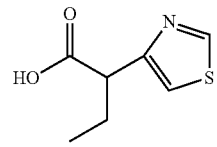

2-(1,3-Thiazol-4-yl)butanoic acid was prepared from commercially available 1,3-thiazol-4-ylacetic acid and ethyl iodide using a procedure analogous to that used to prepare Intermediate 26. $^1$H NMR (500 MHz, CDCl$_3$) δ: 0.95 (t, J=7.3, 3H), 1.25 (t, J=7.3, 3H), 1.95-2.05 (m, 1H), 2.08-2.17 (m, 1H), 3.88 (t, J=7.6, 1H), 4.15-4.23 (m, 2H), 7.22 (d, J=1.8, 1H), 8.77 (d, J=1.8, 1H).

Intermediate 71

4-Methyl-1H-1,2,3-triazole-1-yl acetic acid (i-71)

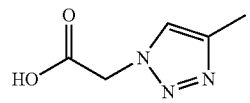

Step A: Ethyl [4-methyl-5-(trimethylsilyl)-1H-1,2,3-triazole-1-yl]acetate

To a solution of 2.0 g (18 mmol) of 1-(trimethylsilyl)-1-proyne in toluene (20 mL) was added 2.3 g (18 mmol) of ethyl azido-acetate. The reaction mixture was heated at 120° C. overnight then cooled to ambient temperature. All volatiles were removed under reduced pressure and the residue was purified by column chromatography on silica gel eluting with a 5-25% acetone in hexanes gradient to yield the title compound as a colorless oil (0.77 g, 18%). $^1$HNMR (500 MHz, CDCl$_3$): δ 5.01 (s, 2H), 4.2 (m, 2H), 2.25 (s, 3H), 1.22 (m, 3H), 0.295 (s, 9H).

Step B: Ethyl [4-methyl-1H-1,2,3-triazole-1-yl]acetate

To a solution of 0.77 g (3.2 mmol) of ethyl [4-methyl-5-(trimethylsilyl)-1H-1,2,3-triazole-1-yl]acetate from step A above in 2 mL of THF was added 1.3 mL (32 mmol) of a solution of 50% hydrofluoric acid in water. The resulting mixture was stirred at room temperature for 3 h and then evaporated to dryness in vacuo. Next, 5 mL of a 2.0 N ammonia in methanol solution was added and then the mixture was again evaporated to dryness in vacuo. The mixture was dissolved in dichloromethane, filtered and then evaporated in vacuo to afford the title compound as a clear gum (0.51 g. 93%). $^1$HNMR (500 MHz, CDCl$_3$) δ: 7.5 (s, 1H), 5.05 (s, 2H), 4.23 (m, 2H), 2.30 (s, 3H), 1.30 (m, 3H).

Step C: [4-Methyl-1H-1,2,3-triazole-1-yl]acetic acid

To a solution of 0.51 g (3.0 mmol) of ethyl [4-methyl-1H-1,2,3-triazole-1-yl]acetate from step B above in tetrahydrofuran (10 ml), methanol (6 ml) was added 6 mL (6 mmol) of an aqueous 1.0 M lithium hydroxide solution. The resulting mixture was stirred at ambient temperature for 1 h. The reaction mixture was neutralized with 8 mL of a 2 N hydrochloric acid solution which was then evaporated to remove all volatiles. The aqueous phase was extracted with ethyl acetate and the combined organics were washed with brine, dried over magnesium sulfate, filtered and evaporated to dryness to afford the title compound as a white solid (0.40 g, 95%). LC/MS 142 (M+1).

Intermediate 72

2-[4-(Methoxycarbonyl)-1H-1,2,3-triazol-1-yl]propanoic acid and (i-72)

Intermediate 73

2-[5-(methoxycarbonyl)-1H-1,2,3-triazol-1-yl]propanoic acid (i-73)

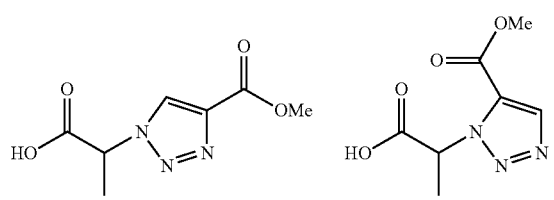

Step A: Methyl 1-(2-tert-butoxy-1-methyl-2-oxoethyl)-1H-1,2,3-triazole-4-carboxylate and methyl 1-(2-tert-butoxy-1-methyl-2-oxoethyl)-1H-1,2,3-triazole-5-carboxylate To a solution of 1.87 g (22.3 mmol) of methyl prop-2-ynoate in 40 mL of toluene was added 1.9 g (11 mmol) of tert-butyl 2-azidopropanate. The reaction mixture was heated at 100° C. for 3 h then cooled to ambient temperature. All volatiles were removed under reduced pressure and the crude residue purified by column chromatography on silica gel eluting with a 5 to 25% acetone in hexanes gradient to afford the title compounds.

Methyl 1-(2-tert-butoxy-1-methyl-2-oxoethyl)-1H-1,2,3-triazole-4-carboxylate (lower Rf) (1.4 g, 50%). $^1$HNMR (500 MHz, CDCl$_3$) δ: 8.30 (s, 1H), 5.46-5.41 (m, 1H), 4.11 (s, 3H), 1.83 (d, 3H), 1.47 (s, 9H). LC-MS: m/z (ES) 256 (MH)$^+$.

Methyl 1-(2-tert-butoxy-1-methyl-2-oxoethyl)-1H-1,2,3-triazole-5-carboxylate (higher Rf) (0.45 g, 16%). $^1$HNMR (500 MHz, CDCl$_3$) δ: 8.15 (s, 1H), 5.77-5.72 (m, 1H), 3.90 (s, 3H), 1.95 (d, J=7.3 Hz, 3H), 1.41 (s, 9H). LC-MS: m/z (ES) 256 (MH)$^+$.

Step B (i-72): 2-[4-(Methoxycarbonyl)-1H-1,2,3-triazol-1-yl]propanoic acid

To a stirred solution of 0.55 g (2.2 mmol) of methyl 1-(2-tert-butoxy-1-methyl-2-oxoethyl)-1H-1,2,3-triazole-P4-carboxylate from step A above in 3 mL of anhydrous 1,4-dioxane was added 2.7 mL (11 mmol) of a 4.0 M hydrogen chloride solution in 1,4-dioxane. The resulting mixture was stirred for 1 h and then evaporated to dryness to afford the title compound as an off-white solid (0.40 g, 93%). $^1$HNMR (500 MHz, CD$_3$OD) δ: 8.67 (s, 1H), 5.60 (q, J=7.3 Hz, 1H), 3.90 (s, 3H), 1.88 (d, J=7.3 Hz, 3H). LC-MS: m/z (ES) 200 (MH)$^+$.

Step B (i-73): 2-[5-(Methoxycarbonyl)-1H-1,2,3-triazol-1-yl]propanoic acid

To a stirred solution of 0.40 g (1.6 mmol) of methyl 1-(2-tert-butoxy-1-methyl-2-oxoethyl)-1H-1,2,3-triazole-5-carboxylate from step A above in 3 mL of anhydrous 1,4-dioxane was added 2.7 mL (11 mmol) of a 4.0 M hydrogen chloride solution in 1,4-dioxane. The resulting mixture was stirred for 1 h and then evaporated to dryness to afford the title compound as an off-white solid (0.27 g, 87%). LC-MS: m/z (ES) 200 (MH)$^+$.

Intermediate 74

2-[4-(Aminocarbonyl)-1H-1,2,3-triazol-1-yl]propanoic acid (i-74)

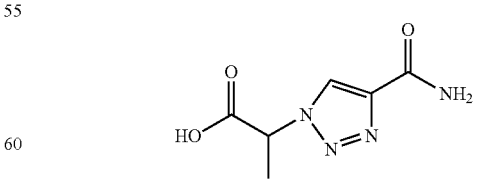

2-[4-(Aminocarbonyl)-1H-1,2,3-triazol-1-yl]propanoic acid was prepared from commercially available propiolamide and tert-butyl 2-azidopropanate using a procedure analogous to that used to prepare Intermediate 52. $^1$HNMR (500 MHz, CD₃OD) δ: 8.48 (s, 1H), 5.50 (q, J=7.3 Hz, 1H), 1.85 (d, J=7.3 Hz, 3H). LC-MS: m/z (ES) 185 (MH)⁺.

Intermediates 75 and 76

2-(4-Methyl-1H-1,2,3-triazol-1-yl)propanoic acid (i-75) and 2-(5-methyl-1H-1,2,3-triazol-1-yl)propanoic acid (i-76)

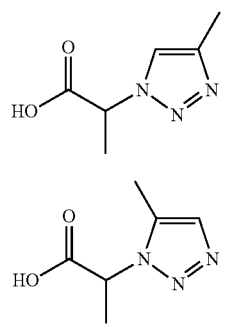

Step A: Methyl 2-[4-methyl-5-(trimethylsilyl)-1H-1,2,3-triazol-1-yl]propanoate and methyl 2-[5-methyl-4-(trimethylsilyl)-1H-1,2,3-triazol-1-yl]propanoate To a solution of 1.9 g (17 mmol) of trimethyl(prop-1-yn-1-yl)silane in 20 mL of toluene was added 2.3 g (18 mmol) of methyl 2-azidopropanoate. The reaction mixture was heated at 120° C. for 3 h. The mixture was cooled and the solvent was evaporated under reduced pressure. The residue was purified by column chromatography on silica gel eluting with a 5-25% acetone in hexanes gradient to yield the title compounds as ~6:1 mixture of methyl 2-[4-methyl-5-(trimethylsilyl)-1H-1,2,3-triazol-1-yl]propanoate to methyl 2-[5-methyl-4-(trimethylsilyl)-1H-1,2,3-triazol-1-yl]propanoate and is a colorless oil (3.0 g, 80%). LC-MS: m/z (ES) 242 (MH)⁺.

Step B: Methyl 2-(4-methyl-1H-1,2,3-triazol-1-yl)propanoate and methyl 2-(5-methyl-1H-1,2,3-triazol-1-yl)propanoate To a solution of 1.3 g (5.4 mmol) of methyl 2-[4-methyl-5-(trimethylsilyl)-1H-1,2,3-triazol-1-yl]propanoate and methyl 2-[5-methyl-4-(trimethylsilyl)-1H-1,2,3-triazol-1-yl]propanoate from step A above in 2 mL of THF was added 2.2 mL (54 mmol) of a solution of 50% hydrofluoric acid in water. The resulting mixture was stirred at room temperature for 15 min and then evaporated to dryness in vacuo. Next, 8 mL of a 2.0 N ammonia in methanol solution was added and then the mixture was again evaporated to dryness in vacuo. The mixture was dissolved in dichloromethane, filtered and then evaporated in vacuo to afford the title compounds as a ~8:1 mixture of methyl 2-(4-methyl-1H-1,2,3-triazol-1-yl)propanoate to methyl 2-(5-methyl-1H-1,2,3-triazol-1-yl)propanoate. The mixture is a clear gum (0.67 g, 73%). LC-MS: m/z (ES) 170 (MH)⁺.

Step C: 2-(4-Methyl-1H-1,2,3-triazol-1-yl)propanoic acid and 2-(5-methyl-1H-1,2,3-triazol-1-yl)propanoic acid To a solution of 0.76 g (4.5 mmol) of methyl 2-(4-methyl-1H-1,2,3-triazol-1-yl)propanoate and methyl 2-(5-methyl-1H-1,2,3-triazol-1-yl)propanoate from step B above in 12 mL of ethanol was added 13.5 mL (13.5 mmol) of an aqueous 1.0 M lithium hydroxide solution. The resulting mixture was stirred at ambient temperature for 1 h. The reaction mixture was acidified with a 2 N hydrochloric acid solution until a pH of 4 was achieved and then evaporated to remove all volatiles. The aqueous phase was extracted with ethyl acetate and the combined organics were washed with brine, dried over magnesium sulfate, filtered and evaporated to dryness to afford the title compounds as an ~8:1 mixture of 2-(4-methyl-1H-1,2,3-triazol-1-yl)propanoic acid and 2-(5-methyl-1H-1,2,3-triazol-1-yl)propanoic acid. The mixture is an off-white solid (0.50 g, 58%). LC-MS: m/z (ES) 156 (MH)⁺.

Intermediate 77

Tert-butyl (2S,5R)-2-(4-{[(2S)-2-aminopropanoyl]amino}benzyl)-5-[(R) hydroxy(phenyl)methyl]pyrrolidine-1-carboxylate (i-77)

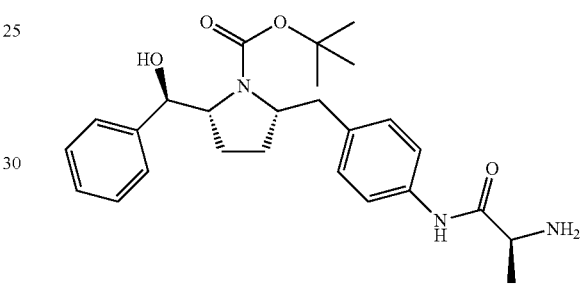

Step A: Tert-butyl (2S,5R)-2-{4-[((2S)-2-{[(9H-fluoren-9-yloxy)carbonyl]amino}propanoyl)amino]benzyl}-5-[(R)-hydroxy(phenyl)methyl]pyrrolidine-1-carboxylate To a solution of 1.85 g (4.82 mmol) of intermediate i-13a in 20 mL of dichloromethane was added 1.0 mL (7.24 mmol) of triethylamine followed by 1.67 g (5.07 mmol) of commercially available 9H-fluoren-9-yl[(1S)-2-chloro-1-methyl-2-oxoethyl]carbamate. The resulting mixture was stirred for 1.5 h then all volatiles were removed in vacuo. The residue was diluted with water and then extracted with ethyl acetate. The combined organic layers were washed with brine, dried over magnesium sulfate, filtered and evaporated to afford the crude title compound which was used without further purification (3.2 g). LC-MS: m/z (ES) 676 (MH)⁺.

Step B: Tert-butyl (2S,5R)-2-(4-{[(2S)-2-aminopropanoyl]amino}benzyl)-5-[(R)-hydroxy(phenyl)methyl]pyrrolidine-1-carboxylate To a stirred solution of 3.15 g (4.65 mmol) of tert-butyl (2S,5R)-2-{4-[((2S)-2-{[(9H-fluoren-9-yloxy)carbonyl]amino}propanoyl)amino]benzyl}-5-[(R)-hydroxy(phenyl)methyl]pyrrolidine-1-carboxylate from step A above in 3 mL of anhydrous THF was added 0.396 g (4.65 mmol) of piperidine. The mixture was heated to 35° C. under an atmosphere of nitrogen for 2 h then all volatiles were removed Intermediate 78

Tert-butyl (2R,5S)-2-[(R)-hydroxy(phenyl)methyl]-5-(4-{1(2S)-2-[(methylamino)propanoyl]amino}benzyl)pyrrolidine-1-carboxylate (i-78)

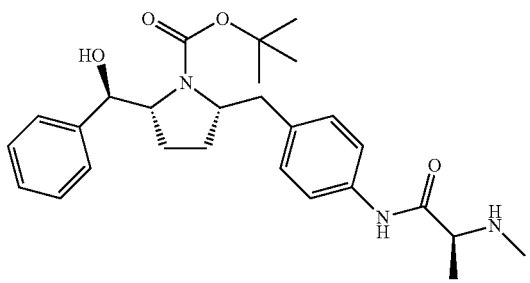 [SMILES: CN[C@@H](C)C(=O)Nc1ccc(C[C@@H]2CC[C@H]([C@H](O)c3ccccc3)N2C(=O)OC(C)(C)C)cc1]

Step A: Tert-butyl (2S,5R)-2-[4-({(2S)-2-[[(9H-fluoren-9-yloxy)carbonyl](methyl)amino]propanoyl}amino)benzyl]-5-[(R)-hydroxy(phenyl)methyl]pyrrolidine-1-carboxylate To a stirred solution of 0.192 g (0.5 mmol) of intermediate 17 in 4 mL of dichloromethane under an atmosphere of nitrogen was added 0.203 g (0.625 mmol) of commercially available (2S)-2-[[(9H-fluoren-9-yloxy)carbonyl](methyl)amino]propanoic acid followed by 0.014 g (0.10 mmol) of 1-hydroxy-7-azabenzotriazole and 0.144 g (0.750 mmol) of 1-(3-dimethylaminopropyl)-3-ethylcarbodiimide hydrochloride. The resulting suspension was stirred at ambient temperature for 24 h. The crude reaction mixture was diluted with 25 mL of dichloromethane, washed with water then dried over magnesium sulfate. The mixture was filtered and evaporated to dryness in vacuo to afford the crude title compound which was used without further purification. LC-MS: m/z (ES) 690 (MH)+.

Step B: Tert-butyl (2R,5S)-2-[(R)-hydroxy(phenyl)methyl]-5-(4-{[(2S)-2-(methylamino)propanoyl]amino}benzyl)pyrrolidine-1-carboxylate To a solution of 0.410 g (0.593 mmol) of tert-butyl (2S,5R)-2-[4-({(2S)-2-[[(9H-fluoren-9-yloxy)carbonyl](methyl)amino]propanoyl}amino)benzyl]-5-[(R)-hydroxy(pyridin-3-yl)methyl]pyrrolidine-1-carboxylate from step A above in 3 mL of anhydrous THF was added 0.152 g (1.78 mmol) of piperidine. The resulting mixture was stirred at ambient temperature for 24 h and then was diluted with 25 mL of dichloromethane. The mixture was washed with water then dried over magnesium sulfate. The mixture was filtered and evaporated to dryness in vacuo to afford the crude title compound which was used without further purification. LC-MS: m/z (ES) 468 (MH)+.

Intermediate 79

Tert-butyl (2R,5S)-2-[(R)-hydroxy(phenyl)methyl]-5-(4-{[(2R)-2-(methylamino)propanoyl]amino}benzyl)pyrrolidine-1-carboxylate (i-79)

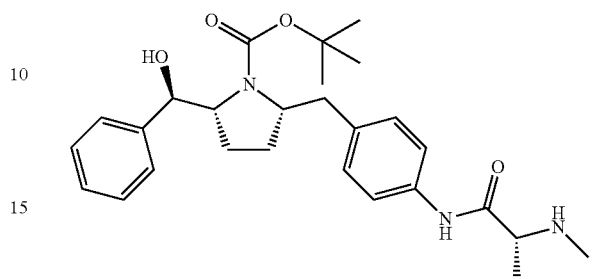

Intermediate 79 was prepared from Intermediate i-13a and commercially available (2R)-2-[[(9H-fluoren-9-yloxy)carbonyl](methyl)amino]propanoic acid following the procedure outlined for the synthesis of Intermediate 78. LC-MS: m/z (ES) 468 (MH)+.

IntermediateS 80a and 80b

Tert-butyl (2S,5R)-2-(4-amino-3-bromobenzyl)-5-[(R)-hydroxy(phenyl)methyl]pyrrolidine-1-carboxylate (i-80a)

Tert-butyl (2R,5R)-2-(4-amino-3-bromobenzyl)-5-[(R)-hydroxy(phenyl)methyl]pyrrolidine-1-carboxylate (i-80b)

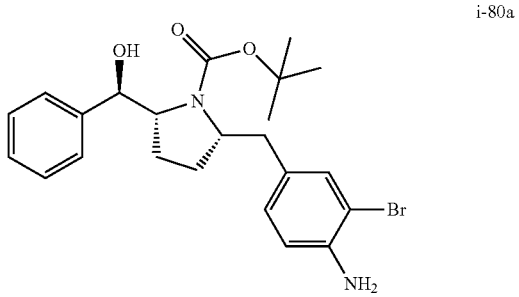 [SMILES: CC(C)(C)OC(=O)N1[C@H](Cc2ccc(N)c(Br)c2)CC[C@@H]1[C@H](O)c1ccccc1]

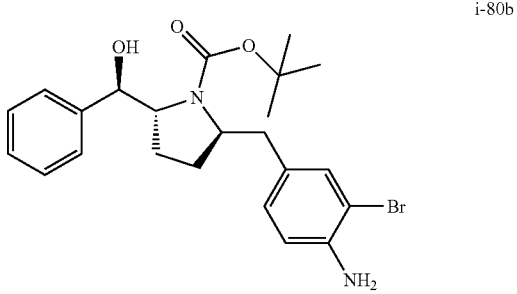 [SMILES: CC(C)(C)OC(=O)N1[C@@H](Cc2ccc(N)c(Br)c2)CC[C@@H]1[C@H](O)c1ccccc1]

Step A: Tert-butyl (2S,5R)-2-(4-amino-3-bromobenzyl)-5-[(R)-hydroxy(phenyl)methyl]pyrrolidine-1-carboxylate (i-80a)

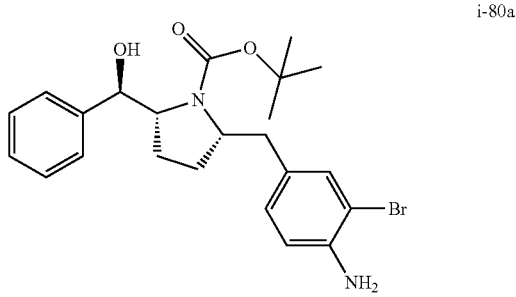

i-80a

To a solution of tert-butyl (2S,5R)-2-(4-aminobenzyl)-5-[(R)-hydroxy(phenyl)methyl]pyrrolidine-1-carboxylate (intermediate i-13a, 214 mg, 0.559 mmol) in DMF (2 mL) cooled to 0° C. via ice/water bath was added NBS (100 mg, 0.559 mmol) and the resulting solution stirred for 1.5 h allowing to warm to rt. The mixture was evaporated under vacuum and the residue purified via Biotage Horizon MPLC using a gradient of 0-40% ethyl acetate in hexane to afford the product (232 mg, 90%) as a white foam. LC-MS: m/z (ES) 483 (MNa)$^+$ and 485 (MNa+2)$^+$.

Step B: Tert-butyl (2R,5R)-2-(4-amino-3-bromobenzyl)-5-[(R)-hydroxy(phenyl)methyl]pyrrolidine-1-carboxylate (i-80b)

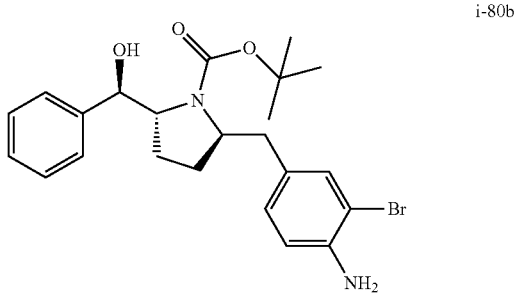

i-80b

To a solution of tert-butyl (2R,5R)-2-(4-aminobenzyl)-5-[(R)-hydroxy(phenyl)methyl]pyrrolidine-1-carboxylate (intermediate i-13b, 108 mg, 0.282 mmol) in DMF (1.5 mL) cooled to 0° C. via ice/water bath was added NBS (55.3 mg, 0.311 mmol) and the resulting solution stirred for 3 h allowing to warm to rt. The mixture was evaporated under vacuum and the residue purified via Biotage Horizon MPLC using a gradient of 0-40% ethyl acetate in hexane to afford the product (83.9 mg, 64%) as a white foam. LC-MS: m/z (ES) 483 (MNa)$^+$ and 485 (MNa+2)$^+$.

Biological Assays:

The following in vitro assays are suitable for screening compounds that have selective β3 agonist activity:

Functional Assay:

cAMP production in response to ligand is measured according to Barton, et al. (1991, Agonist-induced desensitization of D2 dopamine receptors in human Y-79 retinoblastoma cells. Mol. Pharmacol. v3229:650-658) modified as follows. cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation Media (Specialty Media). Cells are then counted and resuspended in assay buffer (Hank's Balanced salt solution supplemented with 5 mM HEPES, 0.1% BSA) containing a phosphodiesterase inhibitor (IBMX, 0.6 mM). The reaction is initiated by mixing 6,000 cells in 6 µL with 6 µL Alexa Fluor labeled cAMP antibody (LANCE™ kit) which is then added to an assay well containing 12 µL of compound (diluted in assay buffer to 2× final concentration). The reaction proceeds for 30 min at room temperature and is terminated by the addition of 24 µL detection buffer (LANCE™ kit). The assay plate is then incubated for 1 h at room temperature and time-resolved fluorescence measured on a Perkin Elmer Envision reader or equivalent. The unknown cAMP level is determined by comparing fluorescence levels to a cAMP standard curve.

The non-selective, full agonist β-adrenergic ligand isoproterenol is used at all three receptors to determine maximal stimulation. The human β3 adrenergic receptor (AR) selective ligand (S)—N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of 10-10 M to 10-5 and the selective ligand (S)—N-[4-[2-[[2-hydroxy-3-(4-hydroxyphenoxy)propyl]amino]ethyl]phenyl]-4-iodobenzenesulfonamide is titrated at the β3 receptor at concentration of 10-10 M to 10-5 M. Unknown ligands are titrated at all 3 β-adrenergic receptor subtypes at a final concentration in the assay of 10-10 M to 10-5 M to determine the EC$_{50}$. The EC$_{50}$ is defined as the concentration of compound that gives 50% activation of its own maximum. Data are analyzed using Microsoft Excel and Graphpad Prism or an internally developed data analysis software package.

Binding Assay:

Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 min on ice. The flasks are scraped to remove the cells and the cells then homogenized using a Teflon/glass homogenizer. Membranes are collected by centrifuging at 38,000×g for 15 min at 4° C. The pelleted membranes are resuspended in TME buffer (50 mM Tris, pH 7.4, 5 mM MgCl$_2$, 2 mM EDTA) at a concentration of 1 mg protein/mL. Large batches of membranes can be prepared, aliquoted and stored at −70° C. for up to a year without loss of potency. The binding assay is performed by incubating together membranes (2-5 µg of protein), the radiolabelled tracer $^{125}$I-cyanopindolol ($^{125}$I-CYP, 45 pM), 200 µg of WGA-PVT SPA beads (GE Healthcare) and the test compounds at final concentrations ranging from 10-10 M to 10-5 M in a final volume of 200 µL of TME buffer containing 0.1% BSA. The assay plate is incubated for 1 h with shaking at room temperature and then placed in a Perkin Elmer Trilux scintillation counter. The plates are allowed to rest in the Trilux counter for approximately 10 h in the dark prior to counting. Data are analyzed using a standard 4-parameter non-linear regression analysis using either Graphpad Prism software or an internally developed data analysis package. The IC$_{50}$ is defined as the concentration of the compound capable of inhibiting 50% of the binding of the radiolabelled tracer ($^{125}$I-CYP). A compound's selectivity for the β3 receptor may be determined by calculating the ratio (IC$_{50}$ β1 AR, β2 AR)/(EC$_{50}$ β3 AR).

Example 1

2-(2-Amino-1,3-thiazol-4-yl)-N-[4-({(5R)-[(R)-hydroxy(phenyl)methyl]pyrrolidin yl}methyl)phenyl]acetamide

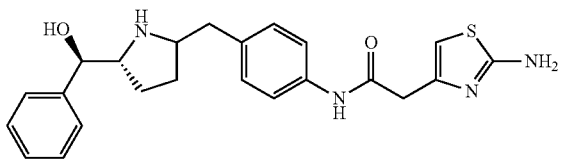

Step A: Tert-butyl (5R)-2-(4-{[(2-amino-1,3-thiazol-4-yl)acetyl]amion}benzyl)-5-[(R)-{[tert-butyl(dimethyl)silyl]oxy}(phenyl)methyl]pyrrolidine-1-carboxylate

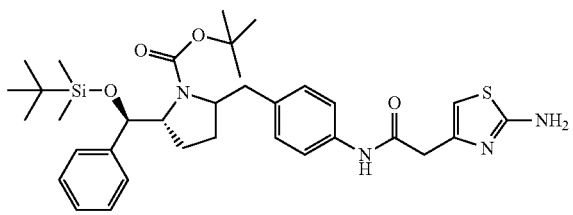

To a solution of 10 mg (5:1 mixture cis/trans, 0.02 mmol) of tert-butyl(5R)-2-(4-aminobenzyl)-5-[(R)-{[tert-butyl(dimethyl)silyl]oxy}(phenyl)methyl]pyrrolidine-1-carboxylate (i-3) and (2-amino-1,3-thiazol-4-yl)acetic acid (3.18 mg, 0.02 mmol) in 0.5 mL anhydrous DMF was added a 0.5 M solution of HOAt in DMF (0.04 mL, 0.02 mmol) followed by EDC (5.8 mg, 0.03 mmol) and DIEA (3.5 µL, 0.02 mmol). The resulting mixture was stirred at room temperature under nitrogen atmosphere for 16 h. The mixture was washed with water and extracted with dichloromethane (2×2 mL). The organics were combined, dried over sodium sulfate, filtered and concentrated in vacuum. The residue was purified by preparative TLC plate (500 uM) eluting with 5% MeOH in dichloromethane to afforded the product (10.3 mg, 81%). m/z (ES) 637 (MH)$^+$, 659 (MNa)$^+$.

Step B: 2-(2-Amino-1,3-thiazol-4-yl)-N-[4-({(5R)-[(R)hydroxy(phenyl)methyl]pyrrolidinyl}methyl)phenyl]acetamide

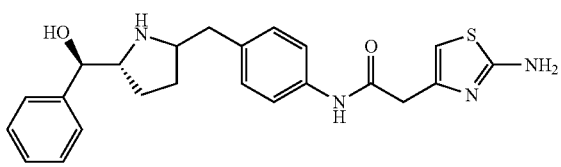

To a solution of 7 mg (0.01 mmol) of tert-butyl (5R)-2-(4-{[(2-amino-1,3-thiazol-4-yl)acetyl]amion}benzyl)-5-[(R)-{[tert-butyl(dimethyl)silyl]oxy}(phenyl)methyl]pyrrolidine-1-carboxylate in 0.20 mL methanol (from Step A) was added 0.20 mL conc. HCl and the reaction mixture stirred at room temperature for 1 h. Azeotrop with toluene (2×) to remove water. The residue was taken up in acetonitrile/water/MeOH (9:1:1) and purified on the Gilson HPLC eluting with a 0-50% gradient of acetonitrile/water with 0.05% TFA buffer. The fractions containing the product were combined, frozen, and lyophilized to give a white foam (3.3 mg, 71%). m/z (ES) 423 (MH)$^+$. (~5:1 mixture) $^1$HNMR (500 MHz, CD$_3$OD) δ: 7.56 (br d, J=8.2 Hz, 2H), 7.44 (d, 7.8 Hz, 2H), 7.39 (t, J=7.6 Hz, 2H) 7.35-7.32 (m, 0.8H) 7.32-7.29 (m, 0.2H minor isomer), 7.26 (d, J=8.0 Hz, 1.7H), 7.14 (d, J=8.1 Hz, 0.3H minor isomer) 6.67 and 6.66 (br s, 0.2/0.8H, totaling 1H), 4.72 (d, J=8.5 Hz, 1H), 3.80-3.70 (m, 4H) 3.14 (dd, J=6.1, 13.8 Hz, 1H), 2.95 (dd, J=9.1, 13.8 Hz, 1H), 2.08-2.00 (m, 1H), 1.86-1.74 (m, 3H).

Using the Biological Assays described above, the human β3 functional activity of Example 1 was determined to be between 1 to 10 nM.

Example 2

2-(2-Amino-1,3-thiazol-4-yl)-N-[4-({(2S,5R)-[(R)-hydroxy(phenyl)methyl]pyrrolidin yl}methyl)phenyl]acetamide

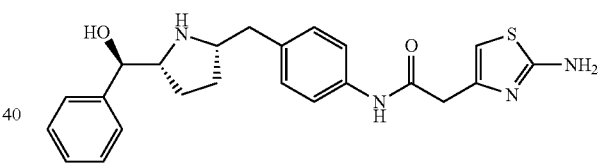

Step A: Tert-butyl (2S,5R)-2-(4-{[(2-amino-1,3-thiazol-4-yl)acetyl]amion}benzyl)-5-[(R)-{[tert-butyl(dimethyl)silyl]oxy}(phenyl)methyl]pyrrolidine-1-carboxylate

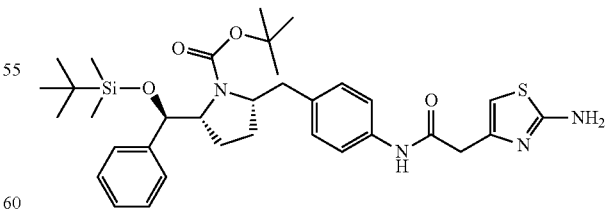

The title compound was prepared from tert-butyl (2S,5R)-2-(4-aminobenzyl)-5-[(R)-{[tert-butyl(dimethyl)silyl]oxy}(phenyl)methyl]pyrrolidine-1-carboxylate (i-4a) and (2-amino-1,3-thiazol-4-yl)acetic acid according to the procedure of Example 1, step A. The crude product was purified by preparative TLC plate eluting with 5% MeOH in dichloromethane to afforded the product (4.1 mg, 21%). m/z (ES) 637 (MH)$^+$, 659 (MNa)$^+$.

Step B: 2-(2-Amino-1,3-thiazol-4-yl)-N-[4-({(2S, 5R)-[(R)hydroxy(phenyl)methyl]pyrrolidinyl}methyl)phenyl]acetamide

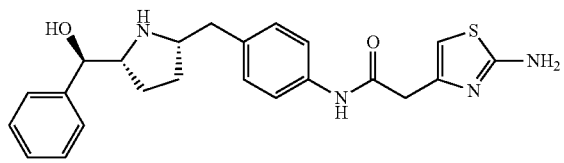 [SMILES: Nc1nc(CC(=O)Nc2ccc(C[C@@H]3CC[C@H]([C@H](O)c4ccccc4)N3)cc2)cs1]

The title compound was prepared from 4 mg of tert-Butyl (2S,5R)-2-(4-{[(2-amino-1,3-thiazol-4-yl)acetyl]amion}benzyl)-5-[(R)-{[tert-butyl(dimethyl)silyl]oxy}(phenyl)methyl]pyrrolidine-1-carboxylate (from Step A) according to the procedure of Example 1, step B. The crude product was purified on the Gilson HPLC eluting with a 0-50% gradient of acetonitrile/water with 0.05% TFA buffer. The fractions containing the product were combined, frozen, and lyophilized to give a white foam (3.3 mg, 71%). m/z (ES) 423 (MH)$^+$. $^1$HNMR (500 MHz, CD$_3$OD) δ: 7.55 (br d, J=8.2 Hz, 2H), 7.44 (d, 7.8 Hz, 2H), 7.39 (t, J=7.6 Hz, 2H) 7.35-7.33 (m, 1H), 7.25 (d, J=8.0 Hz, 2H), 6.65 (br s, 1H). 4.72 (d, J=8.5 Hz, 1H), 3.80-3.72 (m, 4H) 3.14 (dd, J=6.1, 13.8 Hz, 1H), 2.96 (dd, J=9.1, 13.8 Hz, 1H), 2.07-2.00 (m, 1H), 1.85-1.73 (m, 3H).

Using the Biological Assays described above, the human β3 functional activity of Example 2 was determined to be between 1 to 10 nM.

Example 3

2-(2-Amino-1,3-thiazol-4-yl)-N-[4-({(5R)-[(R)-hydroxy(phenyl)methyl]pyrrolidin yl}methyl)phenyl]acetamide

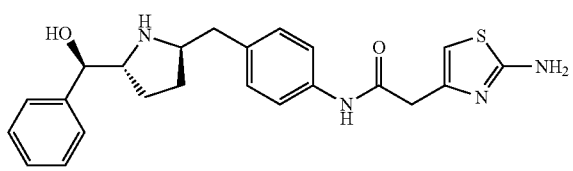 [SMILES: Nc1nc(CC(=O)Nc2ccc(C[C@H]3CC[C@H]([C@H](O)c4ccccc4)N3)cc2)cs1]

Step A: Tert-butyl (2R,5R)-2-(4-{[(2-amino-1,3-thiazol-4-yl)acetyl]amion}benzyl)-5-[(R)-{[tert-butyl(dimethyl)silyl]oxy}(phenyl)methyl]pyrrolidine-1-carboxylate

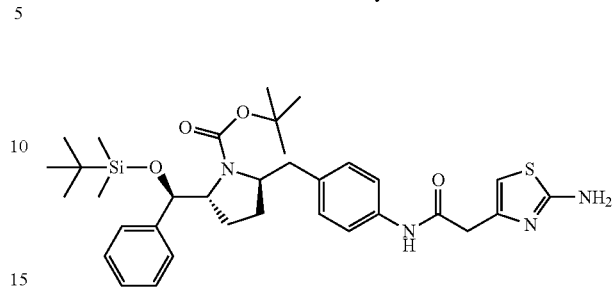

The title compound was prepared from tert-butyl (2R,5R)-2-(4-aminobenzyl)-5-[(R)-{[tert-butyl(dimethyl)silyl]oxy}(phenyl)methyl]pyrrolidine-1-carboxylate (i-4-b) and (2-amino-1,3-thiazol-4-yl)acetic acid according to the procedure of Example 1, step A. The crude product was purified by preparative TLC plate eluting with 5% MeOH in dichloromethane to afforded the product (7.5 mg, 83%). m/z (ES) 637 (MH)$^+$, 659 (MNa)$^+$.

Step B: 2-(2-Amino-1,3-thiazol-4-yl)-N-[4-({(2R, 5R)-[(R)hydroxy(phenyl)methyl]pyrrolidinyl}methyl)phenyl]acetamide

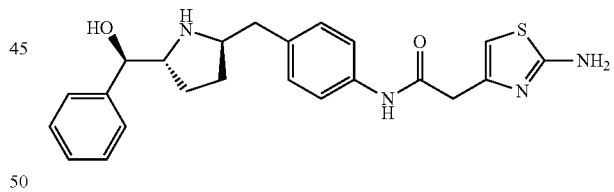

The title compound was prepared from 7 mg of tert-butyl (2R,5R)-2-(4-{[(2-amino-1,3-thiazol-4-yl)acetyl]amion}benzyl)-5-[(R)-{[tert-butyl(dimethyl)silyl]oxy}(phenyl)methyl]pyrrolidine-1-carboxylate (from Step A) according to the procedure of Example 1, step B. The crude product was purified on the Gilson HPLC eluting with a 0-50% gradient of acetonitrile/water with 0.05% TFA buffer. The fractions containing the product were combined, frozen, and lyophilized to give a white foam (4.11 mg, 89%). m/z (ES) 423 (MH)$^+$. δ: 7.56 (br d, J=8.0 Hz, 2H), 7.42 (d, 7.8 Hz, 2H), 7.39 (t, J=7.8 Hz, 2H) 7.32-7.29 (m, 1H), 7.16 (d, J=8.0 Hz, 1H) 6.67 (br s, 1H). 4.70 (d, J=8.5 Hz, 1H), 3.76-3.69 (m, 4H) 3.16 (dd, J=6.3, 13.8 Hz, 1H), 2.94 (dd, J=8.9, 13.8 Hz, 1H), 2.08-2.00 (m, 1H), 1.86-1.74 (m, 3H).

Using the Biological Assays described above, the human β3 functional activity of Example 3 was determined to be between 11 to 100 nM.

Example 4

2-Amino-N-[4-{((2S,5R)-5-[(R)-hydroxy(phenyl) methyl]pyroolidin-2-yl)methyl)phenyl]-5,6-dihydro-4H-cyclopenta[α][1,3]thiazole-4-carboxamide

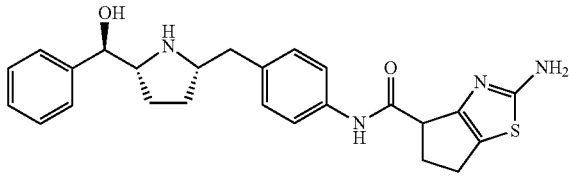 [SMILES: Nc1nc2c(s1)CCC2C(=O)Nc1ccc(C[C@@H]2CC[C@H]([C@H](O)c3ccccc3)N2)cc1]

Step A: Tert-butyl-(2S,5R)-2-(4[({2-[(tert-butoxycarbonyl)amino-]-5,6-dihydro-4H-cyclopenta [α][1,3] thiazol-4-yl}carbonyl)amino]benzyl}-5-[(R)-hydroxy(phenyl)methyl]pyrrolidine-1-carboxylate

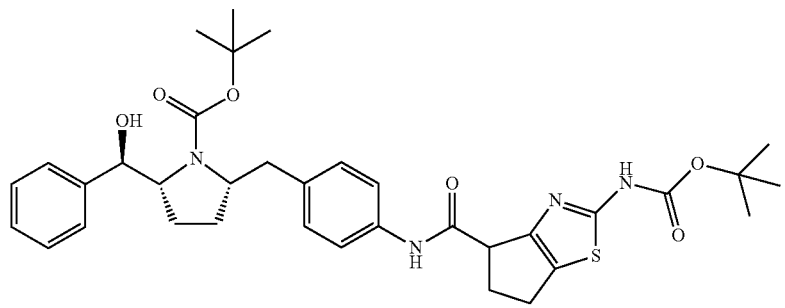 [SMILES: CC(C)(C)OC(=O)Nc1nc2c(s1)CCC2C(=O)Nc1ccc(C[C@@H]2CC[C@H]([C@H](O)c3ccccc3)N2C(=O)OC(C)(C)C)cc1]

To a solution of 220 mg (0.58 mmol) of tert-butyl (2S,5R)-2-(4-aminobenzyl)-5-[(R)-hydroxy(phenyl)methyl]pyrrolidine-1-carboxylate (i-13a) and 164 mg (0.58 mmol) of 2-[(tert-butoxycarbonyl)amino]-5,6-dihydro-4H-cyclopenta[α][1,3]thiazole-4-carboxylic acid (i-8) in anhydrous DMF (5 mL) was added EDC (165 mg, 0.86 mL), HOBt (132 mg, 0.86 mmol) and Hunig's Base (0.3 mL, 1.7 mmol) and the resulting mixture stirred at room temperature overnight. Poured into water (50 mL) and extracted with EtOAc (3×30 mL), combined EtOAc layers washed with water (2×50 mL), sat. NaCl (25 mL), dried over MgSO4, filtered and evaporated. Residue purified by MPLC (Biotage Horizon: FLASH 25+M) eluent: 100% Hexanes (100 mL), gradient 0 to 35% EtOAc in Hexanes (750 mL), then 35% EtOAc in Hexanes (600 mL). Diastereoisomers separated by chiral HPLC on AD column (eluent:25% IPA in Heptane) first eluting isomer (134 mg, 36%) second eluting isomer (126 mg, 34%) both as white foams.

Step B: 2-Amino-N-[4-{((2S,5R)-5-[(R)-hydroxy (phenyl)methyl]pyroolidin-2-yl)methyl)phenyl]-5,6-dihydro-4H-cyclopenta[α][1,3]thiazole-4-carboxamide

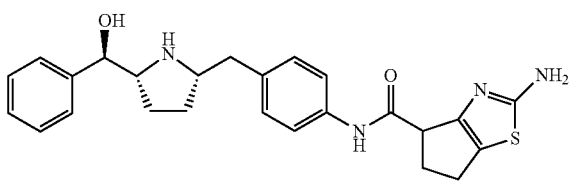 [SMILES: Nc1nc2c(s1)CCC2C(=O)Nc1ccc(C[C@@H]2CC[C@H]([C@H](O)c3ccccc3)N2)cc1]

To a solution of 126 mg (0.19 mmol) of tert-butyl-(2S,5R)-2-(4[({2-[(tert-butoxycarbonyl)amino]-5,6-dihydro-4H-cyclopenta[α][1,3]thiazol-4-yl}carbonyl)amino]benzyl}-5-[(R)-hydroxy(phenyl)methyl]pyrrolidine-1-carboxylate (from step A, second eluting isomer) in DCM (3 mL) was added trifluoroacetic acid (3.0 mL, 38 mmol) the resulting mixture stirred at room temperature for 4 h. The mixture was evaporated and passed through an SCX cartridge eluting with 2 M $NH_3$ in methanol to free up the base. Product purified by PREP-TLC 2×[20×20 cm×1000 micron] eluent: 15% MeOH in DCM+1% $NH_4OH$ and product lyophilized to give (65 mg, 75%) as a white fluffy solid. m/z (ES) 449 $(MH)^+$. $^1$HNMR (500 MHz, DMSO-d6) δ: 10.00 (s, 1H), 7.51 (d, J=8.2, 2H), 7.30 (m, 4H), 7.21 (t, J=6.9, 1H), 7.12 (d, J=8.2, 2H), 6.86 (s, 1H), 4.23 (d, J=7.3, 1H), 3.78 (m, 1H), 3.21 (m, 1H), 3.10 (m, 1H) 2.78 (m, 1H), 2.66 (m, 2H), 2.57 (m, 2H), 2.49 (m, 1H), 1.59 (m, 1H), 1.40 (m, 1H), 1.39 (m, 2H).

Product from step A [first eluting isomer] (134 mg, 0.207 mmol) was deprotected in similar fashion to give (44 mg, 48%) as a white fluffy solid. m/z (ES) 449 $(MH)^+$.

Using the Biological Assays described above, the human β3 functional activity of Example 4 was determined to be less than 1 nM.

Examples 5-96

Using procedures similar to those described above and general knowledge known in the art, the following examples were prepared from the appropriate starting materials.

Using the Biological Assays described above, the human β3 functional activity of each compound was determined and shown in the following table as the following ranges:

less than 1 nM (+);

1-10 nM (++);

11-100 nM (+++);

101-1000 nM (++++); and greater than 1000 nM but less than 3000 nM (+++++).

TABLE 4
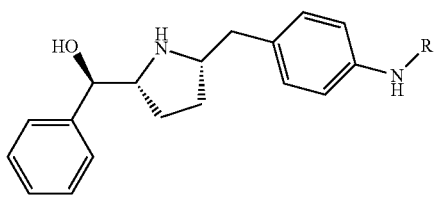
| EXAMPLE NUMBER | R | MW | MS (ES (MH)+) | Human β Binding |
|---|---|---|---|---|
| 5 | benzotriazol-2-yl-CH2-C(O)-C(CH3)2- | 441.52 | 442.54 | ++ |
| 6 | indazol-1-yl-CH2-C(O)-C(CH3)2- | 440.54 | 441.55 | ++ |
| 7 | 2-(pyrrolidin-1-yl)phenyl-C(O)-C(CH3)2- | 455.59 | 456.61 | ++++ |
| 8 | (4-methylthiazol-2-yl)-CH2-C(O)-C(CH3)2- | 421.25 | 422.26 | +++ |
| 9 | (2,4-dimethylthiazol-5-yl)-CH2-C(O)-C(CH3)2- | 435.25 | 436.22 | ++++ |
| 10 | (2,4-dimethylthiazol-5-yl)-CH2-C(O)-C(CH3)2- | 435.25 | 436.23 | ++ |
| 11 | 2-(1,2,3-triazol-2-yl)phenyl-C(O)-C(CH3)2- | 453.55 | 454.49 | +++ |

TABLE 4-continued
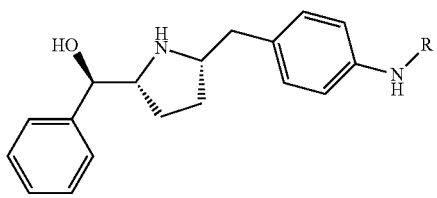
| EXAMPLE NUMBER | R | MW | MS (ES (MH)+ | Human β Binding |
|---|---|---|---|---|
| 12 | 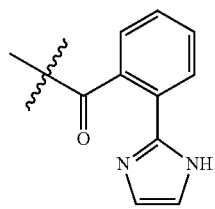 [SMILES: *C(=O)c1ccccc1-c1ncc[nH]1] | 452.56 | 453.52 | +++ |
| 13 | 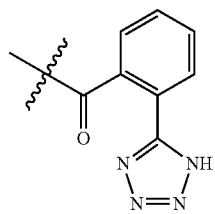 [SMILES: *C(=O)c1ccccc1-c1nnn[nH]1] | 454.54 | 455.51 | +++ |
| 14 | 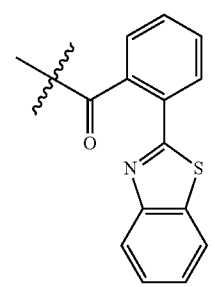 [SMILES: *C(=O)c1ccccc1-c1nc2ccccc2s1] | 519.67 | 520.65 | ++++ |
| 15 | 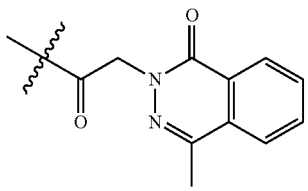 [SMILES: *C(=O)Cn1nc(C)c2ccccc2c1=O] | 482.59 | 483.44 | ++ |
| 16 | 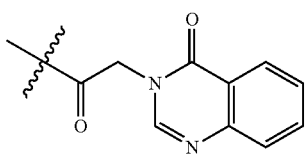 [SMILES: *C(=O)Cn1cnc2ccccc2c1=O] | 468.56 | 469.50 | ++ |
| 17 | 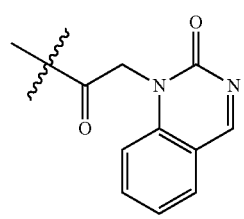 [SMILES: *C(=O)Cn1c(=O)ncc2ccccc21] | 468.56 | 469.51 | ++ |

TABLE 4-continued

| EXAMPLE NUMBER | R | MW | MS (ES (MH)+) | Human β Binding |
|---|---|---|---|---|
| 18 | phthalazinone-benzyl | 558.69 | 559.60 | ++ |
| 19 | 5,6-dimethyl-thieno[2,3-d]pyrimidin-4(3H)-one | 512.64 | 513.60 | ++ |
| 20 | pyridazin-3(2H)-one | 418.49 | 419.24 | ++ |
| 21 | 5-methyl-4H-1,2,4-triazol-3-yl | 405.50 | 406.44 | +++ |
| 22 | 5-phenyl-4H-1,2,4-triazol-3-yl | 467.58 | 468.52 | + |
| 23 | 5-(4-chlorophenyl)-4H-1,2,4-triazol-3-yl | 502.02 | 501.96 (M) 503.94 (M + 2) | +++ |
| 24 | 5-(thiazol-4-yl)-4H-1,2,4-triazol-3-yl | 474.54 | 475.50 | ++ |
| 25 | 5-(pyridin-4-yl)-4H-1,2,4-triazol-3-yl | 468.56 | 469.50 | +++ |

TABLE 4-continued
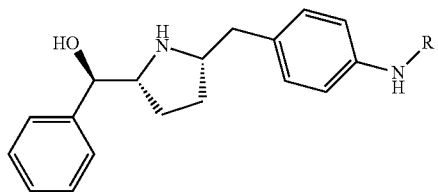
| EXAMPLE NUMBER | R | MW | MS (ES (MH)+) | Human β Binding |
|---|---|---|---|---|
| 26 | 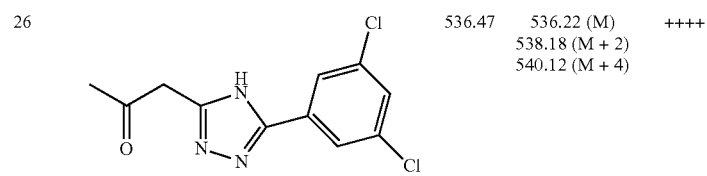 | 536.47 | 536.22 (M)<br>538.18 (M + 2)<br>540.12 (M + 4) | ++++ |
| 27 | 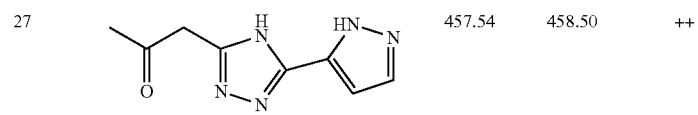 | 457.54 | 458.50 | ++ |
| 28 | 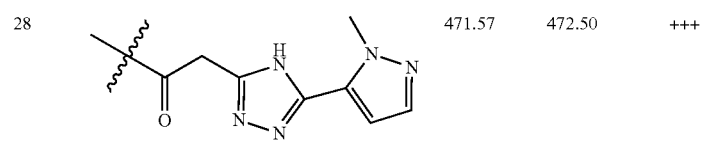 | 471.57 | 472.50 | +++ |
| 29 | 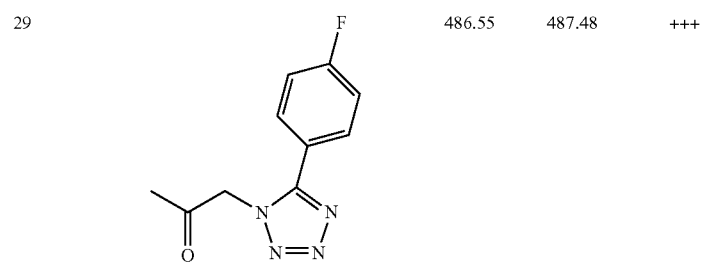 | 486.55 | 487.48 | +++ |
| 30 | 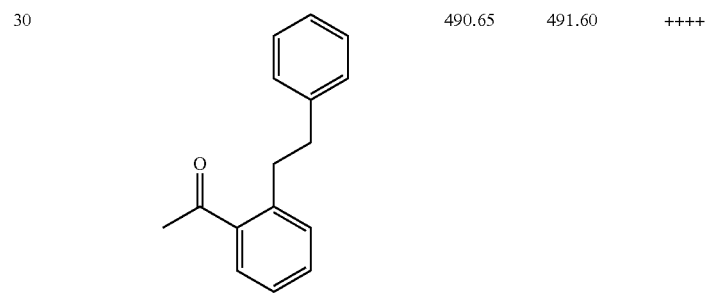 | 490.65 | 491.60 | ++++ |
| 31 | 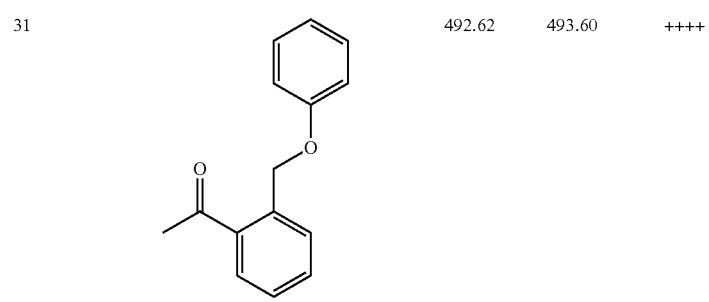 | 492.62 | 493.60 | ++++ |

TABLE 4-continued
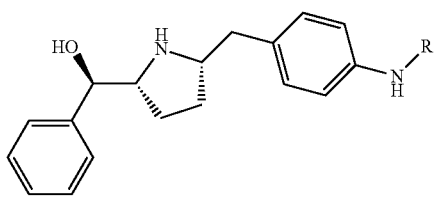
| EXAMPLE NUMBER | R | MW | MS (ES (MH)+) | Human β Binding |
|---|---|---|---|---|
| 32 | | 479.63 | 480.58 | +++ |
| 33 | | 481.60 | 482.54 | +++ |
| 34 | | 467.58 | 468.50 | +++ |
| 35 | | 524.48 | 524.75 (M) 526.55 (M + 2) | +++ |
| 36 | | 485.62 | 486.84 | ++ |

TABLE 4-continued
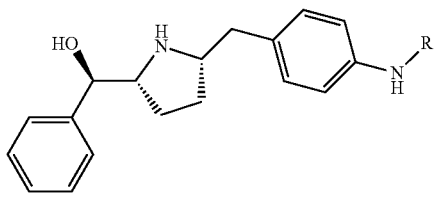
| EXAMPLE NUMBER | R | MW | MS (ES (MH)+) | Human β Binding |
|---|---|---|---|---|
| 37 | 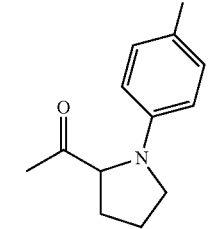 | 490.04 | 490.52 (M) 492.48 (M + 2) | ++++ |
| 38 | 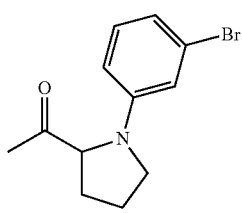 | 534.49 | 534.16 (M) 536.08 (M + 2) | ++ |
| 39 | 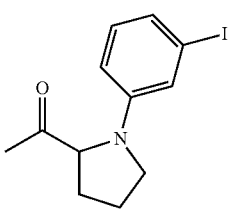 | 581.49 | 582.36 | +++ |
| 40 | 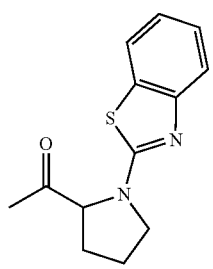 | 512.67 | 513.80 | +++ |
| 41 | 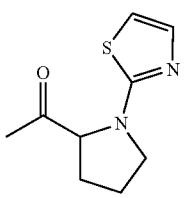 | 462.61 | 463.42 | ++ |

TABLE 4-continued
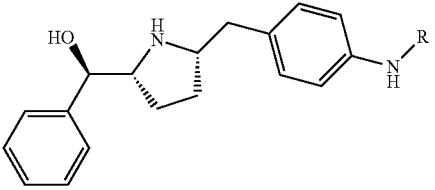
| EXAMPLE NUMBER | R | MW | MS (ES (MH)+) | Human β Binding |
|---|---|---|---|---|
| 42 | 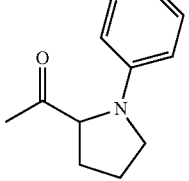 | 534.49 | 534.05 (M) 536.14 (M + 2) | ++++ |
| 43 | 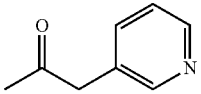 | 401.50 | 402.50 | +++ |
| 44 | 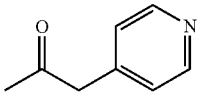 | 401.50 | 402.48 | ++++ |
| 45 | 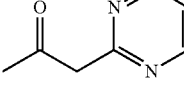 | 401.50 | 402.48 | +++++ |
| 46 | 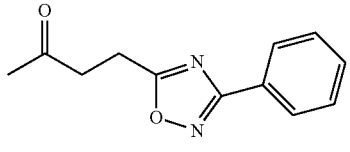 | 402.50 | 403.44 | +++ |
| 47 | 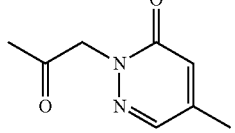 | 482.59 | 483.53 | ++ |
| 48 | 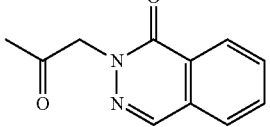 | 432.53 | 433.50 | ++ |
| 49 | 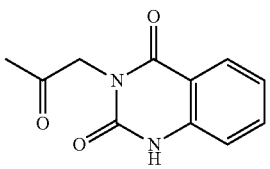 | 468.56 | 469.52 | ++ |
| 50 |  | 484.94 | 485.82 | + |

TABLE 4-continued
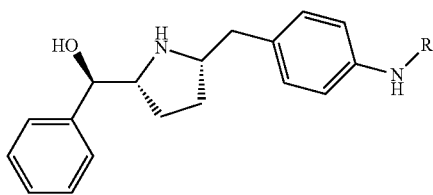
| EXAMPLE NUMBER | R | MW | MS (ES (MH)+ | Human β Binding |
|---|---|---|---|---|
| 51 | 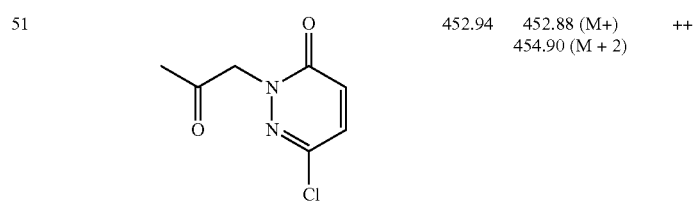 | 452.94 | 452.88 (M+)<br>454.90 (M + 2) | ++ |
| 52 | 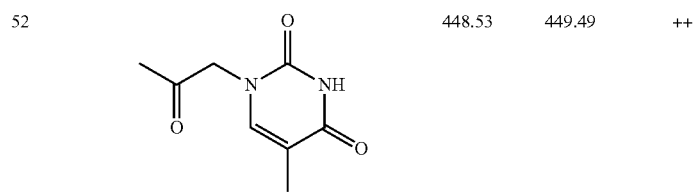 | 448.53 | 449.49 | ++ |
| 53 | 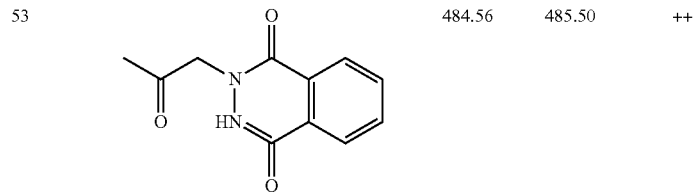 | 484.56 | 485.50 | ++ |
| 54 | 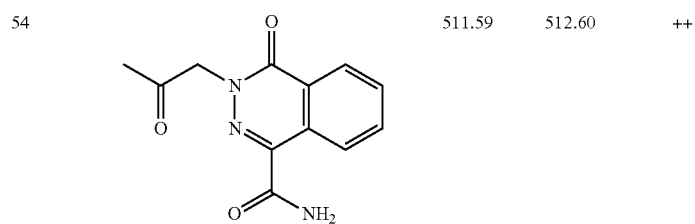 | 511.59 | 512.60 | ++ |
| 55 | 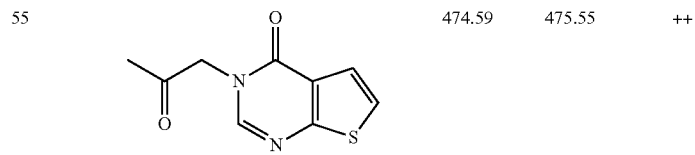 | 474.59 | 475.55 | ++ |
| 56 | 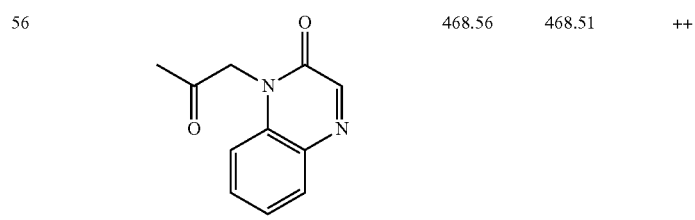 | 468.56 | 468.51 | ++ |

TABLE 4-continued
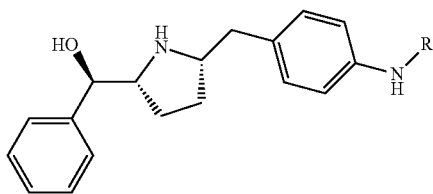
| EXAMPLE NUMBER | R | MW | MS (ES (MH)+) | Human β Binding |
|---|---|---|---|---|
| 57 | | 484.56 | 485.52 | ++ |
| 58 | | 482.59 | 483.60 | ++ |
| 59 | | 469.55 | 470.54 | ++ |
| 60 | | 472.55 | 473.55 | ++ |
| 61 | | 468.56 | 468.51 | ++++ |
| 62 | | 468.56 | 468.50 | ++ |
| 63 | | 434.50 | 435.50 | ++ |

TABLE 4-continued
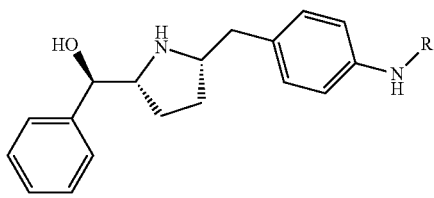
| EXAMPLE NUMBER | R | MW | MS (ES (MH)+) | Human β Binding |
|---|---|---|---|---|
| 64 | ![structure] | 418.50 | 419.48 | ++ |
| 65 | ![structure] | 418.50 | 419.48 | ++ |
| 66 | ![structure] | 418.50 | 419.49 | ++++ |
| 67 | ![structure] | 418.50 | 419.48 | +++ |
| 68 | ![structure] | 407.48 | 408.50 | +++ |
| 69 | ![structure] | 422.49 | 423.47 | ++++ |
| 70 | ![structure] | 418.52 | 419.50 | +++ |
| 71 | ![structure] | 436.51 | 437.48 | ++ |
| 72 | ![structure] | 436.51 | 437.48 | +++ |

TABLE 4-continued
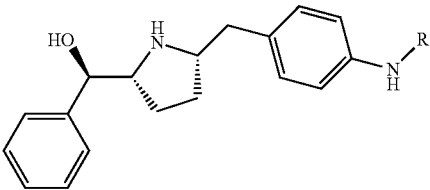
| EXAMPLE NUMBER | R | MW | MS (ES (MH)+ | Human β Binding |
|---|---|---|---|---|
| 73 | 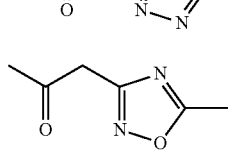 | 391.48 | 392.44 | +++ |
| 74 | 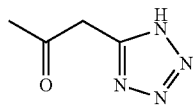 | 406.50 | 407.44 | ++ |
| 75 | 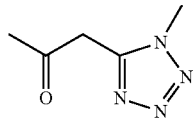 | 392.46 | 393.44 | +++ |
| 76 | 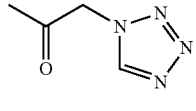 | 406.47 | 407.44 | +++ |
| 77 | 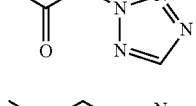 | 392.46 | 393.42 | +++ |
| 78 | 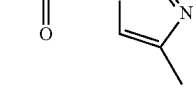 | 392.46 | 393.42 | +++ |
| 79 | 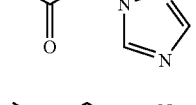 | 405.50 | 406.48 | ++ |
| 80 | 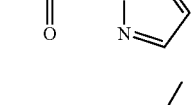 | 391.48 | 392.46 | +++ |
| 81 | 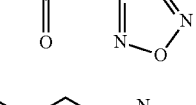 | 391.48 | 392.46 | +++ |
| 82 | 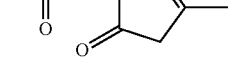 | 406.49 | 407.47 | ++ |
| 83 |  | 420.52 | 421.50 | +++ |

TABLE 4-continued
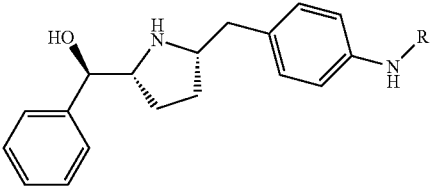
| EXAMPLE NUMBER | R | MW | MS (ES (MH)+ | Human β Binding |
|---|---|---|---|---|
| 84 | 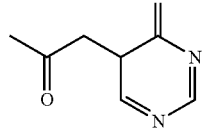 | 418.50 | 419.48 | +++ |
| 85 | 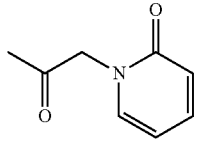 | 421.54 | 422.50 | ++++ |
| 86 | 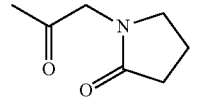 | 417.51 | 418.50 | ++ |
| 87 | 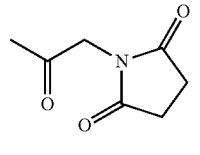 | 407.52 | 408.48 | ++ |
| 88 | 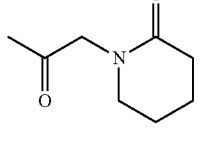 | 421.50 | 421.50 | +++ |
| 89 | 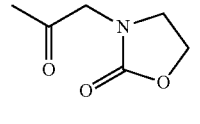 | 421.54 | 422.50 | ++ |
| 90 | 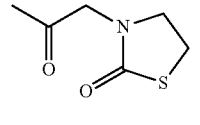 | 409.49 | 410.47 | +++ |
| 91 | 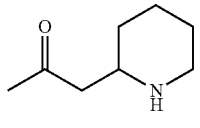 | 425.55 | 426.53 | ++ |
| 92 | 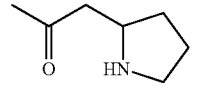 | 393.53 | 394.51 | ++++ |
| 93 | | 379.51 | 380.51 | ++++ |

TABLE 4-continued

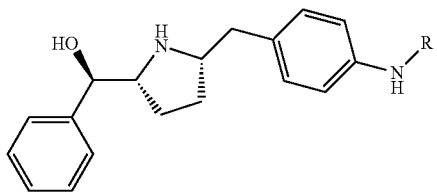

| EXAMPLE NUMBER | R | MW | MS (ES (MH)+) | Human β Binding |
|---|---|---|---|---|
| 94 | | 402.54 | 403.50 | ++ |
| 95 | | 432.53 | 433.51 | +++ |
| 96 | | 428.50 | 429.46 | +++++ |
| 97 | | | | +++++ |
| 98 | | 423.54 | 424.50 | ++ |
| 99 | | 436.38 | 437.40 | +++ |

Example 100

N-(4-(((2S,5R)-5-((R)-hydroxy(phenyl)methyl)pyrrolidin-2-yl)methyl)phenyl)-2-(3-methyl-1H-1,2,4-triazol-1-yl)propanamide

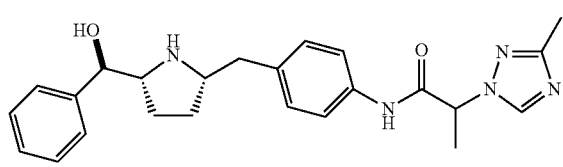 [SMILES: Cc1ncn(C(C)C(=O)Nc2ccc(C[C@@H]3CC[C@H]([C@H](O)c4ccccc4)N3)cc2)n1]

A mixture of i-13a (2.00 g, 5.23 mmol), 2-(3-methyl-1H-1,2,4-triazol-1-yl)propanoic acid i-56 (1.00 g, 5.23 mmol), HOAt (1.307 mL, 0.784 mmol), and EDC (2.005 g, 10.46 mmol) in DMF (20 mL) was stirred at room temperature for 10 min. The reaction mixture was quenched with aqueous sodium bicarbonate and extracted with EtOAc. The crude product was purified by column chromatography (0-3% MeOH (10% NH4OH) in DCM. After evaporation, the product was further purified by chiral HPLC (AD column, 30% IPA./Heptanes) to give the pure boc protected intermediate, which was dissolved in a minimal volume of dioxane and 4 M HCl in dioxane was added. After 2 h at room temperature, the reaction mixture was concentrated under reduced pressure to give the HCl salt of the title compound. Basic reverse phase HPLC (0.1% NH$_4$OH in H$_2$O, MeCN) yielded the desired free base of the title compound. $^1$H-NMR (500 MHz, CD$_3$OD) δ 8.51 (s, 1H), 7.49 (d, J=13 Hz, 2H) 7.35-7.29 (m, 4H), 7.26-7.20 (m, 4H), 5.20 (q, J=7.5 Hz, 1H), 4.20 (d, J=7.5 Hz, 1H), 3.27-3.22 (m, 2H), 2.80-2.72 (m, 2H), 2.34 (s, 3H), 1.82 (d, J=7.5 Hz, 3H), 1.79-173 (m, 1H), 1.52-1.48 (m, 3H). ESI-MS calculated for $C_{24}H_{29}N_5O_2$: Exact Exact Mass: 419.23. found 420.35.

Using the Biological Assays described above, the human β3 functional activity of Example 100 was determined to be between 1 to 10 nM.

Examples 101 and 102

(3S)—N-[4-({(2S,5R)-5-[(R)-hydroxy(phenyl)methyl]pyrrolidin-2-yl}methyl)phenyl]-5-oxo-1,2,3,5-tetrahydroindolizine-3-carboxamide (Example 101) and (3R)—N-[4-({(2S,5R)-5-[(R)-hydroxy(phenyl)methyl]pyrrolidin-2-yl}methyl)phenyl]-5-oxo-1,2,3,5-tetrahydro indolizine-3-carboxamide (Example 102)

Example 101

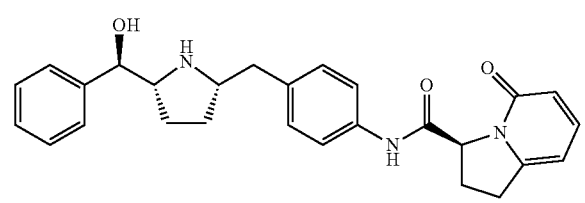

Example 102

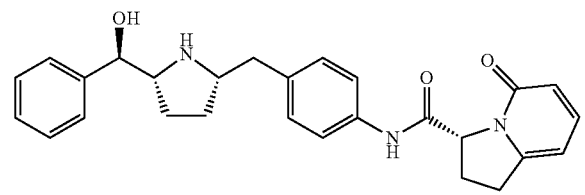

Step A: Tert-butyl (2R,5S)-2-[(R)-hydroxy(phenyl)methyl]-5-[4-({[(3S)-5-oxo-1,2,3,5-tetrahydroindolizin-3-yl]carbonyl}amino)benzyl]pyrrolidine-1-carboxylate (isomer 1) and tert-butyl (2R,5S)-2-[(R)-hydroxy(phenyl)methyl]-5-[4-({[(3R)-5-oxo-1,2,3,5-tetrahydroindolizin-3-yl]carbonyl}amino)benzyl]pyrrolidine-1-carboxylate (isomer 2)

Isomer 1

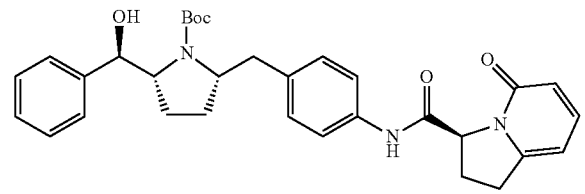

Isomer 2

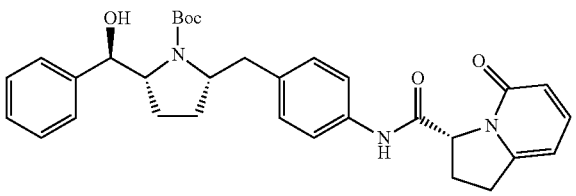

To a solution of 0.610 g (1.60 mmol) of Intermediate i-13a and 0.300 g (1.67 mmol) of Intermediate i-46 in 3.2 mL of anhydrous N,N-dimethylformamide under an atmosphere of nitrogen was added 0.033 g (0.24 mmol) of 1-hydroxy-7-azabenzotriazole followed by 0.336 g (1.75 mmol) of 1-(3-dimethylaminopropyl)-3-ethylcarbodiimide hydrochloride. The resulting suspension was stirred at ambient temperature for 30 min, quenched with water, and extracted with ethyl acetate (3×10 mL). The combined organic layers were washed with brine, dried over magnesium sulfate, filtered and evaporated in vacuo. The crude residue was purified by silica gel chromatography eluting with a 50-100% gradient of ethyl acetate in hexanes to afford the title compounds as a mixture of diastereomers in a 97:3 ratio. The two diastereomers were separated by chiral HPLC employing a Daicel CHIRAL-PAK® AD® column (eluent: 40% IPA in Heptane). The first eluting diastereomer was designated as Isomer 2 and is a colorless solid (0.020 g, 2.3%). LC-MS: m/z (ES) 544.2 (MH)⁺. The second eluting diastereomer was designated as Isomer 1 and is a colorless solid (0.650 g, 75%). LC-MS: m/z (ES) 544.2 (MH)⁺.

Step B (Ex. 101): (3S)—N-[4-({(2S,5R)-5-[(R)-hydroxy(phenyl)methyl]pyrrolidin-2-yl}methyl)phenyl]-5-oxo-1,2,3,5-tetrahydroindolizine-3-carboxamide Example 101

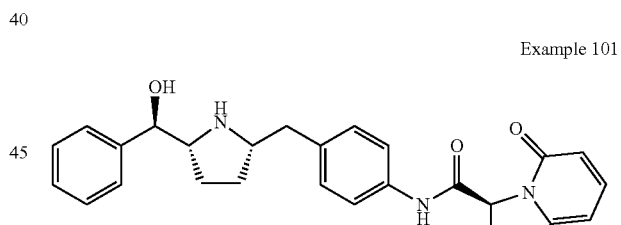

A solution of 0.500 g (0.920 mmol) of Isomer 1 from step A above in 2 mL of isopropanol under an atmosphere of nitrogen was added 4.0 mL of a 4.0 M solution of anhydrous hydrogen chloride in 1,4-dioxane. The reaction mixture was stirred for 1 h and then evaporated to dryness in vacuo. The crude reaction mixture was purified by reverse phase HPLC (TMC Pro-Pac C18; 0-75% 0.01% trifluoroacetic acid in acetonitrile/0.01% trifluoroacetic acid in water gradient). The pure fractions were lyophilized overnight then dissolved in a mixture of 10 mL of chloroform and 4 mL of a saturated aqueous bicarbonate solution. The biphasic mixture was stirred vigorously for 10 min, then the layers were separated. The aqueous phase was extracted with chloroform (3×10 mL) and the combined organic layers were washed with brine, dried over magnesium sulfate, filtered and evaporated in vacuo to afford the title compound (Example 101) as a white solid (0.39 g, 95%). ¹H-NMR (500 MHz, CD₃OD) δ 7.89 (s, 1H), 7.54 (dd, J=8.8, 7.2 Hz, 1H), 7.50 (d, J=8.2 Hz, 2H), 7.34-7.29 (m, 4H), 7.26-7.23 (m, 1H), 7.20 (d, J=8.2 Hz, 2H), 6.38-3.36 (m, 2H), 5.24 (dd, J=9.4, 2.8 Hz, 1H), 4.20 (d, J=7.8 Hz, 1H), 3.35-3.23 (m, 3H), 3.19-3.12 (m, 1H), 2.82-2.71 (m, 2H), 2.60-2.51 (m, 1H), 2.37-2.32 (m, 1H), 1.79-1.72 (m, 1H), 1.52-1.43 (m, 3H). LC-MS: m/z (ES) 444.0 (MH)+.

Step B (Ex. 102): (3R)—N-[4-({(2S,5R)-5-[(R)-hydroxy(phenyl)methyl]pyrrolidin-2-yl}methyl)phenyl]-5-oxo-1,2,3,5-tetrahydroindolizine-3-carboxamide Example 102

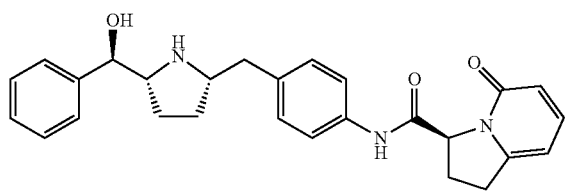

The same procedure was employed for the deprotection of Isomer 2 from step A above to afford the title compound (Example 102) as a single diastereomer. LC-MS: m/z (ES) 444.0 (MH)+.

Using the Biological Assays described above, the human β3 functional activity of Examples 101 and 102 were determined to be between 1 to 10 nM and less than 1 nM, respectively.

Example 103

(6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-α]pyrimidine-6-carboxamide

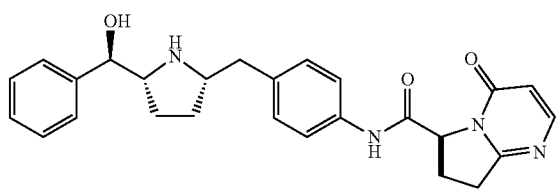 [SMILES: O=C(Nc1ccc(C[C@@H]2CC[C@H]([C@H](O)c3ccccc3)N2)cc1)[C@@H]1CCc2nccc(=O)n21]

Step A: tert-butyl(2R,5S)-2-[(R)-hydroxy(phenyl)methyl]-5-[4-({[(6S)-4-oxo-4,6,7,8-tetrahydropyrrolo[1,2-a]pyrimidin-6-yl]carbonyl}amino)benzyl]pyrrolidine-1-carboxylate

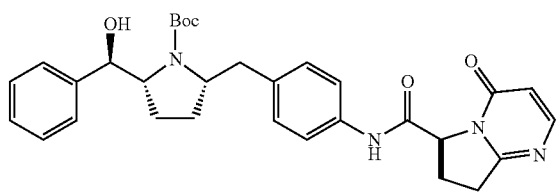 [SMILES: CC(C)(C)OC(=O)N1[C@H](Cc2ccc(NC(=O)[C@@H]3CCc4nccc(=O)n43)cc2)CC[C@@H]1[C@H](O)c1ccccc1]

To a solution of i-13a (21.4 g, 55.9 mmol) in N,N-dimethylformamide (100 ml) at 0° C. was added [(6S)-4-oxo-4,6,7, 8-tetrahydropyrrolo[1,2-α]pyrimidine-6-carboxylic acid (11.1 g, 61.5 mmol), followed by 1-hydroxybenzotriazole (i-44, 7.55 g, 55.9 mmol), N-(3-dimethylaminopropyl)-N-ethylcarbodiimide hydrochloride (16.1 g, 84.0 mmol) and N,N-diisopropylethylamine (29.2 ml, 168 mmol). The reaction mixture was stirred from 0° C. to ambient temperature for 2 h. Water (600 ml) was added and it was extracted with dichloromethane (600 ml×2). The combined organic layers were dried over Na$_2$SO$_4$. After removal of the volatiles, the residue was purified by using a Biotage Horizon® system (0-5% then 5% methanol with 10% ammonia/dichloromethane mixture) to afford the title compound which contained 8% of the minor diastereomer. It was further purified by supercritical fluid chromatography (chiral AS column, 40% methanol) to afford the title compound as a pale yellow solid (22.0 g, 72%). $^1$H NMR (CDCl$_3$): δ 9.61 (s, 1H), 7.93 (d, J=6.6 Hz, 1H), 7.49 (d, J=8.4 Hz, 2H), 7.35-7.28 (m, 5H), 7.13 (d, J=8.5 Hz, 2H), 6.40 (d, J=6.7 Hz, 1H), 5.36 (d, J=8.6 Hz, 1H), 4.38 (m, 1H), 4.12-4.04 (m, 2H), 3.46 (m, 1H), 3.15-3.06 (m, 2H), 2.91 (dd, J=13.1, 9.0 Hz, 1H), 2.55 (m, 1H), 2.38 (m, 1H), 1.71-1.49 (m, 13H). LC-MS 567.4 (M+23).

Step B: (6S)—N-[4-({(2S,5R)-5-[(R)-hydroxy(phenyl)methyl]pyrrolidin-2-yl}methyl)phenyl]-4-oxo-4,6,7,8-tetrahydropyrrolo[1,2-α]pyrimidine-6-carboxamide

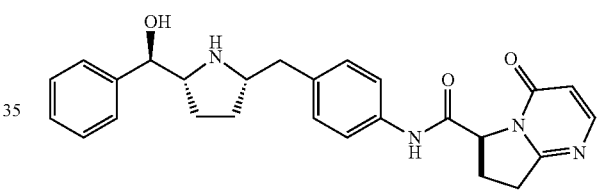

To a solution of the intermediate from Step A (2.50 g, 4.59 mmol) in dichloromethane (40 ml) was added trifluoroacetic acid (15 ml). The reaction mixture was stirred at ambient temperature for 1.5 h. After removal of the volatiles, saturated NaHCO$_3$ was added to make the PH value to 8-9. The mixture was then extracted with dichloromethane. The combined organic layers were dried over Na$_2$SO$_4$. After concentration, crystallization from methanol/acetonitrile afforded the title compound as a white solid (1.23 g, 60%). $^1$H NMR (DMSO-d$_6$): δ 10.40 (s, 1H), 7.91 (d, J=6.7 Hz, 1H), 7.49 (d, J=8.3 Hz, 2H), 7.32-7.26 (m, 4H), 7.21 (m, 1H), 7.15 (d, J=8.4 Hz, 2H), 6.23 (d, J=6.7 Hz, 1H), 5.11 (dd, J=9.6, 2.9 Hz, 1H), 5.10 (br, 1H), 4.21 (d, J=7.1 Hz, 1H), 3.20-3.00 (m, 4H), 2.66-2.51 (m, 3H), 2.16 (m, 1H), 1.57 (m, 1H), 1.38 (m, 1H), 1.29-1.23 (m, 2H). LC-MS 445.3 (M+1).

Using the Biological Assays described above, the human β3 functional activity of Example 103 was determined to be between 11 to 100 nM.

Examples 104-224

Using procedures similar to those described above and general knowledge known in the art, the following examples were prepared from the appropriate starting materials. Diastereomers were separated by chiral HPLC using the methods as described below.

Method A: Diastereoisomers separated by HPLC using a ChiralPAK AD column, eluting with solvent mixtures of IPA, acetonitrile or ethanol in either heptane or hexanes, with first eluting isomer labeled as isomer 1 and second eluting labeled isomer 2.

Method B: Diastereoisomers separated by HPLC using a ChiralCEL OD column, eluting with solvent mixtures of IPA, acetonitrile or ethanol in either heptane or hexanes, with first eluting isomer labeled as isomer 1 and second eluting labeled isomer 2.

Method C: Diastereoisomers separated by HPLC using a Pirkle (R,R)—WHELK-O column, eluting with solvent mixtures of IPA, acetonitrile or ethanol in either heptane or hexanes, with first eluting isomer labeled as isomer 1 and second eluting labeled isomer 2.

Method D: Diastereoisomers separated by HPLC using Daicel CHIRALCEL® OJ® column, eluting with solvent mixtures of IPA or ethanol in either heptane or hexanes, with first eluting isomer labeled as isomer 1 and second eluting labeled isomer 2.

Method E: Diastereoisomers separated by HPLC using Daicel CHIRALPAK® AS® column eluting, with solvent mixtures of IPA or ethanol in either heptane or hexanes, with first eluting isomer labeled as isomer 1 and second eluting labeled isomer 2.

Using the Biological Assays described above, the human β3 functional activity of each compound was determined and shown in the following table as the following ranges:

less than 1 nM (+);
1-10 nM (++);
11-100 nM (+++);
101-1000 nM (++++); and
greater than 1000 nM but less than 3000 nM (+++++).

TABLE 5

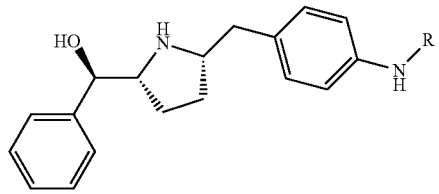

| EXAMPLE NUMBER | R | MW | MS (ES) (MH)+ | CHIRAL COLUMN | Human β3 Functional |
|---|---|---|---|---|---|
| 104 | ![structure with NH2-thiazole] | 436.58 | 437.50 | A | + |
| 105 | ![structure with NH2-thiazole] | 436.58 | 437.80 | A | + |
| 106 | ![indane ketone] Isomer 1 | 426.56 | 427.50 | C | +++ |
| 107 | ![indane ketone] Isomer 2 | 426.56 | 427.50 | C | ++++ |

TABLE 5-continued
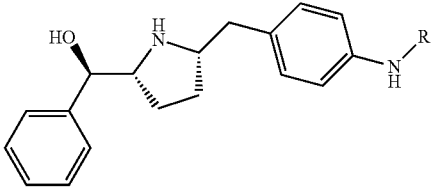
| EXAMPLE NUMBER | R | MW | MS (ES) (MH)+ | CHIRAL COLUMN | Human β3 Functional |
|---|---|---|---|---|---|
| 108 | 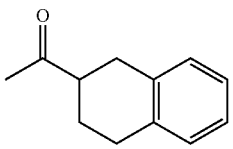<br>Isomer 1 | 440.59 | 441.50 | A | ++++ |
| 109 | 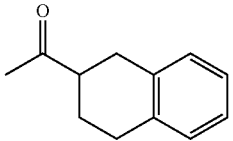<br>Isomer 2 | 440.59 | 441.50 | A | +++++ |
| 110 | 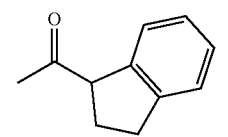<br>Isomer 1 | 426.56 | 427.50 | C | +++ |
| 111 | 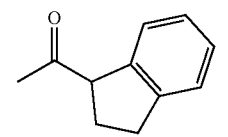<br>Isomer 2 | 426.56 | 427.50 | C | ++++ |
| 112 | 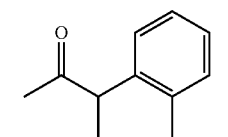<br>Isomer 1 | 440.59 | 441.50 | C | +++ |
| 113 | 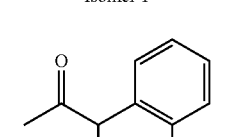<br>Isomer 2 | 440.59 | 441.50 | C | ++++ |
| 114 | 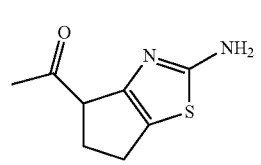<br>Isomer 1 | 448.59 | 449.50 | A | ++ |

TABLE 5-continued

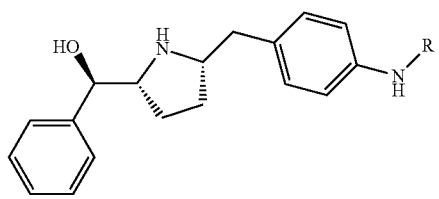

| EXAMPLE NUMBER | R | MW | MS (ES) (MH)+ | CHIRAL COLUMN | Human β3 Functional |
|---|---|---|---|---|---|
| 115 | (acetyl-2-amino-5,6-dihydro-4H-cyclopenta[d]thiazole) Isomer 2 | 448.59 | 449.50 | A | + |
| 116 | (acetyl-2-amino-4,5,6,7-tetrahydrobenzothiazole) Isomer 1 | 462.62 | 463.60 | A | ++ |
| 117 | (acetyl-2-amino-4,5,6,7-tetrahydrobenzothiazole) Isomer 2 | 462.62 | 463.60 | A | + |
| 118 | (acetyl-2-methyl-5,6-dihydro-4H-cyclopenta[d]thiazole) Isomer 1 | 447.60 | 448.60 | A | ++ |
| 119 | (acetyl-2-methyl-5,6-dihydro-4H-cyclopenta[d]thiazole) Isomer 2 | 447.60 | 448.60 | A | + |
| 120 | (acetyl-2-methyl-4,5,6,7-tetrahydrobenzothiazole) Isomer 1 | 461.63 | 462.60 | A | +++ |

TABLE 5-continued

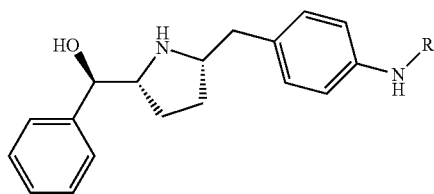

| EXAMPLE NUMBER | R | MW | MS (ES) (MH)+ | CHIRAL COLUMN | Human β3 Functional |
|---|---|---|---|---|---|
| 121 | 2-methyl-4,5,6,7-tetrahydrobenzothiazol-4-yl acetyl, Isomer 2 | 461.63 | 462.60 | A | ++ |
| 122 | 2-(4-fluorophenyl)-5,6-dihydro-4H-cyclopenta[d]thiazol-6-yl acetyl, Isomer 1 | 527.67 | 528.60 | A | ++++ |
| 123 | 2-(4-fluorophenyl)-5,6-dihydro-4H-cyclopenta[d]thiazol-6-yl acetyl, Isomer 2 | 527.67 | 528.60 | A | ++++ |
| 124 | 3-methyl-6,7-dihydro-5H-pyrrolo[2,1-c][1,2,4]triazol-7-yl acetyl, Isomer 1 | 431.54 | 432.50 | C | ++ |
| 125 | 3-methyl-6,7-dihydro-5H-pyrrolo[2,1-c][1,2,4]triazol-7-yl acetyl, Isomer 2 | 431.54 | 432.50 | C | ++ |
| 126 | 3-methyl-6,7-dihydro-5H-pyrrolo[2,1-c][1,2,4]triazol-5-yl acetyl, Isomer 1 | 431.54 | 432.50 | C | +++ |

TABLE 5-continued
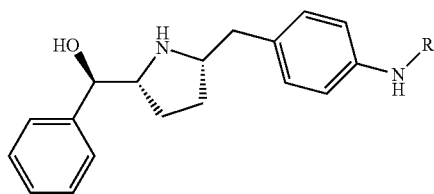
| EXAMPLE NUMBER | R | MW | MS (ES) (MH)+ | CHIRAL COLUMN | Human β₃ Functional |
|---|---|---|---|---|---|
| 127 | Isomer 2 | 431.54 | 432.50 | C | ++++ |
| 128 | Isomer 1 | 417.48 | 418.46 | C | +++ |
| 129 | Isomer 2 | 417.48 | 418.45 | C | +++ |
| 130 | Isomer 1 | 418.50 | 419.48 | B | ++ |
| 131 | Isomer 2 | 418.50 | 419.48 | B | ++ |
| 132 | Isomer 1 | 427.55 | 428.50 | A | + |
| 133 | Isomer 2 | 427.55 | 428.51 | A | + |

TABLE 5-continued

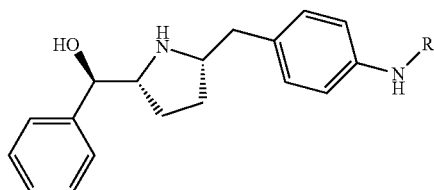

| EXAMPLE NUMBER | R | MW | MS (ES) (MH)+ | CHIRAL COLUMN | Human β₃ Functional |
|---|---|---|---|---|---|
| 134 | (acetyl-dihydrocyclopenta[b]pyridin-2(1H)-one) Isomer 1 | 443.55 | 444.53 | A | ++++ |
| 135 | (acetyl-dihydrocyclopenta[b]pyridin-2(1H)-one) Isomer 2 | 443.55 | 444.53 | A | ++++ |
| 136 | (acetyl-dihydrocyclopenta[c]pyrazole) Isomer 1 | 416.48 | 417.40 | A | +++ |
| 137 | (acetyl-dihydrocyclopenta[c]pyrazole) Isomer 2 | 416.48 | 417.40 | A | +++ |
| 138 | (acetyl-methyl-dihydrocyclopenta[c]pyrazole) Isomer 1 | 430.56 | 431.50 | A | +++ |
| 139 | (acetyl-methyl-dihydrocyclopenta[c]pyrazole) Isomer 2 | 430.56 | 431.50 | A | ++ |
| 140 | (acetyl-methyl-dihydrocyclopenta[d]isoxazole) Isomer 1 | 431.54 | 432.52 | A | +++ |

TABLE 5-continued

| EXAMPLE NUMBER | R | MW | MS (ES) (MH)+ | CHIRAL COLUMN | Human β₃ Functional |
|---|---|---|---|---|---|
| 141 | 3-methyl-acetyl-cyclopentaisoxazole, Isomer 2 | 431.54 | 432.52 | A | ++ |
| 142 | acetyl-cyclopenta-thiazole-COOH, Isomer 1 | 477.59 | 461.60 (M − OH) 478.57 | C | ++++ |
| 143 | acetyl-cyclopenta-thiazole-COOH, Isomer 2 | 477.59 | 461.60 (M − OH) 478.57 | C | +++ |
| 144 | acetyl-cyclopenta-thiazole-Br, Isomer 1 | 512.47 | 512.44 (M+) 514.47 (M + 2) | C | ++ |
| 145 | acetyl-cyclopenta-thiazole-Br, Isomer 2 | 512.47 | 512.44 (M+) 514.47 (M + 2) | C | + |
| 146 | acetyl-cyclopenta-thiazole-F, Isomer 1 | 451.57 | 452.53 | C | + |
| 147 | acetyl-cyclopenta-thiazole-F, Isomer 2 | 451.57 | 452.53 | C | + |

TABLE 5-continued

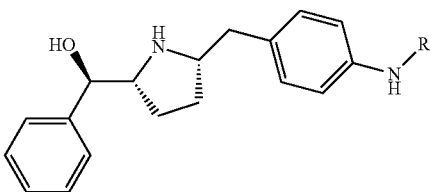

| EXAMPLE NUMBER | R | MW | MS (ES) (MH)+ | CHIRAL COLUMN | Human β3 Functional |
|---|---|---|---|---|---|
| 148 | acetyl-cyclopenta[d]thiazole (isomer) | 433.39 | 434.40 | Made from chiral starting material | + |
| 149 | acetyl-cyclopenta[d]thiazole (isomer) | 433.39 | 434.40 | Made from chiral starting material | +++ |
| 150 | 3-methyl-triazolo-piperidine acetyl, Isomer 1 | 445.57 | 446.55 | C | ++ |
| 151 | 3-methyl-triazolo-piperidine acetyl, Isomer 2 | 445.57 | 446.55 | C | ++ |
| 152 | tetrazolo-piperidine acetyl, Isomer 1 | 432.53 | 433.50 | B | +++ |
| 153 | tetrazolo-piperidine acetyl, Isomer 2 | 432.53 | 433.50 | B | +++ |
| 154 | imidazo-piperidine acetyl, Isomer 1 | 430.56 | 431.50 | A | +++++ |

TABLE 5-continued

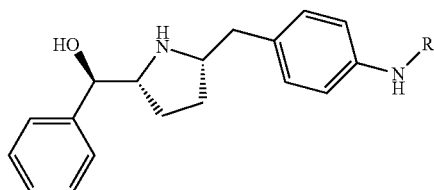

| EXAMPLE NUMBER | R | MW | MS (ES) (MH)+ | CHIRAL COLUMN | Human β3 Functional |
|---|---|---|---|---|---|
| 155 | (acetyl-imidazo[1,2-a]pyridine tetrahydro) Isomer 2 | 430.56 | 431.50 | A | ++++ |
| 156 | (acetyl-pyrazolo tetrahydro) Isomer 1 | 430.56 | 431.50 | A | ++ |
| 157 | (acetyl-pyrazolo tetrahydro) Isomer 2 | 430.56 | 431.50 | A | +++ |
| 158 | (pyrimidinone methyl-acetyl) Isomer 1 | 432.53 | 433.50 | A | ++ |
| 159 | (pyrimidinone methyl-acetyl) Isomer 2 | 432.53 | 433.50 | A | ++ |
| 160 | (pyrimidinone methyl-acetyl) Isomer 1 | 432.53 | 433.50 | B | ++ |
| 161 | (pyrimidinone methyl-acetyl) Isomer 2 | 432.53 | 433.50 | B | + |

TABLE 5-continued
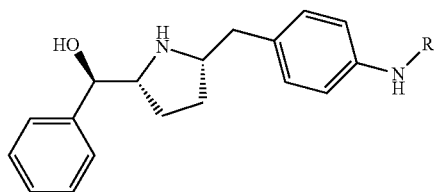
| EXAMPLE NUMBER | R | MW | MS (ES) (MH)+ | CHIRAL COLUMN | Human β₃ Functional |
|---|---|---|---|---|---|
| 162 | Isomer 1 (pyridazinone) | 432.53 | 433.50 | B | ++ |
| 163 | Isomer 2 (pyridazinone) | 432.53 | 433.50 | B | ++ |
| 164 | Isomer 1 (methylpyridazinone) | 446.55 | 447.53 | E | ++ |
| 165 | Isomer 2 (methylpyridazinone) | 446.55 | 447.53 | E | ++ |
| 166 | Isomer 1 (quinazolinone) | 482.53 | 483.50 | D | ++ |
| 167 | Isomer 2 (quinazolinone) | 482.53 | 483.50 | D | + |
| 168 | Isomer 1 (triazole) | 405.50 | 406.46 | C | ++ |

TABLE 5-continued

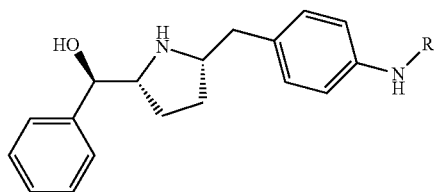

| EXAMPLE NUMBER | R | MW | MS (ES) (MH)+ | CHIRAL COLUMN | Human β3 Functional |
|---|---|---|---|---|---|
| 169 | (1H-1,2,4-triazol-3-yl methyl ketone, Isomer 2) | 405.50 | 406.46 | C | ++ |
| 170 | (methyl-1H-1,2,4-triazolyl methyl ketone, Isomer 1) | 419.52 | 420.46 | C | ++ |
| 171 | (methyl-1H-1,2,4-triazolyl methyl ketone, Isomer 2) | 419.52 | 420.46 | C | ++ |
| 172 | (1H-tetrazol-1-yl methyl ketone, Isomer 1) | 406.50 | 407.50 | C | ++ |
| 173 | (1H-tetrazol-1-yl methyl ketone, Isomer 2) | 406.50 | 407.50 | C | ++ |
| 174 | (N-methyl tetrazolyl methyl ketone, Isomer 1) | 420.52 | 420.50 | C | +++ |
| 175 | (N-methyl tetrazolyl methyl ketone, Isomer 2) | 420.52 | 420.50 | C | ++ |

TABLE 5-continued
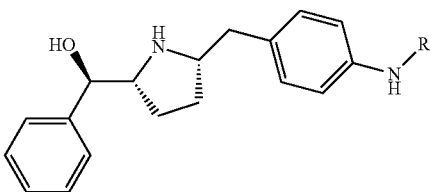
| EXAMPLE NUMBER | R | MW | MS (ES) (MH)+ | CHIRAL COLUMN | Human β₃ Functional |
|---|---|---|---|---|---|
| 176 | Isomer 1 (1,2,4-triazol-1-yl propan-2-one) | 405.50 | 406.46 | A | ++ |
| 177 | Isomer 2 (1,2,4-triazol-1-yl propan-2-one) | 405.50 | 406.46 | A | ++ |
| 178 | Isomer 1 (1,2,3-triazol-2-yl propan-2-one) | 405.50 | 406.46 | A | ++ |
| 179 | Isomer 2 (1,2,3-triazol-2-yl propan-2-one) | 405.50 | 406.46 | A | ++ |
| 180 | Isomer 1 (pyrazol-1-yl propan-2-one) | 404.32 | 405.50 | A | ++ |
| 181 | Isomer 2 (pyrazol-1-yl propan-2-one) | 404.52 | 405.50 | A | ++ |
| 182 | Isomer 1 (1,2,3-triazol-1-yl propan-2-one) | 405.50 | 406.46 | A | +++ |
| 183 | Isomer 2 (1,2,3-triazol-1-yl propan-2-one) | 405.50 | 406.46 | A | ++ |

TABLE 5-continued

| EXAMPLE NUMBER | R | MW | MS (ES) (MH)+ | CHIRAL COLUMN | Human β3 Functional |
|---|---|---|---|---|---|
| 184 | (3-methyl-1H-pyrazol-5-yl, methyl ketone) Isomer 1 | 418.54 | 419.54 | A | +++ |
| 185 | (3-methyl-1H-pyrazol-5-yl, methyl ketone) Isomer 2 | 418.54 | 419.54 | A | ++ |
| 186 | (1-methyl-pyrazol-3-yl, methyl ketone) Isomer 1 | 418.54 | 419.54 | A | ++++ |
| 187 | (1-methyl-pyrazol-3-yl, methyl ketone) Isomer 2 | 418.54 | 419.54 | A | ++ |
| 188 | (triazole-CO2CH3) Isomer 1 | 463.59 | 464.60 | A | ++ |
| 189 | (triazole-CO2CH3) Isomer 2 | 463.59 | 464.60 | A | +++ |
| 190 | (triazole-COOH) Isomer 1 | 449.50 | 433.48 (M − OH) 450.52 | Made chirally from seperated esters above | +++ |

TABLE 5-continued

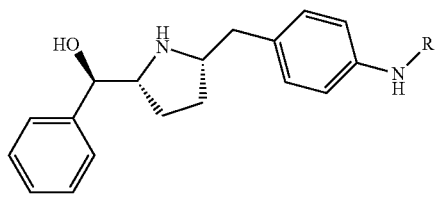

| EXAMPLE NUMBER | R | MW | MS (ES) (MH)+ | CHIRAL COLUMN | Human β3 Functional |
|---|---|---|---|---|---|
| 191 | ![structure] Isomer 2 (triazole-COOH) | 449.50 | 443.48 (M - OH) 450.52 | Made chirally from seperated esters above | +++ |
| 192 | ![structure] Isomer 1 (triazole-CONH2) | 448.59 | 449.60 | Made chirally from seperated esters above | ++ |
| 193 | ![structure] Isomer 2 (triazole-CONH2) | 448.59 | 449.60 | Made chirally from seperated esters above | +++ |
| 194 | ![structure] Isomer 1 (triazole-CO2CH3) | 463.59 | 464.60 | A | +++ |
| 195 | ![structure] Isomer 2 (triazole-CO2CH3) | 463.59 | 464.60 | A | ++ |
| 196 | ![structure] Isomer 1 (triazole-CO2H) | 449.50 | 433.48 (M - OH) 450.52 | Made chirally from seperated esters above | ++ |
| 197 | ![structure] Isomer 2 (triazole-CO2H) | 449.50 | 433.48 (M - OH) 450.52 | Made chirally from seperated esters above | ++ |

TABLE 5-continued

Structure: HO-CH(phenyl)-[pyrrolidine-NH]-CH2-C6H4-NH-R

| EXAMPLE NUMBER | R | MW | MS (ES) (MH)+ | CHIRAL COLUMN | Human β3 Functional |
|---|---|---|---|---|---|
| 198 | [1-(carbamoyl-triazol-1-yl)propan-2-yl]carbonyl, Isomer 1 | 448.59 | 449.60 | Made chirally from seperated esters above | +++ |
| 199 | [1-(carbamoyl-triazol-1-yl)propan-2-yl]carbonyl, Isomer 2 | 448.59 | 449.60 | Made chirally from seperated esters above | ++ |
| 200 | 2-(thiazol-2-yl)propanoyl, Isomer 1 | 421.57 | 422.55 | A | + |
| 201 | 2-(thiazol-2-yl)propanoyl, Isomer 2 | 421.57 | 422.55 | A | ++ |
| 202 | 2-(2-oxopyridin-1-yl)propanoyl, Isomer 1 | 431.54 | 432.50 | A | ++ |
| 203 | 2-(2-oxopyridin-1-yl)propanoyl, Isomer 2 | 431.54 | 432.50 | A | ++ |
| 204 | 2-(pyridin-2-yl)propanoyl, Isomer 1 | 415.54 | 416.50 | A | ++ |

TABLE 5-continued

| EXAMPLE NUMBER | R | MW | MS (ES) (MH)+ | CHIRAL COLUMN | Human β3 Functional |
|---|---|---|---|---|---|
| 205 | (2-pyridyl methyl ketone, Isomer 2) | 415.54 | 416.50 | A | ++ |
| 206 | (pyrazinyl methyl ketone, Isomer 1) | 416.53 | 417.50 | A | ++ |
| 207 | (pyrazinyl methyl ketone, Isomer 2) | 416.53 | 417.50 | A | ++ |
| 208 | (oxazolidinone methyl ketone, Isomer 1) | 423.52 | 424.50 | A | ++ |
| 209 | (oxazolidinone methyl ketone, Isomer 2) | 423.52 | 424.50 | A | +++ |
| 210 | (pyrimidinone methyl ketone, Isomer 1) | 418.50 | 419.47 | A | +++ |
| 211 | (pyrimidinone methyl ketone, Isomer 2) | 418.50 | 419.47 | A | +++ |

TABLE 5-continued
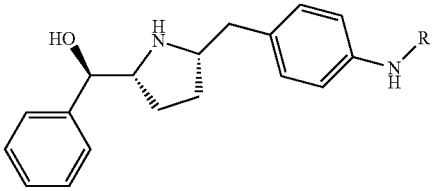
| EXAMPLE NUMBER | R | MW | MS (ES) (MH)+ | CHIRAL COLUMN | Human β₃ Functional |
|---|---|---|---|---|---|
| 212 | 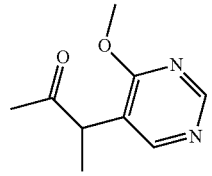<br>Isomer 1 | 446.55 | 447.51 | A | +++ |
| 213 | 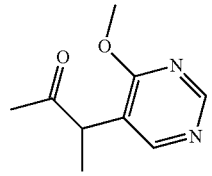<br>Isomer 2 | 446.55 | 447.51 | A | +++ |
| 214 | 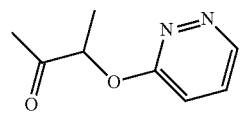<br>Isomer 1 | 432.53 | 433.53 | B | ++++ |
| 215 | 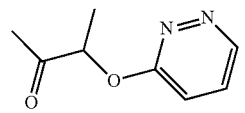<br>Isomer 2 | 432.53 | 433.53 | B | +++ |
| 216 | 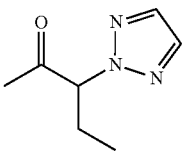<br>Isomer 1 | 419.53 | 420.50 | A | ++ |
| 217 | 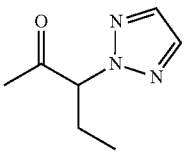<br>Isomer 2 | 419.53 | 420.50 | A | ++ |
| 218 | 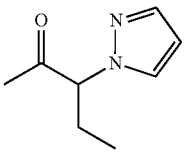<br>Isomer 1 | 418.54 | 419.50 | A | ++ |

TABLE 5-continued
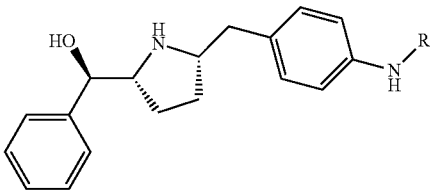
| EXAMPLE NUMBER | R | MW | MS (ES) (MH)+ | CHIRAL COLUMN | Human β₃ Functional |
|---|---|---|---|---|---|
| 219 | (pyrazolyl pentanone) Isomer 2 | 418.54 | 419.50 | A | ++ |
| 220 | (thiazolyl pentanone) Isomer 1 | 418.54 | 419.50 | A | + |
| 221 | (thiazolyl pentanone) Isomer 2 | 418.54 | 419.50 | A | ++ |
| 222 | (2-amino thiazolyl, F-substituted) | 468.60 | 469.56 | C | + |
| 223 | (pyrazolyl, OCH₃) | 448.51 | 449.50 | A | ++ |
| 224 | (pyrazolyl, OCH₃) | 448.51 | 449.50 | A | +++ |

Examples 225-232

Using procedures similar to those described in the above examples and general knowledge known in the art, the following examples were prepared from appropriate starting materials. Diastereomers were separated by chiral HPLC using the methods as described previously.

Using the Biological Assays described above, the human β3 functional activity of each compound was determined and shown in the following table as the following ranges:

11-100 nM (+++);

101-1000 nM (++++); and greater than 1000 nM but less than 3000 nM (+++++).

TABLE 6

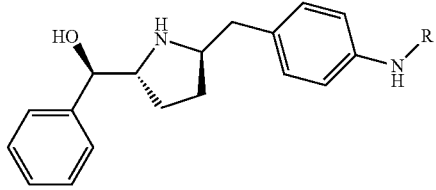

| EXAMPLE NUMBER | R | MW | MS (ES) (MH)+ | CHIRAL COLUMN | Human β3 Functional |
|---|---|---|---|---|---|
| 225 | 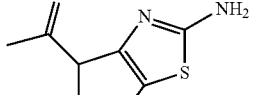<br>Isomer 1 | 448.59 | 449.50 | C | +++ |
| 226 | 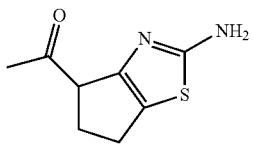<br>Isomer 2 | 448.59 | 449.50 | C | ++++ |
| 227 | 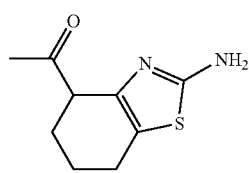<br>Isomer 1 | 462.62 | 463.60 | B | ++++ |
| 228 | 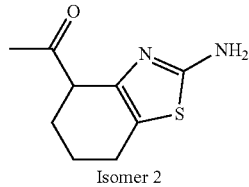<br>Isomer 2 | 462.62 | 463.60 | B | +++++ |
| 229 | 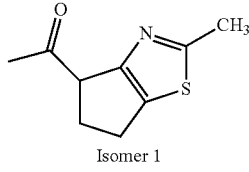<br>Isomer 1 | 447.60 | 448.60 | B | +++ |

TABLE 6-continued
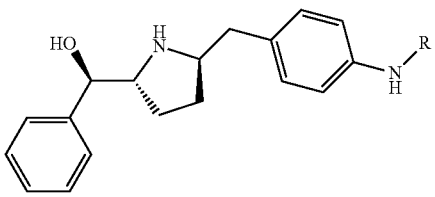
| EXAMPLE NUMBER | R | MW | MS (ES) (MH)+ | CHIRAL COLUMN | Human β₃ Functional |
|---|---|---|---|---|---|
| 230 | 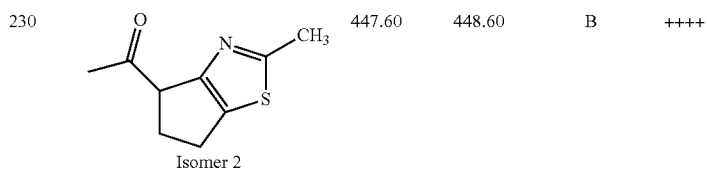<br>Isomer 2 | 447.60 | 448.60 | B | ++++ |
| 231 | 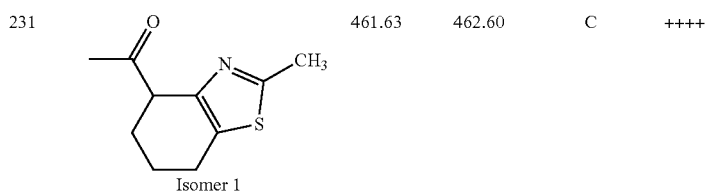<br>Isomer 1 | 461.63 | 462.60 | C | ++++ |
| 232 | 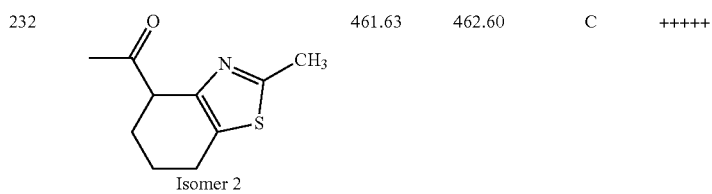<br>Isomer 2 | 461.63 | 462.60 | C | +++++ |
Example 233
N-[4-({(2S,5R)-5-[(R)-hydroxy(phenyl)methyl]pyrrolidin-2-yl}methyl)phenyl]-4-{4-[4-(trifluoromethyl)phenyl]-1,3-thiazol-2-yl}benzenesulfonamide
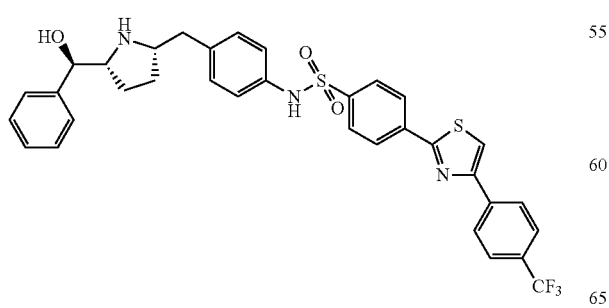

Step A: Tert-butyl (2R,5S)-2-[(R)-{[tert-butyl(dimethyl)silyl]oxy}(phenyl)methyl-5-(4-{(4-{4-[4-(trifluoromethyl)phenyl]-1,3-thiazol-2-yl}phenyl)sulfonyl]amino}benzyl)pyrrolidine-1-carboxylate

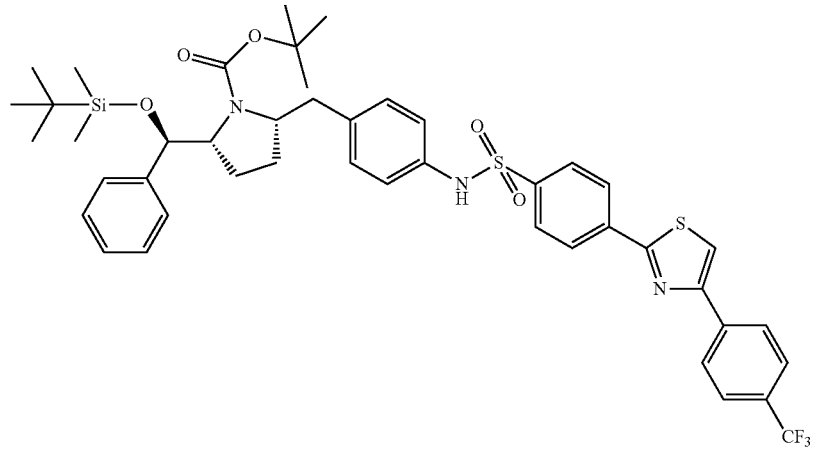 [SMILES: CC(C)(C)OC(=O)N1[C@H](Cc2ccc(NS(=O)(=O)c3ccc(-c4nc(-c5ccc(C(F)(F)F)cc5)cs4)cc3)cc2)CC[C@@H]1[C@H](O[Si](C)(C)C(C)(C)C)c1ccccc1]

To a solution of 10 mg (0.02 mmol) of tert-butyl (2S,5R)-2-(4-aminobenzyl)-5-[(R)-{[tert-butyl(dimethyl)silyl]oxy}(phenyl)methyl]pyrrolidine-1-carboxylate (i-4a) (5:1 mixture cis/trans) in anhydrous DMF was added i-6, (9.4 mg, 0.02 mmol) followed by pyridine (3.2 mg, 0.04 mmol) and the reaction stirred for 1 h at room temperature under nitrogen atmosphere. The reaction was quenched with 1N HCl (0.5 mL) and extracted with dichloromethane (2×2 mL). The dichloromethane layer was dried over magnesium sulfate, filtered and concentrated. Preparative TLC plate (500 uM) purification eluting with 40% ethyl acetate in hexane afforded the product (16.2 mg, 93%). m/z (ES) 865 (MH)+, 765 (M-Boc)+.

Step B: N-[4-({(2S,5R)-5-[(R)-hydroxy(phenyl)methyl]pyrrolidin-2-yl}methyl)phenyl]-4-{4-[4-(trifluoromethyl)phenyl]-1,3-thiazol-2-yl}benzenesulfonamide

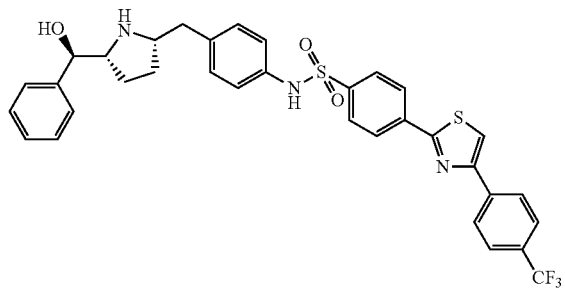 [SMILES: O=S(=O)(Nc1ccc(C[C@@H]2CC[C@H]([C@H](O)c3ccccc3)N2)cc1)c1ccc(-c2nc(-c3ccc(C(F)(F)F)cc3)cs2)cc1]

To a solution of 16 mg (0.02 mmol) of tert-butyl (2R,5S)-2-[(R)-{[tert-butyl(dimethyl)silyl]oxy}(phenyl)methyl-5-(4-{[(4-{4-[4-(trifluoromethyl)phenyl]-1,3-thiazol-2-yl}phenyl)sulfonyl]amino}benzyl)pyrrolidine-1-carboxylate (from Step A) in 0.25 mL methanol was added 0.25 mL conc. HCl and the reaction mixture stirred at room temperature for 30 min. Azeotrop with toluene (2×) to remove water. The residue was taken up in acetonitrile/water/MeOH (9:1:1) and purified on the Gilson HPLC eluting with a 0-50% gradient of acetonitrile/water with 0.05% TFA buffer. The fractions containing the product were combined, frozen, and lyophilized to give a white foam (7.3 mg, 61%). m/z (ES) 650 (MH)+. $^1$HNMR (500 MHz, CD$_3$OD) δ: 8.22 (br d, J=7.8 Hz, 2H), 8.15-8.10 (m, 3H), 7.86 (d, J=7.8 Hz, 2H), 7.72 (d, J=7.8 Hz, 2H), 7.38-7.30 (m, 4H), 7.16 (br d, J=7.8 Hz, 2H), 7.09 (br d, J=7.8 Hz, 2H), 4.56 (d, J=8.1 Hz, 1H), 3.54-3.45 (m, 2H), 2.93 (dd, J=6.4, 13.0 Hz, 1H), 2.82 (dd, J=7.7, 13.0 Hz, 1H), 1.90-1.82 (m, 1H), 1.68-1.53 (m, 3H).

Using the Biological Assays described above, the human β3 functional activity of Example 233 was determined to be between 1 to 10 nM.

Example 234

N-[4-({(2R,5R)-5-[(R)-hydroxy(phenyl)methyl]pyrrolidin-2-yl}methyl)phenyl]-4-{4-[4-(trifluoromethyl)phenyl]-1,3-thiazol-2-yl}benzenesulfonamide

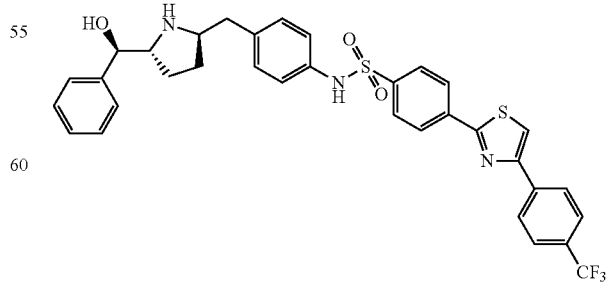

Step A: Tert-butyl (2R,5R)-2-[(R)-{[tert-butyl(dimethyl)silyl]oxy}(phenyl)methyl-5-(4-{[(4-{4-[4-(trifluoromethyl)phenyl]-1,3-thiazol-2-yl}phenyl)sulfonyl]-amino}benzyl)pyrrolidine-1-carboxylate

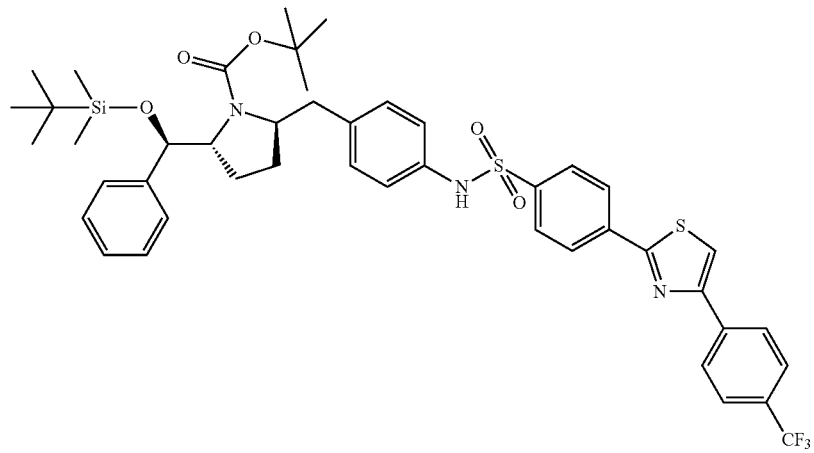 [SMILES: CC(C)(C)OC(=O)N1[C@@H](Cc2ccc(NS(=O)(=O)c3ccc(-c4nc(-c5ccc(C(F)(F)F)cc5)cs4)cc3)cc2)CC[C@@H]1[C@H](O[Si](C)(C)C(C)(C)C)c1ccccc1]

The title compound was prepared from tert-butyl (2R,5R)-2-(4-aminobenzyl)-5-[(R)-{[tert-butyl(dimethyl)silyl]oxy}(phenyl)methyl]pyrrolidine-1-carboxylate (i-4-b) and 4-{4-[4-(trifluoromethyl)phenyl]-1,3-thiazol-2-yl}benzenesulfonyl chloride (i-6) according to the procedure of Example 212, step A. The crude product was purified by preparative TLC plate eluting with 40% ethyl acetate in hexane to afforded the product (8.1 mg, 81%). m/z (ES) 865 (MH)$^+$, 765 (M-Boc)$^+$.

Step B: N-[4-({(2R,5R)-5-[(R)-hydroxy(phenyl)methyl]pyrrolidin-2-yl}methyl)phenyl]-4-{4-[4-(trifluoromethyl)phenyl]-1,3-thiazol-2-yl}benzenesulfonamide

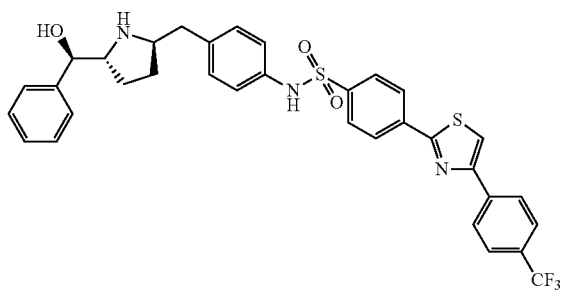 [SMILES: O=S(=O)(Nc1ccc(C[C@H]2CC[C@H]([C@H](O)c3ccccc3)N2)cc1)c1ccc(-c2nc(-c3ccc(C(F)(F)F)cc3)cs2)cc1]

The title compound was prepared from 8 mg of tert-butyl (2R,5R)-2-[(R)-{[tert-butyl(dimethyl)silyl]oxy}(phenyl) methyl-5-(4-{[(4-{4-[4-(trifluoromethyl)phenyl]-1,3-thiazol-2-yl}phenyl)sulfonyl]amino}benzyl)pyrrolidine-1-carboxylate (from Step A) according to the procedure of Example 233, step B. The crude product was purified on the Gilson HPLC eluting with a 0-50% gradient of acetonitrile/water with 0.05% TFA buffer. The fractions containing the product were combined, frozen, and lyophilized to give a white foam (6.3 mg, 71%). $^1$HNMR (500 MHz, CD$_3$OD) δ: 8.20 (br d, J=7.7 Hz, 2H), 8.16-8.10 (m, 3H), 7.88 (d, J=7.7 Hz, 2H), 7.70 (d, J=7.6 Hz, 2H), 7.30-7.25 (m, 4H), 7.14 (br d, J=7.7 Hz, 2H), 7.10 (br d, J=7.6 Hz, 2H), 4.58 (d, J=8.0 Hz, 1H), 3.55-3.44 (m, 2H), 2.90 (dd, J=5.9, 12.4 Hz, 1H), 2.81 (dd, J=7.6, 12.6 Hz, 1H), 1.88-1.83 (m, 1H), 1.69-1.52 (m, 3H).

Using the Biological Assays described above, the human β3 functional activity of Example 234 was determined to be between 11 to 100 nM.

Examples 235-250

Using procedures similar to those described above and general knowledge known in the art, the following examples were prepared from the appropriate starting materials.

Using the Biological Assays (β$_3$AR-cAMP) as described above, the human β3 functional activity of each compound was determined and shown in the following table as the following ranges:

11-100 nM (+++);

101-1000 nM (++++); and greater than 1000 nM but less than 3000 nM (+++++).

TABLE 7
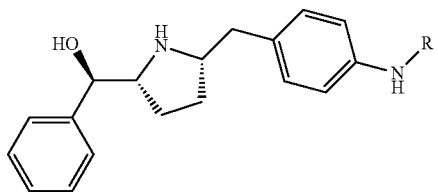
| EXAMPLE NUMBER | R | MW | MS (ES) (MH)+ | Human β₃ Functional |
|---|---|---|---|---|
| 235 | methylsulfonyl-naphthalene | 472.60 | 473.60 | ++++ |
| 236 | methylsulfonyl-isoquinoline | 473.60 | 474.60 | +++++ |
| 237 | methylsulfonyl-quinoline (8-) | 473.60 | 474.60 | ++++ |
| 238 | methylsulfonyl-quinoline (5-) | 473.60 | 474.60 | ++++ |
| 239 | methylsulfonyl-benzothiazole | 479.60 | 480.60 | +++ |
| 240 | (methylsulfonyl)phenyl-pyrazole | 488.61 | 489.60 | ++++ |
| 241 | (methylsulfonyl)phenyl-oxazole | 489.60 | 490.60 | +++ |

TABLE 7-continued
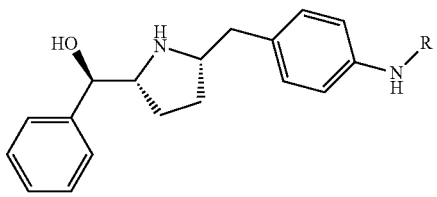
| EXAMPLE NUMBER | R | MW | MS (ES) (MH)+ | Human β₃ Functional |
|---|---|---|---|---|
| 242 | | 504.60 | 505.60 | ++++ |
| 243 | | 514.60 | 515.60 | ++++ |
| 244 | | 515.66 | 516.62 | ++++ |
| 245 | | 558.55 | 558.49 | +++ |
| 246 | | 426.54 | 427.48 | ++++ |
| 247 | | 475.03 | 474.98 (M) 477.01 (M + 2) | +++++ |
| 248 | | 437.57 | 438.50 | ++++ |
| 249 | | 437.57 | 438.50 | +++++ |

TABLE 7-continued

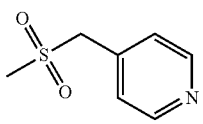

| EXAMPLE NUMBER | R | MW | MS (ES) (MH)+ | Human β3 Functional |
|---|---|---|---|---|
| 250 | (methylsulfonylmethyl-pyridin-4-yl) | 437.50 | 438.50 | ++++ |

Example 251

N-[4-({(2S,5R)-5-[(R)-hydroxy(phenyl)methyl]pyrrolidin-2-yl}methyl)phenyl]-N'-(3-methoxyphenyl)urea

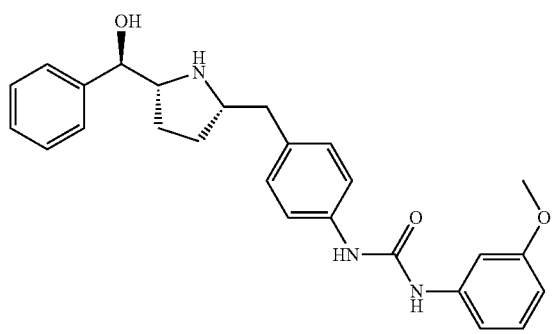 [SMILES: COc1cccc(NC(=O)Nc2ccc(C[C@@H]3CC[C@H]([C@H](O)c4ccccc4)N3)cc2)c1]

Step A: N-[4-({(2S,5R)-5-[(R)-hydroxy(phenyl)methyl]pyrrolidin-2-yl}methyl)phenyl]-N'-(3-methoxyphenyl)urea To a solution of 30 mg (0.078 mmol) of tert-butyl (2S,5R)-2-(4-aminobenzyl)-5-[(R)-hydroxy(phenyl)methyl]pyrrolidine-1-carboxylate (i-13a) in $CH_2Cl_2$ (0.5 mL) was added 14 mg (0.094 mmol) of 1-isocyanato-3-methoxybenzene. The reaction mixture was stirred at ambient temperature for 2.5 h. It was then added TFA (0.4 mL) and was stirred at ambient temperature for another 3 h. After removal of the volatiles, it was purified by reverse-phase HPLC (TMC Pro-Pac C18; 10-80% 0.1% trifluoroacetic acid in acetonitrile/0.1% trifluoroacetic acid in water gradient). The pure fractions were lyophilized overnight to give the title compound as a white solid. LC/MS 432.3 (M+1).

Using the Biological Assays described above, the human β3 functional activity of Example 251 was determined to be between 11 to 100 nM.

Examples 252-262

Using procedures similar to those described above and general knowledge known in the art, the following examples were prepared from the appropriate starting materials.

Using the Biological Assays described above, the human β3 functional activity of each compound was determined and shown in the following table as the following ranges:

1-10 nM (++);
11-100 nM (+++); and
101-1000 nM (++++).

TABLE 8

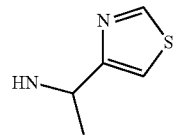

| EXAMPLE NUMBER | R | MW | MS (ES) (MH)+ | Human β3 Functional |
|---|---|---|---|---|
| 252 | 1-(thiazol-4-yl)ethylamino | 436.58 | 437.56 | ++++ |

TABLE 8-continued
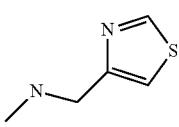
| EXAMPLE NUMBER | R | MW | MS (ES) (MH)+ | Human β3 Functional |
|---|---|---|---|---|
| 253 | 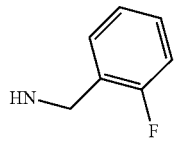 | 436.58 | 437.54 | +++ |
| 254 | 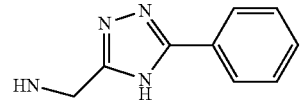 | 433.53 | 434.53 | ++++ |
| 255 | 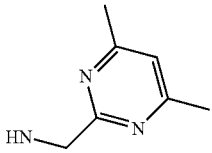 | 482.55 | 483.60 | ++ |
| 256 | 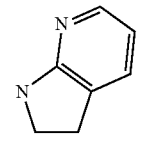 | 445.52 | 446.50 | +++ |
| 257 | 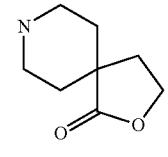 | 428.59 | 429.60 | ++++ |
| 258 | 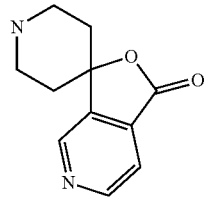 | 463.60 | 464.60 | ++++ |
| 259 | 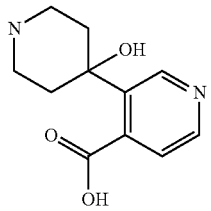 | 512.63 | 513.60 | ++++ |
| 260 |  | 529.60 | 530.60 | +++ |

TABLE 8-continued

| EXAMPLE NUMBER | R | MW | MS (ES) (MH)+ | Human β₃ Functional |
|---|---|---|---|---|
| 261 | | 656.68 | 657.70 | +++ |
| 262 | | 639.66 | 640.70 | ++ |

Example 263

2-Fluoro-N-((1S)-2-{[4-({(2S,5R)-5-[(R)-hydroxy(phenyl)methyl]pyrrolidin-2-yl}methyl)phenyl]amino}-1-methyl-2-oxoethyl)benzamide Step A: Tert-butyl (2S,5R)-2-[4-({(2S)-2-[(2-fluorobenzoyl)amino]propanoyl}amino)benzyl]-5-[(R)-hydroxy(phenyl)methyl]pyrrolidine-1-carboxylate, trifluoroacetic acid salt

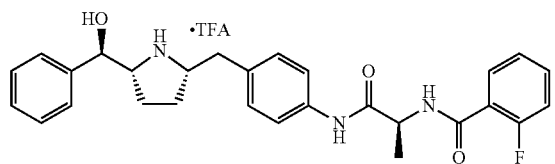 [SMILES: C[C@H](NC(=O)c1ccccc1F)C(=O)Nc1ccc(C[C@@H]2CC[C@H]([C@H](O)c3ccccc3)N2)cc1]

To a solution of 0.090 g (0.20 mmol) of intermediate 77 in 2 mL of dichloromethane was added 0.027 mL (0.20 mmol) of triethylamine followed by 0.032 g (0.20 mmol) of commercially available 2-fluorobenzoyl chloride. The resulting mixture was stirred for 1 h then all volatiles were removed in vacuo. The crude reaction mixture was purified by reverse phase HPLC (TMC Pro-Pac C18; 0-90% 0.1% trifluoroacetic acid in acetonitrile/0.1% trifluoroacetic acid in water gradient) and the pure fractions were lyophilized overnight to afford the title compound as a white solid (0.035 g, 30%). LCMS: m/z (ES) 576 (MH)+.

Step B: 2-Fluoro-N-((1S)-2-{[4-({(2S,5R)-5-[(R)-hydroxy(phenyl)methyl]pyrrolidin-2-yl}methyl)phenyl]amino}-1-methyl-2-oxoethyl)benzamide, trifluoracetic acid salt

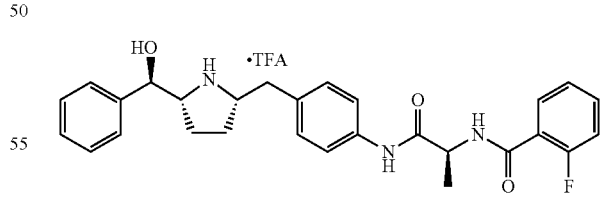

To a stirred solution of 0.033 g (0.057 mmol) of tert-butyl (2S,5R)-2-[4-({(2S)-2-[(2-fluorobenzoyl)amino]propanoyl}amino)benzyl]-5-[(R)-hydroxy(phenyl)methyl]pyrrolidine-1-carboxylate, trifluoroacetic acid salt from step A above in 2.5 mL of dichloromethane was added 0.5 mL of trifluoroacetic acid. The resulting mixture was stirred for 1 h then all volatiles were removed in vacuo. The crude reaction mixture was purified by reverse phase HPLC (TMC Pro-Pac C18; 0-70% 0.1% trifluoroacetic acid in acetonitrile/0.1% trifluoroacetic acid in water gradient) and the pure fractions were lyophilized overnight to afford the title compound as a white solid (0.027 g, 67%). LCMS: m/z (ES) 476 (MH)+.

Using the Biological Assays described above, the human β3 functional activity of Example 263 was determined to be less than 1 nM.

Example 264

(2S)-2-{[(4-Fluorophenyl)sulfonyl]amino}-N-[4-({(2S,5R)-5-[(R)-hydroxy(phenyl)methyl]pyrrolidin-2-yl}methyl)phenyl]propanamide

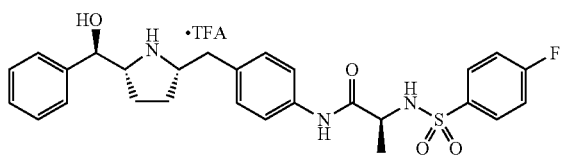 [SMILES: C[C@H](NS(=O)(=O)c1ccc(F)cc1)C(=O)Nc1ccc(C[C@@H]2CC[C@H]([C@H](O)c3ccccc3)N2)cc1]

Step A: Tert-butyl (2S,5R)-2-{4-[((2S)-2-{[(4-fluorophenyl)sulfonyl]amino}propanoyl)amino]benzyl}-5-[(R)-hydroxy(phenyl)methyl]pyrrolidine-1-carboxylate, trifluoroacetic acid salt

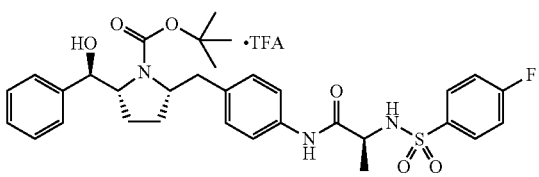 [SMILES: C[C@H](NS(=O)(=O)c1ccc(F)cc1)C(=O)Nc1ccc(C[C@@H]2CC[C@H]([C@H](O)c3ccccc3)N2C(=O)OC(C)(C)C)cc1]

To a solution of 0.085 g (0.19 mmol) of intermediate 77 in 3 mL of dichloromethane was added 0.039 mL (0.28 mmol) of triethylamine followed by 0.036 g (0.19 mmol) of commercially available 4-fluorobenzenesulfonyl chloride. The resulting mixture was stirred for 1 h then all volatiles were removed in vacuo. The crude reaction mixture was purified by reverse phase HPLC (TMC Pro-Pac C18; 0-90% 0.1% trifluoroacetic acid in acetonitrile/0.1% trifluoroacetic acid in water gradient) and the pure fractions were lyophilized overnight to afford the title compound as a white solid (0.047 g, 35%). LCMS: m/z (ES) 612 (MH)+.

Step B: (2S)-2-{[(4-Fluorophenyl)sulfonyl]amino}-N-[4-({(2S,5R)-5-[(R)-hydroxy(phenyl)methyl]pyrrolidin-2-yl}methyl)phenyl]propanamide

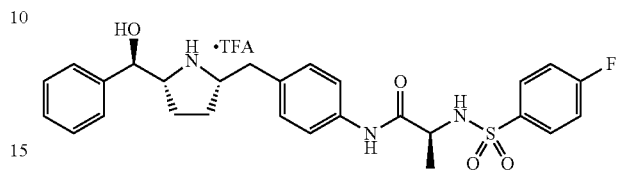

To a stirred solution of 0.047 g (0.065 mmol) of tert-butyl (2S,5R)-2-{4-[((2S)-2-{[(4-fluorophenyl)sulfonyl]amino}propanoyl)amino]benzyl}-5-[(R)-hydroxy(phenyl)methyl]pyrrolidine-1-carboxylate, trifluoroacetic acid salt from step A above in 2.5 mL of dichloromethane was added 0.5 mL of trifluoroacetic acid. The resulting mixture was stirred for 1 h, then all volatiles were removed in vacuo. The crude reaction mixture was purified by reverse phase HPLC (TMC Pro-Pac C18; 0-70% 0.1% trifluoroacetic acid in acetonitrile/0.1% trifluoroacetic acid in water gradient) and the pure fractions were lyophilized overnight to afford the title compound as a white solid (0.030 g, 62%). LCMS: m/z (ES) 512 (MH)+.

Using the Biological Assays described above, the human β3 functional activity of Example 264 was determined between 11 and 100 nM.

Examples 265-273

Using procedures similar to those described above and general knowledge known in the art, the following examples were prepared from the appropriate starting materials.

Using the Biological Assays described above, the human β3 functional activity of each compound was determined and shown in the following table as the following ranges:
less than 1 nM (+);
1-10 nM (++);
11-100 nM (+++); and
101-1000 nM (++++).

TABLE 9

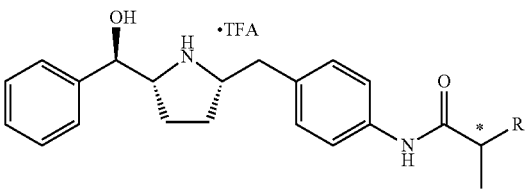

| Example | *Diastereomer | R | MW | MS (MH)+ | Human β3 Functional |
|---------|---------------|---|-----|----------|---------------------|
| 265 | S | 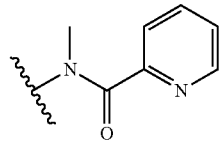 [SMILES: *N(C)C(=O)c1ccccn1] | 472 | 473 | ++++ |

TABLE 9-continued
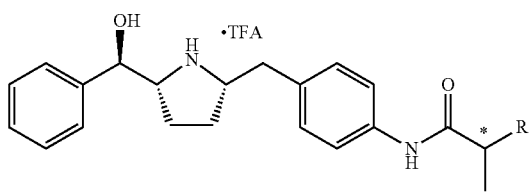
| Example | *Diastereomer | R | MW | MS (MH)+ | Human β3 Functional |
|---|---|---|---|---|---|
| 266 | S | 2-F-C6H4-C(O)-N(CH3)- | 490 | 491 | +++ |
| 267 | S | 2,6-F2-C6H3-C(O)-NH- | 493 | 494 | + |
| 268 | S | pyrimidin-2-yl-C(O)-NH- | 459 | 460 | + |
| 269 | S | pyrazin-2-yl-C(O)-NH- | 459 | 460 | ++ |
| 270 | S | -NH2 | 353 | 354 | +++ |
| 271 | S | 1H-pyrazol-3-yl-C(O)-NH- | 447 | 448 | + |
| 272 | S | C6H5-C(O)-NH- | 457 | 458 | + |
| 273 | S | C6H5-CH2-S(O)2-NH- | 507 | 508 | +++ |

Examples 274 and 275

2-(2-Amino-1,3-thiazol-4-yl)-N-[4-({(5R)-[(R)-hydroxy(3-fluorophenyl)methyl]pyrrolidin yl}methyl)phenyl]acetamide

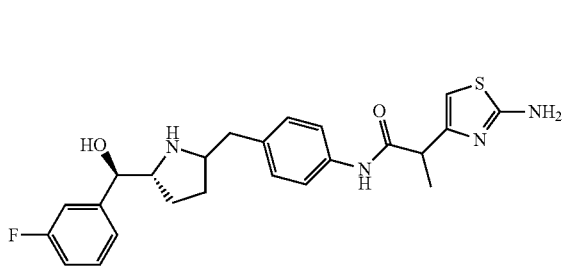

Step A: Tert-butyl (2S,5R)-2-[(R)-{[tert-butyl(dimethyl)silyl]oxy}(3-fluorophenyl)methyl]-5-(4-{[2-(1,3-thiazol-4-yl)propanoyl]amino}benzyl)pyrrolidine-1-carboxylate

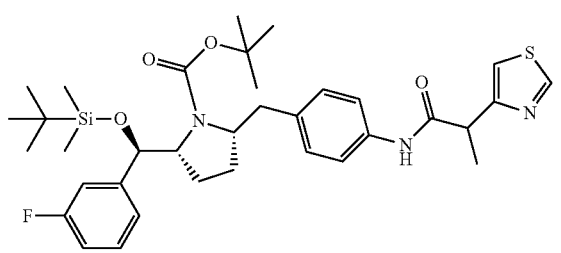 [SMILES: CC(C(=O)Nc1ccc(C[C@@H]2CC[C@H]([C@H](O[Si](C)(C)C(C)(C)C)c3cccc(F)c3)N2C(=O)OC(C)(C)C)cc1)c1cscn1]

To a solution of 50 mg (0.10 mmol) of tert-butyl(5R)-2-(4-aminobenzyl)-5-[(R)-{[tert-butyl(dimethyl)silyl]oxy}(3-fluorophenyl)methyl]pyrrolidine-1-carboxylate (i-4-c) and 2-(1,3-thiazol-4-yl)propanoic acid (15 mg, 0.10 mmol) in 3 mL anhydrous DMF was added a 0.5 M solution of HOAt in DMF (0.2 mL, 0.10 mmol) followed by EDC (25 mg, 0.15 mmol) and DIEA (16.5 µL, 0.1 mmol). The resulting mixture was stirred at room temperature under nitrogen atmosphere for 16 h. The mixture was washed with water and extracted with dichloromethane (2×5 mL). The organics were combined, dried over sodium sulfate, filtered and concentrated in vacuum. The residue was purified by preparative TLC plate (500 uM) eluting with 5% MeOH in dichloromethane to yield the product as a mixture of diastereomers. The two diastereomers were then separated by chiral HPLC employing a Daicel CHIRALPAK® AD® column (eluent: 40% IPA in Heptane). The first eluting diastereomer was designated as Isomer 1 and is a colorless solid. LC-MS: m/z (ES) 655 (MH)⁺, 677 (MNa)⁺. The second eluting diastereomer was designated as Isomer 2 and is also a colorless solid. m/z (ES) 654 (MH)⁺, 676 (MNa)⁺.

Step B: N-[4-({(2S,5R)-5-[(R)-(3-fluorophenyl)(hydroxy)methyl]pyrrolidin-2 yl}methyl)phenyl]-2-(1,3-thiazol-4-yl)propanamide (isomer 1) (Example 274)

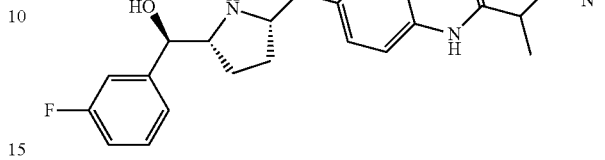

To a solution of 8 mg (0.01 mmol) of tert-butyl (2S,5R)-2-(4-{[2-(2-amino-1,3-thiazol-4-yl)propanoyl]amino}benzyl)-5-[(R)-{[tert-butyl(dimethyl)silyl]oxy}(3-fluorophenyl)methyl]pyrrolidine-1-carboxylate (isomer 1) in 0.20 mL methanol from Step A was added 0.20 mL conc. HCl and the reaction mixture stirred at room temperature for 1 h. Azeotrop with toluene (2×) to remove water. The residue was taken up in acetonitrile/water/MeOH (9:1:1) and purified on the Gilson HPLC eluting with a 0-50% gradient of acetonitrile/water with 0.05% TFA buffer. The fractions containing the product were combined, frozen, and lyophilized to give a white foam (Example 274) (5.1 mg, 88%). m/z (ES) 440 (MH)⁺.

Using the Biological Assays described above, the human β3 functional activity of Example 274 was determined to be between 11 and 100 nM.

Step C: N-[4-({(2S,5R)-5-[(R)-(3-fluorophenyl)(hydroxy)methyl]pyrrolidin-2 yl}methyl)phenyl]-2-(1,3-thiazol-4-yl)propanamide (isomer 1) (Example 275)

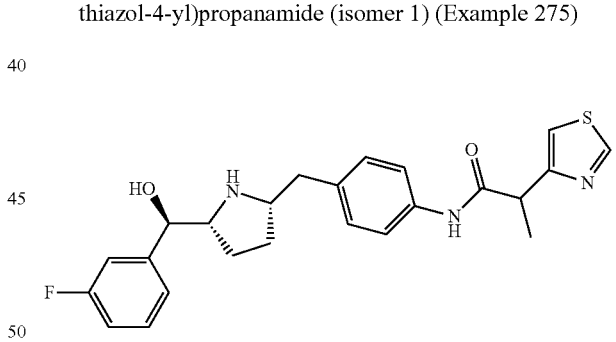

To a solution of 8 mg (0.01 mmol) tert-butyl (2S,5R)-2-(4-{[2-(2-amino-1,3-thiazol-4-yl)propanoyl]amino}benzyl)-5-[(R)-{[tert-butyl(dimethyl)silyl]oxy}(3-fluorophenyl)methyl]pyrrolidine-1-carboxylate (isomer 2) in 0.20 mL methanol from Step A was added 0.20 mL conc. HCl and the reaction mixture stirred at room temperature for 1 h. Azeotrop with toluene (2×) to remove water. The residue was taken up in acetonitrile/water/MeOH (9:1:1) and purified on the Gilson HPLC eluting with a 0-50% gradient of acetonitrile/water with 0.05% TFA buffer. The fractions containing the product were combined, frozen, and lyophilized to give a white foam (Example 275) (4.3 mg, 79%). m/z (ES) 440 (MH)⁺.

Using the Biological Assays described above, the human β3 functional activity of Example 275 was determined to be less than 1 nM.

Examples 276-281

Using procedures similar to those described above and general knowledge known in the art, the following examples were prepared from the appropriate starting materials. Diastereomers were separated by chiral HPLC using the methods as described below.

Method A: Diastereoisomers separated by HPLC using a ChiralPAK AD column, eluting with solvent mixtures of IPA, acetonitrile or ethanol in either heptane or hexanes, with first eluting isomer labeled as isomer 1 and second eluting labeled isomer 2.

Using the Biological Assays ($\beta_3$AR-cAMP) as described above, the human $\beta$3 functional activity of each compound was determined and shown in the following table as the following ranges:

less than 1 nM (+);
1-10 nM (++); and
11-100 nM (+++).

TABLE 10

| EXAMPLE NUMBER | R | MW | MS (ES) (MH)⁺ | Human $\beta_3$ Functional |
|---|---|---|---|---|
| 276 | (2-amino-thiazole fused cyclopentane acetyl), Isomer 1 | 466.39 | 467.50 | +++ |
| 277 | (2-amino-thiazole fused cyclopentane acetyl), Isomer 2 | 466.39 | 467.50 | + |
| 278 | (thiazole fused cyclopentane acetyl) | 451.38 | 452.50 | +++ |
| 279 | (thiazole fused cyclopentane acetyl) | 451.38 | 452.50 | + |
| 280 | (methyl-triazolyl acetyl) | 423.21 | 424.20 | ++ |
| 281 | (pyridazinone acetyl) | 436.19 | 437.20 | ++ |

Examples 282-287

Using procedures similar to those described above and general knowledge known in the art, the following examples were prepared from the appropriate starting materials. Diastereomers were separated by chiral HPLC using the methods as described below.

Method A: Diastereoisomers separated by HPLC using a ChiralPAK AD column, eluting with solvent mixtures of IPA, acetonitrile or ethanol in either heptane or hexanes, with first eluting isomer labeled as isomer 1 and second eluting labeled isomer 2.

Using the Biological Assays described above, the human $\beta$3 functional activity of each compound was determined and shown in the following table as the following ranges:

less than 1 nM (+);
1-10 nM (++); and
11-100 nM (+++).

TABLE 11

| EXAMPLE NUMBER | R | MW | MS (ES) (MH)⁺ | Human $\beta_3$ Functional |
|---|---|---|---|---|
| 282 | (2-amino-thiazole fused cyclopentane acetyl), Isomer 1 | 466.39 | 467.50 | +++ |

TABLE 11-continued

Core structure: 4-fluorophenyl-(hydroxymethyl)-pyrrolidinyl-methyl-phenyl-NHR

| EXAMPLE NUMBER | R | MW | MS (ES) (MH)+ | Human β3 Functional |
|---|---|---|---|---|
| 283 | 2-amino-cyclopenta-thiazole acetyl (Isomer 2) | 466.39 | 467.50 | + |
| 284 | cyclopenta-thiazole acetyl | 451.38 | 452.50 | + |
| 285 | thiazolyl-methyl-ketone (Isomer 1) | 439.39 | 440.40 | +++ |
| 286 | thiazolyl-methyl-ketone | 439.39 | 440.40 | + |
| 287 | pyridazinone-acetyl (Isomer 2) | 436.19 | 437.20 | ++ |

Examples 288-293

Using procedures similar to those described above and general knowledge known in the art, the following examples were prepared from the appropriate starting materials. Diastereomers were separated by chiral HPLC using the methods as described below.

Method A: Diastereoisomers separated by HPLC using a ChiralPAK AD column, eluting with solvent mixtures of IPA, acetonitrile or ethanol in either heptane or hexanes, with first eluting isomer labeled as isomer 1 and second eluting labeled isomer 2.

Using the Biological Assays described above, the human β3 functional activity of each compound was determined and shown in the following table as the following ranges:
less than 1 nM (+); and
11-100 nM (+++).

TABLE 12

| EXAMPLE NUMBER | R | MW | MS (ES) (MH)+ | R¹ | R² | Human β3 Functional |
|---|---|---|---|---|---|---|
| 288 | 2-amino-cyclopenta-thiazole acetyl (Isomer 1) | 484.41 | 485.40 | F | H | +++ |
| 289 | 2-amino-cyclopenta-thiazole acetyl | 484.41 | 485.40 | F | H | + |

TABLE 12-continued

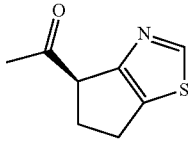

| EXAMPLE NUMBER | R | MW | MS (ES) (MH)+ | R¹ | R² | Human β₃ Functional |
|---|---|---|---|---|---|---|
| | Isomer 2 | | | | | |
| 290 | 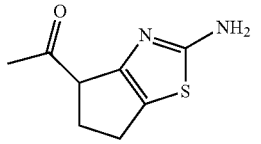 | 469.39 | 470.40 | F | H | + |
| 291 | 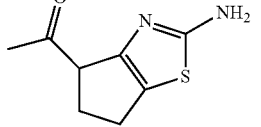 Isomer 1 | 484.41 | 485.40 | H | F | +++ |
| 292 | 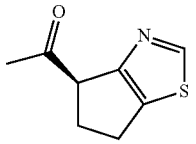 Isomer 2 | 484.41 | 485.40 | H | F | + |
| 293 | | 469.39 | 470.40 | H | F | + |

Examples 294-305

Using procedures similar to those described above and general knowledge known in the art, the following examples were prepared from the appropriate starting materials. Diastereomers were separated by chiral HPLC using the methods as described below.

Method A: Diastereoisomers separated by HPLC using a ChiralPAK AD column, eluting with solvent mixtures of IPA, acetonitrile or ethanol in either heptane or hexanes, with first eluting isomer labeled as isomer 1 and second eluting labeled isomer 2.

Method C: Diastereoisomers separated by HPLC using a Pirkle (R,R)—WHELK-O column, eluting with solvent mixtures of IPA, acetonitrile or ethanol in either heptane or hexanes, with first eluting isomer labeled as isomer 1 and second eluting labeled isomer 2.

Using the Biological Assays described above, the human β3 functional activity of each compound was determined and shown in the following table as the following ranges:

less than 1 nM (+);

1-10 nM (++); and 11-100 nM (+++).

TABLE 13

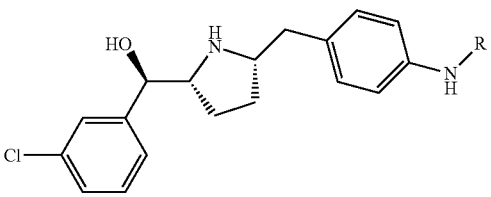

| EXAMPLE NUMBER | R | MW | MS (ES) | Column | Human β$_3$ Functional |
|---|---|---|---|---|---|
| 294 | ![acetyl-2-amino-cyclopentathiazole] Isomer 1 | 482.15 | 482.20 (M)$^+$ 484.20 (M + 2)$^+$ | A | +++ |
| 295 | ![acetyl-2-amino-cyclopentathiazole] Isomer 2 | 482.15 | 482.20 (M)$^+$ 484.20 (M + 2)$^+$ | A | + |
| 296 | ![acetyl-cyclopentathiazole] | 467.14 | 467.10 (M)$^+$ 469.10 (M + 2)$^+$ | Made from chiral starting material | +++ |
| 297 | ![acetyl-cyclopentathiazole] | 467.14 | 467.10 (M)$^+$ 469.10 (M + 2)$^+$ | Made from chiral starting material | + |
| 298 | ![acetyl-2-bromo-cyclopentathiazole] Isomer 1 | 545.05 | 545.00 (M)$^+$ 547.00 (M + 2)$^+$ 549.00 (M + 4)$^+$ | C | + |
| 299 | ![acetyl-2-bromo-cyclopentathiazole] Isomer 2 | 545.05 | 545.00 (M)$^+$ 547.00 (M + 2)$^+$ 549.00 (M + 4)$^+$ | C | +++ |
| 300 | ![acetyl-2-fluoro-cyclopentathiazole] Isomer 1 | 485.13 | 485.10 (M)$^+$ 487.10 (M + 2)$^+$ | C | ++ |
| 301 | ![acetyl-2-fluoro-cyclopentathiazole] Isomer 2 | 485.13 | 485.10 (M)$^+$ 487.10 (M + 2)$^+$ | C | +++ |

TABLE 13-continued

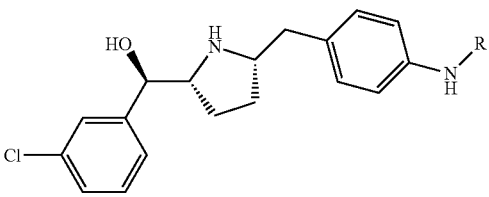

| EXAMPLE NUMBER | R | MW | MS (ES) | Column | Human β₃ Functional |
|---|---|---|---|---|---|
| 302 | 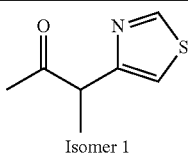<br>Isomer 1 | 455.13 | 455.10 (M)⁺<br>457.10 (M + 2)⁺ | A | ++ |
| 303 | 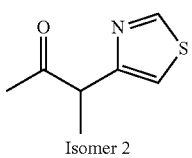<br>Isomer 2 | 455.13 | 455.10 (M)⁺<br>457.10 (M + 2)⁺ | A | +++ |
| 304 | 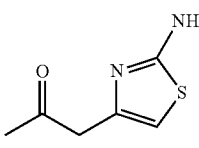 | 456.13 | 456.10 (M)⁺<br>456.10 (M + 2)⁺ | n/a | ++ |
| 305 | 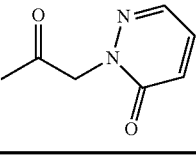 | 452.19 | 452.20 (M)⁺<br>454.20 (M + 2)⁺ | n/a | +++ |

Examples 306-311

Using procedures similar to those described above and general knowledge known in the art, the following examples were prepared from the appropriate starting materials. Diastereomers were separated by chiral HPLC using the methods as described below.

Method A: Diastereoisomers separated by HPLC using a ChiralPAK AD column, eluting with solvent mixtures of IPA, acetonitrile or ethanol in either heptane or hexanes, with first eluting isomer labeled as isomer 1 and second eluting labeled isomer 2.

Using the Biological Assays described above, the human β3 functional activity of each compound was determined and shown in the following table as the following ranges:
less than 1 nM (+);
1-10 nM (++); and
11-100 nM (+++).

TABLE 14

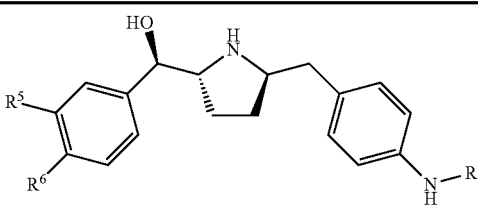

| EXAMPLE NUMBER | R | MW | MS (ES) (MH)⁺ | R⁵ | R⁶ | Human β₃ Functional |
|---|---|---|---|---|---|---|
| 306 | 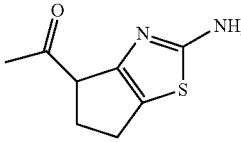 | 466.57 | 467.50 | F | H | + |

TABLE 14-continued
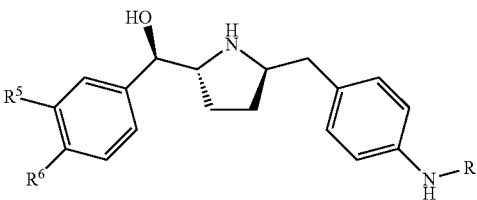
| EXAMPLE NUMBER | R | MW | MS (ES) (MH)+ | R5 | R6 | Human β3 Functional |
|---|---|---|---|---|---|---|
| | Isomer 1 | | | | | |
| 307 | 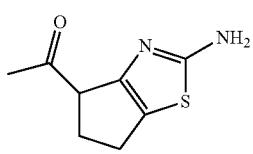<br>Isomer 2 | 466.57 | 467.50 | F | H | +++ |
| 308 | 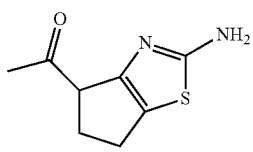<br>Isomer 1 | 466.57 | 467.50 | H | F | ++ |
| 309 | 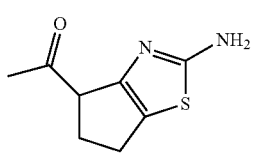<br>Isomer 2 | 466.57 | 467.50 | H | F | +++ |
| 310 | 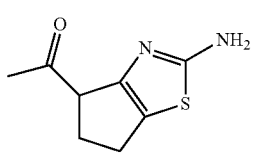<br>Isomer 1 | 482.15 | 482.20 (M)+<br>484.20<br>(M + 2)+ | Cl | H | + |
| 311 | 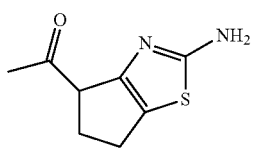<br>Isomer 2 | 482.15 | 482.20 (M)+<br>484.20<br>(M + 2)+ | Cl | H | ++ |

Example 312

2-(2-Amino-1,3-thiazol-4-yl)-N-[2-bromo-4-({(2S, 5R)-5-[(R)-hydroxy(phenyl)methyl]pyrrolidin-2-yl}methyl)phenyl]acetamide

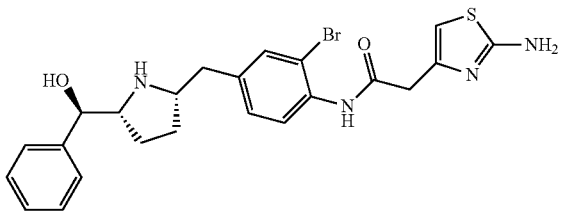 [SMILES: Nc1nc(CC(=O)Nc2ccc(C[C@@H]3CC[C@H]([C@H](O)c4ccccc4)N3)cc2Br)cs1]

Step A: Tert-butyl (2S,5R)-2-(4-{[(2-amino-1,3-thiazol-4-yl)acetyl]amino}-3-bromobenzyl)-5-[(R)-hydroxy(phenyl)methyl]pyrrolidine-1-carboxylate

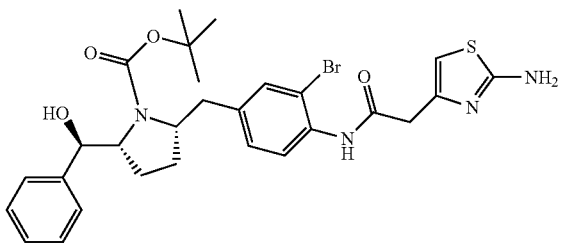 [SMILES: CC(C)(C)OC(=O)N1[C@H](Cc2ccc(NC(=O)Cc3csc(N)n3)c(Br)c2)CC[C@@H]1[C@H](O)c1ccccc1]

To a solution of 115 mg (0.25 mmol) of tert-butyl (2S,5R)-2-(4-amino-3-bromobenzyl)-5-[(R)-hydroxy(phenyl)methyl]pyrrolidine-1-carboxylate (i-80a) and (2-amino-1,3-thiazol-4-yl)acetic acid (77 mg, 0.30 mmol) in 3.0 mL anhydrous DMF was added HOBt (44 mg, 0.32 mmol) followed by EDC (66 mg) and DIEA (0.22 mL, 1.25 mmol). The resulting mixture was stirred at room temperature under nitrogen atmosphere for 16 h. The mixture was washed with water and extracted with dichloromethane (2×2 mL). The organics were combined, dried over sodium sulfate, filtered and concentrated in vacuum. The residue was purified by Gilson reverse phase HPLC eluting with a gradient of 10-90% acetonitrile in water with 0.05% TFA buffer to afforded the product (105 mg, 81%). m/z (ES) 601 (M)$^+$ and 603 (M+2)$^+$, also 623 (MNa)$^+$ and 625 (MNa+2)$^+$.

Step B: 2-(2-Amino-1,3-thiazol-4-yl)-N-[2-bromo-4-({(2S,5R)-5-[(R)-hydroxy(phenyl)methyl]pyrrolidin-2-yl}methyl)phenyl]acetamide

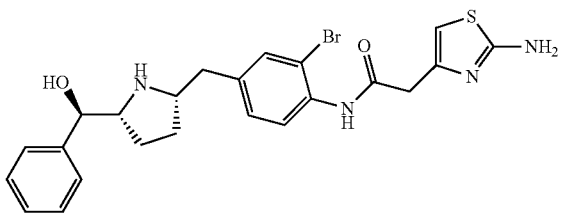 [SMILES: Nc1nc(CC(=O)Nc2ccc(C[C@@H]3CC[C@H]([C@H](O)c4ccccc4)N3)cc2Br)cs1]

To a solution of 105 mg (0.175 mmol) of tert-butyl (2S, 5R)-2-(4-{[(2-amino-1,3-thiazol-4-yl)acetyl]amino}-3-bromobenzyl)-5-[(R)-hydroxy(phenyl)methyl]pyrrolidine-1-carboxylate (from Step A) in 2.0 mL DCM was added 1.0 mL TFA and the reaction mixture stirred at room temperature for 2 h. Azeotrop with toluene (2×) to excess acid. The residue was then taken up in acetonitrile/water/MeOH (9:1:1) and purified on the Gilson HPLC eluting with a 10-90% gradient of acetonitrile/water with 0.05% TFA buffer. The fractions containing the product were combined, frozen, and lyophilized to give a white foam (77 mg, 88%). m/z (ES) 501 (M)$^+$ and 503 (M+2)$^+$, also 523 (MNa)$^+$ and 525 (MNa+2)$^+$.

Using the Biological Assays described above, the human β3 functional activity of Example 312 was determined to be between 11 to 100 nM.

Example 313

2-(2-Amino-1,3-thiazol-4-yl)-N-[2-bromo-4-({(2R, 5R)-5-[(R)-hydroxy(phenyl)methyl]pyrrolidin-2-yl}methyl)phenyl]acetamide

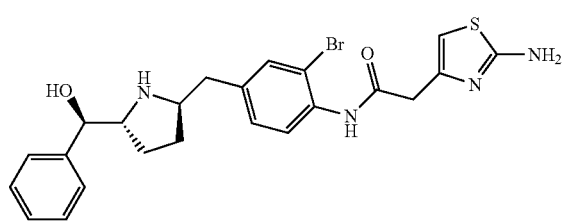 [SMILES: Nc1nc(CC(=O)Nc2ccc(C[C@H]3CC[C@H]([C@H](O)c4ccccc4)N3)cc2Br)cs1]

Step A: Tert-butyl (2R,5R)-2-(4-{[(2-amino-1,3-thiazol-4-yl)acetyl]amino}-3-bromobenzyl)-5-[(R)-hydroxy(phenyl)methyl]pyrrolidine-1-carboxylate

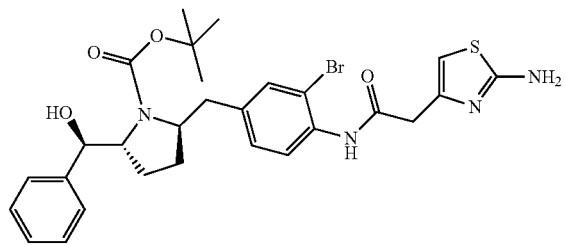 [SMILES: CC(C)(C)OC(=O)N1[C@@H](Cc2ccc(NC(=O)Cc3csc(N)n3)c(Br)c2)CC[C@@H]1[C@H](O)c1ccccc1]

To a solution of 81 mg (0.18 mmol) of tert-butyl (2R,5R)-2-(4-amino-3-bromobenzyl)-5-[(R)-hydroxy(phenyl)methyl]pyrrolidine-1-carboxylate (i-80b) and (2-amino-1,3-thiazol-4-yl)acetic acid (45 mg, 0.18 mmol) in 2.0 mL anhydrous DMF was added HOBt (31 mg, 0.23 mmol) followed by EDC (45 mg) and DIEA (0.16 mL, 0.88 mmol). The resulting mixture was stirred at room temperature under nitrogen atmosphere for 16 h. The mixture was washed with water and extracted with dichloromethane (2×2 mL). The organics were combined, dried over sodium sulfate, filtered and concentrated in vacuum. The residue was purified by Gilson reverse phase HPLC eluting with a gradient of 10-90% acetonitrile in water with 0.05% TFA buffer to afforded the product (75 mg, 81%). m/z (ES) 601 (M)+ and 603 (M+2)+, also 623 (MNa)+ and 625 (MNa+2)+.

Step B: 2-(2-Amino-1,3-thiazol-4-yl)-N-[2-bromo-4-({(2R,5R)-5-[(R)-hydroxy(phenyl)methyl]pyrrolidin-2-yl}methyl)phenyl]acetamide

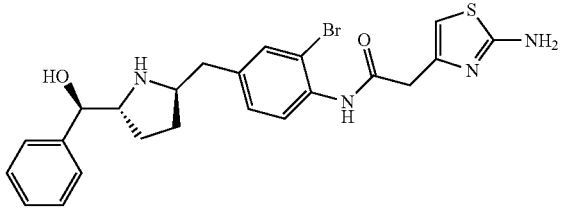 [SMILES: Nc1nc(CC(=O)Nc2ccc(C[C@H]3CC[C@H]([C@H](O)c4ccccc4)N3)cc2Br)cs1]

To a solution of 75 mg (0.124 mmol) of tert-butyl (2R,5R)-2-(4-{[(2-amino-1,3-thiazol-4-yl)acetyl]amino}-3-bromobenzyl)-5-[(R)-hydroxy(phenyl)methyl]pyrrolidine-1-carboxylate (from Step A, Example 313) in 2.0 mL DCM was added 1.0 mL TFA and the reaction mixture stirred at room temperature for 2 h. Azeotrop with toluene (2×) to excess acid. The residue was then taken up in acetonitrile/water/MeOH (9:1:1) and purified on the Gilson HPLC eluting with a 10-90% gradient of acetonitrile/water with 0.05% TFA buffer. The fractions containing the product were combined, frozen, and lyophilized to give a white foam (56 mg, 90%). m/z (ES) 501 (M)+ and 503 (M+2)+, also 523 (MNa)+ and 525 (MNa+2)+.

Using the Biological Assays ($\beta_3$AR-cAMP) as described above, the human $\beta$3 functional activity of Example 313 was determined to be between 101 to 1000 nM.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I, or a pharmaceutically acceptable salt thereof, or a stereoisomer thereof, or a pharmaceutically acceptable salt of the stereoisomer thereof:

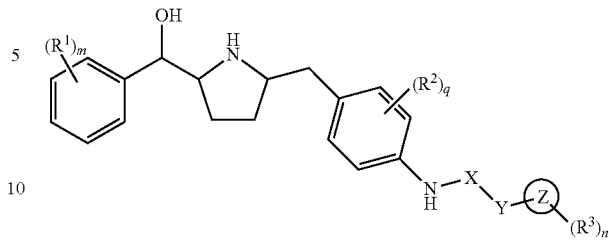

wherein m is 0, 1, 2, 3, or 4;
n is 0, 1, 2, 3, 4, or 5;
p is 0, 1, or 2;
q is 0, 1, 2, 3, or 4;
t is 0, 1, 2, 3, 4, or 5;
X is —CO— or —SO$_2$—;
Y is selected from the group consisting of:
(1) $C_1$-$C_5$ alkanediyl, $C_2$-$C_5$ alkenediyl, and $C_2$-$C_5$ alkynediyl, wherein each of alkanediyl, alkenediyl and alkynediyl is optionally substituted with one to three groups independently selected from halogen, —OR$^a$, —S(O)$_p$—$C_1$-$C_3$ alkyl;
(2) —(CR$^a$R$^a$)$_j$-Q-(CR$^a$R$^a$)$_k$, wherein j and k are integers independently selected from 0, 1 and 2,
(3) a bond, and
(4) phenylene optionally substituted with one to three groups independently selected from R$^1$;
Z is selected from the group consisting of:
(2) a 5- or 6-membered heterocyclic ring with from 1 to 4 heteroatoms selected from oxygen, sulfur and nitrogen;
R$^1$ is selected from the group consisting of:
(1) $C_1$-$C_5$ alkyl optionally substituted with 1 to 5 halogen atoms,
(2) $C_3$-$C_6$ cycloalkyl,
(3) halogen,
(4) nitro,
(5) cyano,
(6) —C(O)R$^a$,
(7) —C(O)$_2$R$^a$,
(8) —C(O)NR$^a$R$^b$, and
(9) -QR$^b$;
R$^2$ is selected from the group consisting of halogen and $C_1$-$C_5$ alkyl;
R$^3$ is selected from the group consisting of:
(1) $C_1$-$C_6$ alkyl optionally substituted with 1 to 5 groups independently selected from halogen, —OR$^a$, —CO$_2$R$^a$, and —CONR$^a$R$^b$,
(2) —(CH$_2$)$_t$-phenyl or —(CH$_2$)$_t$—O-phenyl, and wherein said phenyl in each is optionally substituted with 1 to 3 groups independently selected from halogen, $C_1$-$C_5$ alkyl optionally substituted with 1 to 5 halogen atoms, and —OR$^a$,
(3) oxo,
(4) thioxo,
(5) halogen,
(6) —CN,
(7) $C_3$-$C_6$ cycloalkyl,
(8) —(CH$_2$)$_t$-heterocyclic ring or —(CH$_2$)$_t$—O-heterocyclic ring, and wherein the heterocyclic ring in each is a 5- or 6-membered ring with from 1 to 4 heteroatoms selected from oxygen, sulfur and nitrogen, and wherein said heterocyclic ring is optionally ortho-fused to a benzene ring, and optionally substituted with 1 to 3 groups independently selected from halogen, $C_1$-$C_5$ alkyl optionally substituted with 1 to 5 halogen atoms, and —$OR^a$, (9) —$OR^a$,

(10) —$C(O)OR^a$,

(11) —$C(O)R^a$,

(12) —$C(O)NR^aR^b$,

(12) —$NR^aR^b$,

(13) —$NR^aC(O)R^b$,

(14) —$NR^aC(O)OR^b$, and

(15) —$NR^aC(O)NR^aR^b$;

$R^a$ is selected from the group consisting of hydrogen and $C_1$-$C_6$ alkyl optionally substituted with 1 to 5 halogen atoms;

$R^b$ is selected from the group consisting of:

(1) hydrogen, (2) $C_1$-$C_6$ alkyl optionally substituted with 1 to 5 groups selected from the group consisting of:
  (a) hydroxy,
  (b) halogen,
  (c) —$CO_2R^a$,
  (d) —$S(O)_p$—$C_1$-$C_3$ alkyl;
  (e) $C_3$-$C_8$ cycloalkyl,
  (f) $C_1$-$C_6$ alkoxy optionally substituted with 1 to 5 halogens, and
  (g) phenyl optionally substituted with 1 to 5 groups independently selected from the group consisting of halogen, nitro, —$NR^aR^a$, $R^a$, trifluoromethyl, trifluoromethoxy, $C_1$-$C_5$ alkyl and —$OR^a$, (3) $C_3$-$C_8$ cycloalkyl, and (4) phenyl optionally substituted with 1 to 5 groups selected from the group consisting of:
  (a) halogen,
  (b) nitro,
  (c) —$NR^aR^a$,
  (d) —OH,
  (e) $C_1$-$C_6$ alkoxy optionally substituted with 1 to 5 halogens,
  (f) —$S(O)_p$—$C_1$-$C_6$ alkyl; and
  (g) $C_1$-$C_6$ alkyl optionally substituted with up to 5 groups selected from hydroxy, halogen, trifluoromethyl, cyano, —$CO_2R^a$, $C_3$-$C_8$ cycloalkyl, and -$QR^c$; $R^c$ is selected from the group consisting of:
    (1) Z optionally substituted with up to 5 groups selected from halogen, trifluoromethyl, cyano, $C_1$-$C_5$ alkyl and $C_1$-$C_5$ alkoxy, and
    (2) $C_1$-$C_6$ alkyl; and Q is selected from the group consisting of:

(1) —$N(R^a)$—, (2) —O—, and (3) —$S(O)_p$—.

2. The compound of claim 1 having Formula Ia, or a pharmaceutically acceptable salt thereof, or a stereoisomer thereof, or a pharmaceutically acceptable salt of the stereoisomer thereof:

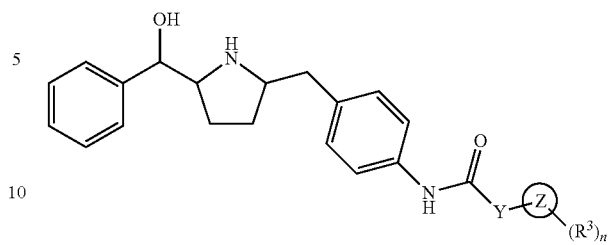

wherein Y, Z, $R^3$ and n are as defined in claim 1.

3. The compound of claim 2 wherein Y is methylene, —$CH(CH_3)$— or a bond.

4. The compound of claim 2 wherein Z is selected from the group consisting of thiazolyl, oxazolyl, 1,2,4-triazolyl, 1,2,3-triazolyl, tetrazolyl, pyrrolidinyl, imidazolyl, pyrazolyl, 1,2,4-oxadiazolyl, and 1,2,5-oxadiazolyl.

5. The compound of claim 2 wherein $R^3$ is selected from the group consisting of:

(1) $C_1$-$C_6$ alkyl optionally substituted with halogen or —$OR^a$, (2) oxo, (3) halogen, (4) —$OR^a$, (5) —$C(O)NR^aR^a$, and (6) —$NR^aR^a$;

wherein $R^a$ is as defined in claim 2.

6. A compound of Formula Ia, or a pharmaceutically acceptable salt thereof, or a stereoisomer thereof, or a pharmaceutically acceptable salt of the stereoisomer thereof:

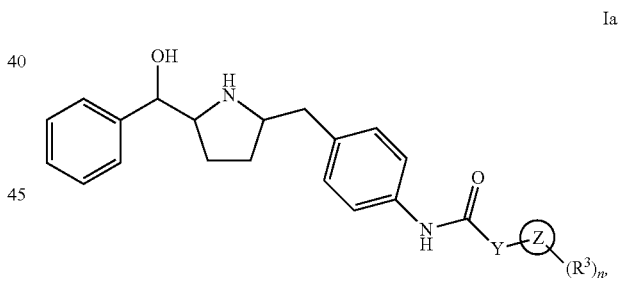

wherein n is 0, 1 or 2;

Y is selected from the group consisting of methylene, —$CH(CH_3)$— and a bond;

Z is selected from the group consisting of thiazolyl, 1,2,4-triazolyl, and pyrazolyl; and $R^3$ is selected from the group consisting of:
  (1) methyl,
  (2) oxo, and
  (3) —$NH_2$.

7. The compound of claim 6, wherein n is 1;

Y is —$CH(CH_3)$—;

Z is 1,2,4-triazolyl; and $R^3$ is methyl.

8. A compound of claim 1 selected from the group consisting of:

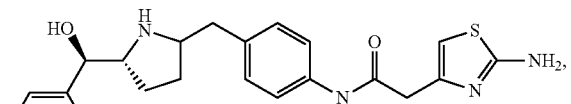

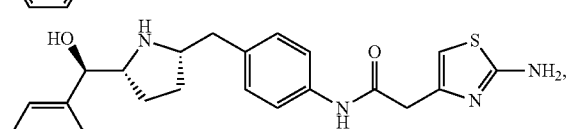

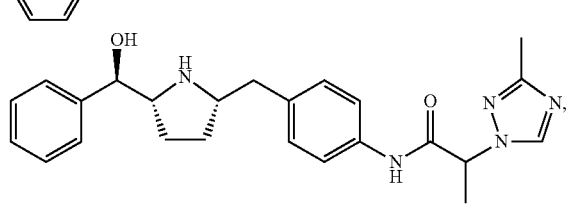

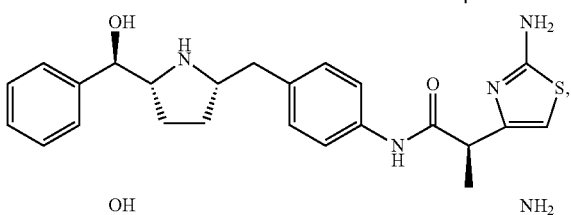

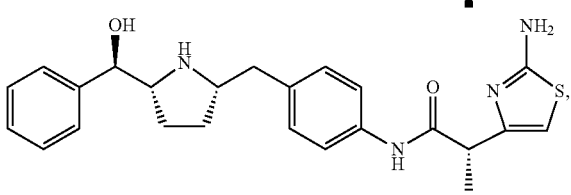

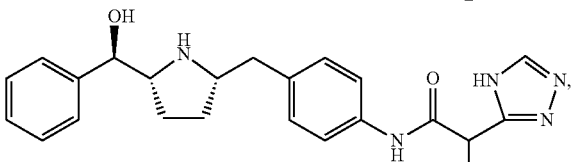

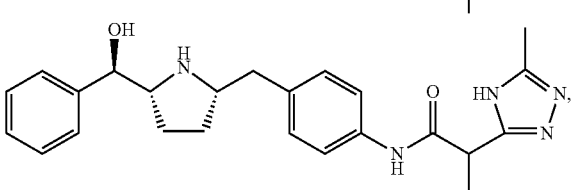

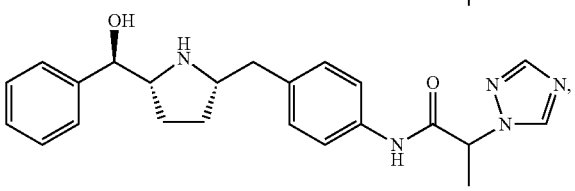

and

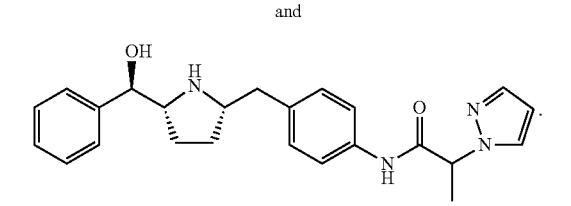

or a pharmaceutically acceptable salt thereof, or a pharmaceutically acceptable stereoisomer thereof, or a pharmaceutically acceptable salt of the stereoisomer thereof.

9. A compound of claim 8, wherein the compound is selected from the group consisting of:

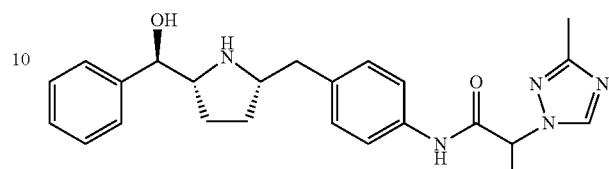

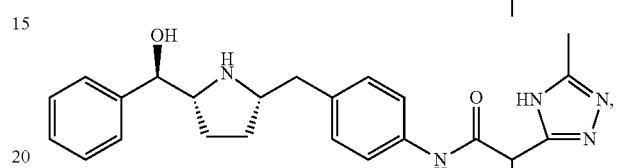

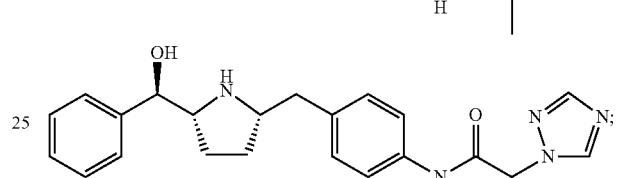

and

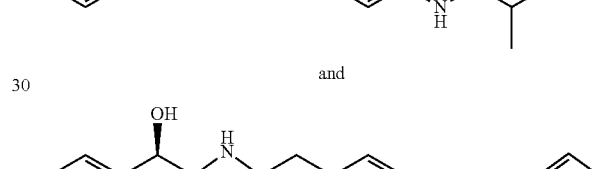

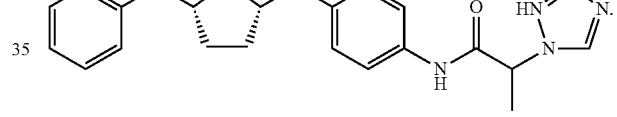

or a pharmaceutically acceptable salt thereof, or a pharmaceutically acceptable stereoisomer thereof, or a pharmaceutically acceptable salt of the stereoisomer thereof.

10. A compound of claim 9, wherein the compound is selected from the group consisting of:

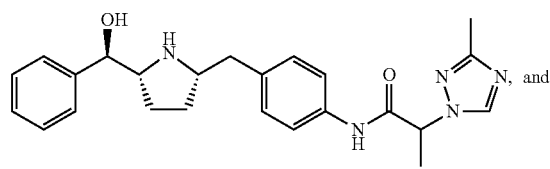, and

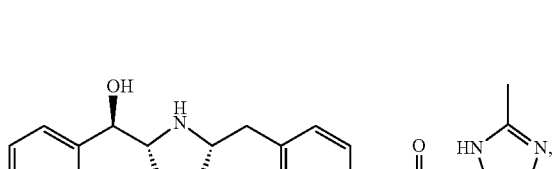

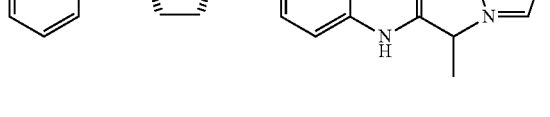

or a pharmaceutically acceptable salt thereof, or a pharmaceutically acceptable stereoisomer thereof, or a pharmaceutically acceptable salt of the stereoisomer thereof.

11. A compound of claim 10, wherein the compound is:

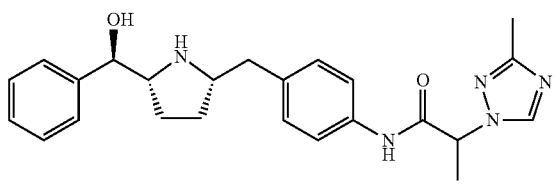

or a pharmaceutically acceptable salt thereof, or a pharmaceutically acceptable stereoisomer thereof, or a pharmaceutically acceptable salt of the stereoisomer thereof.

12. A compound of claim 10, wherein the compound is:

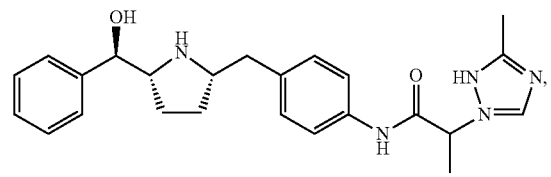

or a pharmaceutically acceptable salt thereof, or a pharmaceutically acceptable stereoisomer thereof, or a pharmaceutically acceptable salt of the stereoisomer thereof.

13. A compound of claim 9, wherein the compound is selected from the group consisting of:

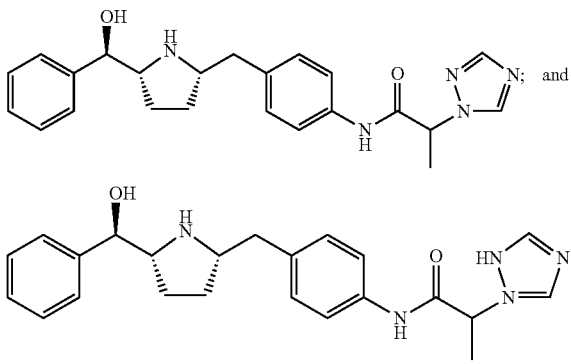

or a pharmaceutically acceptable salt thereof, or a pharmaceutically acceptable stereoisomer thereof, or a pharmaceutically acceptable salt of the stereoisomer thereof.

14. A compound of claim 13, wherein the compound is selected from the group consisting of:

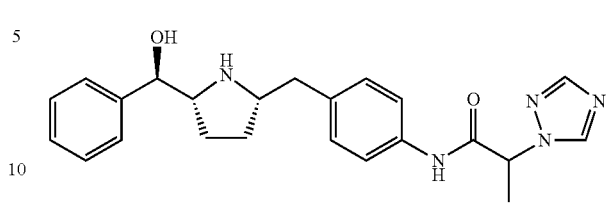

or a pharmaceutically acceptable salt thereof, or a pharmaceutically acceptable stereoisomer thereof, or a pharmaceutically acceptable salt of the stereoisomer thereof.

15. A compound of claim 13, wherein the compound is selected from the group consisting of:

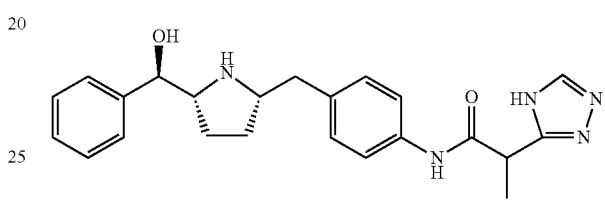

or a pharmaceutically acceptable salt thereof, or a pharmaceutically acceptable stereoisomer thereof, or a pharmaceutically acceptable salt of the stereoisomer thereof.

16. A pharmaceutical composition comprising a compound of claim 1 and a pharmaceutically acceptable carrier.

17. A method for the treatment or prevention of a disease or disorder mediated by the activation of β3-adrenoceptor, wherein said method comprises administering to a patient in need thereof a therapeutically effective amount of a compound of claim 1.

18. The method of claim 17 wherein the disease or disorder is selected from the group consisting of (1) overactive bladder, (2) urinary incontinence, (3) urge urinary incontinence, and (4) urinary urgency.

19. A method for the treatment or prevention of a disease or disorder mediated by the activation of β3-adrenoceptor, wherein the method comprises administering to a patient in need thereof a therapeutically effective amount of a compound of claim 1 and a second active agent.

20. The method of claim 19, wherein the second active agent is a muscarinic receptor antagonist.

* * * * *